US012272463B2

(12) United States Patent
Shelton, IV et al.

(10) Patent No.: US 12,272,463 B2
(45) Date of Patent: Apr. 8, 2025

(54) METHODS FOR SURGICAL SIMULATION

(71) Applicant: Cilag Gmbh International, Zug (CH)

(72) Inventors: Frederick E. Shelton, IV, Hillsboro, OH (US); Charles J. Scheib, Loveland, OH (US); Jason L. Harris, Lebanon, OH (US); Kevin M. Fiebig, Cincinnati, OH (US); Dwight Alan Meglan, Westwood, MA (US)

(73) Assignee: Cilag GmbH International, Zug (CH)

( * ) Notice: Subject to any disclaimer, the term of this patent is extended or adjusted under 35 U.S.C. 154(b) by 682 days.

(21) Appl. No.: 17/332,594

(22) Filed: May 27, 2021

(65) Prior Publication Data
US 2022/0370138 A1 Nov. 24, 2022

Related U.S. Application Data

(60) Provisional application No. 63/191,681, filed on May 21, 2021.

(51) Int. Cl.
*G16H 50/50* (2018.01)
*A61B 18/14* (2006.01)
(Continued)

(52) U.S. Cl.
CPC ............ *G16H 50/50* (2018.01); *A61B 18/14* (2013.01); *A61B 34/25* (2016.02); *A61B 34/30* (2016.02);
(Continued)

(58) Field of Classification Search
CPC ........ G16H 50/50; G16H 15/00; G16H 20/40; G16H 30/40; G16H 40/20; G16H 40/63;
(Continued)

(56) References Cited

U.S. PATENT DOCUMENTS 8,311,791 B1 * 11/2012 Avisar .................... A61B 90/37
707/700
9,104,791 B2  8/2015 Cohen et al.
(Continued)

FOREIGN PATENT DOCUMENTS

CN      110638529 A  *  1/2020  ............. A61B 90/37
DE   102015208804 A1    11/2016
(Continued)

OTHER PUBLICATIONS

Gallagher, A. et al., "Fundamentals of Surgical Simulation", Gallagher, et al., "Fundamentals of Surgical Simulation, Principles and Practices Improving Medical Outcome- Zero Tolerance", DOI 10.1007/978-0-85729-763-1_12, @ Springer-Verlag London Limited 2012, 384 pages.
(Continued)

*Primary Examiner* — Kibrom K Gebresilassie
(74) *Attorney, Agent, or Firm* — Condo Roccia Koptiw LLP

(57) ABSTRACT

An interactive and dynamic surgical simulation system may be used in the context of a computer-implemented interactive surgical system. An operating-room-based surgical data system may aggregate surgical activity data that is indicative of a performance of a live surgical procedure. The surgical simulation device may receive the surgical activity data from the operating-room-based surgical data system. And the surgical simulation device may simulate a surgical task based on surgical activity data. The surgical activity data may be structured by a procedure plan data structure. The procedure plan data structure may be common to the operating-room-based surgical data system and the surgical simulation device. The procedure plan data structure may be configured to covey information indicative of equipment, technique, and surgical steps in a structured format such that the equipment, technique, and surgical steps of the live surgical procedure are reflected in the simulated surgical procedure.

18 Claims, 51 Drawing Sheets

(51) Int. Cl.

| | |
|---|---|
| *A61B 34/00* | (2016.01) |
| *A61B 34/30* | (2016.01) |
| *A61B 34/37* | (2016.01) |
| *A61B 90/00* | (2016.01) |
| *G06F 30/20* | (2020.01) |
| *G06N 20/00* | (2019.01) |
| *G06N 20/10* | (2019.01) |
| *G09B 9/00* | (2006.01) |
| *G09B 19/00* | (2006.01) |
| *G09B 23/30* | (2006.01) |
| *G16H 15/00* | (2018.01) |
| *G16H 20/40* | (2018.01) |
| *G16H 30/40* | (2018.01) |
| *G16H 40/20* | (2018.01) |
| *G16H 40/63* | (2018.01) |
| *G16H 40/67* | (2018.01) |
| *G16H 50/70* | (2018.01) |
| *G16H 70/20* | (2018.01) |
| *A61B 18/12* | (2006.01) |
| *A61B 34/10* | (2016.01) |

(52) U.S. Cl.
CPC .............. *A61B 34/37* (2016.02); *A61B 90/36* (2016.02); *G06F 30/20* (2020.01); *G06N 20/00* (2019.01); *G06N 20/10* (2019.01); *G09B 9/00* (2013.01); *G09B 19/003* (2013.01); *G09B 23/30* (2013.01); *G16H 15/00* (2018.01); *G16H 20/40* (2018.01); *G16H 30/40* (2018.01); *G16H 40/20* (2018.01); *G16H 40/63* (2018.01); *G16H 40/67* (2018.01); *G16H 50/70* (2018.01); *G16H 70/20* (2018.01); *A61B 2018/1253* (2013.01); *A61B 2018/126* (2013.01); *A61B 34/10* (2016.02); *A61B 2034/101* (2016.02); *A61B 2034/102* (2016.02); *A61B 2034/105* (2016.02); *A61B 2034/107* (2016.02); *A61B 2034/252* (2016.02); *A61B 2034/254* (2016.02); *A61B 2034/256* (2016.02); *A61B 2034/258* (2016.02); *A61B 2090/363* (2016.02); *A61B 2090/365* (2016.02); *A61B 2218/002* (2013.01); *A61B 2218/008* (2013.01)

(58) Field of Classification Search
CPC ........ G16H 40/67; G16H 50/70; G16H 70/20; A61B 18/14; A61B 34/25; A61B 34/30; A61B 34/37; A61B 90/36; A61B 34/10; A61B 2018/1253; A61B 2018/126; A61B 2034/101; A61B 2034/105; A61B 2034/107; A61B 2034/252; A61B 2034/254; A61B 2034/256; A61B 2034/258; A61B 2090/363; A61B 2090/365; A61B 2218/002; A61B 2218/008; A61B 34/76; A61B 2017/00203; A61B 2034/102; A61B 2034/2048; A61B 90/30; A61B 2090/364; A61B 2090/372; A61B 2090/502; G06F 30/20; G06F 3/011; G06F 3/016; G06N 20/00; G06N 20/10; G09B 9/00; G09B 19/003; G09B 23/30; G09B 5/06; G09B 23/28

See application file for complete search history.

(56) References Cited

U.S. PATENT DOCUMENTS

| | | |
|---|---|---|
| 9,734,632 B2 | 8/2017 | Thomas et al. |
| 9,881,520 B2 | 1/2018 | Ullrich et al. |
| 10,172,676 B2 | 1/2019 | Ecabert et al. |
| 2008/0235052 A1 | 9/2008 | Node-Langlois et al. |
| 2009/0089092 A1 | 4/2009 | Johnson et al. |
| 2009/0177454 A1 | 7/2009 | Bronstein et al. |
| 2010/0178644 A1 | 7/2010 | Meglan et al. |
| 2012/0016691 A1 | 1/2012 | Sievenpiper et al. |
| 2012/0197619 A1 | 8/2012 | Namer et al. |
| 2014/0272866 A1 | 9/2014 | Kim |
| 2015/0005622 A1 | 1/2015 | Zhao et al. |
| 2016/0314710 A1 | 10/2016 | Jarc et al. |
| 2017/0148213 A1 | 5/2017 | Thomas et al. |
| 2017/0181808 A1 | 6/2017 | Panescu et al. |
| 2017/0319283 A1 | 11/2017 | Suresh et al. |
| 2018/0060455 A1 | 3/2018 | Castillo |
| 2018/0098813 A1* | 4/2018 | Nesichi ................. G09B 23/28 |
| 2018/0247558 A1* | 8/2018 | Livneh .................... G09B 9/24 |
| 2018/0348876 A1 | 12/2018 | Banerjee et al. |
| 2019/0000578 A1* | 1/2019 | Yu .......................... A61B 34/25 |
| 2019/0059997 A1 | 2/2019 | Frushour |
| 2019/0125361 A1 | 5/2019 | Shelton, IV et al. |
| 2019/0200844 A1 | 7/2019 | Shelton, IV et al. |
| 2019/0201118 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0206564 A1 | 7/2019 | Shelton, IV et al. |
| 2019/0206569 A1 | 7/2019 | Shelton, IV et al. |
| 2019/0272917 A1 | 9/2019 | Couture et al. |
| 2019/0325574 A1 | 10/2019 | Jin et al. |
| 2019/0362651 A1 | 11/2019 | Barral et al. |
| 2019/0380792 A1 | 12/2019 | Poltaretskyi et al. |
| 2020/0174451 A1 | 6/2020 | Chanin |
| 2020/0237452 A1 | 7/2020 | Wolf et al. |
| 2020/0242686 A1 | 7/2020 | García Giraldez et al. |
| 2020/0275976 A1 | 9/2020 | Mckinnon et al. |
| 2020/0405403 A1 | 12/2020 | Shelton, IV et al. |
| 2022/0233119 A1 | 7/2022 | Shelton, IV et al. |
| 2022/0370131 A1 | 11/2022 | Shelton, IV et al. |
| 2022/0370132 A1 | 11/2022 | Shelton, IV et al. |
| 2022/0370133 A1 | 11/2022 | Scheib et al. |
| 2022/0370134 A1 | 11/2022 | Shelton, IV et al. |
| 2022/0370135 A1* | 11/2022 | Shelton, IV ............ G06F 30/20 |
| 2022/0370136 A1 | 11/2022 | Scheib et al. |
| 2022/0370137 A1 | 11/2022 | Shelton, IV et al. |
| 2022/0375570 A1 | 11/2022 | Shelton, IV et al. |
| 2022/0375620 A1 | 11/2022 | Scheib et al. |
| 2022/0384022 A1 | 12/2022 | Matsuura et al. |
| 2023/0293236 A1 | 9/2023 | Wright et al. |

FOREIGN PATENT DOCUMENTS

| | | | | |
|---|---|---|---|---|
| EP | 2269693 A1 * | 1/2011 | ........... | A61N 5/1031 |
| EP | 3367387 A1 * | 8/2018 | ............. | A61B 34/25 |
| EP | 3506290 A1 | 7/2019 | | |
| EP | 3649994 A1 * | 5/2020 | .......... | F21V 33/0072 |
| JP | 2021509034 A * | 3/2021 | ............. | G16H 20/30 |
| KR | 101940706 B1 | 4/2019 | | |
| WO | 2011108994 A1 | 9/2011 | | |
| WO | WO 2020072255 A1 * | 4/2020 | ............. | G16H 20/40 |
| WO | WO 2020163358 A1 * | 8/2020 | ............... | G06N 5/01 |

OTHER PUBLICATIONS

Andersen, Daniel et al., "Augmented Visual Instruction for Surgical Practice and Training", IEEE Workshop on Virtual and Augmented Realities for Good, Reutlingen, Germany, Mar. 18, 2018, 5 pages.

Elhelw, Mohamed A. , "Overview of Surgical Simulation", Center for Informatics Science, Nile University, Giza, Egypt, May 2020, 26 pages.

Reiter, Austin et al., "Surgical Structured Light for 3D Minimally Invasive Surgical Imaging", IEEE/RSJ International Conference on Intelligent Robot and Systems(IROS 2014), Chicago, IL, Sep. 14-18, 2014, pp. 1282-1287.

(56) References Cited

OTHER PUBLICATIONS

Wang, Yang et al., "High Resolution Acquisition, Learning, and Transfer of Dynamic 3-D Facial Expressions", Eurographics, vol. 23, No. 3, 2004, pp. 677-686.

* cited by examiner

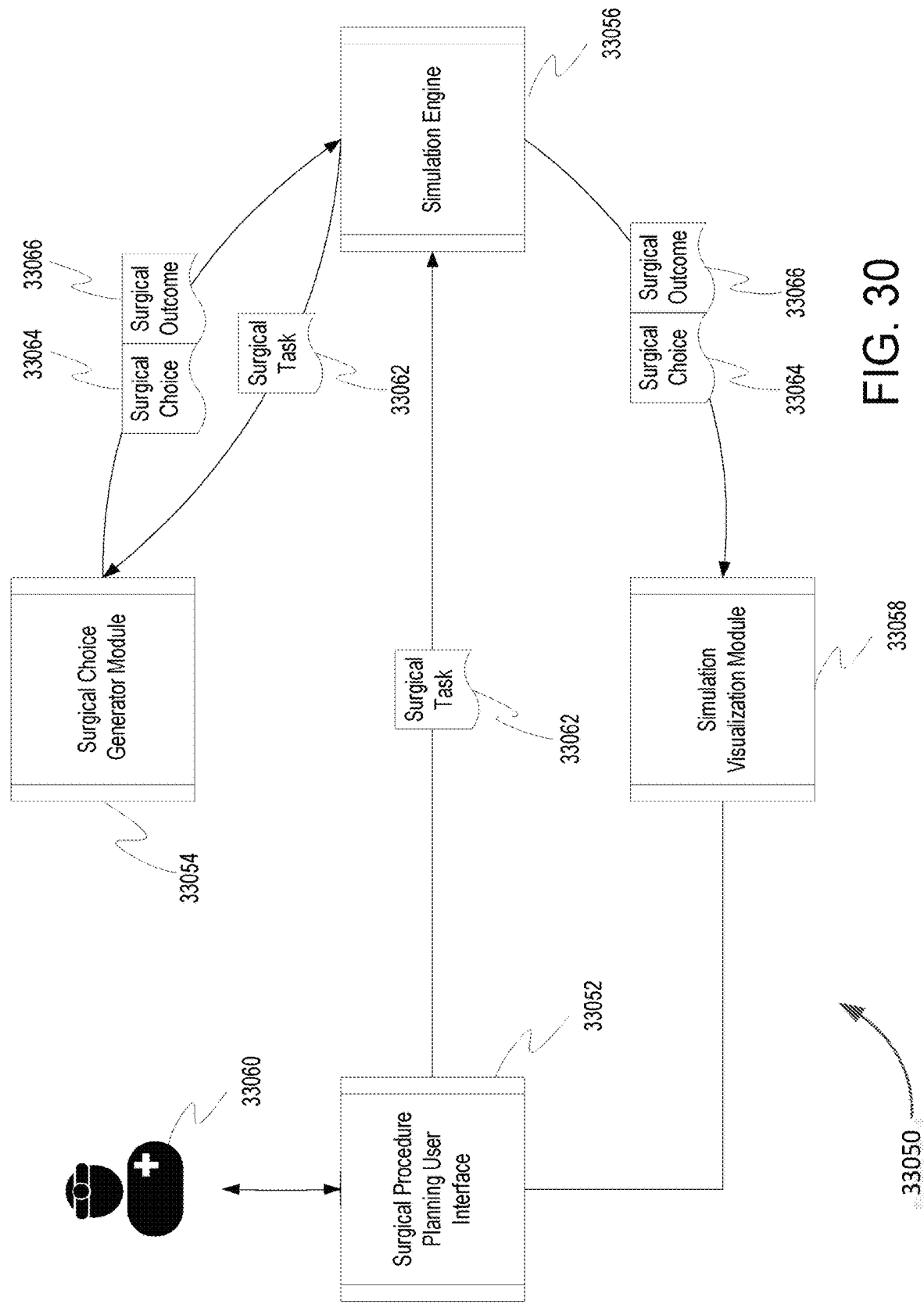

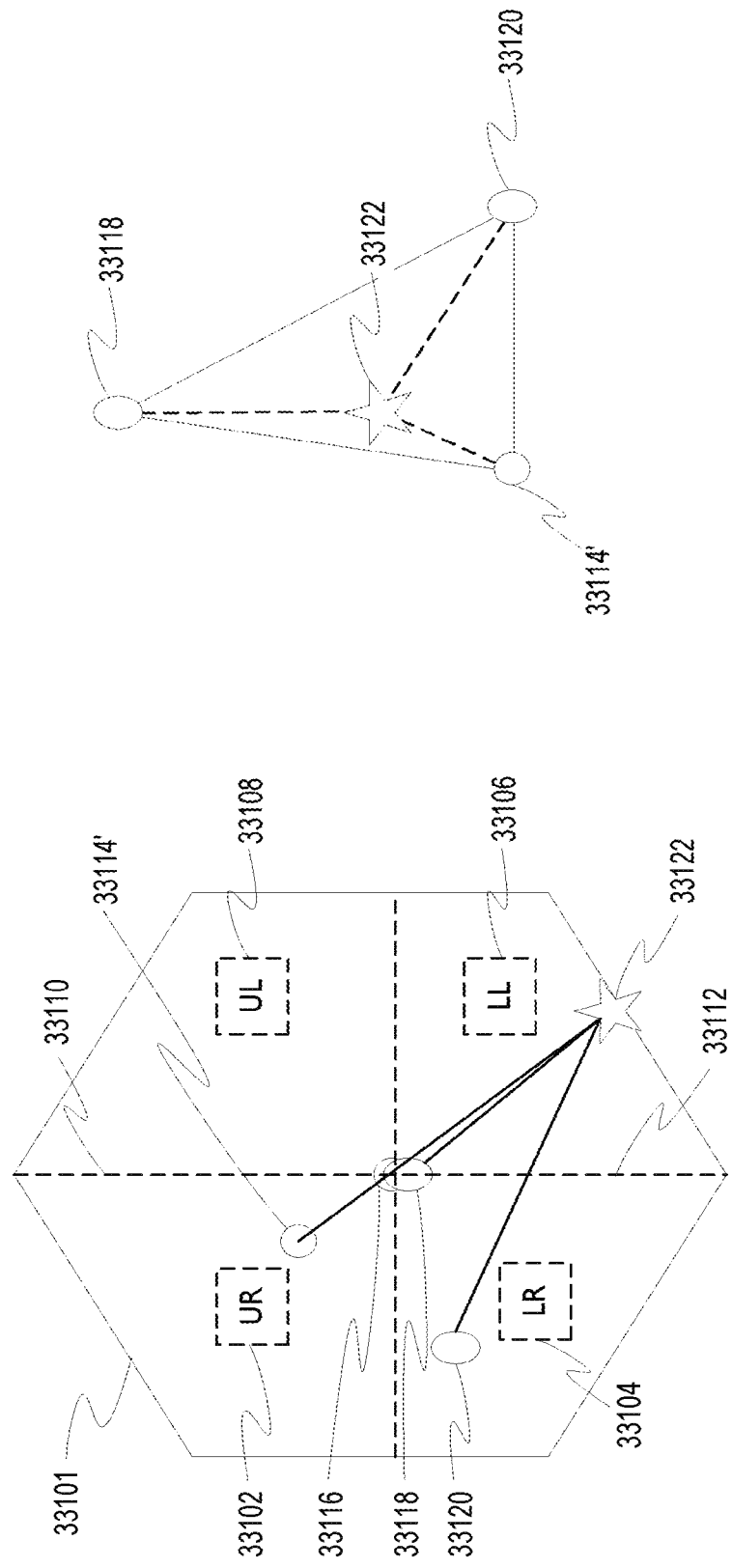

FIG. 46

| | Simulated Sigmoid Colectomy 1 | Simulated Sigmoid Colectomy 2 |
|---|---|---|
| Initiate 34652 | Make Incisions: ▶ Replay | Make Incisions: ▶ Replay |
| | Scope port: umbilicus; 12mm; 2m1s (avg + 15s) | Scope port: umbilicus; 12mm; 1m31s (avg - 15s) |
| | Grasper port: upper right; 5mm; 1m1s (avg + 8s) | Grasper port: upper midline; 5mm; 45s (avg - 8s) |
| | Harmonic port: lower right; 12mm; 1m46s (avg + 8s) | Harmonic port: lower right; 12mm; 1m30s (avg - 8s) |
| Access 34654 | Dissect Mesentery: 38m1s (avg+ 8m49s) | Dissect Mesentery: 20m23s (avg - 8m49s) |
| | Direction: medial-to-lateral | Direction: medial-to-lateral |
| | IMA branches identified: Yes | IMA branches identified: No |
| | Ureter identified: Yes | Ureter identified: Yes |
| | Complications: None | Complications: Some (moderate bleeding) |
| Mobilize Colon 34656 | Ligate IMA: 6m31s (avg+ 39s) | Ligate IMA: 5m13s (avg - 39s) |
| | Branches before root | Root before branches |
| | thinnest branch to thickest | thickest branch to thinnest |
| | Complications: None (minimum bleeding) | Complications: Some (moderate bleeding) |
| | Mobilize Upper Sigmoid: | Mobilize Upper Sigmoid: |
| | . . . | . . . |
| | Mobilize Descending Colon: | Mobilize Descending Colon: |
| | . . . | . . . |
| | Mobilize Rectum and Sigmoid: | Mobilize Rectum and Sigmoid: |
| | . . . | . . . |
| Resect Sigmoid 34658 | Transect Bowel: . . . | Transect Bowel: . . . |
| | . . . | . . . |
| | Remove Sigmoid: . . . | Remove Sigmoid: . . . |
| | . . . | . . . |
| | Set anvil for circular stapler: . . . | Set anvil for circular stapler: . . . |
| | . . . | . . . |
| Perform Anastomosis 34660 | Prepare rectum: . . . | Prepare rectum: . . . |
| | . . . | . . . |
| | Insert circular stapler: . . . | Insert circular stapler: . . . |
| | . . . | . . . |
| | Align anvil with rectum: . . . | Align anvil with rectum: . . . |
| | . . . | . . . |
| | Attach anvil to circular stapler: . . . | Attach anvil to circular stapler: . . . |
| | . . . | . . . |
| | Fire circular stapler: . . . | Fire circular stapler: . . . |
| | . . . | . . . |
| Conclude 34662 | Inflate colon: . . . | Inflate colon: . . . |
| | . . . | . . . |
| | Check for leaks: . . . | Check for leaks: . . . |
| | . . . | . . . |
| | Remove trocars: . . . | Remove trocars: . . . |
| | . . . | . . . |
| | Close incisions: . . . | Close incisions: . . . |
| | . . . | . . . |

34650 · 34672 · 34674

| Independent variables | | Target variable |
|---|---|---|
| IMA ligation root v. branch order | IMA ligation branches order | Bleeding amount |
| Root before branches | Thinnest to thickest | Moderate |
| Branches before root | Thickest to thinnest | Minimum |
| Branches before root | Thinnest to thickest | Minimum |
| Branches before root | Thinnest to thickest | Minimum |
| Root before branches | Thinnest to thickest | Moderate |
| ... | ... | ... |

FIG. 47A

| | Coefficients | P-value |
|---|---|---|
| IMA ligation root v. branch order | 3.45 | 0.01 |
| IMA ligation branches order | 0.14 | 0.64 |

FIG. 47B

METHODS FOR SURGICAL SIMULATION

CROSS-REFERENCE TO RELATED APPLICATIONS

This application claims the benefit of Provisional U.S. Patent Application No. 63/191,681, May 21, 2021, the disclosure of which is incorporated herein by reference in its entirety.

This application is related to the following, filed contemporaneously, the contents of each of which are incorporated by reference herein:

U.S. patent application Ser. No. 17/332,524, filed May 27, 2021, titled SURGICAL SIMULATION OBJECT RECTIFICATION SYSTEM U.S. patent application Ser. No. 17/332,399, filed May 27, 2021, titled SURGICAL SIMULATION NAVIGATION SYSTEM U.S. patent application Ser. No. 17/332,441, filed May 27, 2021, titled SURGICAL SIMULATION SYSTEM WITH COORDINATED IMAGING U.S. patent application Ser. No. 17/332,462, filed May 27, 2021, titled SURGICAL SIMULATION SYSTEM WITH SIMULATED SURGICAL EQUIPMENT COORDINATION U.S. patent application Ser. No. 17/332,197, filed May 27, 2021, titled SIMULATION-BASED SURGICAL PROCEDURE PLANNING SYSTEM U.S. patent application Ser. No. 17/332,407, filed May 27, 2021, titled SIMULATION-BASED DIRECTED SURGICAL DEVELOPMENT SYSTEM U.S. patent application Ser. No. 17/332,449, filed May 27, 2021, titled SURGICAL ADVERSE EVENT SIMULATION SYSTEM U.S. patent application Ser. No. 17/332,496, filed May 27, 2021 titled SIMULATION-BASED SURGICAL ANALYSIS SYSTEM U.S. patent application Ser. No. 17/332,480, filed May 27, 2021, titled DYNAMIC ADAPTATION SYSTEM FOR SURGICAL SIMULATION

BACKGROUND

Surgical simulations, such as computer-based, three-dimensional simulations of a surgical environment and/or surgical procedure for example, present an opportunity to advance the surgical arts. Surgical simulations have potential to benefit surgical training, planning, development, and the like. For example, surgical simulations may be used to train surgeons in new procedures and/or to improve the performance of procedures they already know. Surgical simulations may be used as a virtual "dress rehearsal" to help a surgeon prepare for an upcoming procedure. And surgical simulations may be used to experiment with unproven procedures and techniques.

However, surgical simulation platforms are complex systems that face many limitations in capabilities, scope, and applicability. For example, many platforms are technology "silos," specifically programmed and tailored to address a particular learning objective or to simulate the operation of a singular piece of equipment, such as simulating the operation of a surgical robot. Limitations, such as these, may diminish a platform's effectiveness as a tool to advance the surgical arts. And such limitations may represent significant technological roadblocks to the integration of simulation-based applications into other aspects of the surgical process, such a pre-operative planning, intra-operative support, post-operative analysis, and the like.

Accordingly, innovation in surgical simulation technology, such as technical advancements that address surgical simulation capabilities, scope, and applicability for example, may accelerate further progress in the surgical arts.

SUMMARY

An interactive and dynamic surgical simulation system is disclosed. The surgical simulation system may be used in the context of a computer-implemented interactive surgical system. For example, the surgical simulation system may enable dynamic adaptation. For example, the surgical simulation system may provide rectification of surgical simulation objects. For example, the surgical simulation system may enable enhanced navigation. For example, the surgical simulation system may provide coordinated surgical imagining. For example, the surgical simulation system may enable simulated surgical equipment coordination. For example, the surgical simulation system may provide simulation-based surgical procedure planning. For example, the surgical simulation system may enable simulation-based directed surgical development. For example, the surgical system may provide simulation of surgical adverse events. For example, the surgical system may enable simulation-based surgical analysis.

The computer-implemented interactive surgical system may include an operating-room-based surgical data system. The operating-room-based surgical data system may aggregate surgical activity data. The surgical activity data may be indicative of a performance of a live surgical procedure.

The surgical simulation device may be in communication with the operating-room-based surgical data system. The surgical simulation device may receive the surgical activity data from the operating-room-based surgical data system. And the surgical simulation device may simulate a surgical task based on surgical activity data.

The surgical activity data may be structured by a procedure plan data structure. The procedure plan data structure may be common to the operating-room-based surgical data system and the surgical simulation device. For example, the operating-room-based surgical data system may be configured to employ the procedure plan data structure to record discrete elements of the live surgery for structured analysis. And for example, the surgical simulation device may be configured to employs the procedure plan data structure to establish a setting and an objective for a simulation session. The procedure plan data structure may be configured to covey information indicative of equipment, technique, and surgical steps in a structured format such that the equipment, technique, and surgical steps of the live surgical procedure are reflected in the simulated surgical procedure.

BRIEF DESCRIPTION OF THE DRAWINGS

FIG. 30 illustrates an example data flow of simulation-assisted surgical procedure planning.

FIGS. 32A and 32B illustrate an example set of surgical choices for a surgical task for use with a computer-implemented interactive surgical system and/or a surgical simulator.

FIG. 46 is an example output of an example surgical procedure simulation review user interface.

FIGS. 47A and 47B illustrate an example implementation of an aspect of surgical procedure simulation review.

DETAILED DESCRIPTION

Surgical simulation systems, devices, and methods may include aspects of integration with other medical equipment, data sources, processes, and institutions. Surgical simulation systems, devices, and methods may include aspects of integration with a computer-implemented interactive surgical system and/or with one or more elements of a computer-implemented interactive surgical system, for example.

Figure 1:
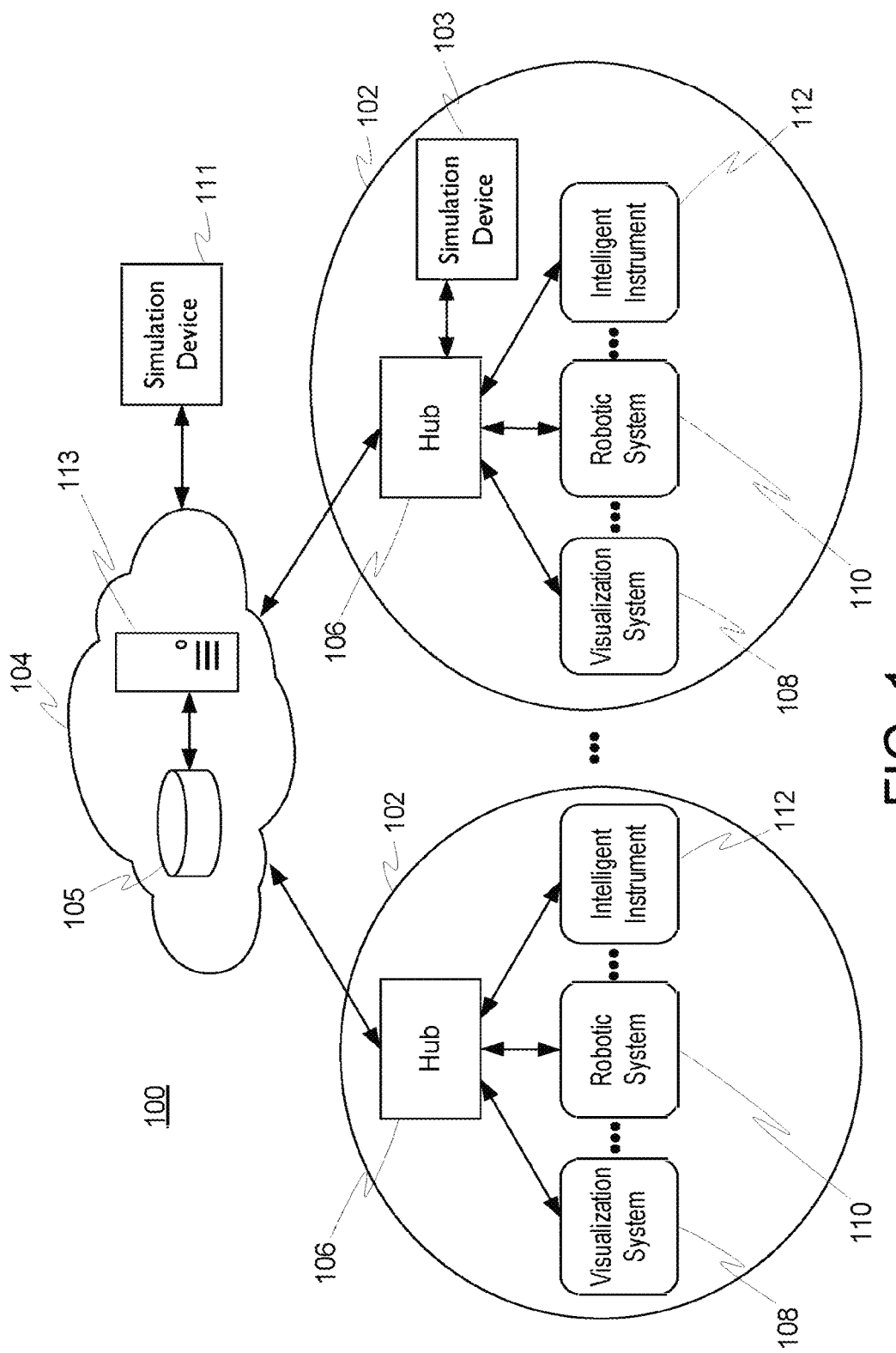
FIG. 1 is a block diagram of a computer-implemented interactive surgical system.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113.

One or more simulation devices 103, 111 may be in communication with and/or integrated as part of the computer-implemented interactive surgical system 100. For example, the simulation device 103 may be an element of the one or more surgical systems 102. For example, the simulation device 103 may be in communication with one or more surgical hubs 106. For example, the simulation device 111 may be in communication with the computer-implemented interactive surgical system 100 via the cloud 104.

In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
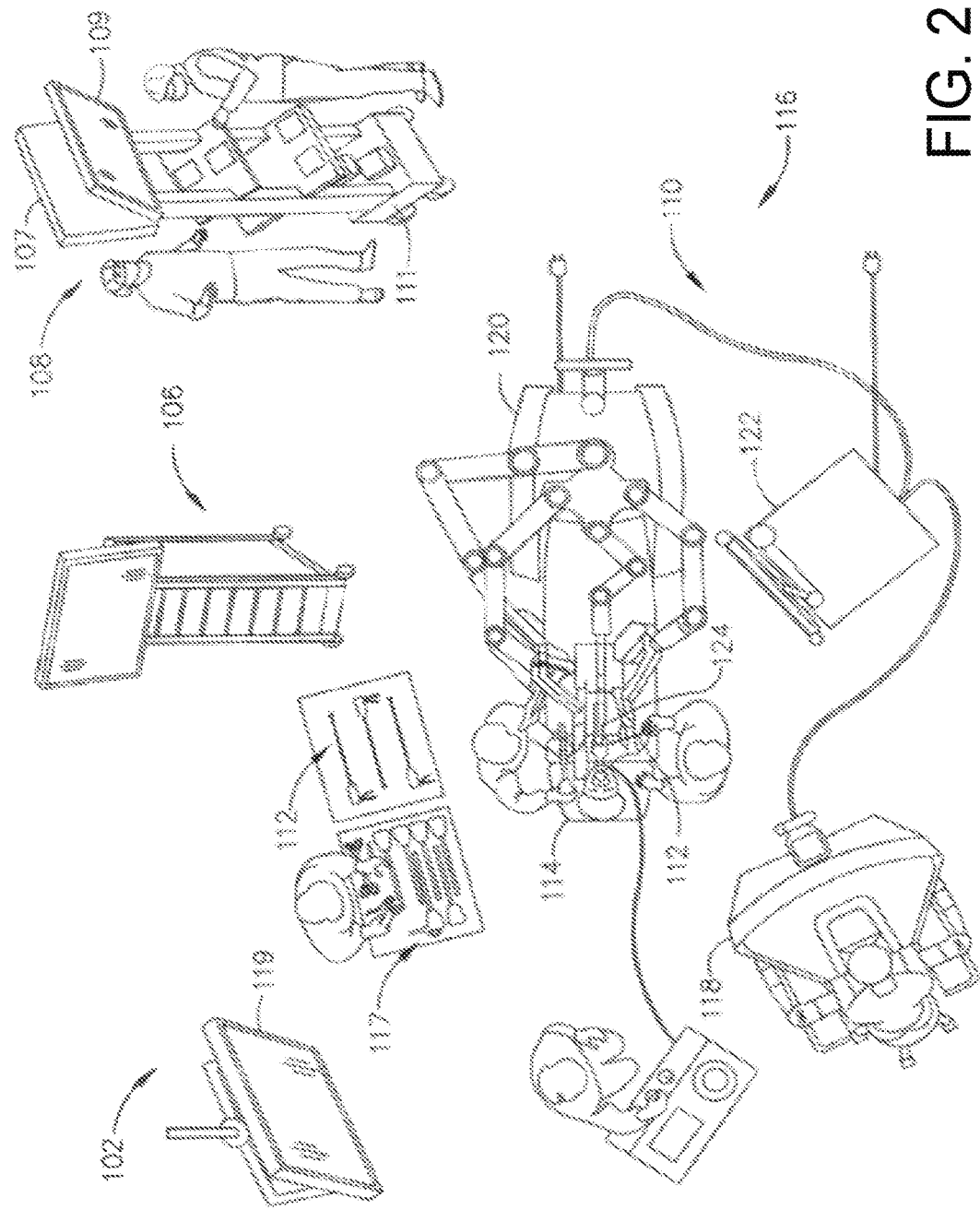
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in .S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
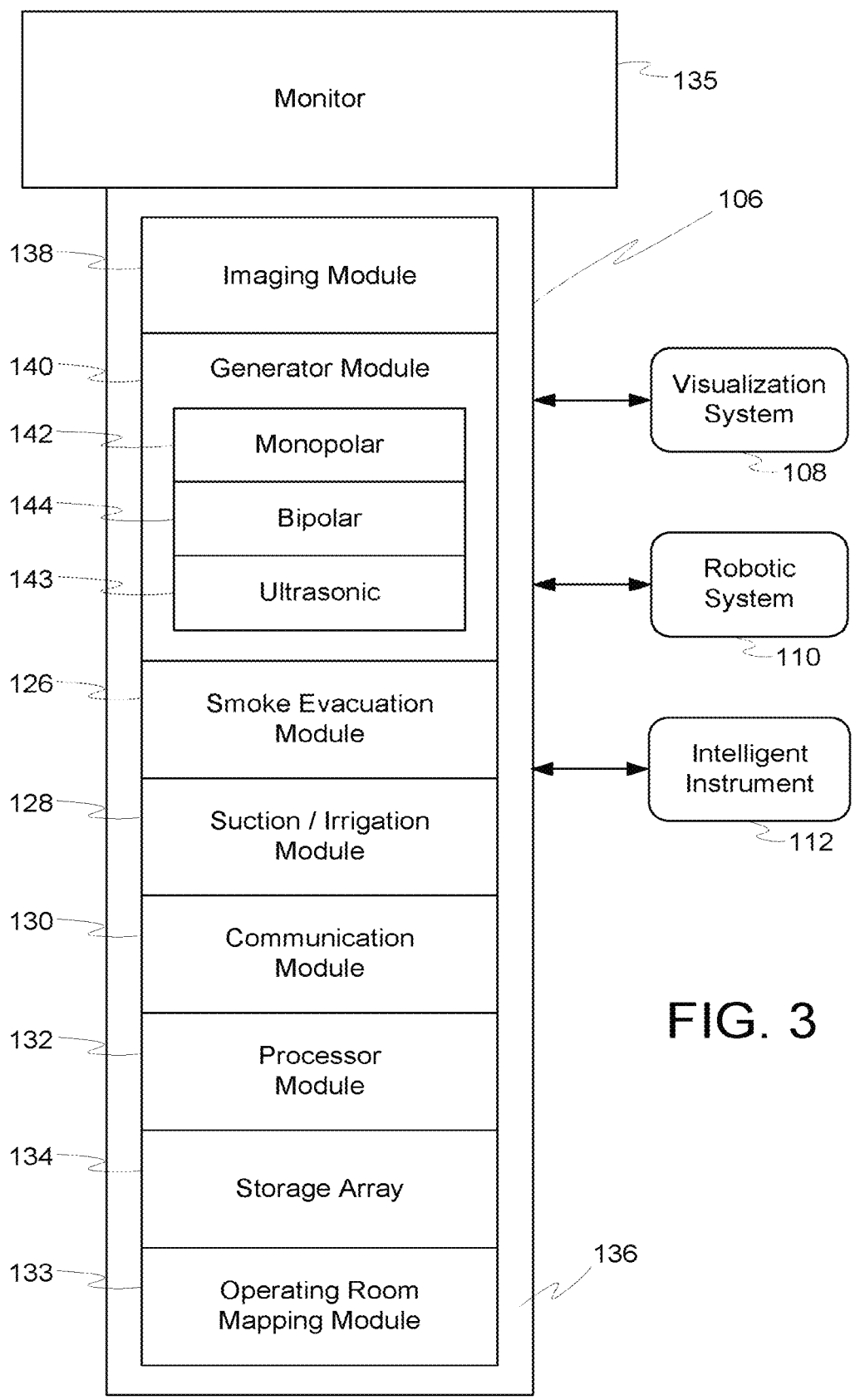
FIG. 3 shows an example surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module con-figured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate com-munication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
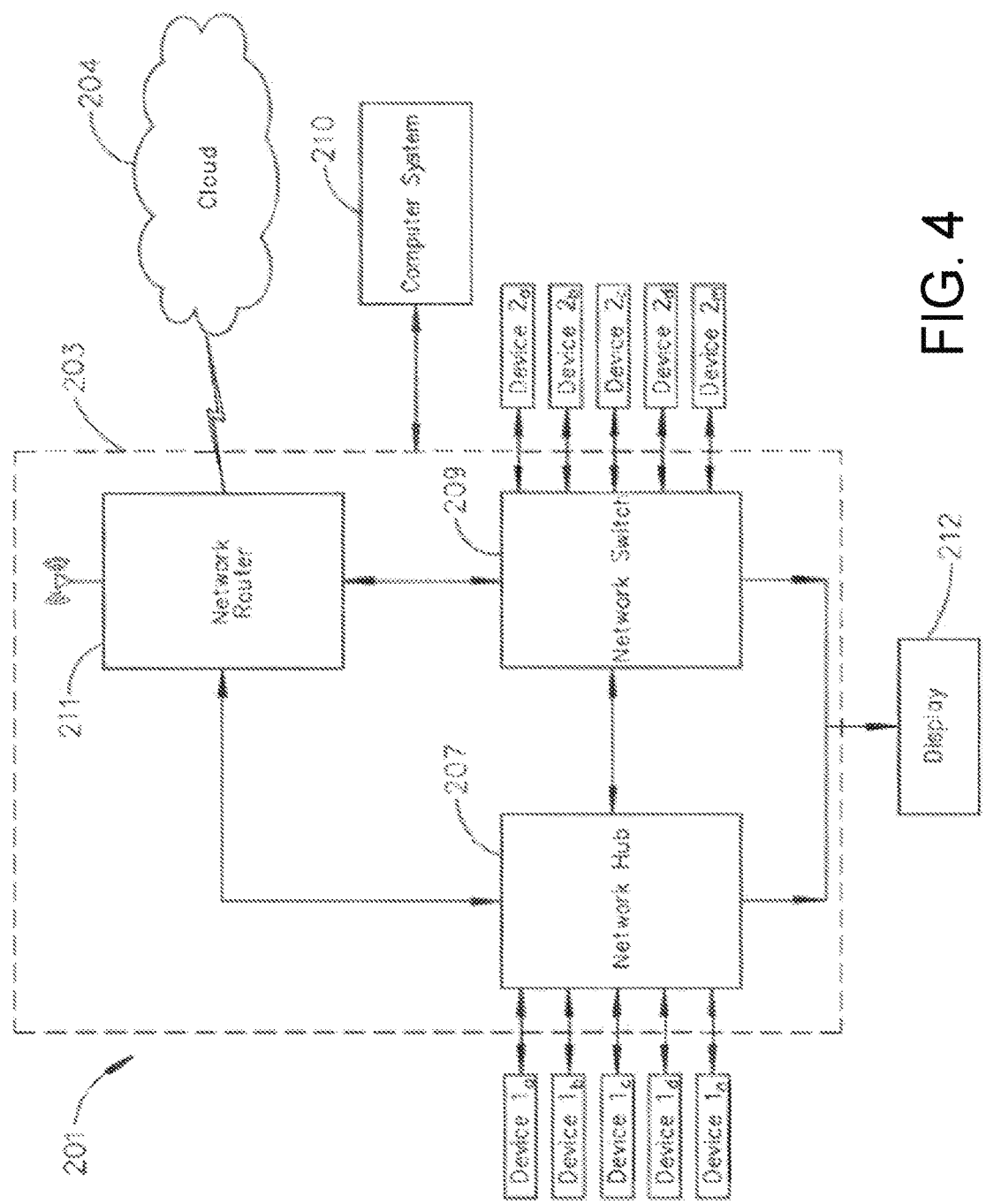
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHZ) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
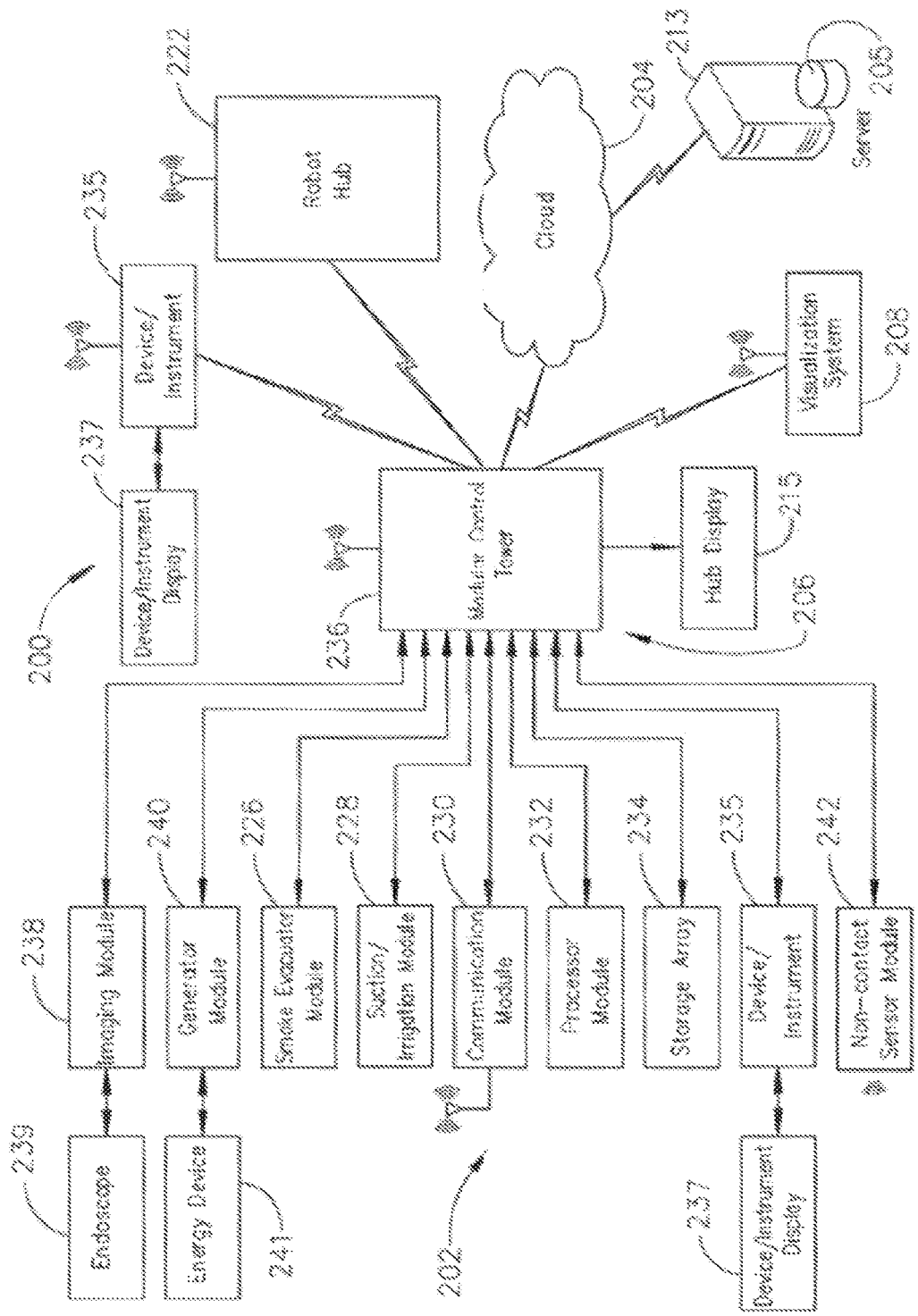
FIG. 5 illustrates an example computer-implemented interactive surgical system.
Figure 6:
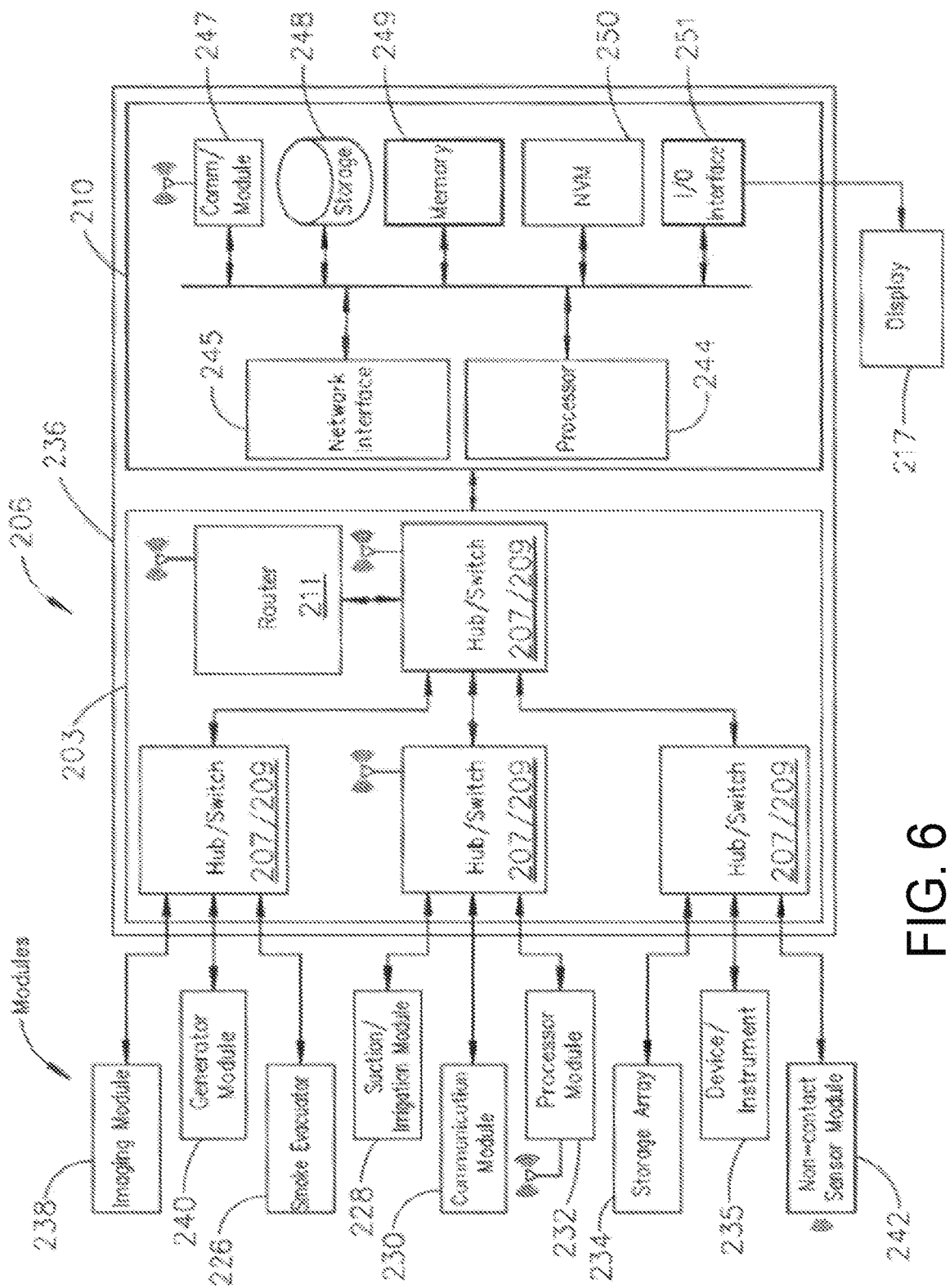
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in .S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
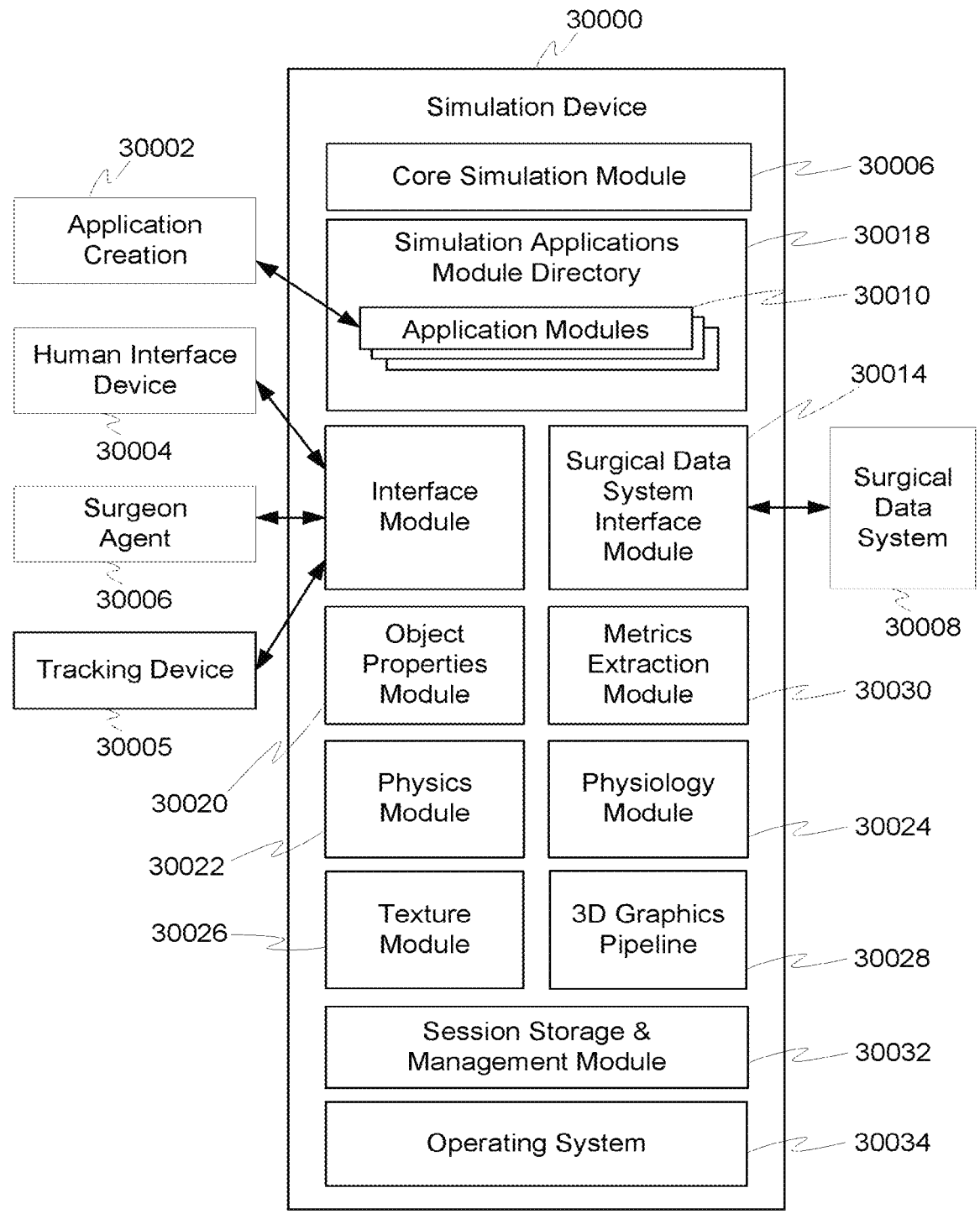
FIG. 7. is a block diagram of an example surgical simulator system.

FIG. 7. is a block diagram of an example surgical simulator system. The surgical simulator system may include a simulation device 30000. The surgical simulator system may include an application creation device 30002, a human interface device 30004, a surgeon agent device 30006, and/or a surgical data system 30008.

The simulation device 30000 may provide core simulation functionality. For example, the loading/running of one or more simulations, the reception and processing of user control information input, the generation and transmission of visual, audible, and/or haptic information output, the collection of simulation operation and activity information, and the primary simulation cycle processing may be performed by the simulation device 30000.

The application creation device 30002 may provide simulation authoring functionality. Individual simulation applications may be stored as application modules 30010 at the simulation device 30000. The application modules 30010 may be created, modified, and/or deleted by the application creation device 30002. The application modules 30010 may include computer readable and/or executable instructions to direct an operation of the simulation device 30000. For example, the application modules 30010 may include any filetype suitable for storing information to run a surgical simulation, for example, simulation scripts, programming code, structure data files such as Extensible Markup Language (XML) files, database files, and the like.

The application creation device 30002 may include a graphical user interface with controls to author application modules 30010. The application creation device 3002 may communicate with the simulation device 30000 to retrieve, modify, and/or load application modules 30010 for simulation operation. For example, the graphical user interface may include interface structures to allow a user to select simulation activities, to input various simulation parameters, to set simulation objectives, and to confirm simulation execution. The application creation device 30002 may be provided as a stand-alone device and/or integrated with one or more other devices of the surgical simulation system, such as integrated with the simulation device 30000 for example.

The human interface device 30004 may include any hardware, software, and/or combination thereof that enables a human user to interact with a simulation provided by the simulation device 30000. The human interface device 30004 may enable a user to provide control input to the simulation device 300000 and/or to receive output information (such as visual, audible, and/or haptic information) from the simulation device 30000. In one example, the human interface device 30004 may include a traditional desktop computer.

The human interface device 30004 may include suitable physical equipment. For example, the human interface device 30004 may include physical equipment that mimic physically and/or virtually aspects of a surgical procedure. For example, such equipment may include bench-top units, part-task virtual reality units, high fidelity virtual reality units, high fidelity full-size patient units, suite units, high fidelity full operating room units, full physics virtual reality units, surgical robot console units, and the like. For example, the human interface device 30004 may include devices such as the computer-based simulator interfaces disclosed by Gallager et al, "Simulations for Procedural Training," Fundamentals of Surgical Simulation, Principles and Practice, Springer (2012).

The human interface device 30004 may include physical equipment that mimics, physically and/or virtually, surgical instruments. For example, the human interface device 30004 may include physical devices that mimic surgical instruments, appliances, and consumables, such as access equipment, such as trocars, hand-access ports, insufflation needles, and guiding sheaths; adjunctive hemostats, such as patches, gelatins, and powders; craniomaxillofacial appliances, like distractors and plates; balloons and inflators; catheters, like diagnostic catheters, access catheters, vascular catheters, and therapeutic catheters; energy sealing and dissecting devices, like tissue sealers, shears, blades, and forceps; orthopedic equipment, like reduction wires, compression screws, plates, implants, drills, burrs, rods, and connectors; ligation instruments, like open and endoscopic clip appliers; microwave ablation equipment; ancillary endoscopic instruments, like drains, sutures, ligature, needle holders, retrievers, and suture clips; surgical stapling equipment, like open staplers, endoscopic staplers, cutter staplers, powered staplers, circular staplers, vascular staplers, linear staplers, staple cartridges, and staple line reinforcement applicators; wound closure materials, like suture, adhesives, needles, and knotless tissue control devices; imaging devices, like minimally invasive imaging devices; and the like. For example, the human interface device 30004 may include virtual reality handheld controllers, that when operated with a virtual reality headset, mimics the surgical instruments, appliances, and consumables, such as those disclosed above.

The human interface device 30004 may include a display that communicates visual representations of the simulation to the user. The human interface device 30004 may include a computer display. The human interface device 30004 may include a virtual reality headset display. For example, the virtual reality headset display may be used display the surgical environment, such as that disclosed in FIG. 2, herein. A user with such a virtual reality headset display may view and/or interact with any of the elements in the surgical operating room 116, including, for example, the patient, the robotic system 110, the surgeon's console 118, the surgical robotic hub 122, one or more surgical tools 117, the imaging device 124, the patient side cart 120, one or more displays 119, 107, 109, and the like.

The human interface device 30006 may present visual information that represents the point of the view of the surgeon. The human interface device 30006 may present visual information from a simulated imaging device, such as an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, ureteroscope, and their related instruments, controls, and the like. The human interface device 30006 may present visual information from a simulated supplemental intra-operative imaging equipment, like computed tomography (CT) units, magnetic resonance imaging (MRI) units, image-guided surgery units, intra-operative ultrasound units; fluoroscopy units, and the like. Such point-of-view visual information, surgical imaging information, and supplemental intra-operative imaging information may be displayed in any combination to the user suitable for the simulation's operation. For example, such information may be presented to the user as a single full-screen view, a tiled window view, a picture-in-a-picture view, or registered to a simulated display unit in a virtual reality view.

The human interface device 30004 may include a physical and/or virtual reality surgical robot surgeon console. For example, an example surgeon-console-like human interface device 30004 may include a display, such as a stereo vision display and control inputs, including hand-held manipulators, foot pedals, and the like. For example, the surgeon-console-like human interface device 30004 may include an interface of the surgeon's console 118, disclosed herein. The human interface device 30004 may enable voice controls via, for example, a microphone and speech recognition functionality. The human interface device 30004 may provide audible feedback via, for example, a speaker. The human interface device 30004 may provide haptic feedback via, for example, vibration, force feedback, air vortex rings, and ultrasound techniques.

As implemented, the human interface device 30004 may be provided as a stand-alone device and/or integrated with one or more other devices of the surgical simulation system, such as integrated with the simulation device 30000 for example. The simulation device 30000 may include an interface module 30012 to communicate with the human interface device 30004. In an example, human interface device 30004 may be integrated into one or more elements of the computer-implemented interactive surgical system 100. For example, the human interface device 30004 may be integrated into the computer system 210. For example, the human interface device 30004 may be integrated into the hub 106. For example, the human interface device 30004 may be integrated into the visualization system 108. The interface module 30012 may communicate with the one or more elements of the computer-implemented interactive surgical system 100 via the surgical data system interface module 30014 for example.

In an embodiment, more than one human interface device 30004 may concurrently engage with the simulation device 30000. For example, a multi-person simulation application The surgeon agent device 30006 may include any hardware and/or software suitable for providing a computer-based control and response to the input and output of the simulation device 30000. The surgeon agent device 30006 may include a computer process that mimics human input to the simulation device 30000. For example, the surgeon agent device 30006 may be able to record and register control inputs, such as basic instrument manipulation. The surgeon agent device 30006 may include a computer process that can access a input/output application programming interface (API) of the simulation device 30000. For example, the API may reveal one or more input/output functions that may be directed according to the surgeon agent device 3006.

The functions may include granular manipulation and physics-based input/output functions, such as functions that directly control the location and movement of instruments. The functions may include less granular surgical-activity-based input/output functions, such as a ligation activity, a suturing activity, a stapling activity, and the like. The functions may include less granular surgical task and/or stage-based input/output functions, such as surgical access function, organ mobilization function, and the like. Each function may include parameter consistent with its level of granularity. The parameters may provide specific details to direct the operation of the function within the simulation. The surgeon agent 30006 may include functionality for generating and operating multiple simulation runs. For example, a user may wish to estimate the duration of various suturing techniques. A surgeon agent device 30006 may be used to script the simulation of any number of different techniques, each of which can be run via the simulation device, and the metrics collected by the simulation device may be used to estimate the difference in durations.

The surgeon agent device 30006 may be provided as a stand along device and/or integrated with one or more other devices of the surgical simulation system, such as integrated with the simulation device 30000 for example. The simulation device 30000 may include an interface module 30012 to communicate with the surgeon agent device 30006. For example, the surgeon agent device 30006 may be integrated as a module of the simulation device 30000. For example, the surgeon agent device 30006 may be integrated into an application module 30010 of the simulation device.

The surgical data system 30008 may include any hardware and/or software suitable for providing external, structured surgical information and functionality to the simulation device 30000. The surgical data system 30008 may include the structure and/or functions described in connection with FIGS. 1-6 herein. For example, the surgical data system 30008 may include one or more elements of a computer-implemented interactive surgical system 100. The surgical data system 30008 may include, for example, a surgical hub 106. For example, the simulation device 30000 include a surgical data system interface module 30014 that enables communication with the surgical hub 106 via the surgical hub's communication module 130. The surgical data system 30008 may include, for example, on or more surgical data repositories. For example, the surgical data system 30008 may include the computer system 210 located in the surgical theater. For example, the surgical data system 30008 may include the remote server 213 in the cloud 204.

A surgical data system 30008, such as the surgical hub 106 for example, may provide data to the simulation device 30000 and/or the application creation device 30002. For example, the data may include any surgical data collected and/or generated by the surgical hub 106. Also for example, the simulation device 30000 may receive similar data directly from any of the networked devices disclosed in FIGS. 1-6. Such data may include information about a live surgical procedure, for example. Such data may include information about a past surgical procedure. Such data may include information about future, scheduled surgical procedures.

Information about the surgical procedures may include information about the patient, the staff, the procedure as planned, the procedure as experienced, and post-operative activity including patient outcomes. For example, the information received and used by the simulation device may include patient records, patient imaging, models of patient anatomy, patient lab results, patient medical history, and the like. For example, the information received and used by the simulation device may include a staff manifest for a procedure, details about the past procedures of the specific staff members, staff metrics, experience, recent scheduling and workload, and historical surgical activity, such instrument use statistics, procedure duration, and the like. For example, the information received and used by the simulation device may include procedure plans, equipment and inventory information, pull-lists, checklists, procedure plan analysis and recommendations. For example, the information received and used by the simulation device may include any data collected or generated during a live procedure, such as procedure progress, milestones, patient information, vitals, operating theater setup, staff movement, imaging, instrument use, surgical technique, such as that captured by video, recorded manually, and/or inferred from smart-instrument reporting for example, duration, abnormal event reporting, and the like. Any data captured during a live procedure may also be stored and made available as a past procedure. For example, the information received and used by the simulation device may include post-operative records, patient recovery information, and patient outcome information, post-operative diagnostic information, such as labs, imaging, etc., The simulation device 30000 may include any computer or processing platform suitable for executing one or more simulations. The simulation may include a computer-modeled environment of a surgical procedure. For example, the simulation may include a model of a patient's anatomy and/or physiology. For example, the simulation may include a model of the actions and/or instruments of one or more healthcare professionals, such as the actions of a surgeon, nurse, other doctor, technician, or the like.

The simulation device 30000 may include one or more functional modules. Each module may include hardware, software, or a combination thereof that enable functionality of the module. One or more modules, operating in concert, may represent a computer framework on which a simulation of a medical procedure may be executed. The modules may include hardware elements, such as a computer processing unit, a graphics processing unit, a field-programmable gate array (FPGAs), communications hardware, memory, and the like. The modules may include software elements that when executed by a processor cause the module to perform certain functions.

The simulation device may include a core simulation module 30016, a simulation applications module directory 30018, the interface module 30012, an object properties module 30020, a physics module 30022, a physiology model 30024, a texture model 30026, a 3D graphics pipeline 30028, the surgical data system interface module 30014, a metrics extraction module 30030, a session storage and management module 30032, for example. The simulation device may include an operating system module 30034.

The core simulation model 30016 may provide primary simulation functionality of the simulation device 30000. For example, the core simulation module 30016 may include code for initializing a simulation, for communicating and interacting with other modules of the simulation device 30000, and/or for managing architectural level simulation parameters. For example, the core simulation module 30016 may include a master event clock to provide time alignment and/or coordination of the operation of the modules of the simulation device 30000. For example, the core simulation module 30016 may establish the overall simulation frame rate.

The core simulation module 30016 may include core for providing a master simulation cycle. The core simulation module 30016 may run one or more iteration of the master simulation cycle. Each iteration of the master simulation cycle may represent an individual time slice for simulation. In an example, the core simulation module 30016 may run the master simulation cycle according to the flow disclosed in FIG. 10.

The simulation applications module directory 30018 may manage the storing, retrieving, and/or linking of the one or more application modules 30010. Each application module 30010 may include code that directs the application-level aspects of a simulation. For example, an application module 30010 may include the functionality to provide a simulation of specific anatomy, of specific teaching scope, of specific equipment, or the like. In an example simulation device 30000, an application-specific simulation device 30000 may operate with a single application module 30010 with or without a simulation application module directory 30010. The simulation application module directory 30018 may operate based on interaction with the core simulation module 30016 and/or the application creation device 30002.

The interface module 30012 may provide functionality for interacting with the human interface device 30004 and/or the surgeon agent device 30006. For example, the interface module 30012 may include one or more drivers to translate information received from human interface device 30004 into software commands, interrupts, and the like. For example, the interface module 30012 may include a software application programming interface (API) for interacting with the surgeon agent 30006. The interface module 30012 may provide information received from the human interface module 30004 and/or the surgeon agent device 30006 to other modules of the simulation device 30000. For example, the interface module 30012 may receive a control input from the human interface module 30004 and/or the surgeon agent device 30006 that represents movement of a simulated instrument and provide that information to one or more other modules of the simulation device 30000 so the movement may be represented in the simulation.

The interface module 30012 may provide the API to enable a more granular interaction with the surgeon agent device 30006. For example, the API may provide an interface to receive simulation parameters and simulation settings from the surgeon agent device 30006. Such simulation parameters and/or simulation settings may be like those input by the user via the application creation device 30002, for example. For example, the surgeon agent device 30006 may be enabled to run one or more computer-controlled simulation trials through the simulation device 30000. For example, the surgeon agent device 30006 may be enabled to run multiple simulations, each with alternative interactions.

The interface module 30012 may send output from the simulation device 30000 to the human interface device 30004 and/or the surgeon agent device 30006. For example, the output may include visual output, haptic output, audio output, and/or structured data output, or the like.

The object properties module 30020 may provide functionality for managing the simulated appearance and/or behavior of objects within in the simulation. Simulated objects may include objects such as anatomy, instrument, equipment, consumables, fluids, and the like. An object's appearance may be managed by object properties, such as location, dimensions, scale, material, parent/child relationships, vertices, faces, interactivity, transparency, trajectory, rendering properties, textures, surface reflectivity, motion blur, layering, and the like. An object's behavior may be managed by object properties, such as physics properties, mass, motion, collision behavior, elasticity, viscosity, surface tension, rigging constraints, hardness, shear strength, tearing behavior, grain, and the like.

The physics module 30022 may provide functionality to calculate the physical responses and/or interaction of objects within the simulation. The physical module may determine such responses and/or interactions according to classical mechanics, fluid mechanics, soft body dynamics, Brownian motion, collision detection, cloth behavior, finite element analysis, and the like. The physics module 30022 may include commercial and/or open-source modules, such as PhysX™, Simulation Open Framework Architecture (SOFA)™, VisSim™, and the like.

The physiology module 30024 may provide functionality to calculate physiological responses and/or interactions of the anatomy and/or patient as a whole in the simulation. The physiology module 30024 may provide physiological models for key organs and/or systems. The physiological models may include mathematical models, statistical models, or the like. For example, the physiology module 30024 may module the patient's vitals to calculate their response and/or interaction to activities performed during the simulation. For example, a circulatory model may calculate blood pressure in response to a severed vessel in the simulation. The physiology module 30024 and the physics module 30022 may coordinate with each other during the calculation of each state of the simulation. For example, blood pressure calculated by the circulatory model may be used to determine fluid dynamics properties calculated by the physics module 30022 and managed by the object properties module 30020.

The texture module 30026 may provide functionality to determine, retrieve, and/or generate the appropriate surfacing of objects within the simulation. The texture module 30026 may include one or more surfacing modalities that may be controlled according to parameters of the simulation. The surfacing modalities may include artificially generated surfaces, surfaces based on real-world imagery, and combinations thereof. The texture module 30026 may coordinate operation with the physics module 30022 to provide accurate haptic feedback to the user via the user interface module 30012.

The 3D graphics pipeline 30028 may provide functionality for visual rendering of the simulation environment. The 3D graphics pipeline 30028 may receive object properties and a perspective. The 3D graphics pipeline 30028 may determine the visualization to be presented to the user that represents the objects in 3D space as viewed from the camera perspective. The 3D graphics pipeline 30028 may determine geometric aspects of the rendering, such as lighting, projection, clipping, view transformation, and the like. The 3D graphics pipeline 30028 may determine rasterization aspects of the rendering, such as fragmentation, pixel shading, vertex shading, geometry sharing, texture filtering, and the like. The 3D graphics pipeline 30028 may coordinate with the texture module 30026 to provide accurate visual feedback to the user via the interface module 30012.

The surgical data system interface module 30014 may provide interactive connectivity to one or more elements of computer-implemented interactive surgical system 100. Information from the one or more elements of the computer-implemented interactive surgical system 100 may be communicated via the surgical data system interface module 30014 to one more modules of the simulation device 30000 to influence operation of a simulation. For example, the surgical data system interface module 30014 may receive information about a surgical procedure an communicate it to a corresponding application module 30010. For example, the surgical data system interface module 30014 may receive information about an instrument and communicate it to the object properties module 30020. For example, the surgical data system interface module 30014 may receive information about a patient and communicate to the physiology module. For example, the surgical data system interface module 30014 may receive information about tissue imaging and communicate it to the texture module 30026.

Information from the modules of the simulation device 30000 may be provided, via the surgical data system interface 30014, to one or more elements of the computer-implemented interactive surgical system 100. For example, one or more elements of the computer-implemented interactive surgical system 100 may receive statistics related to a simulated procedure plan from the metrics extraction module 30030. For example, one or more elements of the computer-implemented interactive surgical system 100 may receive replayed simulation visualization procedure plan from the session storage and management module 30032. For example, the surgical data system interface module 30014 may provide a communications pathway between the interface module 30012 and one or more elements of the computer-implemented interactive surgical system 100. For example, a surgeon during a live surgical procedure may access simulation information and/or operate a simulation from the operating theater. For example, a surgeon may use the surgeon console 118 to access and/or interact with a simulation that corresponds to the live surgical procedure.

The metrics extraction module 30014 may provide recording functionality of various parameters related to the operation of the simulation. For example, the metrics extraction module 30014 may record metrics related to the simulation as a whole, such as duration, number of activities, number of movements, complexity of movements, staff employed, staff movement, equipment and/or instrument changes, etc. For example, the metrics extraction module 30014 may record metrics related to a particular aspect of the simulation, such as simulated patient vitals, complications, collisions, bleeding, etc. The metrics extraction module 30014 may maintain a master log of metric-related events during a simulation. For metrics extraction module 30014 may record metric-related events according to a configuration from the application module 30010 employed for the simulation.

The session storage and management module 30032 may provide management functionality of the main simulation run-record. For example, the session storage and management module 30032 may store the information to enable a simulation to be rerun, viewed, and/or analyzed in its entirety. The session storage and management module 30032 may store the information about each input, simulation state, and output, such as the input, simulation state, and output disclosed with regard to FIG. 10. The session storage and management module 30032 may enable a previous simulation to be recalled, copied, and initialized with new user input. To illustrate, a surgeon in training may recall a simulation run by an experienced surgeon, pause the simulation at a critical step, and attempt that step on her own. The session storage and management module 30032 may provide overlay functionality between various runs of a particular simulation. Such overlays may highlight similarities and differences and may enhance training.

The operating system module 30034 may manage the hardware and/or software resources for the simulation device 30000. The operating system module 30034 may provide common computing system-level services for the other modules of simulation device 30000. For example, the operating system module 30034 may provide hardware input and output handling, memory allocation, hardware interrupt handling, software interrupt handling, thread processing, single task handling, multi-task handling, and the like. The simulation device 30000 may be a real-time computing device. The operating system module 30034 may include a real-time operating system. For example, the operating system module 30034 may be driven by the events and frame rate established by the core simulation module 30016.

Figure 8:
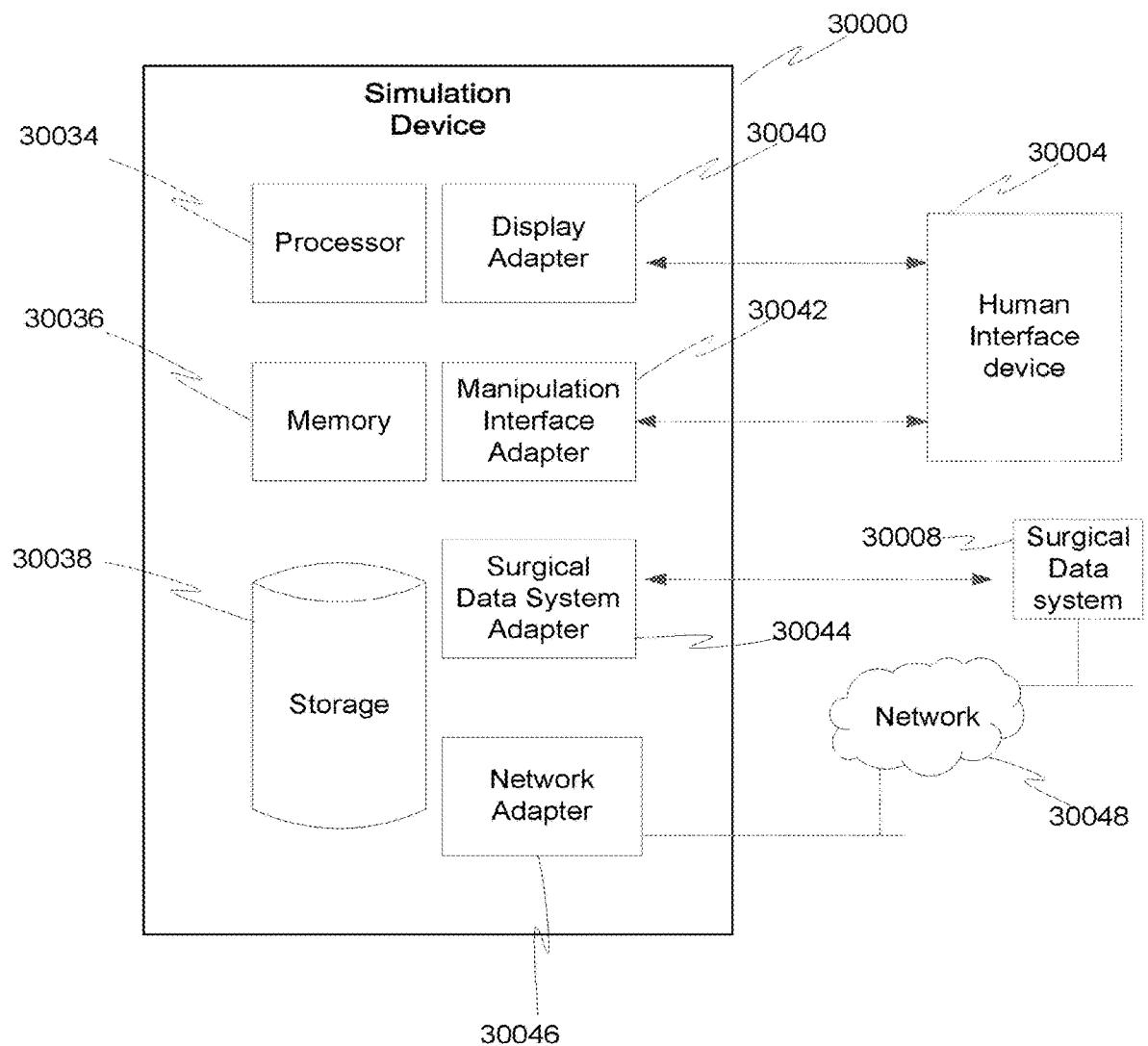
FIG. 8 is a block diagram of an example surgical simulator system.

FIG. 8 is a block diagram of an example surgical simulator system. The simulation device 30000 is depicted with an example hardware architecture. For example, the simulation device 30000 may include a processor 30034, a memory 30036, a storage 30038, a display adapter 30040, a manipulation interface adapter 30042, a surgical data system adapter 30044, and/or a network adapter 30046. One or more of the processor 30034, a memory 30036, a storage 30038, a display adapter 30040, a manipulation interface adapter 30042, a surgical data system adapter 30044, and/or a network adapter 30046 may be used to enable operation of the modules of the simulation device 30000 disclosed herein.

The processor 30046 may include computer processing unit, graphics processing unit, any suitable microcontroller, microprocessor, field programmable gate array (FPGA), application specific integrated circuit (ASIC), or the like, and/or any combination thereof that is suitable for processing and delivering a 3D simulated environment for interaction with a computer agent and/or human user. In one example, the processor 30046 may include one or more processing units. The processor 30046 may be a processor of any suitable depth to perform the digital processing requirements disclosed herein. For example, the processor 30046 a 32-bit processor, a 64-bit processor, a 128-bit processor, or the like.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The memory 30036 may include any component or collection of components suitable for storing data. For example, the memory 30036 may include volatile memory and/or nonvolatile memory. The memory 30036 may include random-access memory (RAM), read-only memory (ROM), erasable programmable read-only memory (EPROM), (electrically erasable programmable read-only memory) EEPROM, flash memory, or the like.

The storage 30038 may include any component or collection of components suitable for storing large quantities of data. For example, storage 30038 may include hard disk drives (HDD), solid state drives (SSD), network-attached storage (NAS), or the like. The storage 30038 may include a database structure and/or a database management system (DBMS).

The display adapter 30040 may include any component or collection of components suitable for outputting the visual representation of a 3D simulation environment. For example, the display adapter 30040 may include a graphics card, a display card, a graphics adapter, or the like. The display adapter 30040 may be used to generates a feed of output images to a display device, such as a display of the human interface device 30004. The display adapter 30040 may include a graphics processing unit (GPU). The display adapter 30040 may include hardware to render a graphics pipeline, for example. The manipulation interface adapter 30042 may include any component or collection of components suitable for receiving manipulation information from the human interface device and/or outputting feedback information to the human interface device. For example, the manipulation interface adapter 30042 may receive motion tracking information from a virtual reality headset and in turn, manipulate the view being displayed to the user. For example, the manipulation interface adapter 30042 may receive control input indicative of a user manipulating a surgical instrument and, in turn, output haptic feedback to the user's handheld device. For example, the manipulation interface adapter 30042 may receive control information from a traditional desktop keyboard and mouse. The manipulation interface adapter may include input/output hardware such as serial input/output ports, parallel input/output ports, universal asynchronous receiver transmitters (UARTs), discrete logic input/output pins, analog-to-digital converters, digital-to-analog converters, universal serial bus (USB) ports, USB-C ports, FireWire ports, High Performance Parallel Interface (HIPPI), Thunderbolt port, Yapbus, Ethernet, Gigabit Ethernet, and/or any other suitable peripheral interface technology.

The surgical data system adapter 30044 may include any component or collection of components suitable for communicating with the surgical data system 30008. The surgical data system adapter 30044 may include communications hardware to establish a physical channel between the simulation device 30000 and the surgical data system 30008. For example, the surgical data system adapter 30044 may include a communication port such as, a USB port, USB-C ports, FireWire ports, HIPPI port, Thunderbolt port, Yapbus port, Ethernet port, Gigabit Ethernet port, and/or any other suitable peripheral interface. The surgical data system adapter 30044 may include hardware, software, and/or a combination thereof to establish a logical channel between the simulation device 30000 and the surgical data system 30008 over the network adapter 30046 and the network 30048.

The network adapter 30046 may include any component or collection of components suitable for communication over a network, such as network 30048 for example. The network adapter 30046 may enable communication over networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

In an embodiment, the network adapter 30046 may include a wireless network adapter, such as a 5G network adapter. Such a 5G network adapter 30046 may use a 5G New Radio (NR) transceiver to provide enhanced mobile broadband (eMBB) with ultra-reliable and low latency communications (URLLC). Such a 5G network adapter 30046 may use wireless bands, such as higher wireless bands like the 3.5 Ghz-7 Ghz and/or the 24 GHZ-48 GHz bands. The network 30048 servicing such a 5G network adapter 30046 may include a public wireless network, a semi-private (e.g., network slicing-based) network, and/or a fully private wireless network.

Figure 9:
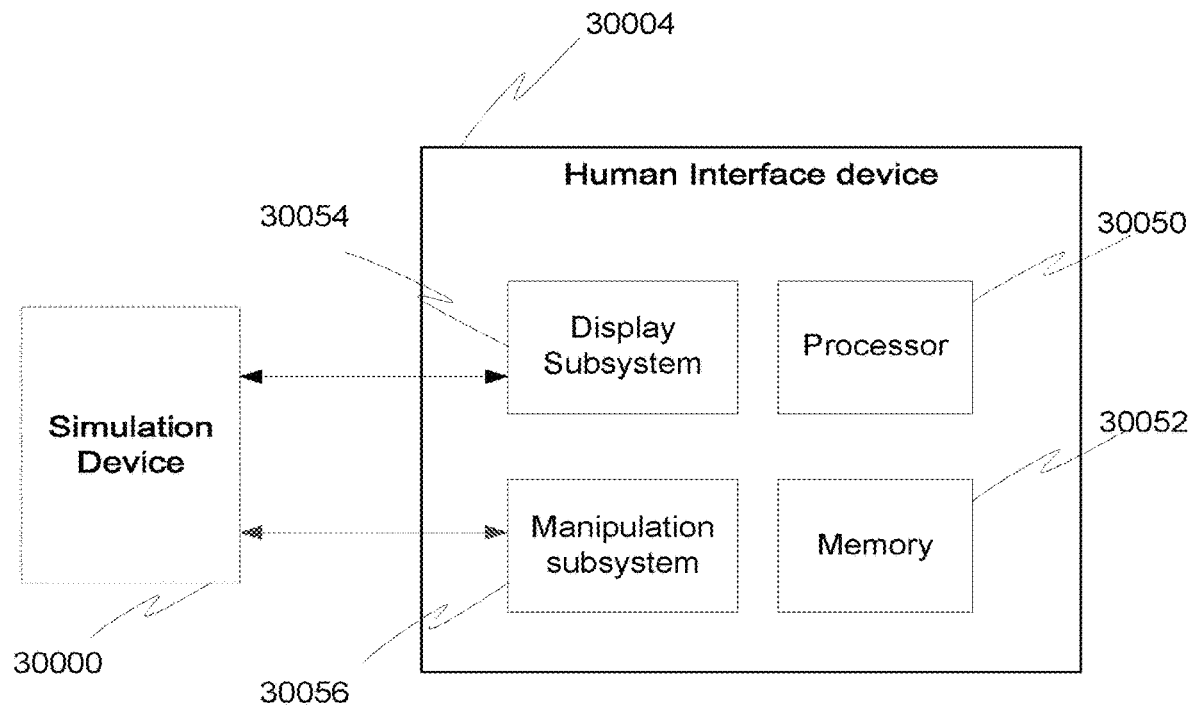
FIG. 9 is a block diagram depicting an example surgical simulator user interface device.

FIG. 9 is a block diagram depicting an example surgical simulator human user interface device 30004. The human user interface device 30004 is depicted with an example hardware architecture. For example, the human user interface device 30004 may include a processor 30050, a memory 30052, a display subsystem 30054, and/or a manipulation subsystem 30056.

The processor 30050 may include computer processing unit, graphics processing unit, any suitable microcontroller, microprocessor, field programmable gate array (FPGA), application specific integrated circuit (ASIC), or the like, and/or any combination thereof that is suitable for handling the processing associated with displaying visual information received from the simulation device 30000, processing manipulation information for sending to the simulation device, processing feedback information received from the simulation device 30000, and the like. The processor 30050 may include a microcontroller to interface with one or more local sensors to sense control manipulation from the user and/or to interface with one or more local actuators to provide feedback from the user.

Such processors may comprise, or may be in communication with, media, for example computer-readable media, that may store instructions that, when executed by the processor, can cause the processor to perform the steps described herein as carried out, or assisted, by a processor. Embodiments of computer-readable media may comprise, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The memory 30036 may include any component or collection of components suitable for storing data. For example, the memory 30036 may include volatile memory and/or nonvolatile memory. The memory 30036 may include random-access memory (RAM), read-only memory (ROM), erasable programmable read-only memory (EPROM), (electrically erasable programmable read-only memory) EEPROM, flash memory, or the like.

The display subsystem 30054 may include any component or collection of components suitable for displaying visual representations of a 3D simulation from the simulation device 30000 to a user. The display subsystem may include display hardware such as a monitor, a digital projector, a smart phone, a digital headset, a virtual reality headset, a stereoscopic display, a robotic surgery surgeon's console display, a surgical display unit, a surgical microscope, and the like.

The manipulation subsystem 30056 may include any component or collection of components suitable for collecting manipulation controls from the user to send to the simulation device 30000 and/or providing feedback information, received from the simulation device 30000, to the user. Manipulation from the user may include any interface with sensors that engage with the user, for example, engaging to indicate a user's intent in the simulation. For example, the interfaces may include keyboards, mice, joysticks, physical equipment that mimics the size, shape, and operation of actual surgical instruments, virtual reality hand-held controllers, smart gloves, motion sensing systems (such as hand tracking systems, for example), a robotic surgery surgeon's console manipulators and/or controls, a physical unit that mimics the size, shape, and operation of an actual robotic surgery surgeon's console manipulators and/or controls, and the like. For example, the interface may include a point of view sensor, such as an accelerometer, in a headset to indicate a user's point of view within the simulation.

Feedback from the simulation device 30000 may include any interface with an actuator that provides sensory input to the user. For example, the feedback may include haptic feedback, force feedback, temperature feedback, moisture feedback, audio feedback, olfactory feedback, and the like. For example, a force feedback and/or haptic actuator in the manipulator of a robotic surgery surgeon's console may be used to simulate the feedback the user would feel if operating such a manipulator in a live procedure. For example, a force feedback and/or haptic actuator in a user device that mimics the size, shape, and operation of actual surgical stapler may be used to simulate the feedback the user would feel if operating such a device on live tissue, including force feedback when engaging the tissue and firing the stapler for example.

Figure 10:
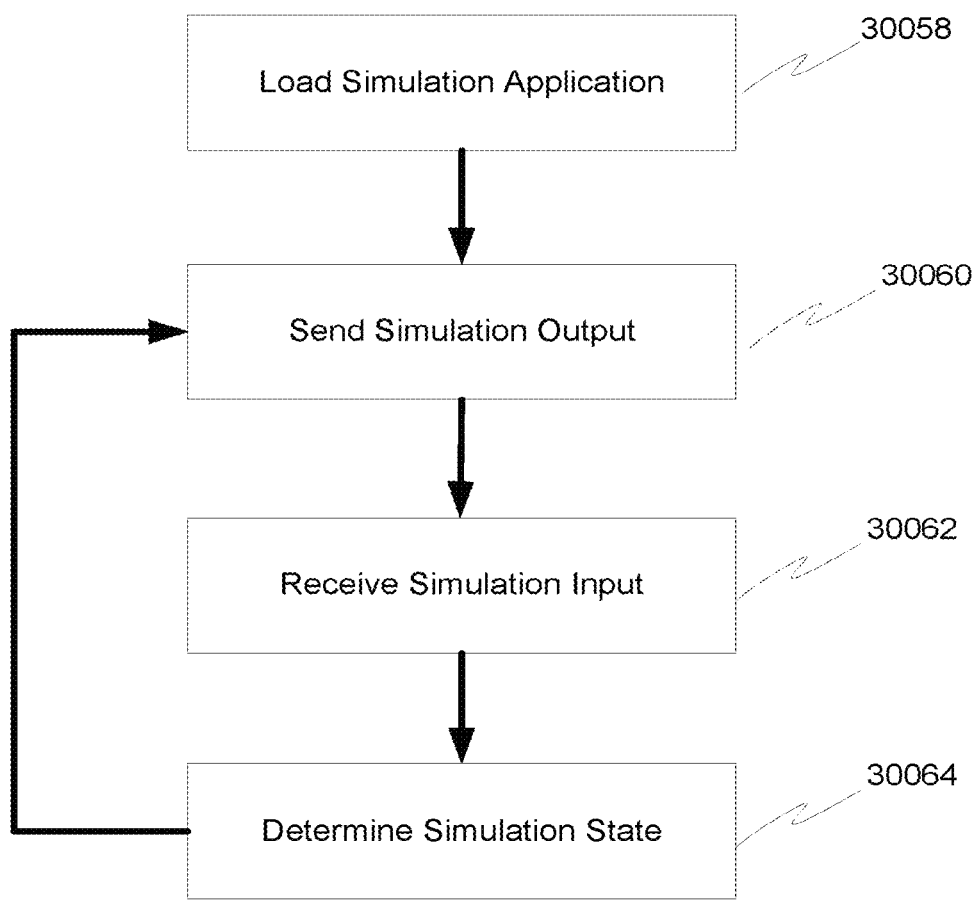
FIG. 10 is a flow chart of an example surgical simulator operation.

FIG. 10 is a flow chart of an example surgical simulator operation. At 30058, a simulation application may be loaded. For example, the core simulation module 30016 may cause data associated with a particular application module 30010 to be loaded into memory 30036. The loaded data may include instructions for the processor 30034 to operate a particular simulation. The loaded data may include a procedural plan for the simulation. For example, the procedural plan may be structured as disclosed herein, for example with regard to FIGS. 11A-B. The loaded data may include an initial state for the simulation.

At 30060, the simulation output may be determined and/or sent. For example, the simulation output may be determined and/or sent by the simulation device 30000. Here, the core simulation module 30016 may reference a current state of the simulation (e.g., an initial state and/or a subsequent state). The core simulation module 30016 may engage one or more other modules to process the current state for output. For example, the core simulation module may engage any of the object properties module 30020, the texture module 30026, the application module 30010, the 3D graphics pipeline 30028, the interface module 30012, and/or the surgical data system interface module 30014 to process the current simulation state into information for output. Information related to the output may be processed and/or stored by the metrics extraction module 30030 and/or the session storage and management module 30032, for example.

In a human-operated simulation session, for example, output information may be sent via the display adapter 30040 and/or the manipulation interface adapter 30042 to the display subsystem 30054 and/or the manipulation subsystem 30056 of the human interface device 30004. In a computer-controlled simulation session, for example, output information may be sent via the interface module 30012 to a surgeon agent 30006. Also for example, in a computer controlled simulation session, output information may be sent (e.g., processed locally) at an application module 30010. In a session accessed via the surgical data system 30008, for example, output information may be sent by the surgical data system interface module 30014 via the surgical data system adapter 30044 and/or the network adapter 30046.

At 30062, simulation input may be received and/or processed. For example, simulation input may be received and/or processed by the simulation device 30000. Here, the core simulation module may engage with the interface device, the surgical data system interface module, and/or the application module 30010 to receive control input. Information related to the input may be processed and/or stored by the metrics extraction module 30030 and/or the session storage and management module 30032, for example.

In a human-operated simulation session, for example, input information may be sent from a manipulation subsystem 30056 of the human interface device 30004 and received via the manipulation interface adapter 30042. In a computer-controlled simulation session, for example, input information may be sent from a surgeon agent 30006 and received via the interface module 30012. Also for example, in a computer controlled simulation session, input information may be received (e.g., processed locally) at an application module 30010. In a session accessed via the surgical data system 30008, for example, input information may be received via the surgical data system adapter 30044 and/or the network adapter 30046 and initially handled by the surgical data system interface module 30014.

At 30064, a subsequent simulation state may be determined. For example, a subsequent simulation state may be determined from the current simulation state and/or the any received input. The core simulation module 30016 may engage one or more of the other modules of the simulation device 30000 to determine the subsequent simulation state. For example, the code simulation module 30016 may engage the application module, the object properties module, the physics module, the physiology module, and the like. The subsequent simulation state may be determined by operation of the processor 30034. Information related to the input may be processed and/or stored by the metrics extraction module 30030 and/or the session storage and management module 30032, for example.

At this stage, the process may loop to receiving input at 30060. Each iteration of this flow may represent a corresponding time cycle in the simulation. The framerate of the simulation may be set to a level suitable for the goal of the simulation and the processing capabilities of the surgical simulation device 30000. Lower framerates may enable processing that achieves a live human interaction simulation. Higher framerates may enable greater simulation fidelity. For example, when operating computer-controlled simulations, with a surgeon agent 30006 for example, a higher framerate may be used, even if the higher framerate causes the processing time of the simulation to exceed the real-world time it is simulating.

Figure 11A:
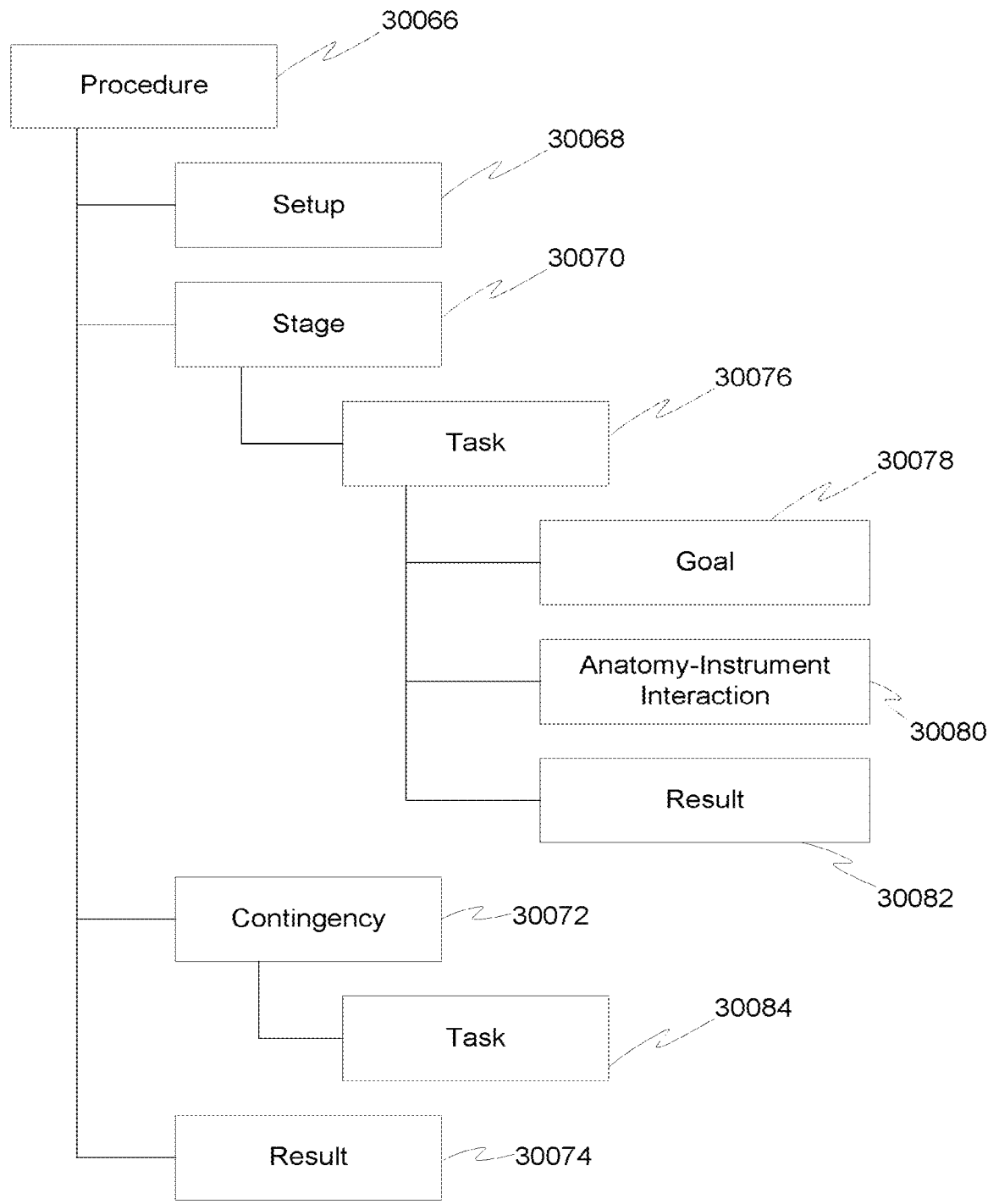
FIGS. 11A-B illustrate example surgical procedural plan data structures for use with a computer-implemented interactive surgical system and/or a surgical simulator.
Figure 11B:
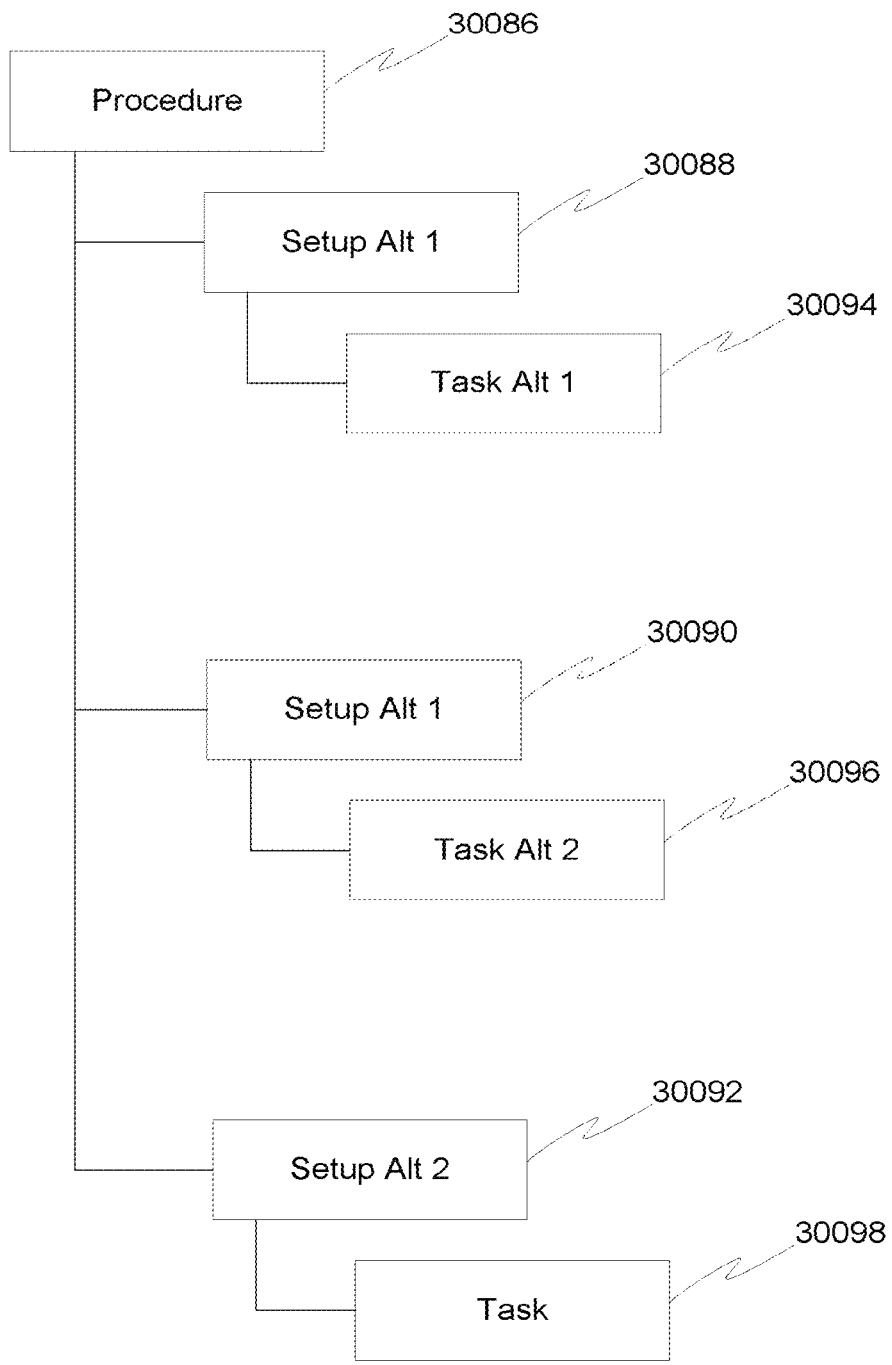

FIGS. 11A-B illustrate example surgical procedural plan data structures for use with a computer-implemented interactive surgical system and/or a surgical simulator. A surgical procedure plan may include information that outlines the staff, equipment, technique, and steps that may be used to perform a surgical procedure. For example, the procedure plan may include a staff manifest indicating what roles and/or what specific health care professionals are to be involved in the procedure. The procedure plan may include a listing of equipment, such as durable surgical equipment, imaging equipment, instruments, consumables, etc. that may be used during the procedure. For example, the procedure plan may include a pick list for a surgical technician to use to assemble the appropriate tools and materials for the surgeon and the surgery when prepping the operating theater. The procedure plan may include information about the procedure's expected technique. For example, the procedure plans for the same surgical goal may include different methods of access, mobilization, inspection, tissue joining, wound closure, and the like.

The procedure plan may reflect a surgeon's professional judgement with regard to an individual case. The procedure plan may reflect a surgeon's preference for and/or experience with a particular technique. The procedure plan may map specific surgical tasks to roles and equipment. The procedure plan may provide an expected timeline for the procedure.

The procedure plan may include one or more decision points and/or branches. Such decision points and/or branches may provide surgical alternatives that are available for particular aspects of the procedure, where selection of one of the alternatives may be based on information from the surgery itself. For example, the choice of one or more alternatives may be selected based on the particular planes of the particular patient's anatomy, and the surgeon may select an alternative based on her assessment of the patient's tissue during the live surgery.

The procedural plan may include one or more contingencies. These may include information about unlikely but possible situations that may arise during the live surgery. The contingencies may include one or more surgical tasks that may be employed if the situation does occur. The contingencies may be used to ensure that adequate equipment, staff, and/or consumables are at the ready during the procedure.

The procedure plan may be recorded in one or more data structures. A procedure plan data structure may be used to record data about a future live surgery, about a completed live surgery, about a future simulated surgery, about a completed simulated surgery, and the like. A procedure plan data structure for live surgeries may be used by the computer-implemented interactive surgical system 100. For example, the procedure plan data structure for live surgeries may be used by surgical hub 106 to enhance situational awareness and/or the operational aspects of the computer-implemented interactive surgical system 100. The procedure plan data structure for live surgeries may be used by the surgical hub 106 to record discrete elements of the live surgery for structured analysis.

A procedure plan data structure may be used by a simulation device 30000. For example, the procedure plan data structure may be used by the simulation device 30000 to establish a setting and/or one or more objectives for a simulation session. For example, the procedure plan data structure may be used by the simulation device 30000 to record the discrete elements of the simulated surgery for structured analysis.

The procedure plan data structure may include any structure suitable for capturing data elements related to the procedure. For example, the procedure plan may be recorded in a tree-like data structure, such as the one shown in FIG. 11A, for example. Here, the root of the tree structure represents the core procedure data 30066. The core procedure data 30066 may include information about the procedure as a whole, such as procedure name, procedure code, patient name, date, time, and the like. For a simulation, the core procedure data 30066 may include information about simulation device, such as device ID, software version, user, the simulation run settings, such as frame rate, resolution, connected user interface devices, and the like.

The procedure data may include leaves of the tree structure. The first level of leaves may include data regarding the main aspects of the procedure plan, such as the procedure setup 30068, one or more procedure stages 30070, one or more contingencies 30072, and the data regarding the result of the procedure 30074.

The setup data 30068 may include information related to the preparations and/or initial state of the procedure. For example, the setup data 30068 may include elements such as staff manifest, staff roles and/or staff IDs, operating room ID, an equipment list, a room layout, an initial surgical table position, a listing of instruments and/or consumables prepared in the surgical field, any initial settings associated with equipment, pre-surgical imaging, patient record, etc.

For a simulation, the setup data 30068 may include information related the simulated environment, such as a record of the simulated anatomy, a record of the simulated physiology, pre-surgical imaging, and the like.

The stage data 30070 may include data elements related to a major milestone of the procedure. For example, a stage of a procedure may include a milestone such as establishing access. The stage data 30070 may include information related to the staff, equipment, technique, and steps that may be used to perform the particular stage of the procedure. The stage data 30070 may include a stage ID.

The stage may be further detailed by one or more sub-leaves, such as one or more surgical tasks 30076. The surgical task may represent a discrete surgical step within a given stage. For example, within the stage of access, placing a trocar may be a surgical task. The surgical task data 30076 may include a task ID. The surgical task data 30076 may include information related to the particular task, such as the staff and/or surgeon performing the task, the equipment to be used, the particular technique being applied, the patient vitals at the time the task is being performed, other environment information, and the list. Each task may be further detailed with goal data 30078, data related to an anatomy-instrument interaction 30080, and result data 30082. The goal data 30078 may include information indicative of the relative success of the task performance. The goal data 30078 may include information about expected task duration, acceptable performance specificity, efficiency modality, avoidance of complications, and the like. The result data 30082 may include information related to one or more goals. The result data 30082 may record the surgical performance (e.g., live and/or simulated) relative to the goals.

The task data 30076 may include one or more elements of anatomy-instrument interaction data 30080. The anatomy-instrument interaction data 30080 may represent a granular indication of surgical performance. The anatomy-instrument interaction data 30080 may represent the one or more specific activities used to perform the surgical task. The anatomy-instrument interaction data 30080 may represent the observable behavior of the surgeon.

In an example, the anatomy-instrument interaction data 30080 may include the specific positions, forces, angles, and the like being applied to the anatomy by the surgeon. For example in a live surgery, data recorded from smart instruments by the surgical hub 106 may be captured as anatomy-instrument interaction data 30080. For example, a smart surgical stapler in cooperation with other elements of the computer-implemented interactive surgical system 100 may record stapler position, angle, tip forces, jaw forces, staple cartridge type, closing pressure, firing rate, and the like. In a simulated surgery, similar data elements may be captured.

The contingency data 30072 may indicate any complications that may be relevant to the procedure. Each contingency data 30072 may include one or more task data elements 30084 that address the appropriate response to the particular complication. The contingency data 30072 may indicate deviations from an original procedure plan. Also for example, contingency data may be cross-referenced to one or more tasks 30078 and/or anatomy-instrument interactions 30080. For example, if a certain performance in an anatomy-instrument interactions 30080 could lead to a complication, the nature of that performance and a cross-reference to the contingency may include in the result data 30082 associated with that anatomy-instrument interactions 30080.

The result data 30074 may be indicative of the result of the procedure. Here overall metrics of the surgical performance may be stored, notes, actual and/or simulated patient recovery information, and/or patient outcomes. For example, the result data 30074 may include efficiency information, cost information, surgical duration, workload metrics, percentage of planned consumables used, and the like.

FIG. 11B illustrates a procedural plan data structure with the above disclosed elements, which further establishes structure of alternative steps for completing a particular procedure, task, or activity. As shown, the procedure represented by the procedure data 30086 may include two alternative setups, each indicated by respective setup data-a first setup data 30088, 30090 and a second setup data 30092. The first setup data 30088, 30090 may include two alternative tasks 30094, 30096. The second setup data 30092 may include one task 30098. In this illustration, the procedure represented by procedure data 30086 may be accomplished in three different ways. First via first setup 30088 and the first task 30094. Second via the first setup 30090 and the second task 30096. And third via the second setup 30092 and its corresponding task 30098.

Each path of the tree structure may represent a particular set of alternative ways to perform the procedure. Such a structure may be useful to aid the creation of a particular procedure plan for a particular live and/or simulated surgery. Such a structure may be useful to simulate many possible alternatives of a procedure to assess the differences in results.

Figure 12:
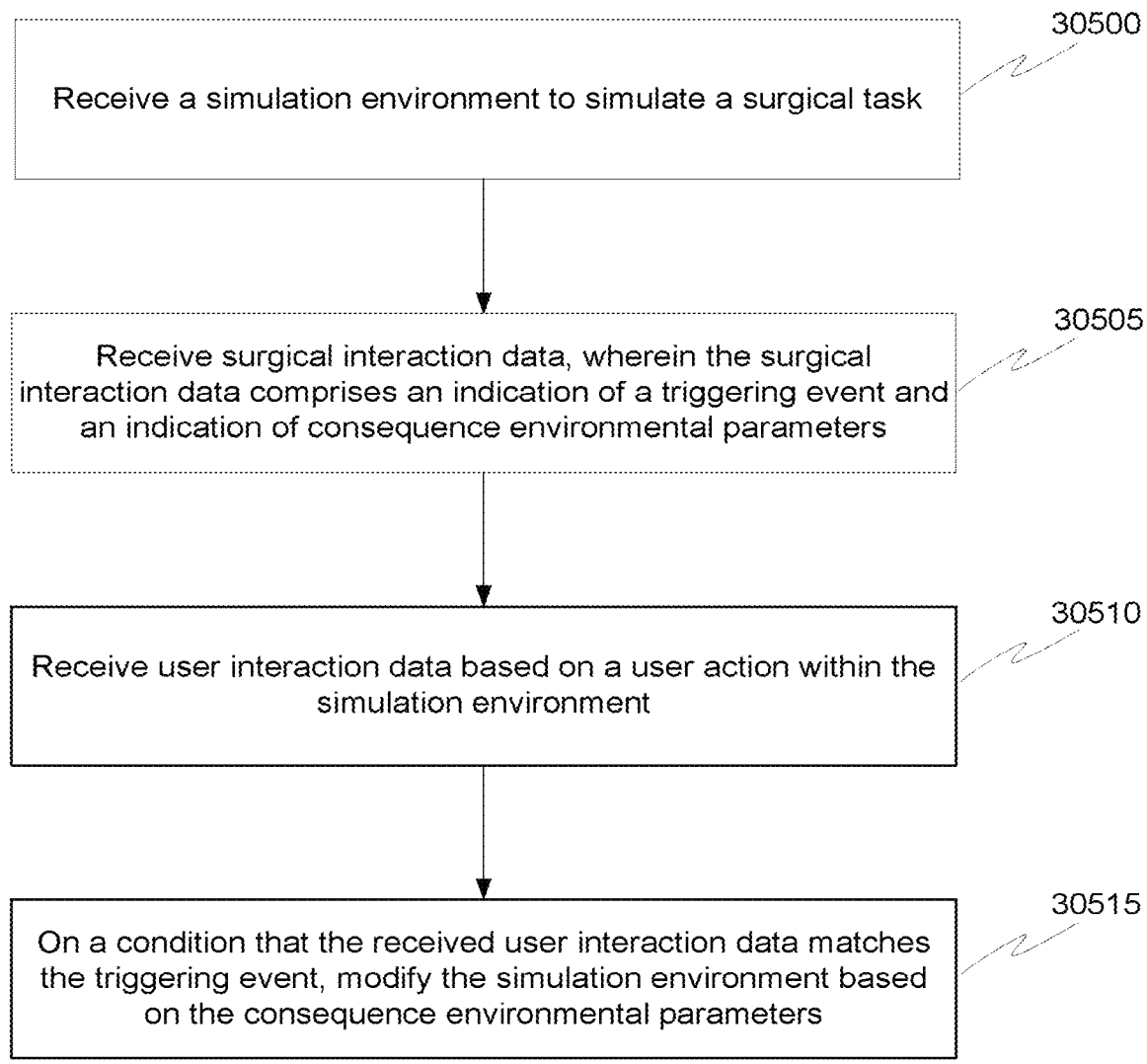
FIG. 12 shows example surgical consequences management in a simulated surgical task.

FIG. 12 shows example surgical consequences management in a simulated surgical task.

At 30500, a simulation environment may be received. In examples, the simulation environment may be used to simulate one or more surgical tasks. The simulation environment may be defined by a set of environmental parameters. For example, the set of environmental parameters may define an anatomy and/or a physiology of a simulated patient. For example, the environmental parameters may define a colon (e.g., properties of a colon) and/or bodily structures surrounding the colon. An example of an environmental parameter that defines a colon may be colon friability. The environmental parameter may be set with a numeric value that, for example, that is representative of the colon's friability.

In examples, the environmental parameters may indicate a condition of the anatomy and/or physiology of the simulated patient. For example, the environmental parameters may indicate that the colon lacks adequate blood supply. For example, the environmental parameters may be set with a numeric value that is representative of the colon's blood supply. In a case where the colon lacks adequate blood supply, the numeric value may be lower than an expected colon blood supply. In examples, the set of environmental parameters may indicate a baseline anatomy and/or physiology. In examples, the consequence environmental parameters may indicate a modified anatomy, for example, that may be a result of a surgical interaction represented by the surgical interaction data.

In examples, defining the set of environmental parameters may involve the object properties module and/or the physiology module, as described with respect to FIG. 7. The environmental parameters may be sent, for example, by the simulator to a display module that may generate images to be used in the simulation environment. The images may represent the anatomy and/or physiology of the patient defined by the environmental parameters and/or consequence environmental parameters as described herein. Generating the images may involve the texture module and/or the 3D graphics pipeline as described with respect to FIG. 7.

The surgical task(s) may be associated with a medical procedure. For example, a medical procedure may involve a surgeon performing one or more surgical tasks to treat a patient's condition. In an example, the medical procedure may be a bariatric surgery. The surgical tasks associated with bariatric surgery may be stomach access, stomach mobilization, and/or gastric transection. The simulator may be aware of the one or more surgical tasks that may be simulated. A user of the simulator may perform each of the surgical tasks, for example, in order to complete the medical procedure. The surgical task(s) may comprise similar characteristics as the task described with respect to FIG. 11A and/or 11B.

In examples, the surgical task(s) may be displayed to a user of the simulator on a display screen. Information relevant to the surgical task(s), such as recommended medical instruments and/or a recommended course of action, may be displayed on the display screen. The display screen may be included on the human interface device as described with respect to FIG. 8.

The surgical task(s) may be associated with a medical procedure context. The medical procedure context may indicate a condition of the simulated patient's anatomy and/or physiology. In examples, the medical procedure context may be associated with the environmental parameters. For example, the medical procedure context may include a subset of the environmental parameters. For example, the medical procedure may be a colorectal surgery and the medical procedure context may include the numeric value associated with colon friability as described herein. In examples, the simulator may generate the medical procedure context from the environmental parameters. In example, the medical procedure context may comprise tissue friability, tissue fragility, blood flow, tissue perfusion, allergic reaction, blood pressure, and/or heart rate.

The medical procedure context may be sent by the simulator to a surgical data system as described with respect to FIG. 7. In examples, the medical procedure and the medical procedure context may be sent to the surgical data system as described with respect to FIG. 7. The surgical data system may use the medical procedure context, for example, when determining surgical interaction data to send to the simulator.

At 30505, surgical interaction data may be received. The surgical interaction data may be received from a surgical data system, as described with respect to FIG. 7. In examples, the surgical interaction data may be sent from the surgical data system to a simulator. The simulator may send a request message to the surgical data system requesting the surgical interaction data. The request message requesting the surgical interaction data may comprise the medical procedure and the medical procedure context. In examples, the request message may be sent periodically. The request message may be sent, for example, after significant user interaction data is received by the simulator as described herein.

The request message requesting the surgical interaction data may be sent based on a surgical task that may be simulated. For example, the simulator may be simulating a colorectal surgery. The colorectal surgery may include the surgical task of mobilizing the colon. The simulator may request surgical interaction data related to mobilizing the colon, for example, if the simulator is simulating mobilizing the colon. In examples, surgical interaction data may be based on the medical procedure context as described herein. For example, the surgical interaction data may be based on a colon with low colon friability as indicated by the medical procedure context. The surgical data system may filter the surgical interaction data based on the medical procedure context and filtered surgical interaction data may be sent to the simulator.

At 30510, user interaction data may be received. User interaction data may be received by a simulator. The user interaction data may involve the physics module as described with respect to FIG. 7. The user interaction data may be based on one or more user actions within a simulation environment. For example, a simulator may be simulating a colorectal surgery. A user may ligate a simulated internal mammary artery (IMA), for example, to perform mobilizing the colon surgical task. The user may use an input device as described with respect to FIG. 14 to perform such actions in the simulation. In such a case, the physics module may measure data related to the user ligating the simulated IMA. For example, the simulator may measure the force exerted by the user on the input device as the user ligates the IMA.

At 30515, user interaction data received by the simulator may be compared against one or more triggering events. The surgical interaction data described herein may comprise the triggering event(s). The triggering event(s) may be generated in a surgical data system as described with respect to FIG. 7. In examples, the surgical data system may store historical data associated with real-life medical procedures and real-life medical procedure contexts. The surgical data system may be owned and/or operated by a medical facility, such as a hospital. In such a case, the historical data may be associated with the real-life medical procedures and medical procedure contexts previously performed by the staff of the medical facility.

The surgical data system may analyze the historical data and may identify correlation(s) between a surgeon's actions and environmental events. The surgical data system may set triggering event(s) and corresponding consequence environment parameters based on the correlations. For example, the surgical data system may identify, based on historical data, that when a surgeon exerts a certain amount of force on an IMA, the IMA tends to tear. In such a case, the surgical data system may set a triggering event that corresponds to the amount of force exerted on the IMA and may set consequence environment parameters corresponding to the IMA tearing. The surgical data system may link the triggering event to the consequence environment parameters. For example, the triggering event corresponding to the amount of force exerted on the IMA may be linked to the consequence environment parameters corresponding to the IMA tearing.

On condition that the user interaction data matches the triggering event, the simulation environment may be modified based on the consequence environment parameters. For example, one or more of the numeric values of the environmental parameters may be updated with one or more numeric values of the consequence environment parameters associated with the triggering event that matched the user interaction data. The modifications may involve the object properties module as described with respect to FIG. 7. The updated values may be sent to a display module that may generate images corresponding to the consequence environment parameters. The generated images may be used by the simulator to depict the modified simulated environment to the user.

In examples, the triggering event may be a force exerted on an IMA and the corresponding consequence environment parameters may indicate the IMA tearing. The simulator may receive user interaction data associated with a user exerting force on the IMA as the user attempts to mobilize a colon during the simulation. The simulator may compare the user interaction data against the triggering event associated with the force exerted on the IMA. The force exerted by the user may match the triggering event. In such a case, the simulator may identify that the user interaction data matches the triggering event and may update the environment parameters with the consequence environment parameters linked to the triggering event. In such a case, the simulation environment may change to show a torn IMA.

In examples, the surgical interaction data may be filtered to filtered surgical interaction data. The filtered surgical interaction data may comprise filtered triggering event(s) and/or filtered consequence environment parameters. The filtered surgical interaction data may be filtered by the simulator and/or by the surgical data system. The surgical data system may filter the surgical interaction data based on the medical procedure and the medical procedure context. For example, the simulator may send to the surgical data system the medical procedure currently being simulated. The simulator may send to the surgical data system medical context associated with the medical procedure. The surgical data system may filter the triggering events and consequence environment parameters stored on it, for example, to correspond to the medical procedure and the medical procedure context.

In examples, one or more probabilities associated with the triggering events may be determined. In examples, the surgical data system as described with respect to FIG. 7 may determine the probabilities based on the historical data described herein. For example, the surgical data system may analyze the historical data and determine that 20% of the time when a surgeon exerts a certain force on the IMA, a tear in the IMA results. The surgical interaction data received by the simulator may comprise the probabilities along with the triggering events and the consequence environment parameters. The probabilities may be linked to the triggering events and consequence parameters. For example, the probability 20% may be linked to the triggering event associated with the force exerted to tear an IMA. In such a case, the simulator may update the environment parameters with the consequence environment parameters 20% of the time when the user interaction data matches the triggering event.

In examples, a triggering threshold associated with one or more triggering events may be determined. The simulator may determine the triggering threshold based on the triggering events. In examples, the surgical data system may determine the triggering threshold based on the triggering events. The surgical interaction data may comprise the triggering threshold. In examples, the surgical data system may send the surgical interaction data, comprising the triggering threshold, to the simulator, for example, after receiving a message from the simulator requesting the surgical interaction data.

The triggering threshold may be compared against the user interaction data. In examples, the simulator may receive user interaction data related to a surgeon performing a simulated surgical task. The simulator may compare the user interaction data against one or more triggering thresholds, for example, which may have been received from a surgical data system as described herein. The simulator may determine that the user interaction data has crossed the respective triggering threshold. In such a case, the simulator may modify the simulation environment based on the consequence environment parameters as described herein.

In examples, surgical interaction criteria based on one or more surgical tasks may be determined. The surgical data system may determine the surgical interaction criteria based on the historical data associated with a medical procedure and a medical procedure context. The surgical interaction data may comprise the surgical interaction criteria. The surgical interaction criteria may be linked to the triggering events and/or the consequence environment parameters.

The simulator may consider the surgical interaction criteria, for example, when deciding whether to modify the simulated environment based on the consequence environment parameters. In examples, the simulator may determine that the user interaction data matches the triggering event. In such a case, the simulator may assess the simulation criteria to determine whether to modify the simulated environment based on the consequence environment parameters. In examples, the simulation interaction criteria may include the duration of time remaining in the simulated medical procedure and/or simulated surgical task. For example, the simulator may modify the simulation environment based on the consequence environment parameters if the time remaining is greater than or equal to an X value. The simulator may not modify the simulation environment based on the consequence environment parameters if the time remaining is less than the X value. The simulation criteria may include the experience level of the user. For example, the simulator may modify the simulation environment based on the consequence environment parameters if the user has an expert experience level. The simulator may not modify the simulation environment based on the consequence environment parameters if the user has a novice experience level.

Figure 13:
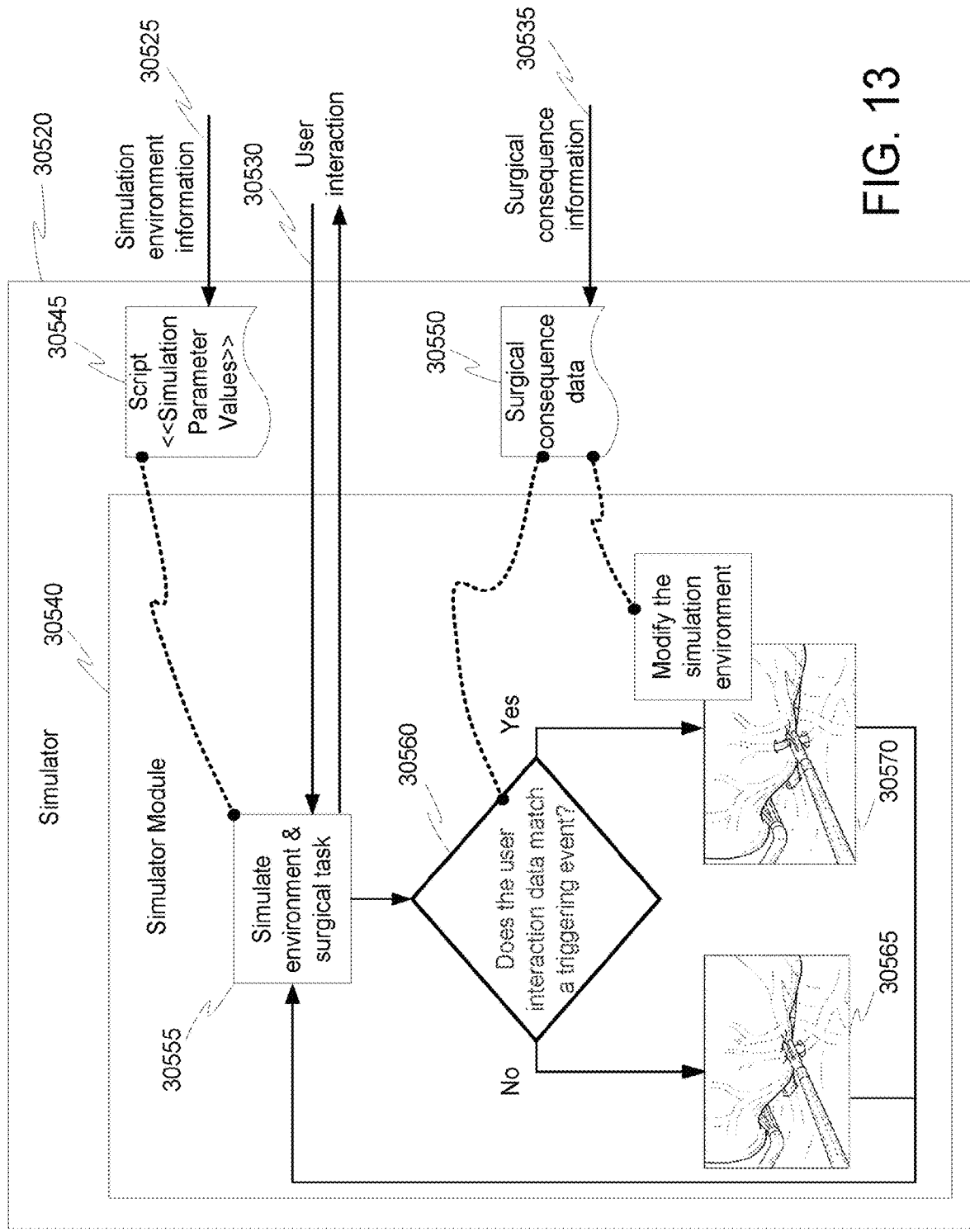
FIG. 13 shows example surgical consequences management in a simulated surgical task.

FIG. 13 shows example surgical consequences management in a simulated surgical task.

A simulator 30520 may comprise a simulator module 30540. The simulator module 30540 may be included in the core simulation module as described with respect to FIG. 7. In examples, the simulator module 30540 may be one or more of the applications modules as described with respect to FIG. 7.

The simulator module 30540 may comprise a simulator script 30545. The simulator script 30545 may include executable instructions that pertain to the simulator 30520. The simulator module 30540 may run the script 30545, for example, when executing a simulation. In examples, the simulator script 30545 may be independent from the simulator module 30540.

The script 30545 may include one or more simulation parameter values. The simulation parameter values may be used to define a simulation environment. The simulation environment may be associated with a medical procedure. For example, a simulator 30520 may simulate a colorectal surgery. In such a case, the simulation environment may include the colon, stomach, rectum, and/or tissues surrounding the colon. In such a case, the simulation environment may include blood arteries involved in colorectal surgery, such as the IMA.

Simulation environment information may be received 30525. The simulation environment information may relate to a medical procedure and a medical procedure context. The simulator may request simulation environment information based on the medical procedure and medical procedure context it intends to simulate. For example, the simulator may intend to simulate a colorectal surgery where scar tissue surrounds the colon. The simulator may send data related to this information to a remote database in a request message. The database may send a response message with simulation environment information related to a colorectal surgery where scar tissue surrounds the colon. The simulation environment information may be set as script simulation parameter values, for example, when received by the simulation.

For example, one of the script simulation parameter values may be a numeric value for the quantity of scar tissue. The simulator may input the numeric value, for example, based on the response message sent from the database.

The simulator module 30540 may simulate a simulation environment 30555 associated with a medical procedure and a medical procedure context. The simulator module 30540 may simulate a surgical task associated with the medical procedure. For example, the simulator module 30540 may simulate colon mobilization for a colorectal surgery medical procedure. The simulator 30520 may display steps for a user to do in order to perform the colon mobilization surgical task.

The user may interact with the simulation. In examples, the user may interact with the simulation via the interface module as described with respect to FIG. 7. In examples, the user may use a user interface device as described with respect to FIG. 8 to interact with the simulation. The simulator module may request user interaction data 30530 related to the user interactions. For example, the user interface device may store the user interaction data 30530 and may send the user interaction data 30530 to the simulator module 30540, for example, as a response to the request for the user interaction data 30530. In examples, the user interface device may periodically send the user interaction data 30530 to the simulator module 30540. In examples, the surgical data system as described in FIG. 7 may store and send the user interaction data 30530 to the simulator module 30540. For example, the user interface device may send the user interaction data 30530 to the surgical data system.

Surgical consequence information 30535 may be received. In examples, the surgical consequence information 30535 may be received from the surgical data system described herein. The surgical consequence information 30535 may include the surgical interaction data described herein. For example, the surgical consequence information 30535 may include one or more triggering events and one or more consequence environment parameters associated with the triggering events. The surgical consequence information 30535 may be received by the simulator 30520 and stored in a surgical consequence database. In such a case, the surgical consequence information 30535 may be referred to as surgical consequence data 30550. The surgical consequence database may allow the simulator 30520 to access the surgical consequence data 30550, for example, if the simulator 30520 wants to use the surgical consequence data 30550 in a simulation.

The simulator module 30540 may request the surgical consequence data 30550. In such a case, the simulator 30520 may send the surgical consequence data 30550 to the simulator module 30540. The simulator module 30540 may compare 30560 the user interaction data 30530 against the surgical consequence data 30550. For example, the simulator module 30540 may compare the user interaction data 30530 against the triggering events. The simulator module 30540 may assess whether the user interaction data 30530 matches the triggering events as described with respect to FIG. 12.

On a condition that the user interaction data 30530 does not match the triggering event, the simulator module 30540 may not modify the simulation environment and output an unmodified simulation environment 30565 as described with respect to FIG. 12. On a condition that the user interaction data 30530 does match the triggering event, the simulator module 30540 may modify the simulation environment based on the surgical consequence data 30550 and output a modified simulation environment 30570 as described with respect to FIG. 12. For example, the simulator module 30540 may assess that the user interaction data 30530 matches the triggering event. In such a case, the simulator module 30540 may send a request for the consequence environment parameters. The request may be sent to the surgical consequence database. The request may be sent to the simulator 30520. The consequence environment parameters may be sent to the simulator module 30540, for example, in response to the request. In examples, the simulator 30520 may direct the surgical consequence database to send the consequence environment parameters to the simulator module 30540.

The consequence environment parameters may be used to modify the simulation environment and output a modified simulation environment 30570. In examples, the simulation environment parameters may be replaced with the consequence environment parameters to modify the simulation environment. As shown in FIG. 13, the consequence environment parameters may be used to modify a simulation environment to show a severed artery. For example, images may be generated, as described with respect to FIG. 12, based on the consequence environment parameters. The consequence environment parameters may be sent to a display module that may be in communication with the simulator module 30540.

Figure 14:
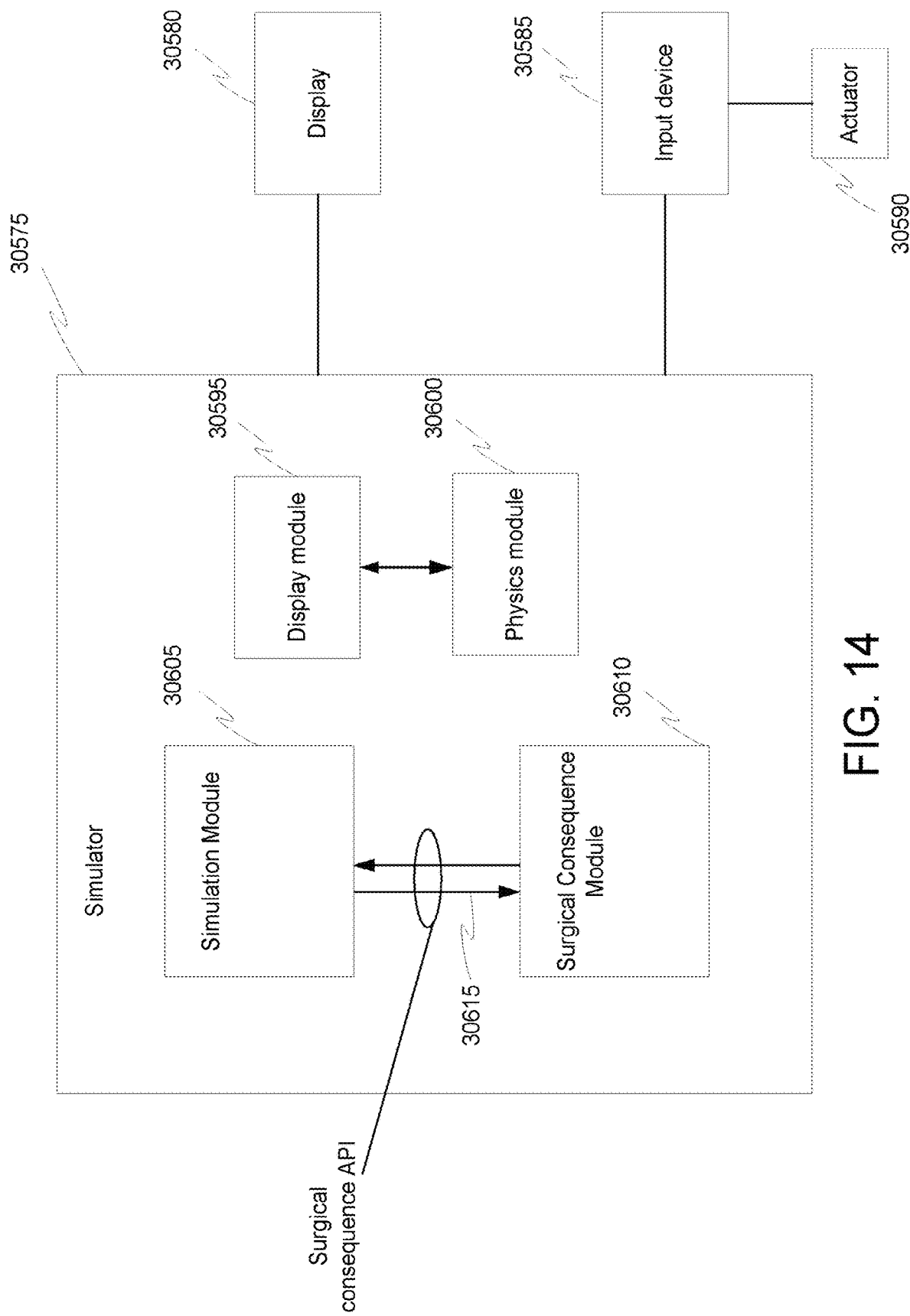
FIG. 14 shows a layout of a simulator design for surgical consequences management in a simulated surgical task.

FIG. 14 shows a layout of the simulator design.

The simulator 30575 may include a simulation module 30605. The simulation module 30605 may be the simulation module 30605 as described with respect to FIG. 13. The simulation module 30605 may be a core simulation module as described with respect to FIG. 7. In examples, the simulation module 30605 may be one or more application modules as described with respect to FIG. 7.

The simulation module 30605 may be in communication with a surgical consequence module 30610. In examples, the surgical consequence module 30610 may be a component of the simulator 30575. In examples, the surgical consequence module 30610 may be separate from the simulator 30575. The surgical consequence module 30610 may be a component of the surgical data system as described with respect to FIG. 7.

The surgical consequence module 30610 may analyze the triggering events and the consequence environment parameters. For example, the surgical consequence module 30610 may link the triggering events with respective consequence environment parameters. The surgical consequence module 30610 may comprise a database structure that stores the triggering events and the consequence environment parameters.

The simulation module 30605 may send a message to the surgical consequence module 30610 requesting the triggering events and the respective consequence environment parameters. The request message may be associated with a query. The request message may comprise a triggering event. In examples, the request message list of triggering events and probabilities associated with each triggering event.

The request message may be defined by a surgical consequence application programming interface (API) 30615. For example, the surgical consequence API 30615 may define the format of the request message. The format may facilitate communication between the simulation module 30605 and the surgical consequence module 30610. In examples, the surgical consequence API 30615 may analyze the request message to confirm that the request message is in a correct format. In examples, the surgical consequence API 30615 may transform the request message into a format.

The surgical consequence API 30615 may provide security to the data being exchanged between the simulation module 30605 and the surgical consequence module 30610. In examples, the surgical consequence API 30615 may allow an authentication key to be used in the communication between the simulation module 30605 and the surgical consequence module 30610. The authentication key may allow the surgical consequence API 30615 to confirm the identity of the module, for example, which helps to prevent hacking attacks. For example, the simulation module 30605 may send an authentication key when sending the request message to the surgical consequence module 30610. The surgical consequence API 30610 may check the authentication key and confirm that the simulation module's identity. The surgical consequence API 30615 may allow the request message to proceed to the surgical consequence module 30610, for example, after checking the authentication key.

The surgical consequence module 30610 may query the database for the triggering event, for example, after receiving the request message from the simulation module 30605. The surgical consequence module 30610 may pinpoint the triggering event that matches the triggering event. The surgical consequence module 30610 may pinpoint the consequence environment parameters linked to the triggering event. The surgical consequence module 30610 may send the triggering event and the consequence environment parameters to the simulation module 30605. In examples, the surgical consequence module 30610 may send only the consequence environment parameters to the simulation module 30605.

The simulator 30575 may include a display module 30595. The display module 30595 may be a component of the simulator 30575. In examples, the display module 30595 may be separate from the simulator 30575. The display module 30595 may be in communication with the three-dimensional (3D) graphics pipeline as described with respect to FIG. 7. In examples, the display module 30595 may be an application module as described with respect to FIG. 7.

The display module 30595 may generate images associated with a simulation environment. For example, the simulator 30575 may intend to simulate a colorectal surgery and may want the simulation environment to represent the environment that the surgeon sees during a colorectal surgery. To represent such an environment, the simulator 30575 may use the display module 30595 to generate images related to colorectal surgery. In examples, the display module 30595 may access a remote storage, for example, where images related to medical procedure are stored. In examples, the display module 30595 may store the images in a local database.

The physics module 30600 may measure user interaction data based on an input device 30585. In examples, the input device 30585 may be a robotic controller. A user may move the robotic controller to perform surgical tasks associated with the simulation. In examples, the robotic controller may resemble a medical instrument associated with the surgical task. For example, the robotic controller may resemble a harmonic scalpel if a user is performing colon mobilization surgical task.

The input device 30585 may include a trigger. The trigger may allow a user apply simulated force with a simulated medical instrument in the simulation. For example, during a simulation of a colon mobilization surgical task, the user may press the trigger of the input. Data associated with the pressing may be received by the user interaction module. The user interaction module may filter the pressing data. The simulator 30575 may use the filtered pressing data to simulate the force with the simulated medical instrument. For example, an environmental parameter of the simulator 30575 may represent the force of the simulated medical instrument. The simulator 30575 may input the filtered pressing data as a value of the environmental parameter.

The input device 30585 may include an actuator 30590. The actuator 30590 may be a rotary actuator and/or a linear actuator. The actuator 30590 may demonstrate to the user how to move the input device 30585 in order to perform the surgical task. Data associated with the actuator's movements may appear on the display 30580 for the user to see.

The simulator 30575 may be in communication with a display 30580. The display 30580 may be accessible to a user of the simulator 30575. The simulator 30575 may output the images generated by the display module 30595 to the display 30580 for the user to see. The display module 30595 may generate the images based on the user interaction data received from the input device 30585. The images may be outputted as a real-time live stream of the simulation to the display 30580. In such a case, the user may be able to see the result of the user's action on the input device 30585. For example, the user may press the trigger and the display module 30595 may generate an image showing the simulated medical instrument firing an energy beam.

Dynamic and adaptive interactive simulations for improved real world procedure feel may be provided. Dynamic adaptive interactive simulation may react to user's interactions. The adaptive simulation reaction may comprise adjustable aspects of the procedure, for example, which may automatically adjust based on the interaction of the simulation user's choices and/or reactions. The reactions may be a summary of real-world data sets that may be an aggregation of compiled data. The adjustable aspects may include regional differences, co-morbidities, medication reaction, and/or other treatments to the simulated patient.

Automatic customization of simulators with patient specific information may be provided. The simulated anatomy may be customized with real world and/or selected parameters, for example, to allow the simulation to be aligned with the patient the simulation is trying to mimic. This may be helpful in training, for example, as the trainer may select complications or other issues the resident may encounter to broaden the resident's expertise. In the case of real-world surgeons simulating a procedure plan for a real patient the customization of the simulation may allow the simulation to be as close to the real patient interaction as the surgeon may get to understand access, patient issues and/or co-morbidities, etc.

Artificial Intelligence compilation and updating with regional, patient demographic, or real-world surgical data may be provided.

The dynamic variables and aspects of the simulation may be updated by a machine learning algorithm that may be capable of adjusting the simulation based on the reactions of the user as well as based on the real-world data sets of previous surgeries. The real-world data sets of previous surgeries may be an aggregation of the procedure done by a surgeon, the surgeries from that facility and/or a compilation of surgeons using hubs within the same network.

The machine learning algorithm may be updated by data from a cloud and/or remote system, for example, which may be compiling best practices, regional data on surgeries, and/or worldwide outcomes and step-of-use from any number of other facilities worldwide.

The reactions of the simulated patient may be adjusted based on the actions, approaches, issues, resolution, etc. of the user of the simulation. The patient parameters may be adjusted based on chosen co-morbidities, regional differences, health status, and/or may be effects by the machine learning based on the medications and/or other treatments received by the simulated patient.

The real-world information may be derived from procedure outcomes, for example, from the region, population etc. and/or may be interpolation and/or aggregation of sub-biomarker measures and outcomes.

The patient parameters may be adjusted based on input from wearables (e.g., physical activity, blood pressure, heard rate, for x weeks pre-op drive probability of complications in simulation and watch out intra op indications). The patient parameters may be adjusted based on input from non-wearables application-based patient inputs such as medications taken and when the medications were taken, diet, exercise, and/or sleep.

Probability-driven local complications and anastomotic variation to display, select, able, and/or toggle able likely variances may be provided. Statistical and/or medial risk probabilities may be used to create a realistic variation of reactions of the body, physiology, organs etc. to the user's actions and/or device usage. The probability reaction may produce a range of adaptations that may differ with each re-use of the system. The range of adaptations may give the interaction a real-world air of interaction with the patient and/or surgery being simulated.

Simulator to create scenario of the patient response to known or unknown allergies/allergic reactions to medications and/or materials may be provided. The simulator may be used to train and develop staff to identify signals and/or reactions. The scenarios may be tailored to a patient based on patient characteristics and/or known allergies.

The predefined simulated patient co-morbidities, allergies, etc. may be defined and the system may utilize these as context as the simulation is executed. For example, if a step, job, and/or medicant may have a differing reaction due to the complicated patient variable, the simulation may include that new modified reaction.

Reactive and predictive variable consequences based on choices may be provided. Reactive variables of the consequences include one or more of the following: blood flow, perfusion, lobectomy (e.g., artery or vein in pulmonary artery in lung, which may fill up like a balloon), vessels or broncus, access (e.g., how the anatomy presents the vessels, which may be out front), different disease states may include differing outcome for vein and artery, micro or macro tissue tension, or technique (e.g., which may predict complication rate of the surgeon based on technique). Reactive variables may be linked. Reactive variables may be predictive of adverse event risk based on simulation user action.

For example, indication of tissue fracture prediction based on specific tissue deflection may indicate a force. The force may cause a deflection and fracture, which may lead to stress. The stress may cause deflection, for example, due to too high of a retraction force on the liver or another heavy organ to access structures underneath.

Adaptive difficulty teaching and/or reactive simulations for procedure familiarity may be provided. The adaptable option and/or reaction may comprise an aspect that allows a user to set the probability of challenges and/or define the type and intensity of the reaction to vary the simulator's response to user choices.

The change of difficulty may include the likelihood of lower probability but higher risk aspects, adverse events, and/or complications being utilized and allowing the user to overcome them. There may be a randomness aspect to the adaptability. For example, if a user ran the same simulation twice and did the same set of steps and interactions, there may a be possibility that the reaction of the simulation may differ.

In examples, bleeding likelihood, tissue fragility and tissue tearing, radiation treatment reactions of tissue friability and the fragility of the tissue or its unusual thinness, ablation therapy, melted, tissue and its impact on coagulation, inflammation, etc. may be included in the adaption and/or reaction.

Figure 15:
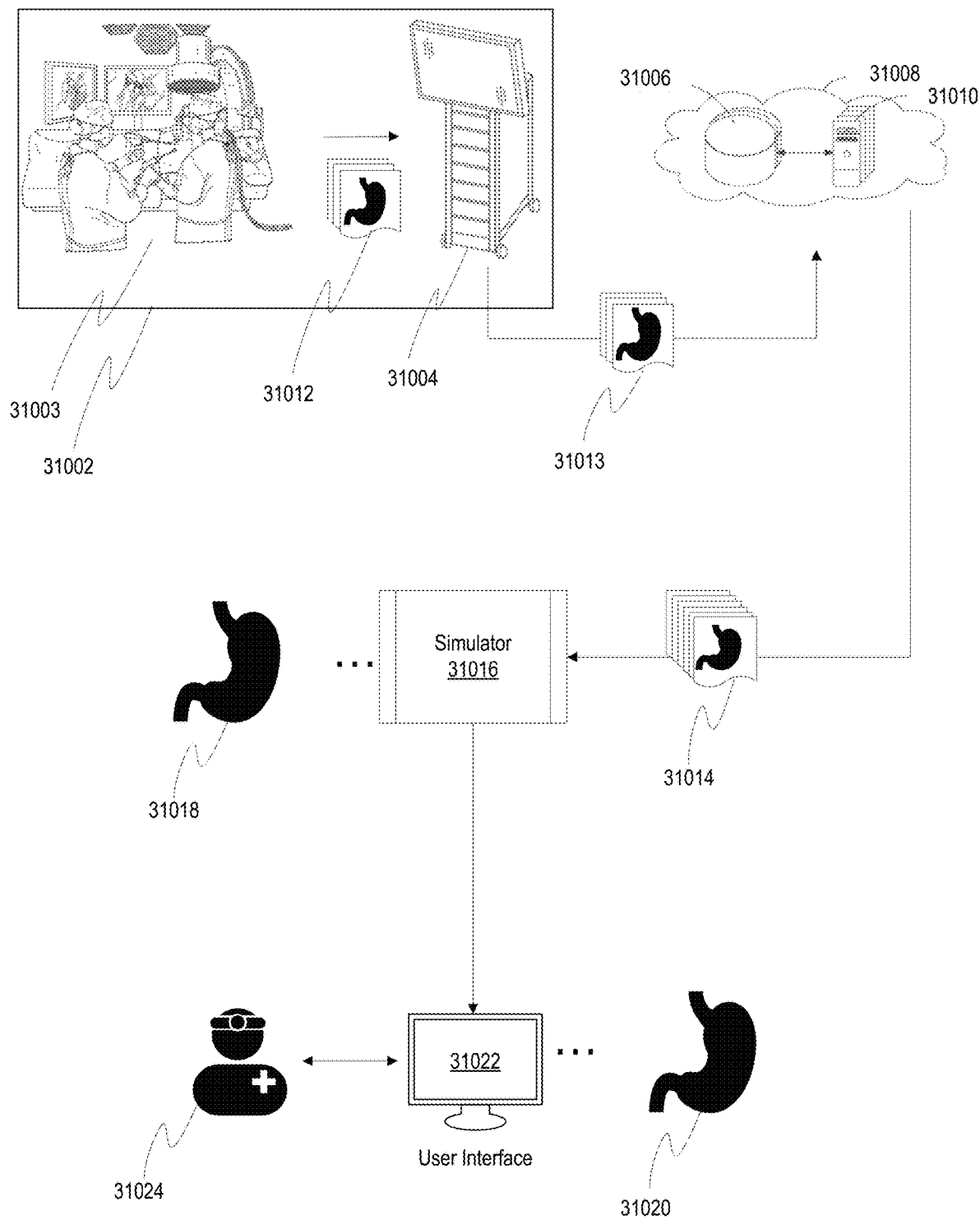
FIG. 15 illustrates an example data flow of an example surgical simulator operation.

FIG. 15 illustrates an example data flow 31000 of an example surgical simulator 31016 operation. The example surgical simulator 31016 may be the simulation device 30000 (e.g., described in FIGS. 7 and 8). The simulator 31016 may include the processor 30034 of the simulation device 30000. Images of a patient's organ(s) and/or tissue(s) may be captured during a surgical procedure. For example, images of a patient's stomach may be captured during a laparoscopic sleeve gastrectomy procedure. As shown in FIG. 15, in an operating room 31002, a surgeon and a surgeon assistant are performing a laparoscopic sleeve gastrectomy procedure 31003. A laparoscope with structured light imaging capability may be used in the procedure 31003. The laparoscope may include an incoming light channel for a pattern of light from a structured light projector and an outgoing light channel for light reflected from a surgical site (e.g., the stomach). The pattern of light from the structured light projector may be a narrow-band light (e.g., a blue light). As such, the light reflected from the stomach may include the distorted pattern of light reflected from the stomach and white light reflected from the stomach.

The images of the stomach as reflected in white light may be filtered and captured by a white light camera and images of the stomach may be presented to the surgeon and/or surgeon assistant in a visualization user interface. The images of the stomach overlaid with the distorted pattern of light may be filtered and captured by a corresponding narrow-band light camera intra-operatively, e.g., in a video format. The white light camera and the narrow-band light camera may be calibrated such that red/green/blue (RGB) color values of the images captured by the white light camera may be looked up for the images captured by the narrow-band light camera. As such, images of the stomach overlaid with the distorted pattern of light and the associated RGB color values may be captured intra-operatively.

The captured images of the patient's organ(s) and/or tissue(s) may be sent to a surgical data system 31004. For example, the captured images of the stomach 31012 overlaid with the distorted pattern of light may be sent to a surgical data system 31004 in the operating room 31002 (e.g., surgical data system 30006 as described in FIG. 7). The pattern of light projected from the structured light projector may also be sent to the surgical data system 31004.

The surgical data system 31004 may send the captured images of patient organ(s) and/or tissue(s) to a remote system 31008. For example, the surgical data system 31004 may send the images of the stomach captured from a plurality of laparoscopic sleeve gastrectomy procedures 31013 to a remote system 31008 (e.g., the cloud 14 as described in FIG. 1). The surgical data system 31004 may also send the pattern of light projected from the structured light projector to the remote system 31008. The remote system 31008 may include a remote server 31010 coupled to a storage device 31006. The plurality of the laparoscopic sleeve gastrectomy procedures may include the procedures performed on the same patient and/or the procedures performed on different patients.

A surgical simulator 31016 may simulate a surgical procedure using two-dimensional (2D) image data of patient organ(s) and/tissue(s) from the remote system 31008. For example, a surgical simulator 31016 may simulate a laparoscopic sleeve gastrectomy procedure using 2D image data of a stomach 31014 from the remote system 31008. The 2D image data of a stomach 31014 may include 2D image data of a stomach from a plurality of surgical data systems, e.g., at a same facility, at different facilities in a same geographic region, or at different facilities in different geographic regions. The 2D image data of a stomach 31014 may be image frames from videos captured intraoperatively using structured light imaging described herein.

The surgical simulator 31016 may generate a simulated human organ for the simulated surgical procedure by generating a baseline deformable three-dimensional (3D) model of the human organ and combining the model with the 2D image data of a human organ from the remote system 31016. For example, the surgical simulator 31016 may generate a simulated stomach by generating a baseline deformable 3D model of a stomach 31018 and combining the model 31018 with the 2D image data of a stomach 31014 from the remote system 31008. The surgical simulator 31016 may reconstruct 3D data of a stomach from the 2D image data of a stomach 31014 from the remote system 31008. The surgical simulator 31016 may map the shape of the baseline deformable 3D model of the stomach 31018 to correspond to the reconstructed 3D data of the stomach 31014 from the remote system 31008. The surgical simulator 31016 may map the surface of the baseline deformable 3D model of the stomach 31018 to correspond to the reconstructed 3D data of the stomach 31014.

The surgical simulator 31016 may output the mapped baseline deformable 3D model of the simulated human organ 31020 after mapping its shape and its surface to correspond to the reconstructed 3D data of the human organ. A simulation user 31024 may interact with the mapped baseline deformable 3D model of the simulated human organ 31020 in a simulated environment.

Figure 16:
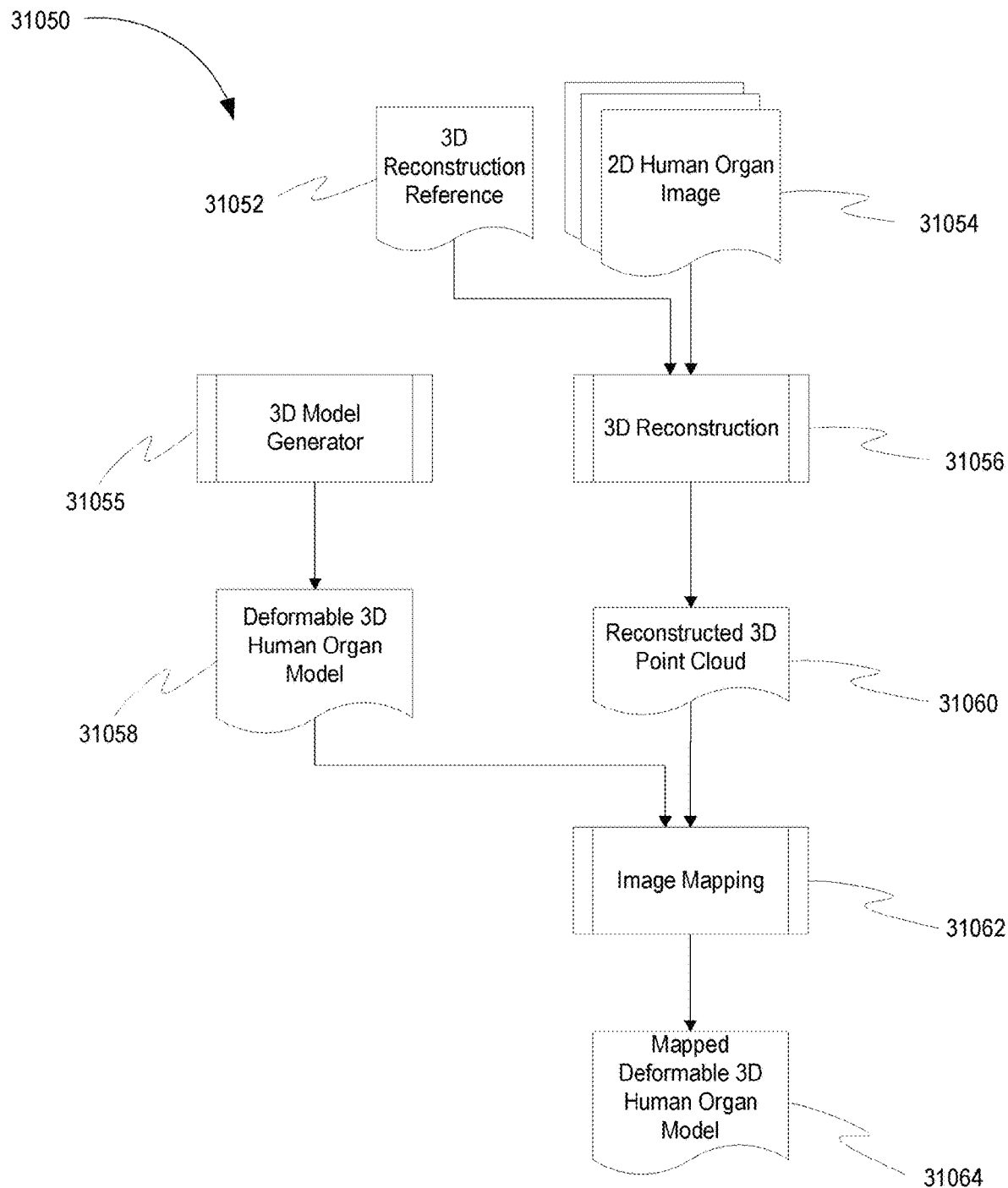
FIG. 16 illustrates an example data flow of an example surgical simulator operation.

FIG. 16 illustrates an example data flow of an example surgical simulator 31050 operation. The example surgical simulator 31050 may be the simulation device 30000 (e.g., described in FIGS. 7 and 8). The example data flow may be performed by the simulation device 30000. The example data flow may be performed by the processor 30034 of the simulation device 30000. The surgical simulator 31050 may include a 3D reconstruction module 31056. The 3D reconstruction module 31056 may receive 2D human organ images 31054 and associated 3D reconstruction reference data 31052. For example, the 2D human organ images 31054 may be the 2D images of stomach 31014 as described in FIG. 15. For example, the associated 3D reconstruction reference data 31052 may be the pattern of light projected from the structured light projector as described in FIG. 15.

The 3D reconstruction module 31056 may reconstruct 3D image data from the received 2D human organ images 31054 and associated 3D reconstruction reference data 31052. For example, the 3D reconstruction module 31056 may recover a 3D point cloud 31060 from 2D stomach images 31014 and the associated 3D reconstruction reference data 31052. In an example, the 3D reconstruction module 31056 may recover a 3D point cloud from the 2D images of stomach 31014 and the pattern of light projected from the structured light projector as described in FIG. 15. 3D points may be recovered at pixels of 2D images of stomach 31014 using any suitable 3D reconstruction algorithm associated with the pattern of light. 3D points recovered from the 2D images of stomach 31014 may include RGB color values from the 2D images of stomach 31014. 3D points recovered from the 2D images of stomach 31014 may include 3D spatial coordinates. 3D points recovered from different 2D images of stomach 31014 may be spatially aligned into a uniform 3D coordinate system, e.g., using image registration algorithms, such as non-rigid registration algorithm and/or feature-based registration algorithm.

The surgical simulator 31050 may include a 3D model generator 31055. The 3D model generator 31055 may generate a deformable 3D human organ model 31058. For example, the 3D model generator 31055 may generate a deformable 3D stomach model 31058 based on a stomach anatomical template (e.g., an anatomical atlas of a stomach). The deformable 3D stomach model 31058 may be deformable volumetric tetrahedron model. The deformable 3D stomach model's 31058 surface vertices may embody the surface shape of the stomach anatomical template. The deformable 3D stomach model's 31058 surface vertices may be generated in a default color and in a default texture.

The surgical simulator 31050 may include an image mapping module 31062. For example, the image mapping module 31062 may receive the reconstructed 3D point cloud 31060 recovered from the 2D images of stomach 31014 and the deformable 3D stomach model 31058.

The mapping module 31062 may generate a mapped deformable 3D human organ model 31064 based on the reconstructed 3D point cloud 31060 and the deformable 3D human organ model 31058. For example, the mapping module 31062 may extract a 3D mesh surface stomach model from the deformable 3D stomach model 31058. The mapping module 31062 may convert the extracted 3D mesh surface stomach model into a corresponding 3D point cloud. Such 3D point cloud may be mapped to the reconstructed 3D point cloud 31060 recovered from the 2D images of stomach 31014 to minimize the difference from the reconstructed 3D point cloud 31060, e.g., using the iterative closest point (ICP) algorithm. The mapped 3D point cloud may be converted back to a 3D mesh surface stomach model and subsequently the 3D mesh surface stomach model may be converted back to a deformable volumetric tetrahedron model. As such, the mapped deformable 3D stomach model 31064 matches closest to the shape, the color, and the texture of the reconstructed 3D point cloud 31060.

The mapped deformable 3D human organ model 31064 may be sent to a visualization module for a user to interact with. For example, the mapped deformable 3D stomach model may be sent a visualization module for a user to interact with in a simulation environment.

Figure 17:
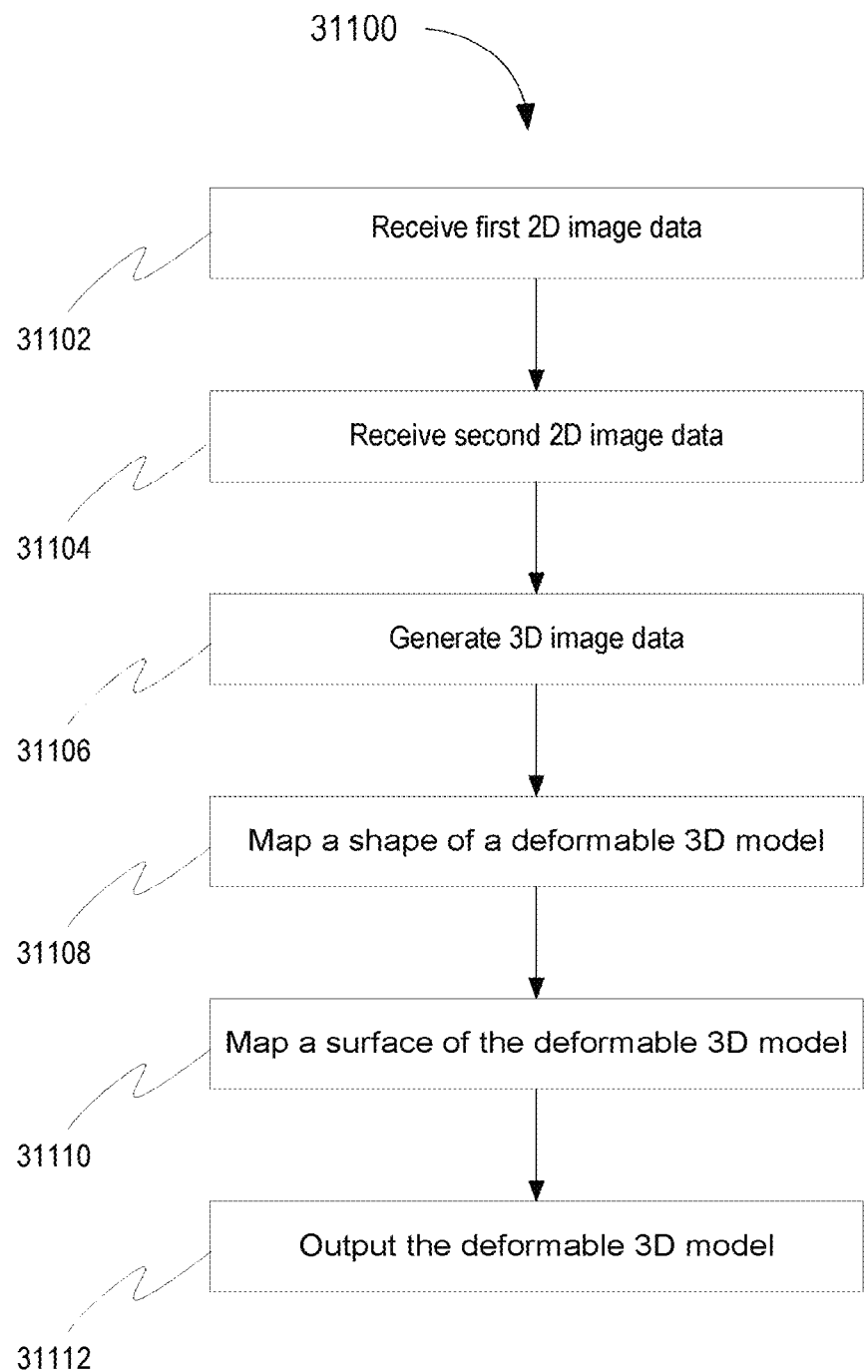
FIG. 17 is a flow chart of an example operation of an example surgical simulator.

FIG. 17 is flow chart of an example operation an example surgical simulator. For example, the example operation may include a process 31100 to generate 3D image data from 2d image data. The process 31100 may map a deformable 3d Model to the 3D image data. The example surgical simulator may be the simulation device 30000 (e.g., described in FIGS. 7 and 8). The process 31100 may be performed by the simulation device 30000. The method 31100 may be performed by the processor 30034 of the simulation device 30000.

At 31102, first two-dimensional (2D) image data of a first human organ of a first patient may be received. The first 2D image data may include first 2D visible image data captured inside the first patient and first three-dimension (3-D) reconstruction reference data. The 2D image data of the first human organ of a first patient may be captured using structured light imaging.

At 31104, second 2D image data of a second human organ of a second patient may be received. The second 2D image data may include second 2D visible image data captured inside the second patient and second 3D reconstruction reference data. For example, the first human organ of the first patient and the second human organ of the second patient may be a same type of human organ. For example, the first 2D image data may further include first invisible image data that is captured inside the first patient. The second 2D image data may further include second invisible image data that is captured inside the second patient. The 3D image data from the aggregation of the first visible image data and the second visible image data may be generated based on the first reference and the second reference, and based on the first invisible image data and the second invisible image data. The 3D image data may further include non-visual information. Sub-surface data of the deformable 3D model of the simulated human organ may be generated based on the non-visual information of the 3D image data.

At 31106, 3D image data from an aggregation of the first visible image data and the second visible image data and based on the first reference and the second reference may be generated. The 3D image data may include spatial information and visual information.

At 31108, a shape of a deformable 3D model of a simulated human organ may be mapped to correspond to the spatial information of the 3D image data. For example, the method may receive tissue property data of the one or more human organs. The tissue property data may be determined at least by tracking a displacement of a physical fiducial marker attached on the one or more human organs. A simulated force is applied to the deformable 3D model may be determined. The shape of the deformable 3D model may be deformed based on the physical property data.

At 31110, a surface of the deformable 3D model of the simulated human organ may be mapped to correspond to the visual information of the 3D image data. For example, patient specific data may be received. The surface of the deformable 3D model of the simulated human organ may be mapped to correspond to the visual information of the 3D image data and the patient specific data.

At 31112, the deformable 3D model may be outputted.

For example, an expected aspect of the simulated surgical procedure may be defined. The expected aspect may be one of a surgical step, a job that is a part of the surgical step, a location in a surgical scene, or a surgical instrument. An input data, from a user, to the simulated surgical procedure may be monitored. the input data to correspond to the expected aspect may be determined. A relevant instruction may be presented to the user.

For example, an expected aspect of the simulated surgical procedure may be defined. The expected aspect may be one of a surgical step, a job that is a part of the surgical step, a location in a surgical site, or a surgical instrument. An input data, from a user, to the simulated surgical procedure may be monitored. The input data may be determined to correspond to the expected aspect. A choice of initiating an instructive interaction with the user may be presented to an instructor.

For example, an expected surgical step of the simulated surgical procedure may be defined. An input data to the simulated surgical procedure from a user may be monitored. The input data may be determined to correspond to the expected surgical step. A choice of viewing a corresponding segment of one or more actual surgical procedure videos may be presented to the user. The one or more actual surgical procedure videos may include segments that are indexed on surgical steps. In an example, the choice of viewing the corresponding segment of the one or more actual surgical procedure videos may be further customized by a surgical complication or a surgical outcome.

The simulator may be configured to provide realistic appearance via integration of real-world information. The simulator may include surgical simulator models with real world images, textures, organ manipulated shapes and organ aspects (e.g., via computer adaptation). The simulator models (e.g., 3D models) of the simulation may have real world imagery overlaid onto the models to provide accuracy and interactive aspects of the surgery and organs. The deformed organ images may be generated through a combination of structured light imaging of real surgeries. The surface textures, features, and look may be generated form an aggregation of real surgical imagery. The overlays may be customized by a user, a facility, a surgical data system (e.g., a hub), or a remote system (e.g., a cloud-based system) based on specific needs of the simulation and/or specific aspects of the simulated procedure and/or patient.

The simulator may be configured to provide digital simulation using video overlay of actual tissue imaging. The video overlay of actual tissue imaging may be adjusted to the deformed state 3D models, e.g., via structured light imaging of an original dataset of actual tissue imaging.

The overlays of actual tissue imaging may be adaptive. The overlays of actual tissue imaging may be derived from aggregated real-world imaging of similar tissues and may include multi-spectral imaging and other imaging technologies of the tissues. The aggregated real-world imaging may be adjusted by a user based on predefined aspects for realism to a specific patient or tissue. The aggregated real-world imaging may be updated from additional data aggregated in a remote system (e.g., a cloud-based system) as more procedures are imaged. The adaptions may be customized by a region, a population age, one or more co-morbidities, and/or treatment effects.

Tissue models may be adjusted to real deformed state and/or real repositioned state with respect to other anatomy through intra-operative scans (e.g., via structured light or time-of-flight distance sensor array(s)). Tissue models may be adjusted to data that are inputted to simulation from Crowd-Sourced Assessment of Technical Skills (CSATS) databases or other live-view databases.

The simulator may be configured to simulate micro tension and/or surface strain, which may induce subsurface shear, deformation, and/or stresses. The simulator may perform such simulator using structured light combined with a physical fiducial marker on organ(s) and/or tissues. Physically attached markers may be added to the structured light tracking of organ(s) and/or tissue(s), e.g., in place of or in combination with the structured-light projected tracking. Tracking using physically attached markers may provide monitoring of strains and stress within the surface of the organs and may enable extrapolation of the sub-surface force implied deformations and motions. Using such tracking, the deformed model generation may more realistically reflect movement and retractions and/or cutting of the organ(s) and/or tissue(s). Surface and sub-surface strains and stresses may be calculated. Using such calculation, the sectioning of the organ may be in an appropriate configuration for viewing. Using such calculation, tissue tensions, blood flow occlusion due to tissue shear, and micro tissue tensions and max strain before tearing, may be shown.

The simulator may be configured to include indexable recording of real-world video of surgeries that may be accessed and reviewed within the simulator (e.g., for learning from real surgeon activities). The indexable recording may include CSATS surgical phases augmented into the simulator (e.g., for learning). The indexable recording may include ethnography.

The indexable recording may include step segmentation viewing of a specific procedure. The step segmentation may allow the user to view one or more examples of how the system suggests to approach the step. Sources of the example videos could be thought leader, crowd sourced, a given hospital's network best practice. The network examples may be related to an economical aspect. Such network examples may promote consistent behaviors in the network. For example, for a specific network, the pay and reimbursement of a procedure may drive examples of how surgeons in that network may handle predefined approaches, treatments, or product utilization. Differing steps may be searched for to pull in example videos. An example of such step may be vascular isolation for mesentery transection. An example of such step may be introduction of the anvil into the colon. An example of such step may be approximation of anvil.

The indexable recording may provide searching for specific difference to pull in an example of how to deal with that difference via a specific doctor's approach.

The indexable recording may be searchable by outcome(s) and/or complication(s).

The simulator may be configured to provide live instruction(s) to a user during a simulation via simulation control(s). The simulation controls may include toggleable labeling, landmark ID, complication callouts, indications of tissue plane orientations, and deviation notification from best practice activities.

The simulator may be configured to operate in an automated tutorial mode. The simulation may have a predefined initiation, or steps to take as the user gets to specific predefined locations, step, instruments, or jobs. The predefined initiation and/or steps may include instructions on one or more of the following: step-by-step operation, interaction with other systems like augmented imaging, or instruments or the use of auxiliary or adjunct tools or materials.

The simulator may be configured to operate in a live instruction mode. The simulation may include interaction with an instructor, such as teaching staff or a residence director. The simulation may allow the user to communicate with the instructor. The simulation may allow for prompting at predetermined times. The simulation may be controlled via exterior controls or indicators, e.g., by an external instructor. The controls may indicate a re-orientation, or may walk the user through the steps. The controls may include orientation, points, marking, labeling, or otherwise guiding the user. The simulation may include verbal overlay.

The simulator may be configured to include cooperative interaction of alternative visualization means in the simulation. For example, the simulation may include multi-spectral imaging overlay or supplementation, or other imaging interactions to provide occluded view of critical structures. Examples of imaging interactions may include post-exposure treatment hospital (PET) uptake number scans, augmented views of a lymph node, An example of the critical structures may include vessels. The simulation may include clinical involvement.

For example, the simulation may include imaging from Indocyanine green (ICG) to indicate blood flow. For example, the simulation may include simulating a best time to systemically introduce ICG. For example, the simulation may include simulating ICG fading (e.g., over a period time). For example, the simulation may include simulating when to directly introduce ICG.

The simulator may be configured to include imaging supplementation of the anatomy of a specific patient to adapt the simulated aggregate base anatomy to be customized for the patient irregularities. The simulation may affect size of the organs, disease state impacts, location or positioning of the organs of the vascular geometries specific to that patient. The simulation may include divergent patient organs and unusual anatomy. The simulation may include input from pre-operative imaging, e.g., multiple bifurcation and/or trifurcation of vascular into lung lobes and segments. The simulation may include intra-operative and/or pre-operative fluoroscopy that provides information of collateral circulation to organs.

Figure 18:
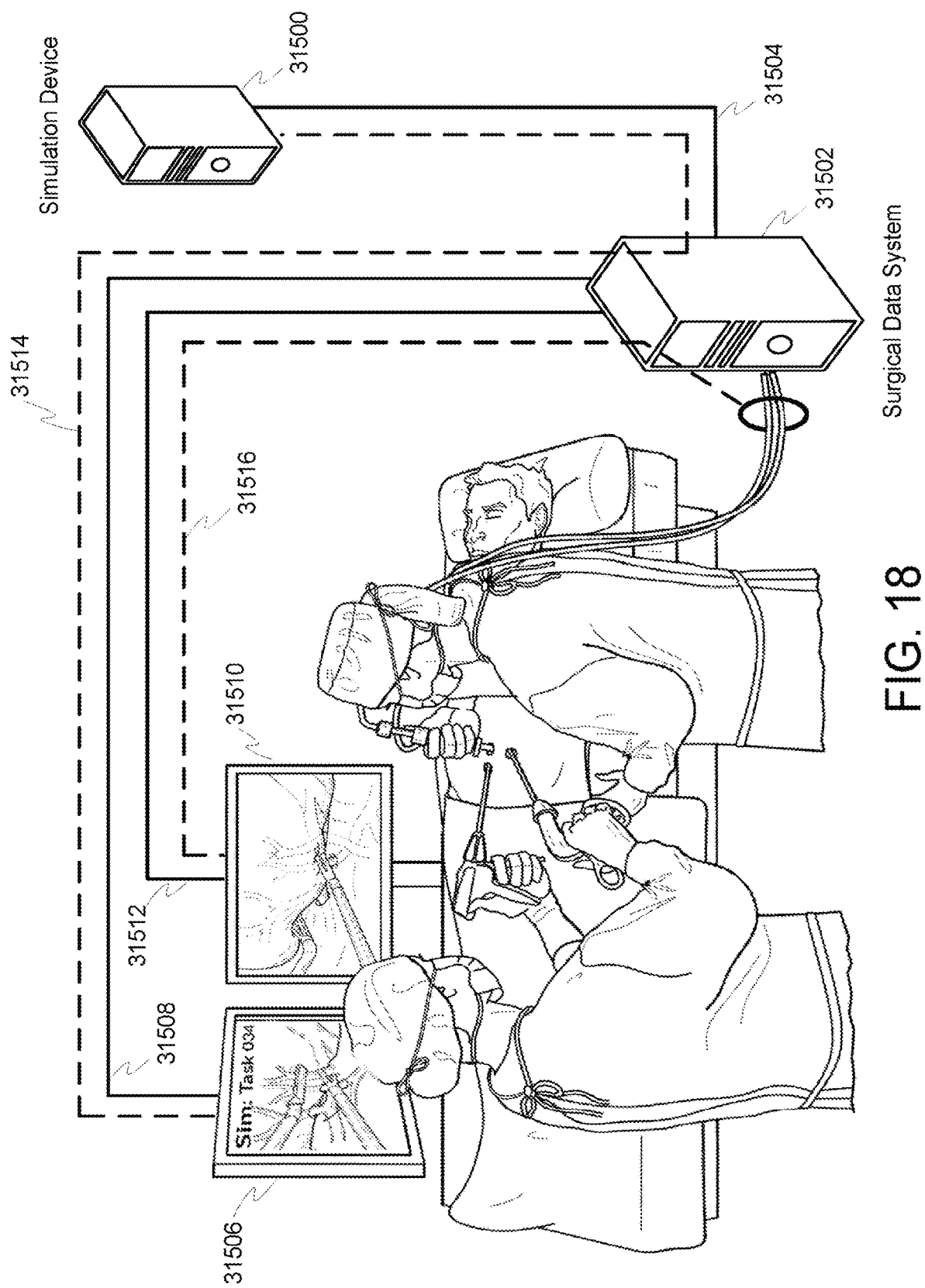
FIG. 18 illustrates a system for providing simulation support in a live surgical procedure

FIG. 18 illustrates a system for providing simulation support in a live surgical procedure. A live surgical procedure may employ a simulation device 31500, a surgical data system, and the like. There may be stored a simulation of a particular surgical procedure. And a surgeon may benefit, when performing that particular procedure, from retrieving the stored simulation and interacting with it during the live procedure. The stored simulation may provide guidance, training, aid in memory and/or recall, and the like. The stored simulation may enable the surgeon to simulate a task and/or technique in temporal proximity to performing the task and/or technique live. The stored simulation may provide expert guidance on a particular task and/or technique, where the simulated anatomy and/or simulated patient conditions aligns with the live patient.

The simulation device 31500 may include a computing platform capable of storing, recalling, and/or running a simulation as disclosed herein. For example, the simulation device 31500 may include simulation device 30000 as disclosed herein. The simulation device 31500 may be in communication with a surgical data system 31502. For example, the simulation device 31500 may be in communication with a surgical data system 31502 via a communications leg 31504.

The surgical data system 31502 may include a surgical computing platform capable of providing surgical situational awareness, live imaging, simulation imaging, and the like. For example, the surgical data system 31502 may include the surgical data system 30008 disclosed herein. For example, the surgical data system 31502 may include one or more components of the computer-implemented interactive surgical system 100 disclosed herein. For example, the surgical data system 31502 may include the surgical hub 106 disclosed herein.

The surgical data system 31502 may be in communication with a simulation human user interface 31506. For example, the surgical data system 31502 may be in communication with the simulation human user interface 31506 via a communications leg 31508. The human interface device 31506 may include the human interface device 30004 disclosed herein. In an example, the human interface device 31506 may include user controls particularly suited for the operating room environment. For example, the human interface device 31506 may include simplified play-back controls. For example, the human interface device 31506 may include a robotic surgery surgeon's console with a simulation/live cutover switch, such that the same console may be used to interact with the simulation and interact with the live patient. In an embodiment, such a human interface device 31506 may enable a video overlay of imaging of the live procedure and imaging of the simulation.

The surgical data system 31502 may be in communication with a surgical display 31510. For example, the surgical data system 31502 may be in communication with the surgical display 31510 via a communications leg 31512. The surgical display 31510 may include one or more components of the computer-implemented interactive surgical system 100 disclosed herein. For example, the surgical display 31510 may include aspects of the visualization system 108, such as the primary display 119, the first non-sterile display 107, the second non-sterile display 109, and the like.

The surgical data system 31502 and/or the simulation device 31500 may be used to access archived portions of a simulation during the procedure, for example, to reorient and/or reanalyze key steps due to unanticipated deviations from the pre-surgery plan. In an example, a procedure plan may be created with surgical choices at key surgical steps. A simulation of this procedure plan may be recorded, archived, and/or later recalled during the actual procedure. For example, such simulated snap shots may be recalled by the surgeon to review and/or update with new data and/or unanticipated issues encountered during the procedure. For example, the simulation may be re-run during the procedure to provide the surgeon with new outcomes, choices, and/or impacts. Also for example, the simulation may be updated with information learned during the procedure, such as revising the simulated patient's anatomy. Such an updated simulation may be rerun during the procedure according to the procedure plan (and, for example, a corresponding surgeon agent). And such an updated simulation may be used to more closely align with the live procedure than the original simulation, for example.

In an example, the surgical data system 31502 and/or the simulation device 31500 may be used capture simulated and/or real-world snapshots of the procedure. Such snapshots may be recalled at a later point in procedure, at a time for example, when one or more organs and/or retractions are distorting and/or occluding the surgeon's view. For example, the operative view may be augmented with one or more snapshots from a preferred point in time, such as a preferred point in time associated with indocyanine green-based (ICG-based) anatomic delineation clarity. And once a critical structure is identified, the surgical data system 31502 and/or the simulation device 31500 may be used to re-apply (e.g., overlay) the snapshot as last viewed in the simulation.

In an example, the surgical data system 31502 and/or the simulation device 31500 may be used to archive certain alternative steps in simulation, such as alternate surgeon choices of approach, retraction, instrument usage, and the like. Such simulated alternative tasks may be accessed during the procedure. A simulation may be updated to align with the current state of the live procedure and then re-run with a selected alternative to provide metrics related to expected results. Such re-run simulations may be re-run automatically with this new information. And the surgical data system 31502 and/or the simulation device 31500 may incorporate such new information to update procedure forecasting.

In an example, new and/or updated simulations may be constructed "on the fly" during a live procedure. Such simulations may enable a surgeon to infer patient responses (e.g., micro-outcomes) and to explore the implication of certain granular surgical step choices. For example, such a simulation may enable a surgeon to determine a cause and/or correlated response to an activity and/or observed behavior in the live procedure.

In an example, the surgical data system 31502 and/or the simulation device 31500 may be used compare to work backwards from a desired outcome and identify one or more steps and/or boundary conditions that are associated with the desired outcome. For example, a comparison, using forward and backward simulation steps, may enable a surgeon to estimate the similarity between an actual and simulated surgical approach and its relation to a particular objective.

The operation of the simulation in concert with the live surgery may be coordinated by the surgical data system 31502, for example. The operation of the simulation in concert with the live surgery may be coordinated with reference to one or more procedure datasets.

Illustrating a use of the surgical data system 31502 and/or the simulation device 31500, the surgical display 31510 may show the present live surgery. The surgical display 31502 may be displaying a current task associated with upper lobe manipulation in a thoracic lobotomy. As shown, the surgeon's present technique is causing poor visualization of the pulmonary vein and/or pulmonary artery structures on the surgical display 31502. At this point, the surgeon may access a simulation of the corresponding task via the simulation human user interface 31506. The stored simulation may include a simulated based on the same and/or similar anatomy, performed by the same surgeon, performed by an expert surgeon, simulated with the same and/or similar instruments, and the like. The present task of the live procedure may be coordinated (e.g., coordinated via common task-based indexing) with a corresponding portion of the stored simulation. In response to the request, the surgical data system 31502 and/or the simulation device 31500 may retrieve the appropriate portion of the simulation and present it to the surgeon for interaction. As shown, the simulation may inform the surgeon of an improved instrument technique that may enhance visualization of the pulmonary vein and/or pulmonary artery structures by showing the simulation of the technique via the simulation human user interface 31506.

The operation of the simulation in concert with the live surgery may be coordinated with reference to a procedure plan for the simulated procedure, the procedure data associated with the actual simulation as executed, the procedure plan data for the live surgical procedure, the situational awareness data from the live surgical procedure, and the like.

Figure 19:
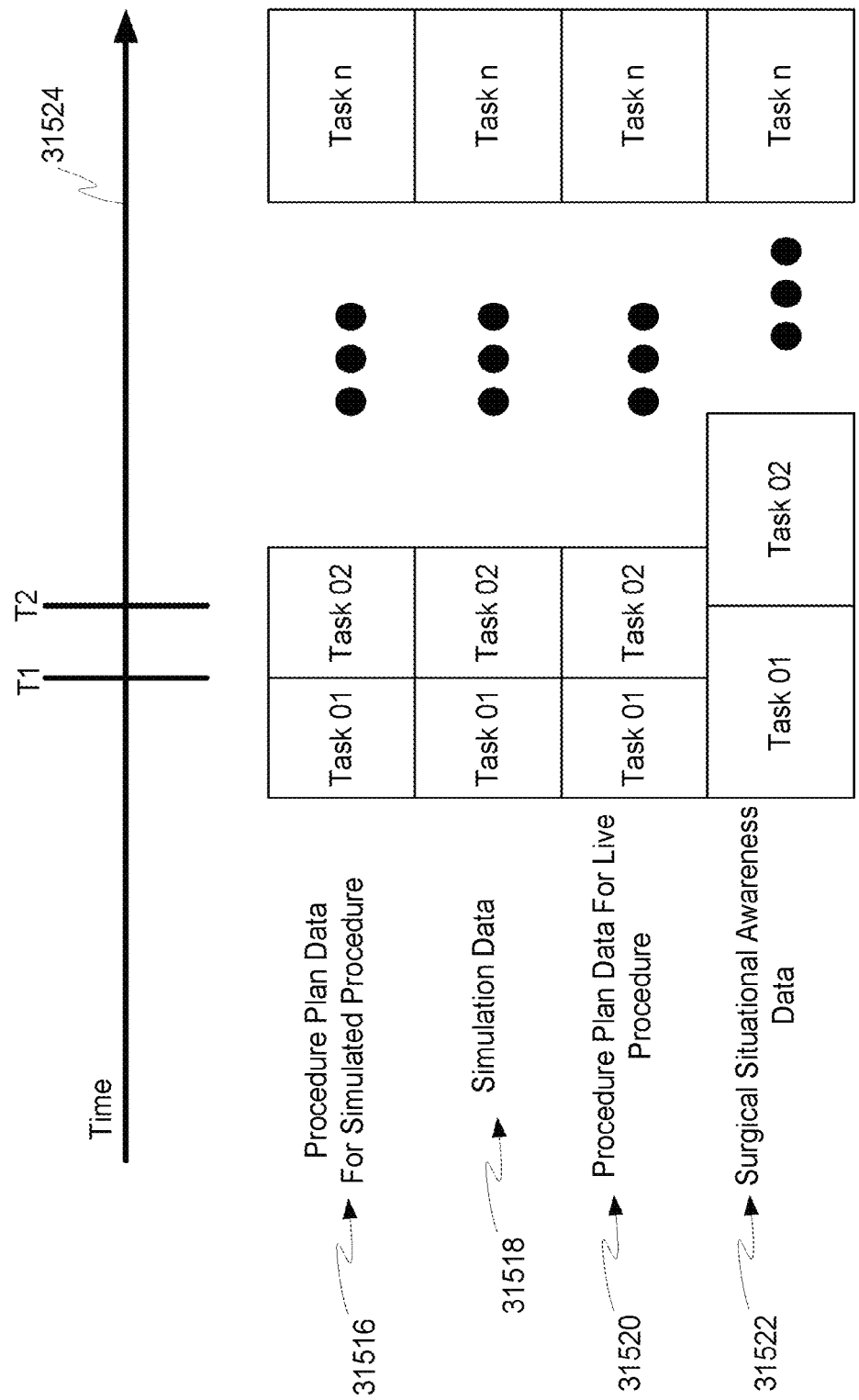
FIG. 19 illustrates time-based surgical and simulation data.

FIG. 19 illustrates time-based surgical and simulation data. Here, example procedure plan data for the simulated procedure 31516, example procedure data associated with the actual simulation as executed 31518, example procedure plan data for the live surgical procedure 31520, and example situational awareness data from the live surgical procedure 31522 are illustrated as a series of tasks with reference to a timeline 31524. The datasets 31516, 31518, 31520, 31522 may be similarly structured. For example, the datasets 31516, 31518, 31520, 31522 may be structured according to a common and/or compatible data structure, such as the example data structure disclosed herein with reference to FIG. 11A.

The simulated procedure plan 31516 planned for task 1 to end and for task 2 to begin at time T1. Similarly, when the simulated procedure was executed as a simulation, for example before the actual live procedure, the simulated task 1 ended and simulated task 2 began at time T1, as recorded by the simulation data 31518. In this example, the procedure plan data 31520 for the live procedure indicated that the task 1 was planned to end and task 2 was planned to begin at time T1. However, during the live surgical procedure, as indicated by the surgical situational awareness data 31522, task 1 ended and task 2 began at time T2, which is different and/or after time T1.

Here, with a time-based reference, a surgeon retrieving a copy of the simulated procedure for viewing and/or interacting during the live procedure would face mismatched timing. Such a surgeon may sync the playback of the simulation to the live procedure by a jog operation forward and/or backward to find the appropriate time T1 in the simulation that matched the corresponding task in the live surgery at time T2.

Figure 20:
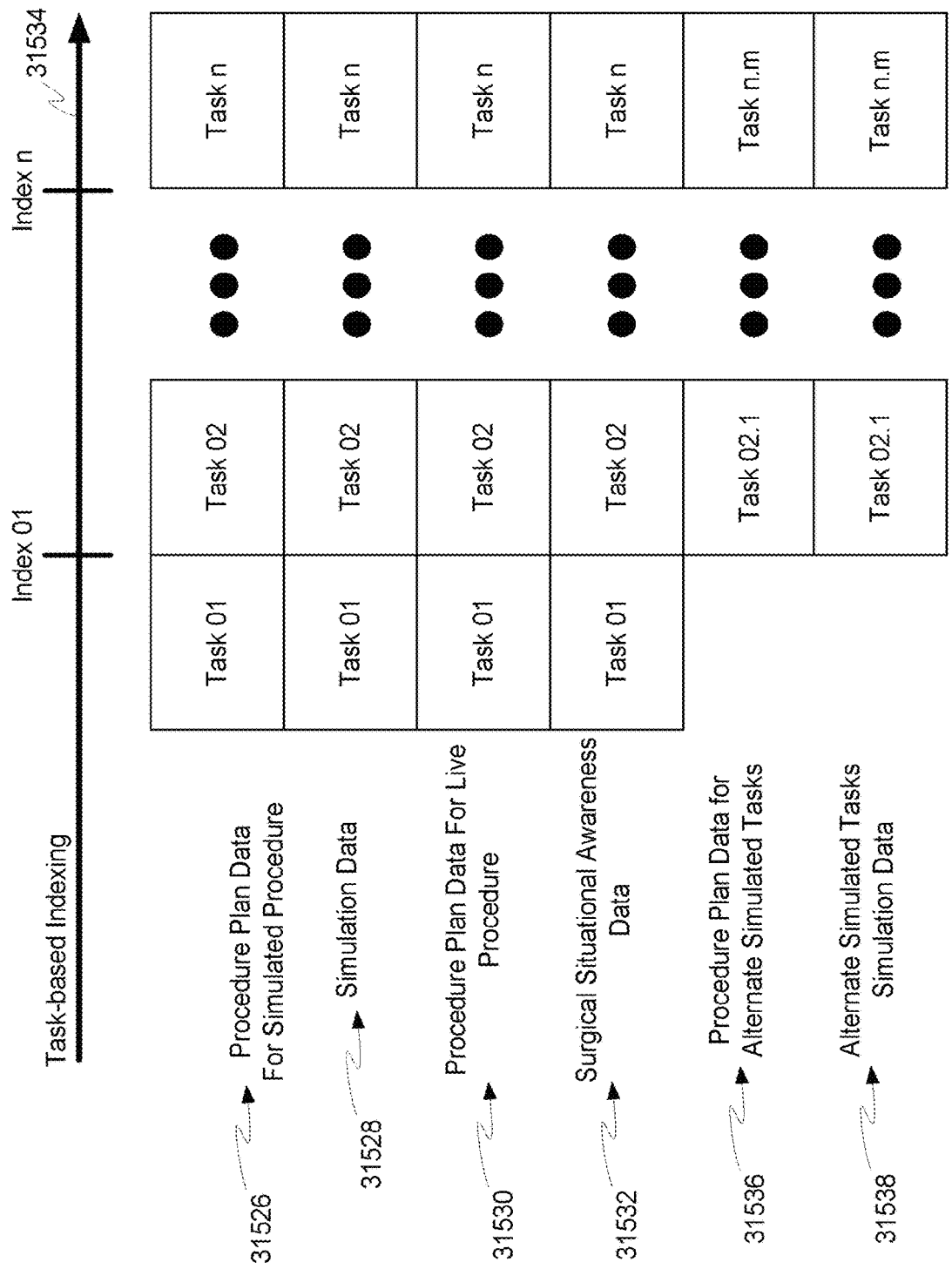
FIG. 20 illustrates a task-based indexing of the time-based surgical and simulation data.

FIG. 20 illustrates a task-based indexing of the time-based surgical and simulation data. Here, example procedure plan data for the simulated procedure 31526, example procedure data associated with the actual simulation as executed 31528, example procedure plan data for the live surgical procedure 31530, and example situational awareness data from the live surgical procedure 31532 are illustrated as a series of tasks with reference to a task-based index 31534. The datasets 31526, 31528, 31530, 31532 may be similarly structured. For example, the datasets 31526, 31528, 31530, 31532 may be structured according to a common and/or compatible data structure, such as the example data structure disclosed herein with reference to FIG. 11A. For example, the datasets 31526, 31528, 31530, 31532 may be structured with a task identifier field that provides unique identifier for individual tasks. For example, datasets 31526, 31528, 31530, 31532 may be structured with a task type field that is a common key for data elements that contain information about various planned, simulated, or actual instances of the same task.

In the simulated procedure plan 31526, the transition for planned task 1 to end and/or for planned task 2 to begin may be indexed at index 01. Similarly, when the simulated procedure was executed as a simulation, the end of simulated task 1 and/or the start of simulated task 2 may be indexed at index 01 in the simulation data 31528. Likewise, the procedure plan data 31530 for the live procedure indexes the end of task 1 as planned and the start of task 2 as planned with index 01. And during the live surgical procedure, as indicated by the surgical situational awareness data 31532, the end of task 1 and/or the beginning of task 2 may be indexed with index 01.

The indexing may be based on the transition from one task to a subsequent task, for example. The indexing may be based on completion of a task. The indexing may be based on the start of a task. The indexing may be common across different data sets. For example, a task may have common indexing for each corresponding instance of that task in different data sets. The procedure data structure may enable such common indexing. In an example, a transition from a particular task to the subsequent task may be commonly indexed with corresponding instances of the task and subsequent task in other data sets regardless of the time planned and/or actually elapsed associated with the task. Similarly, the transition from a particular simulated task to the subsequent simulated task may be commonly indexed with corresponding instances of the live task and subsequent live task in another data set regardless of the time cycle and/or framerate of the simulated task.

Here, with task-based indexing, a surgeon retrieving a copy of the simulated procedure for viewing and/or interacting during the live procedure may use the common index, index 01 for example, to skip to the appropriate portion of the simulation, such as the portion of the simulation that corresponds to the present point in the live procedure.

In an embodiment, the surgeon may run and/or retrieve one or more alternative simulated tasks. The alternative simulated task may be indicated by corresponding procedure plan data for the alternate simulated task 31536. The alternate simulated task may be indicated by the simulation data of the alternate simulated task 31538. Here, the start of the corresponding alternate task as planned for simulation may be similarly indexed at index 01. The start of the corresponding alternate task as simulated may be similarly indexed at index 01. Such alternatives may be recorded via a common data structure. For example, such alternatives may be accommodated by the data structure disclosed herein with reference to FIG. 11B for example. For example, tasks that may serve as alternatives for one another, such as at branching and/or decision points, may be commonly indexed.

Index information may be stored as part of the disclosed datasets 31526, 31528, 31530, 31532, 31536, 31538, for example. Index information may be stored apart from the disclosed datasets 31526, 31528, 31530, 31532, 31536, 31538, for example. Index information may be stored in a centralized data base, for example. Index information in a centralized database may provide cross referencing to unique task identifiers present in the disclosed data sets 31526, 31528, 31530, 31532, 31536, 31538, for example.

Figure 21:
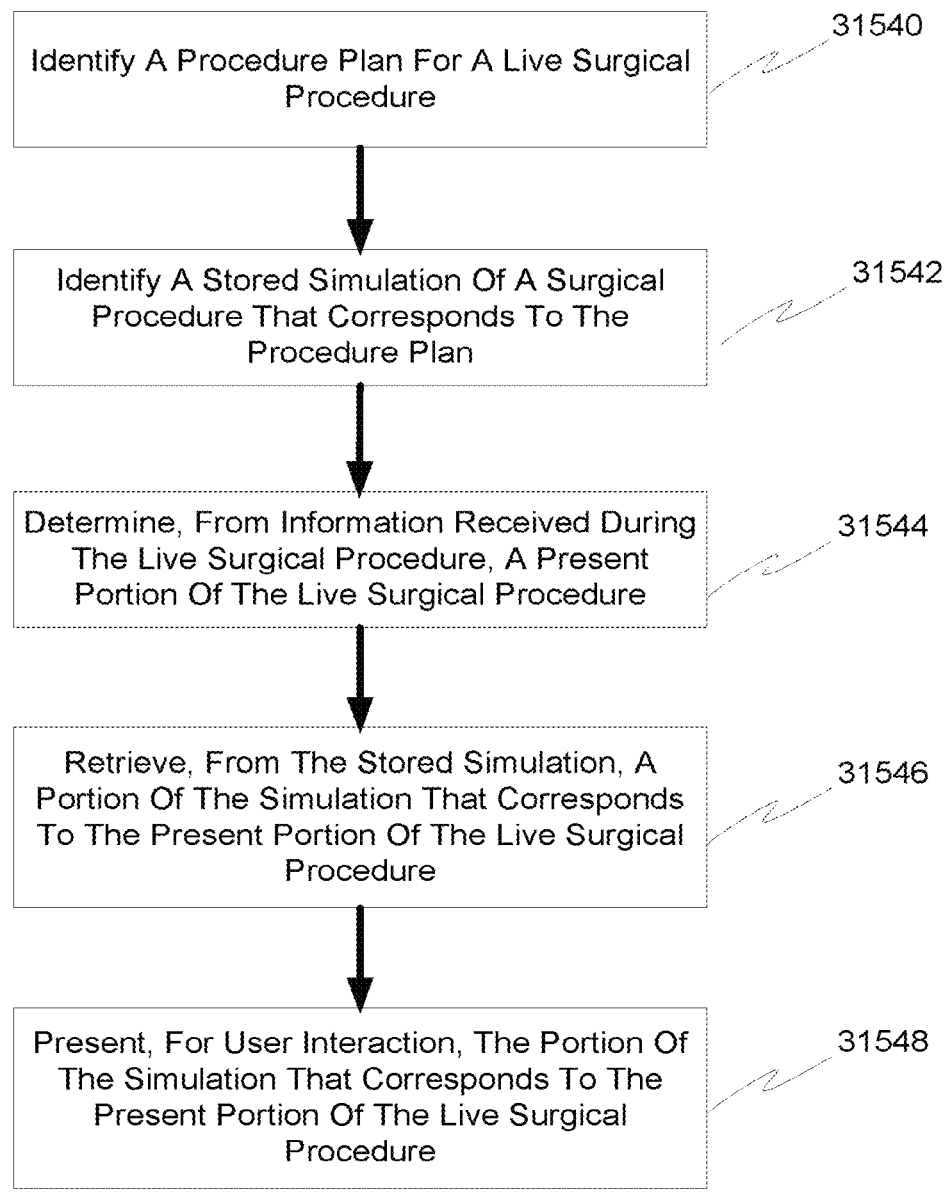
FIG. 21 is a flow diagram of example process for providing simulation support in a live surgical procedure.

FIG. 21 is a flow diagram of example process for providing simulation support in a live surgical procedure. At 31540, a procedure plan for a live surgical procedure may be identified. For example, the procedure plan for the live surgical procedure may be identified, created, copied, modified, or the like, such as part of a pre-surgical planning process. Such a procedure plan for the live surgical procedure may be used by a surgical data system in managing and/or supporting the live surgical procedure. For example, such a procedure plan may be used by the surgical data system to support situational awareness functionality.

At 35142, a stored simulation may be identified. The stored simulation may be a simulation of a surgical procedure that corresponds to the procedure plan identified at 31540, for example. The stored simulation may be a simulation of a surgical plan that corresponds to the procedure plan by having common tasks, for example. The stored simulation may be a simulation of a surgical plan that corresponds to the procedure plan by having setup, such as patient anatomy, for example. The stored simulation may be a simulation of a surgical plan that corresponds to the procedure plan by having tasks that may serve as alternatives to the tasks set forth in the procedure plan, for example.

In an example, the procedure plan may include a set of tasks. The stored simulation may include information indicative of simulated activity. The information of simulated activity may be indexed according to the set of tasks in the procedure plan.

At 31544, a present portion of the live surgical procedure may be determined. For example, the present portion of the live surgical procedure may be determined from information received during the live surgical procedure. For example, the present portion of the live surgical procedure may be determined from information received during the live surgical procedure at a surgical data system, such as a surgical hub 106 for example. For example, the present portion of the live surgical procedure may be determined from surgical situational awareness information received during the live surgical procedure. For example, the present portion of the live surgical procedure may be determined from task index information received during the live surgical procedure.

At 31546, a portion of the stored simulation that corresponds to the present portion of the live surgical procedure may be retrieved. For example, the portion of the stored simulation that corresponds to the present portion of the live surgical procedure may be retrieved based on an analysis of the information received during the live surgical procedure, at 31544 for example. For example, the portion of the stored simulation that corresponds to the present portion of the live surgical procedure may be retrieved based on a common index between the portion of the stored simulation and the present portion of the live surgical procedure.

In an example, the present portion of the live surgical procedure may be determined, at 31546, according to a present task (such as by an index of the present task) from the procedure plan identified at 31542. A portion of the store simulation (e.g., a portion of information indicative of simulated activity) may be retrieved based on an index of the present task.

At 31546, the portion of the stored simulation that corresponds to the present portion of the live surgical procedure may be retrieved. For example, the portion of the stored simulation that corresponds to the present portion of the live surgical procedure may be retrieved from the stored simulation. For example, the portion of the stored simulation that corresponds to the present portion of the live surgical procedure may be retrieved from the stored simulation in a simulation device, such as simulation device 31500, for example.

At 31546, the portion of the simulation that corresponds to the present portion of the live surgical procedure may be presented for user interaction. For example, the portion of the simulation that corresponds to the present portion of the live surgical procedure may be presented for user playback. For example, the portion of the simulation that corresponds to the present portion of the live surgical procedure may be presented for a user to perform simulated activities. For example, the portion of the simulation that corresponds to the present portion of the live surgical procedure may be presented for a user to consider alternative surgical tasks.

The portion of the simulation that corresponds to the present portion of the live surgical procedure may be presented for a user interaction by the surgical data system, such as surgical data system 31502, for example. The portion of the simulation that corresponds to the present portion of the live surgical procedure may be presented for a user interaction by the simulation device, such as simulation device 31500, for example. The portion of the simulation that corresponds to the present portion of the live surgical procedure may be presented for a user interaction by the simulation device in cooperation with a surgical data system, such as by simulation device 31500 in cooperation with surgical data system 31502, for example.

For example, control input may be received during the live procedure. The control input may be for the portion of the simulation that corresponds to the present portion of the live surgical procedure. Based on the control input, a live simulation may be executed. The live simulation may be executed during the live procedure. For example, the live simulation may correspond to the portion of the stored simulation that corresponds to the present portion of the live surgical procedure. In an example, such a control may include a modification of the user activity in the stored simulation. For example, the modification of the user activity may include modifying any of selection, instrument configuration, technique selection, application location, or the like. In an example, such a control may include a modification of the simulation settings of the stored simulation. For example, the modification of the settings may include modifying the simulated anatomy.

A visualization of the present portion of the live surgical procedure may be presented. A presentation of the retrieved portion of simulation may be presented. The visualization of the present portion of the live surgical procedure may be presented concurrently with a presentation of the portion of the simulation that corresponds to the present portion of the live surgical procedure. In an example, a user control may include a timeline user control to view the stored simulation at a time other than that which corresponds to the present portion of the live surgical procedure. In an example, a different portion of the stored simulation may be retrieved based on a user's selection of the timeline control.

In an example, a user control may include a task-based index user control to view the stored simulation at a task other than that which corresponds to the present portion of the live surgical procedure. In an example, a different portion of the stored simulation may be retrieved based on a user's selection of the task-based index user control. In an example, a user control may include a procedure plan user control. The user may use the procedure plan user control to view a different portion of stored simulation that corresponds to that selected by the procedure plan user control. For example, a different portion of the stored simulation may be retrieved based on a user's selection of the procedure plan control.

The process flow at 31540-31548 may be performed at any suitable configured processor, such as a processor of the surgical data system 31502, a processor of the simulation device 31500, a processor of the human interface device 31506, and the like.

Simulation support may refer to the use of a surgical simulation during a live surgical procedure so as to provide active guidance to the surgeon during a surgery. For example, simulation support may refer to having a simulation environment that runs simultaneously and continuously with the live surgical procedure. For example, simulation support may refer to a simulation which is not actively being run simultaneously with the live surgical procedure, but one which can be queried so as to present a portion of a simulation which has been run at least once. Each of these embodiments can be considered to provide support, or guidance, to a surgeon during a live surgical procedure.

User interaction may also refer to user guidance. In other words, the portion of the simulation may be presented or displayed to the surgeon for the purposes of guiding the surgery. It may be understood that a live surgical procedure may refer to a surgical procedure that is happening in real-time. In other words, the live surgical procedure can be happening concurrently with the operation of the simulation.

The processor may be configured to determine a portion of the live surgical procedure through information received (e.g. through image processing or through information received from a surgical hub, configured to determine surgical context).

Figure 22:
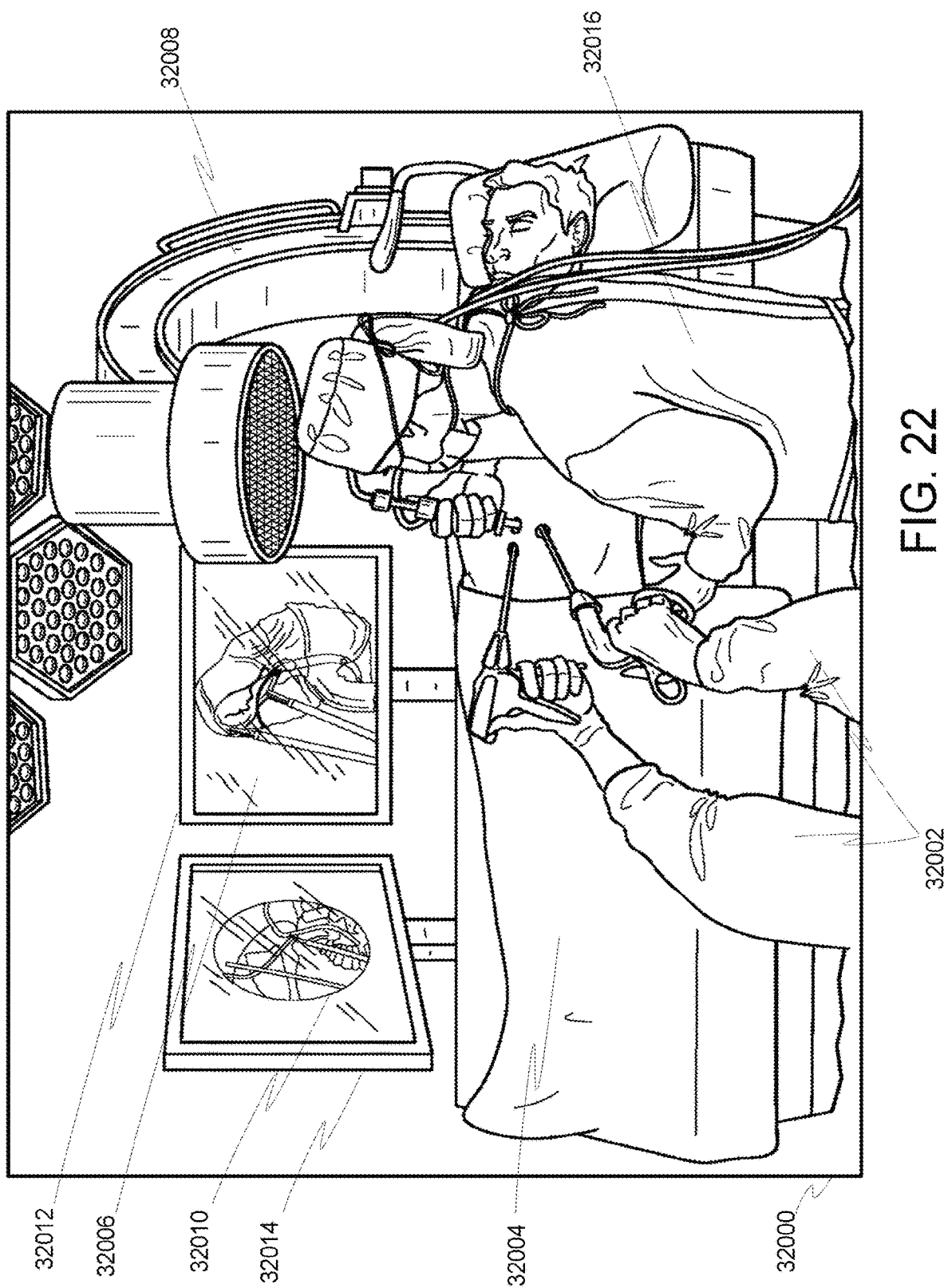
FIG. 22 illustrates an example a virtual reality simulation with supplementary medical imaging.

FIG. 22 illustrates an example a virtual reality simulation with supplementary medical imaging. A virtual reality point-of-view 32000 of a surgical procedure may include one or more simulated elements. For example, the view 32000 may include simulated surgeon arms with instruments 32002, a simulated patient 32002, simulated primary imaging 32006, simulated supplemental imaging equipment 32008, and/or simulated supplemental imaging 32010. View 32000, the simulated primary imaging 32006, and/or the simulated supplemental imaging 32010 may be coordinated such that the view 32000, the simulated primary imaging 32006, and/or the simulated supplemental imaging 32010 reflect different views of a common simulation (e.g., a reflect different views of a common event in the simulated surgical procedure). Such a simulation may enable enhanced training and/or improved patient outcomes by incorporating simulated supplemental imaging 32006 together with simulated primary imaging 32006 within the point-of-view 32000 of the simulation user.

In an example, user interface activities performed by the user may be reflected in corresponding activities performed in the simulation. For example, moving a virtual reality headset may drive changes to the direction of the surgeon's point-of-view 32000 within the simulated environment. Manipulation of virtual reality instruments and/or physical equipment designed to mimic actual instruments may drive corresponding manipulation of the simulated instruments and simulated surgeon arms 32002.

To the extent that a simulated instrument may include primary imaging, such as imaging associated with minimally invasive surgery for example, the simulation may include a display of such primary imaging. The display of primary imaging may be driven by manipulation of the simulated instruments and/or equipment. For example, manipulating a simulated endoscopic surgical stapler in such a virtual reality point-of-view 32000 may drive corresponding simulation of the surgeon's arm 32002 and/or the view of the simulated endoscopic surgical stapler within the simulated primary imaging 32006.

Similarly, the display of supplemental imaging 32010 may be driven by manipulation of the simulated instruments and/or equipment. For example, supplemental imaging may include intra-surgical imaging such as intra-surgical computerized tomography (CT), intra-surgical magnetic resonance imaging (MRI), intra-surgical x-ray, trans-orifice scope, and the like. For example, manipulating a simulated endoscopic surgical stapler in such a virtual reality point-of-view 32000 may drive corresponding simulation of the surgeon's arm 32002 and/or the view of the simulated endoscopic surgical stapler within the simulated supplementary imaging 32006.

In an example, a surgical simulation with fully integrated primary and supplemental imaging may cause both primary imaging 32006 and supplemental imaging 32010 to be driven by manipulation of the simulated instruments and/or equipment. For example, both primary imaging 32006 and supplemental imaging 32010 may be driven within the simulation point-of-view 32000 by user manipulation of the simulated instruments and/or equipment. Also for example, primary imaging 32006, supplemental imaging 32010, and other elements of the simulation point-of-view 32000 may be driven by user manipulation of the simulated instruments and/or equipment.

In an example, the primary imaging 32006 may be registered to appear on a simulated display 32012 within the user's point-of-view 32000. The supplemental imaging 32010 may be registered to appear on a simulated display 32014. The imaging equipment, including their respective displays 32012, 32014 may include simulated equipment user interfaces (not shown). Such interfaces may enable a user to interact with the imaging equipment, and accordingly, may drive corresponding changes to the simulated primary imaging 32006 and/or supplementary imaging 32010

In an example, the simulation may pair one or more types of imaging for cooperative simulation. For example, the simulation may include systems such as multi-spectral light imaging, ultrasound imaging, CT, and/or other pre-operative and/or intra-operative imaging systems. For example, the simulation may include intra-operative multi-spectral light imaging, intra-operative ultrasound, intra-operative CT, intra-operative endoluminal fluoroscopy, intra-operative MRI, and intra-operative x ray, pre-operative ultrasound, pre-operative CT, pre-operative endoluminal fluoroscopy, pre-operative MRI, pre-operative x ray, and the like. The simulation may include multiple operating room displays (e.g., displays 32012, 32014), augmented reality glasses, instrument imaging display, to show coordinated imaging output.

In an embodiment, supplemental imaging 32014 may be put into an idle state. The secondary imaging equipment 32008 may be manipulated in simulation. For example, the user may reposition the equipment in simulation, move the patient relative to the equipment, interact with user controls of the equipment in simulation, adjust its settings, and the like. The simulation may receive such manipulations and drive changes to the supplemental imaging 32014 accordingly.

Similarly, in an embodiment, the simulation may include interaction and/or control of imaging and/or non-imaging equipment inside and/or outside of the simulated sterile field. Such equipment may include elements such as wearable links, uterine manipulators, circular staplers, outside-sterile-field scopes (such as lower gastrointestinal (GI) scopes, bronchial scopes, upper GI scopes, video-assisted thoracoscopic surgery (VATS) scopes), capital equipment for in barrier devices, and the like.

Figure 23:
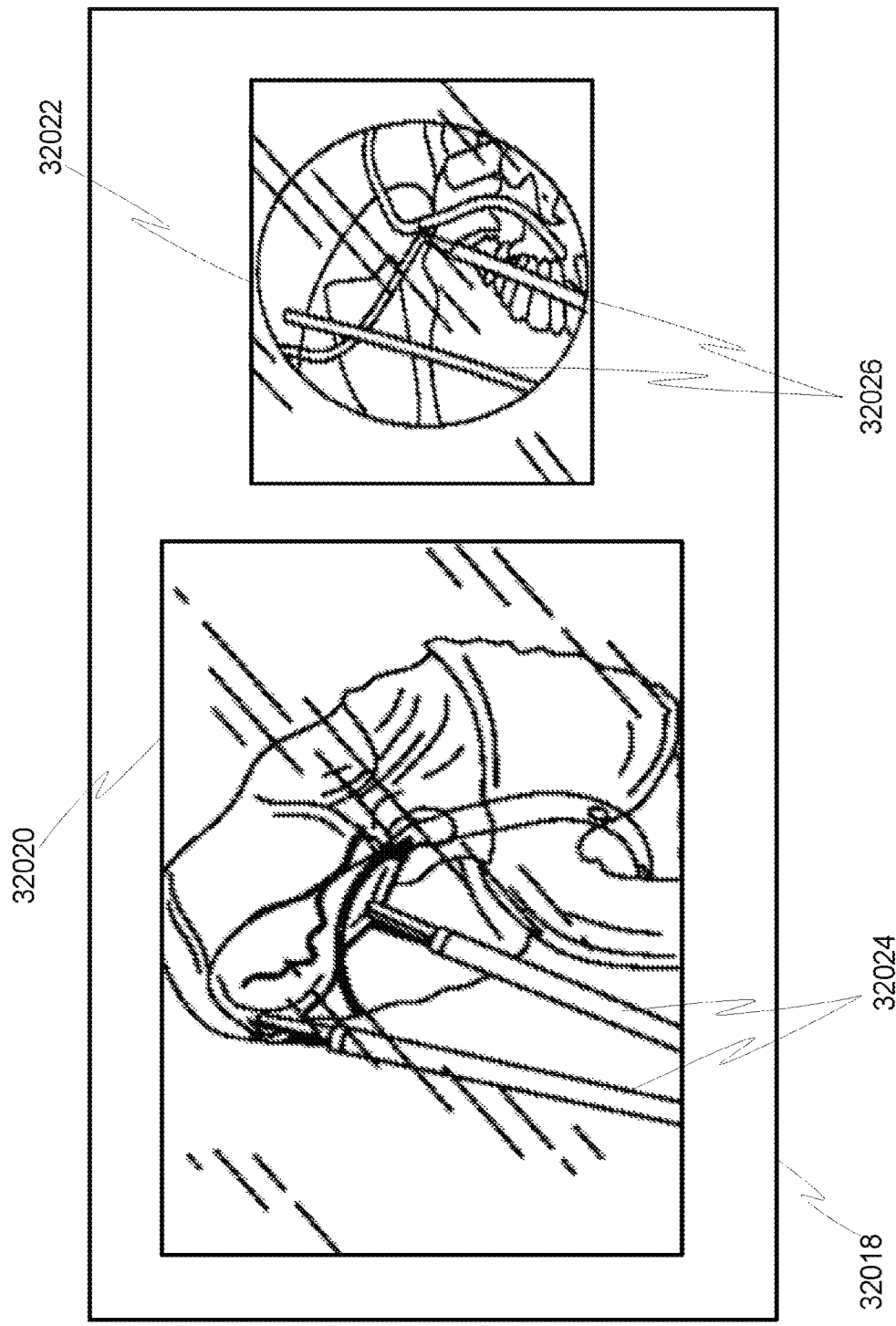
FIG. 23 illustrates an example a scope-view simulation with supplementary medical imaging.

Such equipment may include surgical robotics such as hybrid robotics equipment, flexible robotics equipment, and the like. For example, a simulation may enable multiple windows and/or screens to simulate devices in cooperation (for example as shown in FIG. 23.) For example, a simulation may enable a simulation of a full operating room. When simulating flexible robotic solutions, the simulation may combine activities such that the system provides the user visual information from two separate points of view. In an embodiment, a primary simulation element may provide visual information to an idle flexible robot console for appropriate interaction and/or a secondary element may provide a simulator interface to cooperate with the primary. In an embodiment, such interactions may enable a second simulated assistant. The simulation may enable the surgeon to ask the simulated assistant to control the system. For example, the system may be simulated to have linked control to a primary. For example, the system may be simulated to challenge the surgeon to react to issues that may arise when the assistant has trouble with the surgeon's instructions.

In an embodiment, the primary imaging and/or the supplemental imaging may be projected onto an area of the patient. For example, such projection may be performed within a digital simulated environment. For example, such projection may be performed onto a full-patient-body and/or table-top physical simulator. Such a projection may enable the imaging to be seen on the body and/or surgical site without the overlay on another monitor source. The projection may be made inside and/or outside the sterile field. Such a projection may enable a superimposition of pre-operative and/or intra-operative imaging onto a body using augmented reality (AR) glasses, for example. For example, an AR-based human interface device may enable imaging from multiple sources, identify relevant markers with respect to patient anatomy and instrumentation. An AR-based system may enable projections onto physical models, such as animal training modules, synthetic manual models (e.g., those designed with physical material to simulate dissection, retraction, transection, and the like), synthetic tissue models, vessel models, and the like. Such projection may enhance the training value of such physical models. For example, such models may enable the use of physical instruments on physical media. For example, such modules may enable more realistic and/or actual surgical device activations, such as energy application, stapling etc. For example, such models may enable enhanced training by demonstrating tissue issues, such as excessing tissue tension, incorrect staple cartridge, etc.

In an example, the simulation may enable multi-person interaction. For example, a first healthcare professional may engage in a multi-person simulation with a second healthcare professional. The first healthcare professional may receive a virtual reality view 32000 as shown. The first healthcare professional may also view a simulated representation of the second healthcare professional 32016. When the second healthcare professional 32016 manipulates controls to perform activities within in the simulation, such manipulations may drive changes to the visual representation of the first healthcare professional's virtual reality view 32000, primary imaging 32006, and/or supplemental imaging 32010, for example. Similarly, the second healthcare professional 32016 may also view a simulated representation of the environment, and a corresponding visual representation of the first healthcare professional may be presented in the view of the second healthcare professional 32016. Likewise, manipulation of controls by the first healthcare professional may drive the second healthcare professional's virtual reality view, the second healthcare professional's view of the primary imaging, the second healthcare professional's view of the supplemental imaging, and the like.

Such a multi-person simulation may include one or more additional logic elements to enable multi-person interactions, such as instrument hand-offs, cooperative handling of common tissues, and the like. Such simulations may enable training scenarios and/or objectives relevant to groups, such as communication errors, spatial awareness and conflicts, and the like. Such a simulation may enable a synchronized timing of information display to multiple virtual reality headsets. In an example, simulation performance evaluation may be based on the cooperation of various team combinations. The performance may be correlated with procedure types, equipment sets, specific staff combinations, and the like. A schedule may be determined based on such performance evaluation. For example, a schedule may be determined such that higher performing teams are staffed together.

A simulation system may include one or more tracking devices, such as tracking device 30005 for example. For example, the tracking devices may be part of a sensing system. For example, the simulation device and a surgical data system, such as simulation system 30000 and surgical data system 30008, may include the sensing system devices, processes, functionality, and/or capabilities disclosed in U.S. patent application Ser. No. 17/156,287, filed Jan. 22, 2021, titled METHOD OF ADJUSTING A SURGICAL PARAMETER BASED ON BIOMARKER MEASUREMENTS, which is hereby incorporated by reference in its entirety.

The sensing system may include a wearable sensing system (which may include one or more surgeon sensing systems and one or more patient sensing systems) and the environmental sensing system. The one or more sensing systems may measure data relating to various biomarkers. The one or more sensing systems may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers using one of more of the following sensing technologies: photoplethysmography, electrocardiography, electroencephalography, colorimetry, impedimentary, potentiometry, amperometry, etc.

The inclusion of tracking devices may enable enhanced user information for incorporation into simulation operation, training, performance scoring, and the like. For example, tracking device may engage with a simulation device, such as simulation device 3000, to create, track, and/or monitor environmental settings. Such processing may identify optimal settings for specific individual staff members. For example, such processing may identify optimal settings for specific individual staff members to optimize operating time, minimize risk to patient, reduce stress/strain on staff, and the like.

In an example, an operating room may include one or more environmental settings. The one or more environmental settings may be adjustable. Example environmental settings may include lighting color, lighting brightness, lighting diffusion (e.g., direct lighting, indirect lighting, and the like), surgical display location, surgical display contrast, surgical display brightness, surgical display text size, table height, table position, instrument and/or equipment placement, equipment alarms and notification sounds and/or volume, ambient noise, background music presence, music type, music volume level, temperature, humidity, and the like. Such adjustments to the environmental settings may influence the individuals in the operating rooms. For example, behaviors, response timing, communication clarity, stress, strain, and the like may be influenced. For example, adjustments to the environmental settings may be made to minimize distractions and/or annoyances, to reduce mental stress and/or strain, to minimizes eye strain, to reduce extraneous visual stimuli, and the like.

In an example, the simulation device may adjust various simulated and/or real environmental settings during a user's simulation session. The user's simulation performance may be correlated with the environmental settings to determine one or more target settings for the user. The one or more target settings may include settings that are correlated with a target performance in simulation. Such settings may be saved for the individual, communicated to a surgical data system, such as the surgical hub 116. The surgical data system may enable the user's settings to be implemented when the user is performing a live surgery, for example.

FIG. 23 illustrates an example a scope-view simulation with supplementary medical imaging. Here, a simulation view 32018 of a surgical procedure may include one or more simulated visualizations. For example, the simulated visualizations may include simulated primary imaging 32020 and/or simulated supplemental imaging 32022. Each visualization 32020, 32022 may include a corresponding view of a surgical environment. For example, each visualization 32020, 32022 may include a corresponding view the patient anatomy and/or simulated instruments 32024, 32026. For example, a user manipulation of the user interface may drive corresponding manipulation of the simulated instruments 32024 as visualized in the primary imaging 32020 and/or the simulation instruments 32026 in the supplemental imaging 32022. The primary imaging 32020 may include imaging associated with minimally invasive surgery for example. The supplemental imaging 32020 may include intra-surgical imaging such as intra-surgical computerized tomography (CT), intra-surgical magnetic resonance imaging (MRI), intra-surgical x-ray, trans-orifice scope, and the like. The simulated primary imaging 32020, and the simulated supplemental imaging 32022 may be coordinated such that the simulated primary imaging 32020 and the simulated supplemental imaging 32022 reflect different views of a common simulation (e.g., a reflect different views of a common event in the simulated surgical procedure).

Figure 24:
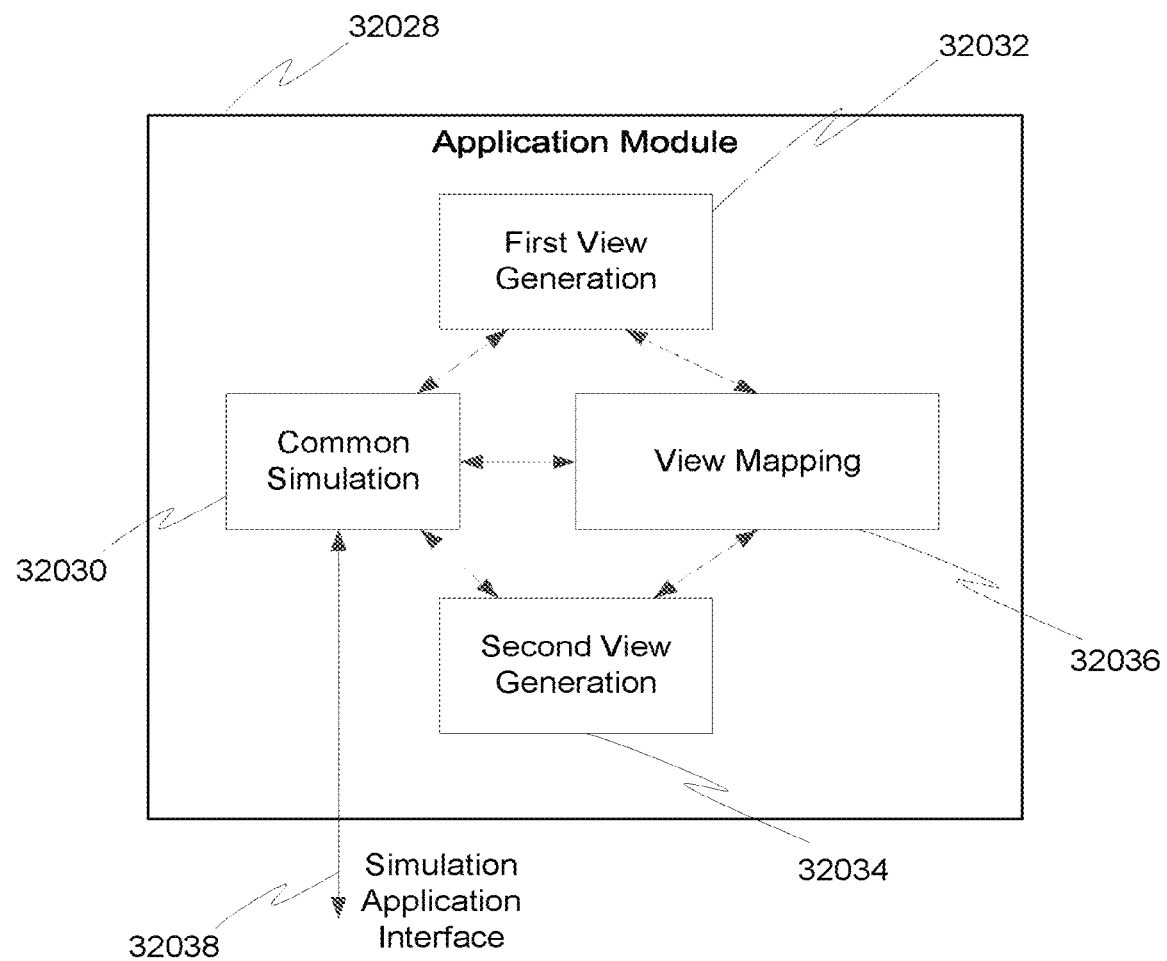
FIG. 24 is a block diagram of an example simulation application module.

FIG. 24 is a block diagram of an example simulation application module 32028. The application module 32028 may be a module of a simulation device, such as the simulation device 30000 disclosed herein. The functionality of the application module 32028 may be provided by a processor, such a processor 30034 disclosed herein.

The application module 32028 may enable a surgical simulation with multiple coordinated views, such as a surgeon point-of-view, primary imaging, supplemental imaging, multi-user point of views, and the like. For example, the application module 32028 may enable multiple coordinated views as shown in view 32000, view 32018, and the like.

The application module 32028 may enable one or more functional elements, such a common simulation element 32030, first view generation element 32032, a second view generation element 32034, and/or a view-mapping element 32026, for example.

The common simulation element 32030 may establish a common primitive-level simulation that may support one or more views. For example, the common simulation element 32030 may engage with the core simulation module 30016 to provide primitive-level simulation, such as environment processing, object processing, physics processing, and/or physiology processing, for example. The common simulation element 32030 may enable primitive-level simulation of an event that may be common for one or more visualizations. For example, the common simulation element 32030 may process one or more simulation objects with regard to environment processing, object processing, physics processing, and/or physiology processing, and the like, such that it may be common element to be visualized by one or more visualizations. In this way, the same simulated anatomy, instruments, and interactions, may be displayed to the user with a visible-light-based visualization and one or more other-than-visible-light-based visualizations, such as MRI, X-ray, CT, and the like.

The first view generation element 32032 may establish a first view associated with the common primitive-level simulation as established by the common simulation element 32030. The first view having first view characteristics, such as a viewpoint location, a viewpoint direction, a viewpoint perspective (e.g., a focal length, zoom, focus, etc.), and/or a viewpoint filter (e.g., color, black/white, visual range, non-visual emulation, such as computerized tomography emulation, a magnetic resonance imaging emulation, an x-ray emulation, and the like). For example, the first view generation element 32032 may engage with the core simulation module 30016 to provide visualization-level simulation, such as object processing, texture processing, 3D graphics pipeline processing, and/or input/output interface processing, for example. For example, the first view generation element 32032 may engage with the core simulation module to provide visualization-level simulation consistent with the first view characteristics.

Similarly, the second view generation element 32034 may establish a second view associated with the common primitive-level simulation as established by the common simulation element 32030. The second view having second view characteristics, such as a viewpoint location, a viewpoint direction, a viewpoint perspective (e.g., a focal length, zoom, focus, etc.), and/or a viewpoint filter (e.g., color, black/white, visual range, non-visual emulation, such as computerized tomography emulation, a magnetic resonance imaging emulation, an x-ray emulation, and the like). For example, the second view generation element 32034 may engage with the core simulation module 30016 to provide visualization-level simulation, such as object processing, texture processing, 3D graphics pipeline processing, and/or input/output interface processing, for example. For example, the second view generation element 32034 may engage with the core simulation module to provide visualization-level simulation consistent with the second view characteristics.

An output of the respective visualization-level simulations associated with the first view generation element 32032 and the second view generation element 32034 may enable a multi-view simulation experience, such as view 32018, for example. For example, the common simulation element 32030 may provide a simulation application interface 32038 for user interaction, including display output, feedback output, control input and the like.

In an example, an output of the respective visualization-level simulations associated with the first view generation element 32032 and the second view generation element 32034 may enable a multi-user simulation experience. For example, the common simulation element 32030 may provide a simulation application interface 32038 for multi-user interaction. The common simulation element 32030 may delineate a first user interaction and the second user interaction, for example. The common simulation element 32030 may associate the first user interaction with the first view generation element 32032. The common simulation element 32030 may associate the second user interaction with the second view generation element 32032.

In an example, an output of the respective visualization-level simulations associated with the first view generation element 32032 and the second view generation element 32034 may enable a multi-view simulation experience, such as view 32000, for example. For example, the simulation may include one or more imaging equipment objects and/or one or more display objects. Each display object may be linked to a corresponding embedded view, supported by a respective view generation element. The view-mapping element may register the visualization-level simulation output from a view generation element of the embedded view to the display object (such as registering the visualization-level simulation output from a view generation element to a surface property of a portion the display object, for example). The view-mapping element may register the view characteristics of the view generation element of the embedded view to an imaging equipment object. Manipulation of the simulated imaging equipment may cause corresponding changes to the view characteristics associated with the view generation element of the embedded view. The results of those changes may be presented as a simulated display on the face of the display object.

To illustrate, a simulated surgical display object may be shaped to represent an operating room flat panel tv display unit. The portion of the display that represents the screen may be designated as a rectangular surface for example. When generating a visual representation of the object, surface properties and textures may be used. The visual processing for this first visualization, for a virtual reality point of view for example, may use a fully-rasterized output of another visualization, the endoscope view of the simulation, and map and/or register that output to the rectangular surface of defined as the screen of the display. The fully-rasterized output would then be subject to the visual processing of the first visualization, including perspective, light and ray tracing, glare, etc. In an example, the fully-rasterized output may be further processed by one or more image filters to provide an image that represents the brightness, contrast, tint, saturation, framerate, and the like of the simulation surgical display.

The application module 32028 may include any number of view generation elements. In an example, an application module 32028 with three view generation elements may enable a main virtual reality point-of-view view, a primary imaging view, and/or a supplemental imaging view, where the virtual reality point-of-view is that of an operating room, where the primary imaging view (e.g., an endoscopic view) is shown on a first simulated display, and the supplemental view is shown on a second simulated display.

Figure 25:
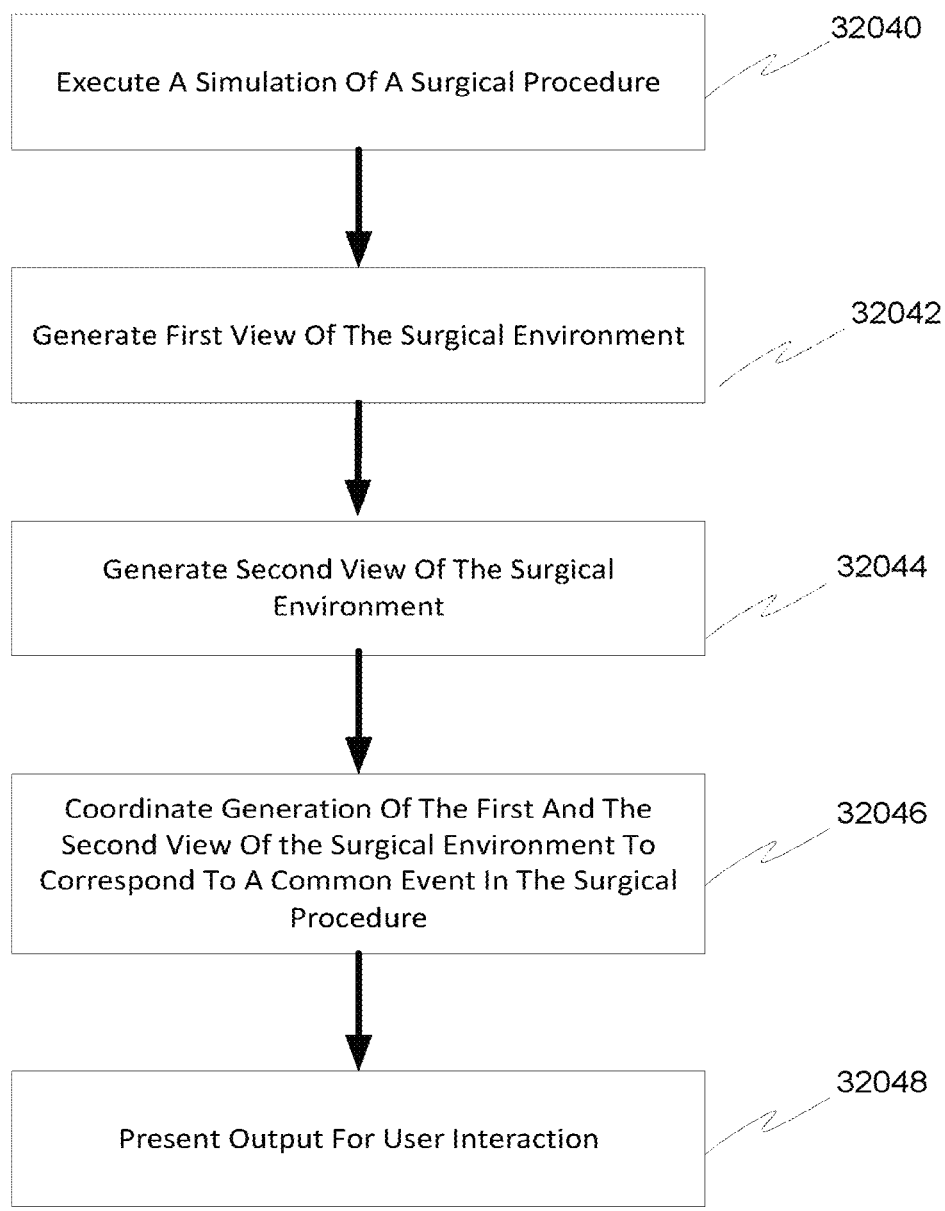
FIG. 25 is a flow chart of an example surgical simulation operation.

FIG. 25 is a flow chart of an example surgical simulation operation. At 32040, a simulation of a surgical procedure may be simulated. For example, the surgical procedure may be simulated in a simulated surgical environment. In an example, live biomarker information associated with the user, may be received. And execution of the simulation may be modified based on the live biomarker information.

At 32042, a first visual representation of a first portion of the simulated surgical environment may be generated. For example, the first visual representation may correspond to a first view within the surgical environment. In an example, the first view may be a point-of-view of a surgeon within the surgical environment. In an example, the first view may be an endoscopic view of the surgical procedure.

At 32044, a second visual representation of a second portion of the simulated surgical environment may be generated. For example, the second visual representation may correspond to a second view within the surgical environment. In an example, the second view may include any of a computerized tomography view, a magnetic resonance imaging view, an x-ray view, or trans-orifice scopic view of the surgical procedure. In an example a third visual representation of a third portion of the simulated surgical environment may be generated.

At 32046, the generation of the first visual representation and the generation of the second visual generation may be coordinated. For example, the generation of the first visual representation and the generation of the second visual generation may be coordinated such that the first visual representation and the second visual representation correspond to a common event in the surgical procedure. For example, the common event may refer to a common time cycle of the simulation. For example, the first visual representation and the second visual representation may be synchronized to correspond to a common event in the surgical procedure. For example, the common event may refer to a common aspect of simulation that is being represented in two separate visual representations. For example, the common event may refer to a common simulation object that undergoes separate visual-based processing and simulation such as a visible-light-based processing, an x-ray-based processing, a CT-based processing, and the like.

In an example, the first view may be a point-of-view of a surgeon within the surgical environment And the second visual representation may be mapped, within the first visual representation for example, to register to a simulated medical equipment display. In an example, the first visual representation and the second visual representation may be synchronized. In an example, the first view may represent a point-of-view of a surgeon within the surgical environment. And the second visual representation may be mapped, within the first visual representation, to register to common anatomy within the simulated surgical environment.

Figure 26:
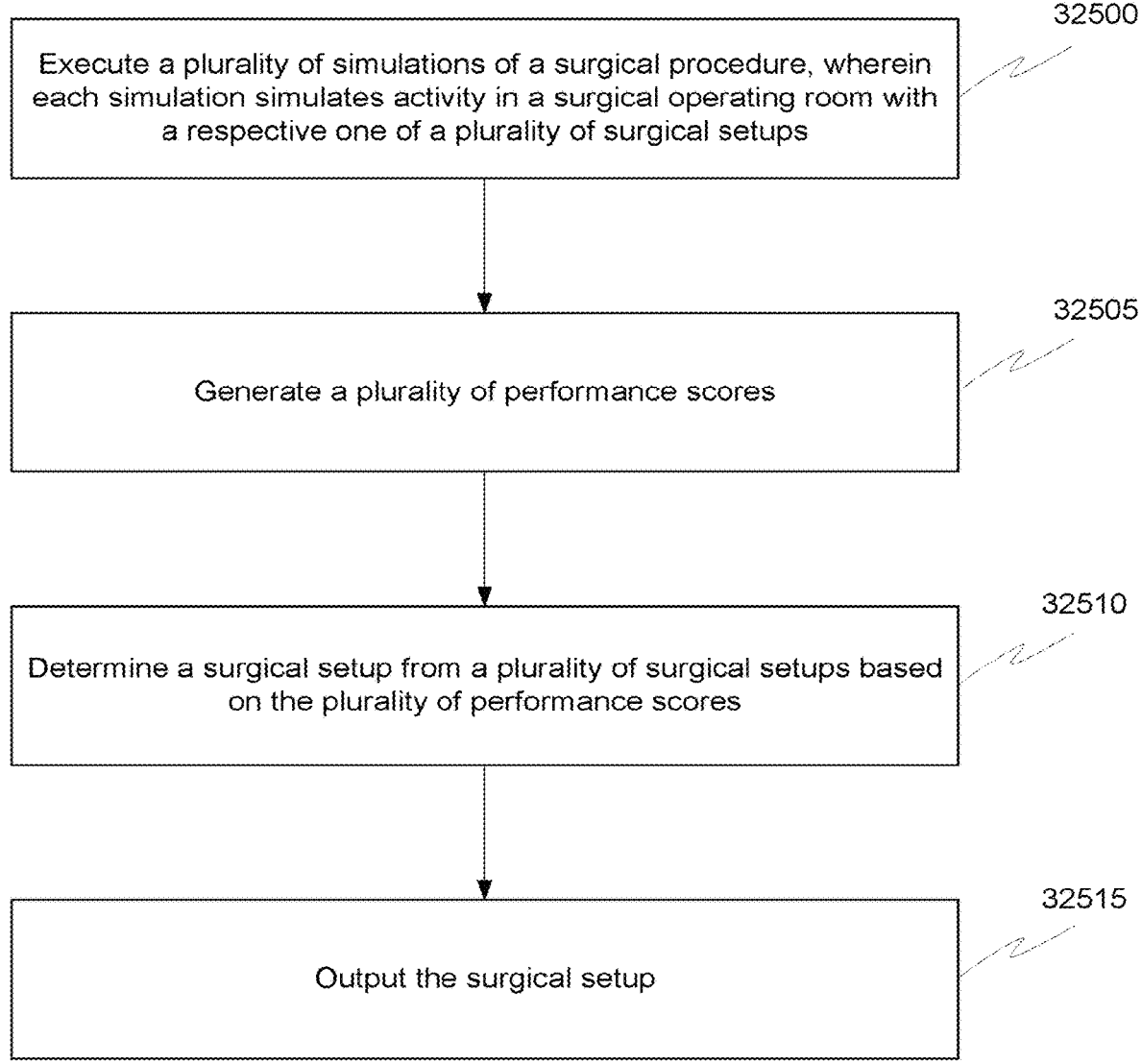
FIG. 26 shows example surgical setup simulations.

At 32048, the first visual representation and the second visual representation may be presented for user interaction. For example, the second visual representation may be presented for user interaction by simulating a traditional user interface for the simulated medical equipment display for the user. For example, the first visual representation and the second visual representation may be presented to any of a virtual reality or augmented reality interface for user interaction. In an example, generation of the first visual representation, generation of the second visual representation, and generation of the third visual representation may be coordinated. And the first visual representation corresponds to a virtual reality point of view within the surgical environment, the second visual representation corresponds to an endoscopic view within the surgical environment, and the third visual representation corresponds to a supplemental imaging view within the surgical environment;

FIG. 26 shows example surgical setup simulations.

At 32500, a plurality of simulations of a surgical procedure may be executed. The surgical procedure may be received from a surgical data system as described with respect to FIG. 7. The surgical procedure may be manually inputted by a user of the simulation. In examples, the surgical procedure may be a colorectal surgery. A plurality of simulations associated with a colorectal surgery may be executed.

Each of the plurality of simulations may simulate activity in a surgical operating room. The activity may be associated with a surgical procedure, for example, a colorectal surgery. The activity may be one or more actions taken by the medical staff, for example, in order to perform the surgical procedure. For example, a colorectal surgery may comprise mobilizing the colon, resecting the colon, and anastomosis. The simulated activity associated with a colorectal surgery may include action(s) taken by the medical staff, for example, in order to perform mobilizing the colon, resecting the colon, and anastomosis.

In an example, the plurality of simulations may use a machine learning framework. For example, the simulations may user the machine learning framework described herein with regard to FIG. 38 for example.

Each of the plurality of simulations may be associated with a respective surgical setup. For example, the simulation may simulate activity in a surgical operating room associated with a respective surgical setup. The surgical setup may comprise a surgical equipment setup and/or a surgical staff setup. In examples, the surgical equipment setup may include one or more surgical equipment involved in performing a surgical procedure. For example, the surgical equipment setup may include a harmonic scalpel, a monopolar or bipolar radiofrequency (RF), a linear stapler, and/or a circular stapler if simulating a colorectal surgery. In examples, the surgical staff setup may include the surgical staff involved in performing a surgical procedure. For example, the surgical staff setup may include a primary surgeon, an assisting surgeon, a nurse, an anesthesiologist, and/or an assistant.

Information related to the surgical setup may be received from a surgical data system as described with respect to FIG. 7. The information may be indicative of the surgical procedure to be performed. The surgical data system may be a surgical hub associated with a medical facility. The surgical data system may store historical surgical setup data associated with real-life surgical procedures performed by the staff of the medical facility. For example, a medical facility may perform X number of colorectal surgeries. The surgical data system associated with the medical facility may store data associated with which medical instruments were used for the respective surgery. The surgical data system associated with the medical facility may store data associated with which medical staff were used for the respective surgery. The simulator may send a request message to the surgical data system requesting the stored data associated with the medical instrument and the stored data associated with the medical staff, for example, if the simulator is simulating a plurality of surgical setups related to a colorectal surgery.

At 32505, a plurality of performance scores may be generated. Each of the plurality of performance scores may correspond to a surgical setup simulated by the simulator. In examples, a surgical setup may comprise a primary surgeon, an assisting surgeon, a nurse, and an assistant. In such a case, a performance score associated with the surgical setup may be generated to be X. In example, a surgical setup may comprise a primary surgeon, an assisting surgeon, and a nurse. In such a case, the performance score associated with the surgical setup may be Y.

Each surgical equipment setup may comprise a number of equipment, respective positions of equipment, and type of equipment. Number of equipment may be the number (e.g., total number) of equipment used during the surgical procedure. In examples, the number of equipment may be the number of unique equipment used during the surgical procedure. Respective positions of equipment may be the location of each equipment with respect to the surgical operating room. Coordinate plane mapping may be used by the simulator to map each equipment location to a coordinate plane system.

Each surgical staff setup may comprise a number of staff, respective positions of staff, and type of staff. Number of staff may be the number (e.g., total number) of staff members involved during the surgical procedure. In examples, the number of staff may be the number of unique staff members involved during the surgical procedure. Respective positions of staff may be the location of each staff member with respect to the surgical operating room. Coordinate plane mapping may be used by the simulator to map each staff member location to a coordinate plane system.

In examples, generating the plurality of surgical setups may comprise receiving a manifest of surgical equipment. Generating the plurality of surgical setups may comprise receiving a manifest of surgical staff. In example, all combinations of surgical setups may be generated using the surgical equipment and/or the surgical staff on the manifest.

Generating the performance scores may be based on surgical costs. The surgical costs may be associated with a surgical duration, a surgical movement, surgical complications, and/or patient outcomes. In examples, the surgical costs may be the duration of the surgical procedure. For example, a performance score of Z may be associated with a surgical procedure that took 90 minutes to complete. In examples, a performance score of T may be associated with a surgical procedure that took 150 minutes to complete. In such a case, the performance score of Z may be associated with a higher value than the performance score of T.

In examples, the surgical costs may include number of collisions. For example, a simulator may simulate performing a surgical task with L number of medical staff members on the left side of the patient and Q number of medical staff members on the right side. The simulator or one application module of the simulator as described with respect to FIG. 7 may count the number of times a medical staff member collided with another medical staff member as the surgical task is simulated. A collision may occur when the coordinate points of a medical staff member match the coordinate points of another medical staff member.

The surgical costs may include the accessibility of each medical staff member to the patient. For example, a simulator may simulate performing a surgical task with 4 medical staff members a S distance from the patient. The simulator may assess how many of the medical staff members are able to access the patient throughout the simulation of the surgical task. The simulator may access to what degree the medical staff member may access the patient.

The surgical costs may include the complication rate associated with the surgical procedure. For example, a performance score of Y may be associated with a surgical procedure with a complication rate of 5%. For example, a performance score of R may be associated with a surgical procedure with a complication rate of 1%. In examples, the performance score of R may be associated with a higher value than the performance score of Y.

Generating the performance scores may be based on a combination of surgical costs. In examples, the surgical costs may be weighted. For example, a surgical cost associated with a greater weight may have more of an impact on generating the performance score when compared to a surgical cost associated with a lesser weight.

At 32510, a first surgical setup may be determined. In examples, the first surgical step may be determined from the plurality of surgical setups based on performance scores associated with each of the plurality of surgical setup. In examples, a first surgical setup associated with a highest value performance score may be determined. For example, each of the plurality of surgical setups may be associated with a complication rate. The surgical setup with the lowest complication rate may be associated with a highest value performance score. In such a case, the surgical setup may be determined.

A scoring function may be received. In examples, the scoring function may be received from the surgical data system as described with respect to FIG. 7. The scoring function may be used to generate the plurality of performance scores. For example, values associated with each surgical setup may be inputted into the scoring function. The scoring function may generate performance score based on the inputted values. The values may be associated with the number of equipment, respective positions of equipment, and type of equipment as described herein. The values may be associated with the number of staff, respective positions of staff, and role of staff as described herein. The values may be associated with the surgical costs as described herein.

At 32515, a first surgical setup may be outputted. In examples, the first surgical setup determined from the plurality of surgical setups as described herein may be outputted. The first surgical setup may be outputted to a display screen accessible by a surgeon. The surgeon may consult the display screen, for example, pre-surgery to determine an optimal surgical setup for the surgery that the surgeon is about to perform. The surgical setup may be sent to a surgical hub associated with a medical facility. In examples, the surgical hub may be a surgical data system as described with respect to FIG. 7.

A procedural plan may be determined based on the outputted surgical setup. The procedural plan may be associated with the surgical procedure. The procedural plan may comprise instructions for a surgeon and/or a medical staff to follow, for example, to prepare for the surgical procedure. The procedural plan may comprise which equipment may be accessible in the surgical OR. The procedural plan may comprise where each equipment may be positioned in the surgical OR. The procedural plan may comprise which surgical staff members may be present in the OR and where each surgical staff member may be located in the surgical OR. The procedural plan may demonstrate the movement of the surgical staff members, for example, as the surgical procedure proceeds. The procedural plan may be sent to a surgical hub, for example, where the procedural plan may be accessed by the surgeon and/or medical staff. The procedural plan may be sent to a computing device accessible by the surgeon and/or medical staff. The procedural plan may be sent to the surgical hub and the computing device simultaneously. The procedural plan may be sent to the surgical hub and/or computing device in real-time.

Figure 27:
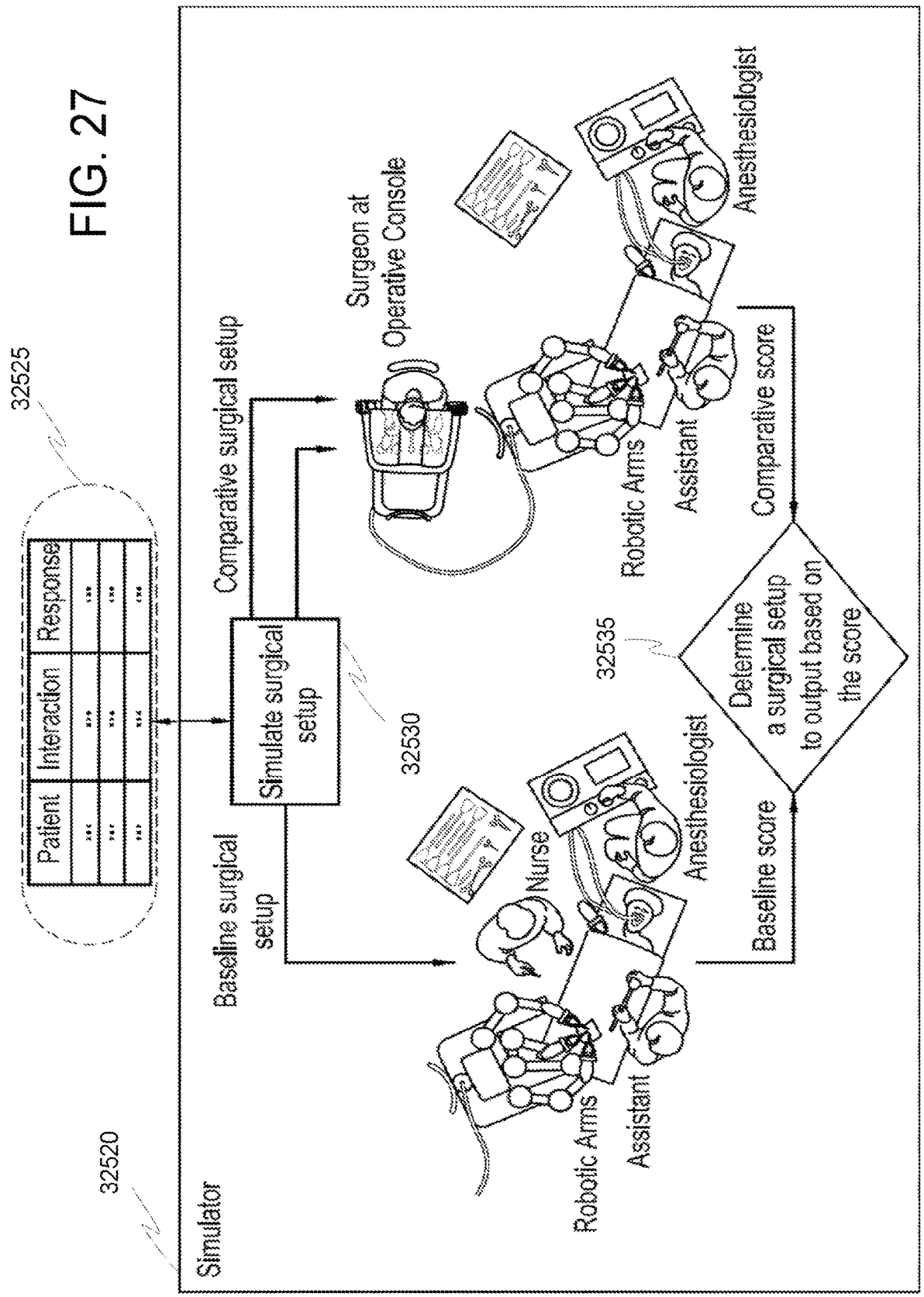
FIG. 27 shows example comparison of simulated surgical setups.

FIG. 27 shows example comparison of simulated surgical setups.

A simulator 32520 may be provided. The simulator 32520 may be the core simulation module as described with respect to FIG. 7.

A surgical setup may be simulated. In examples, simulating the surgical setup may comprise the simulation simulating activity in a surgical operating room associated with the surgical setup as described with respect to FIG. 26. The surgical setup may be simulated via one or more modules. In examples, the modules may include the physics module, physiology module, metrics extraction module, and/or the interface module as described with respect to FIG. 7.

The simulate surgical setup module 32530 may be in communication with a database. The database may record information 32525 related to past surgical procedures. In examples, the database may be included in the surgical data system as described with respect to FIG. 7. The information 32525 may be related to the surgical equipment setup and/or surgical staff setup as described with respect to FIG. 26. For example, the information 32525 may include the surgical setup used during patient X's surgical procedure and the patient's response to the surgical procedure. A response may be a complication that the patient experienced during and/or after the surgical procedure. For example, the database may indicate that for patient X, four surgical staff were involved in the surgical procedure and two harmonic scalpels were used in the surgical procedure. The database may indicate that patient X experienced internal bleeding after the surgical procedure. Information 32525 associated with surgical duration, surgical movement, surgical complications, and/or patient outcomes as described with respect to FIG. 11A may be recorded by the database.

The simulate surgical setup module 32530 may request the information 32530 from the database, for example, if determining parameters for the surgical setup. For example, the parameters may include number of equipment, respective positions of equipment, and type of equipment as described with respect to FIG. 26. For example, the parameters may include number of staff, respective positions of staff, and role of staff as described with respect to FIG. 26.

The simulate surgical setup module 32530 may determine a baseline surgical setup. The baseline surgical setup may be a surgical setup with one or more optimal parameters for a given surgical procedure. The parameters may be optimal for a respective surgical cost. For example, the parameters may be optimal for surgical duration. In such a case, the parameters may be associated with a lowest surgical duration. For example, the parameters may be optimal for surgical complication rate. In such a case, the parameters may be associated with a lowest surgical complication rate.

The baseline surgical setup may be simulated by the simulator 32520 and the simulator 32520 may generate a baseline score. The baseline score may be a performance score as described with respect to FIG. 26. The baseline score may be based on the surgical costs described herein. For example, a surgical duration of X may be associated with a baseline score of 4. For example, a surgical complication rate of Y may be associated with a baseline score of 6.

The simulate surgical setup module 32530 may determine a comparative surgical setup. The comparative surgical setup may include a surgical setup with one or more potential parameters for a given surgical procedure. The potential parameters may be potentially optimal for a respective surgical cost. For example, the parameters may be potentially optimal for surgical duration. For example, the parameters may be potentially optimal for surgical complication rate.

The potential parameters may be different than the optimal parameters in terms of number of equipment, respective positions of equipment, and type of equipment. For example, the potential parameters may include two harmonic scalpels and the optimal parameters may include three harmonic scalpels. The potential parameters may include 30 total equipment. The optimal parameters may include 25 total equipment. In examples, the potential parameters may include a robotic arm located at coordinates x and y. The optimal parameters may include a robotic arm located at r and z.

The comparative surgical setup may be simulated by the simulator 32520 and the simulator 32520 may generate a comparative score. The comparative score may be a performance score as described with respect to FIG. 26. The comparative score may be based on the surgical costs described herein. For example, a surgical duration of L may be associated with a comparative score of 5. For example, a surgical complication rate of Q may be associated with a comparative score of 3.

The simulator 32520 may determine a surgical setup to output 32535 based on the baseline score and the comparative score. In examples, the simulator 32520 may compare the baseline score against the comparative score. In such a case, the simulator 32520 may determine which score is greater and choose the surgical setup associated with the higher score to output 32535. For example, the simulator 32520 may choose the baseline surgical setup to output 32535 if the baseline score is greater than the comparative score. In examples, the simulator 32520 may determine which score is lower and choose the surgical setup associated with the lower score to output 32535. For example, the simulator 32520 may choose the comparative score if the comparative score is lower than the baseline score.

Figure 28:
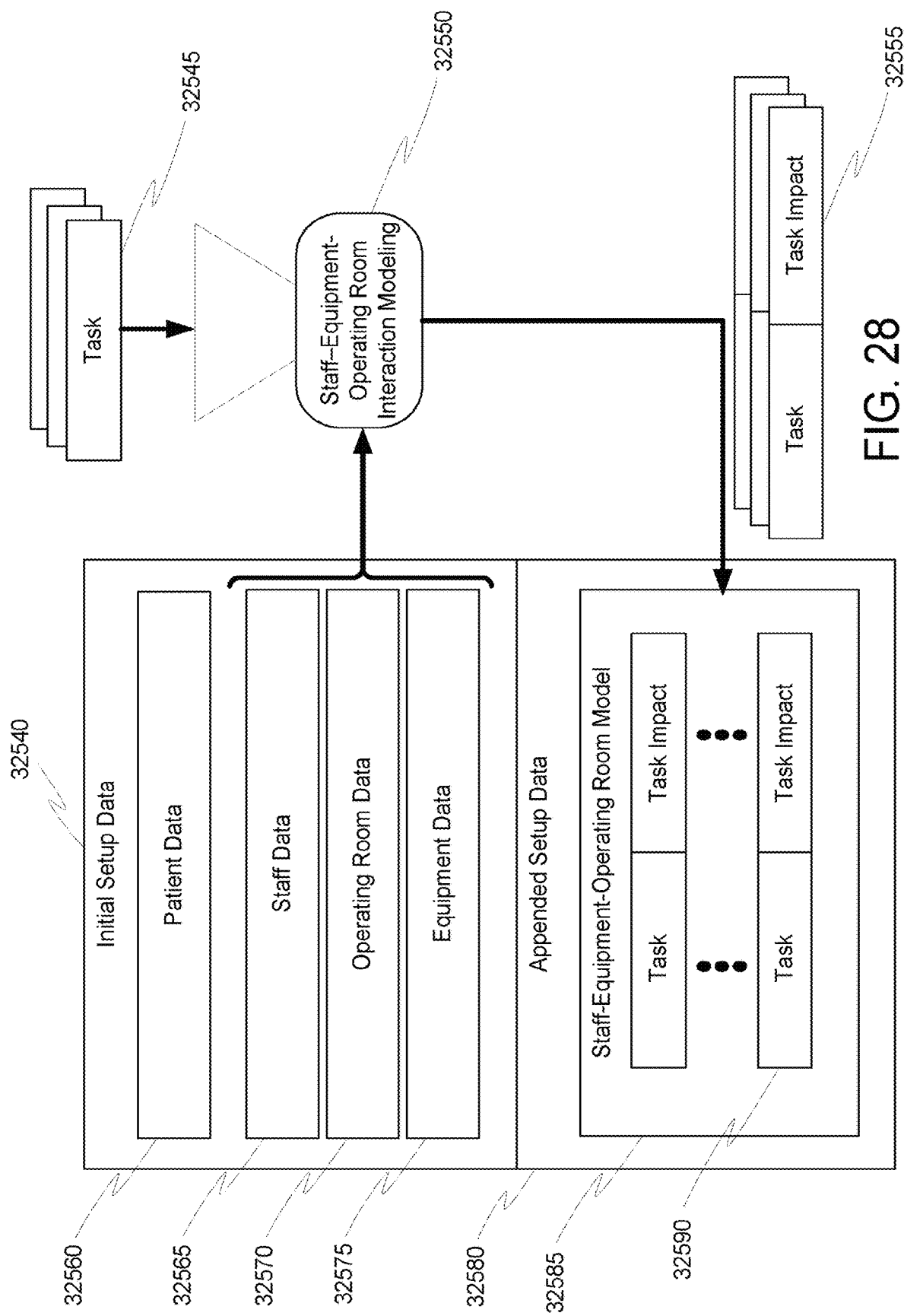
FIG. 28 shows an example surgical setup simulator module.

FIG. 28 shows an example surgical setup simulator module.

One or more tasks 32545 may be associated with a surgical procedure. Each task 32545 may be simulated with a surgical setup, for example, to output a respective task impact 32555. For example, a colorectal surgery may include mobilizing the colon, resecting the colon, and anastomosis tasks. Each of mobilizing the colon, resecting the colon, and anastomosis tasks may be simulated with a surgical setup of two harmonic scalpels and five surgical staff. Task impacts 32555 may be determined for mobilizing the colon, resecting the colon, and anastomosis, respectively.

A staff-equipment operating room interaction modeling 32550 may be used to determine the task impacts 32555. The staff-equipment operating room interaction modeling 32550 may be a module of the simulator. The staff-equipment room operating room interaction modeling may be a module of a remote computer.

The staff-equipment operating room interaction modeling module 32550 may request data from a surgical hub. In examples, the surgical hub may be a surgical data system as described with respect to FIG. 7. The data requested may include staff data 32565, operating room data 32570, and/or equipment data 32575. The staff data 32565 may be data related to the surgical staff setup as described with respect to FIG. 26. The equipment data 32575 may be data related to the surgical equipment data as described with respect to FIG. 26. The operating room data 32570 may be data related to surgical operating room as described with respect to FIG. 26. The operating room data 32570 may include a mapping to a coordinate plane. The mapping may allow the positions of the surgical staff and the surgical equipment to be mapped.

Initial setup data 32540 may be initiated on the simulator. The initial setup data 32540 may include patient data 32560. The initial setup data 32540 may include staff data 32565, operating room data 32570, and/or equipment data 32575 described herein. The staff data 32565, operating room data 32570, and/or equipment data 32575 may be sent to a staff-equipment operating room interaction modeling 32550 as described herein. The patient data 32560 may be received by the simulator. In examples, the patient data 32560 may be sent by the surgical data system with respect to FIG. 7 to the simulator, for example, upon a request message from the simulator for the patient data 32560.

Appended setup data 32580 may be appended in the simulator. An appended setup data module may handle the appended setup data 32580. The appended setup data module may receive the tasks 32545 and task impacts 32555, for example, from the staff-equipment operating room interaction modeling 32550 described herein. The appended setup data module may include a staff-equipment operating room model 32585 that coordinates the tasks 32545 and task impact 32555. In examples, the staff-equipment operating room model 32585 may insert the task 32545 and tasks impacts 32555 in a list. The simulator may be able to assess the task impacts 32555 and determine a first surgical setup, as described with respect to FIG. 26 based on the tasks impacts 32555.

Simulation of patient variables and/or procedures for evaluation of attached equipment behavior may be provided. Automated simulation of patient parameters and/or surgeon tasks and reactions may determine the reaction utilized equipment and devices. Equipment used to perform procedure step may be supplied with a varying adaptive array of patient responses and surgeon interaction to identify and/or monitor the reactions of equipment to the varying condition. Multiple pieces of equipment may be engaged and used to monitor the reactions of a first piece of equipment to the behavior or output from a second piece of equipment. A simulator may be used to assess the different equipment and/or devices used during surgery, for example, for evaluation and/or assessment prior to purchasing.

Utilizing a simulator may be used to evaluate and/or assess equipment and/or devices prior to purchasing, for example, which may give the facility an opportunity to determine the impact the equipment and/or devices may have to the OR environment and/or user interaction. The impact may indicate the benefit and/or value that the equipment and/or devices may add to the facility. Equipment and/or devices may be decided by individuals and/or facility that do not use the equipment. Decisions may be made based on a comparison of cost verses understanding overall impact to the facility. The simulator may be ran utilizing different equipment and/or devices to baseline against the current facilities setup, for example, to understand the overall impact to cost to the facility, e.g., the new equipment may cost less but the new equipment adds time to procedure which may cost more to the facility overall. The simulator may assess and/or compare errors to determine, for example, if the new equipment may cause more errors or downtime due to staff interface than current facilities setup.

Simulation may compare a first set of equipment and a second set of equipment with the same number of support staff to determine the differing combinations of instruments and or equipment that achieve better outcomes, timing, and/or efficiency than the first set of equipment.

In examples, the first set of equipment may be run through the automated simulation resulting in a baseline for behavior. The comparative set may be run through the automated simulation to identify inefficiencies and/or improvements.

The automated simulations may be used to identify the interdependencies of equipment with the need for increased staff to support the equipment. The automated simulations may be used with multiple adaptive runs to determine, for example, if the improved efficiencies of the equipment are durable.

The results of the equipment behavior under these simulated runs may be used to train personnel on what to expect, for example, when using the equipment and to teach the techniques and nuisances of the equipment to new personnel.

Simulation of differing numbers of support staff with a predefined set of equipment to determine the impacts of the equipment on personal needs may be provided. The behavior and required monitoring and/or interaction of the equipment may be simulated to determine the impacts of the new equipment on the support staff within the OR. The simulations may involve delays of the procedure, for example, as HCPs are interacting with the equipment. The simulations may result in lower staff needed to run all of the interrelated equipment.

Figure 29:
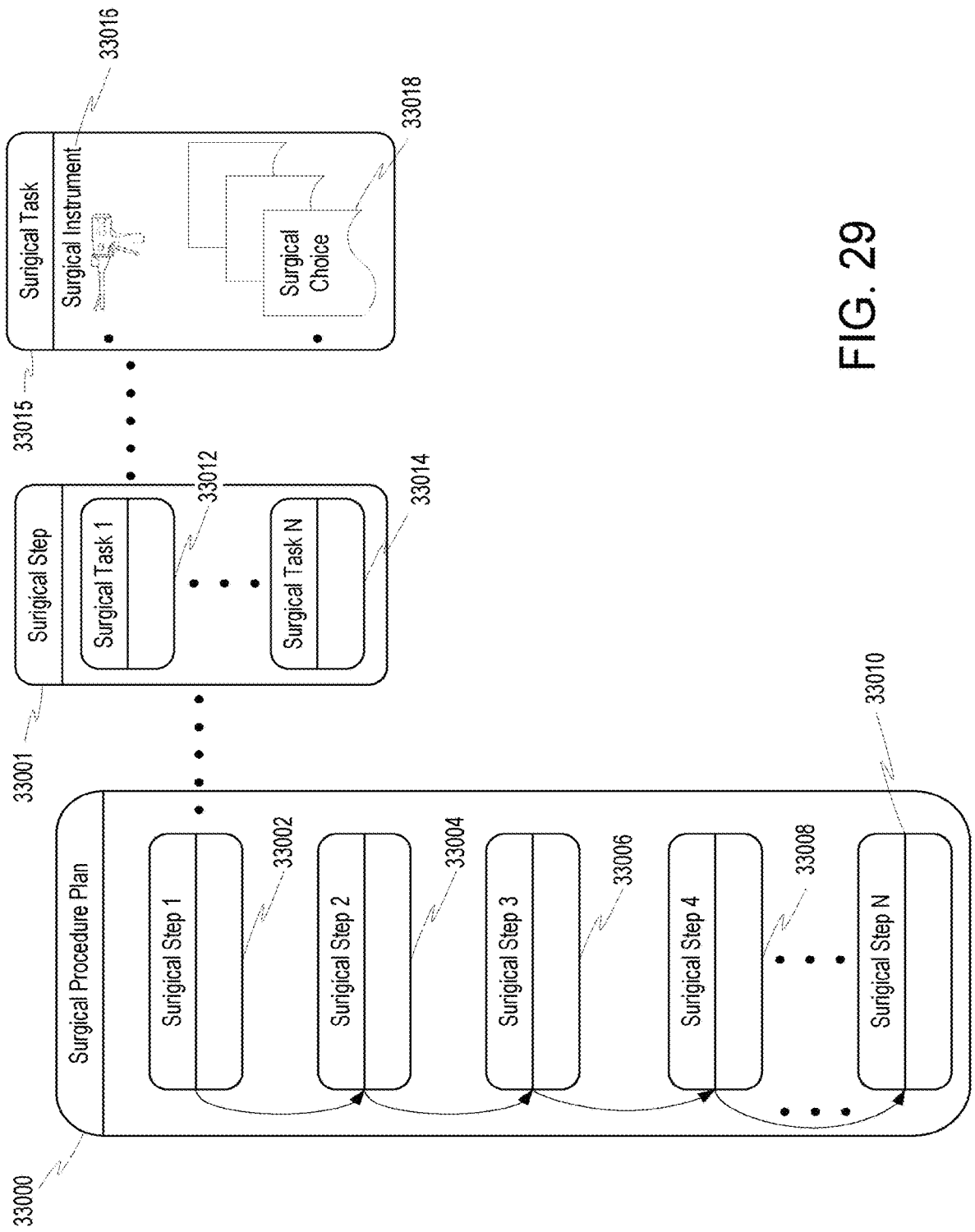
FIG. 29 illustrates an example surgical procedural plan data structures for use with a computer-implemented interactive surgical system and/or a surgical simulator.

FIG. 29 illustrates an example surgical procedural plan 33000 data structures for use with a computer-implemented interactive surgical system and/or a surgical simulator. The computer-implemented interactive surgical system and/or a surgical simulator may be the simulation device 30000 (e.g., described in FIGS. 7 and 8). The surgical procedure plan 33000 may be implemented by the simulation device 30000. The surgical procedure plan 33000 may be implemented by the processor 30034 of the simulation device 30000.

The surgical procedure plan 33000 may include a plurality of surgical steps, such as surgical step 1 (33002), surgical step 2 (33004), surgical step 3 (33006), surgical step 4 (33008), through surgical step N (33010). For example, the surgical procedure plan 33000 may be a surgical procedure plan for a laparoscopic sigmoid colectomy procedure. In such case, the surgical procedure plan 33000 may include the following surgical steps: initiate, access, mobilize colon, resect sigmoid, perform anastomosis, and conclude.

A surgical step may include a plurality of surgical tasks. For example, the surgical step (33001) may include surgical task 1 (33012) through surgical task N (33014). In an example, the surgical step 33001 may be a surgical step "initiate" of the surgical procedure plan 3300 for a laparoscopic sigmoid colectomy procedure. In such case, the surgical step 33001 (33002) may include the following surgical tasks: make incisions, place trocars, and assess adhesions. In an example, the surgical step 33001 may be a surgical step "access" of the surgical procedure plan 3300 for a laparoscopic sigmoid colectomy procedure. In such case, the surgical step 33001 may include the following surgical tasks: dissect adhesions, dissect mesentery, and identify ureter.

A surgical task may include a surgical instrument selection and a plurality of surgical choices. For example, a surgical task 33015 may include a surgical instrument selection 33016 and surgical choices 33018. In an example, surgical task 33015 may be a surgical task of the surgical step "initiate" of the laparoscopic sigmoid colectomy procedure. In such case, the surgical task 33015 may be to make incisions (e.g., for trocar placement). The surgical task 33015 may include a surgical instrument selection 33016 of scalpel. The surgical task 33015 may include a surgical choice 33018 of incision length of 10 mm for a laparoscope port. The surgical task 33015 may include a surgical choice 33018 of incision location of umbilicus for a laparoscope port. The surgical task 33015 may include a surgical choice 33018 of incision length of 5 mm for a grasper port. The surgical task 33015 may include a surgical choice 33018 of incision location of upper right quadrant of abdomen for a grasper port. The surgical task 33015 may include a surgical choice 33018 of incision length of 5 mm for a harmonic energy device port. The surgical task 33015 may include a surgical choice 33018 of incision location of lower right quadrant of abdomen for a harmonic energy device port.

In an example, surgical task 33015 may be a surgical task of the surgical step "access" of the laparoscopic sigmoid colectomy procedure. In such case, the surgical task 33015 may be to dissect mesentery. The surgical task 33015 may include a surgical instrument selection 33016 of grasper. The surgical task 33015 may include a surgical instrument selection 33016 of a harmonic energy device. The surgical task 33015 may include a surgical choice 33018 of performing dissection in the direction of medial-to-lateral. The surgical task 33015 may include a surgical choice 33018 of performing dissection in the direction of lateral-to-medial.

FIG. 30 illustrates an example data flow 33050 of simulation-assisted surgical procedure planning. The data flow 33050 may be performed by the simulation device 30000 (e.g., described in FIGS. 7 and 8). The data flow 33050 may be performed by the processor 30034 of the simulation device 30000.

A surgeon 33060 may use a surgical procedure planning user interface 33052 to create a surgical procedure plan. For example, the surgeon 33060 may create a surgical procedure plan (e.g., surgical procedure plan 33000 as described in FIG. 29) for a laparoscopic sigmoid colectomy procedure.

The surgical procedure planning user interface 33052 may retrieve a surgical procedure plan template and present the surgical procedure plan template to the surgeon 33060. The surgical procedure plan template may include a plurality of pre-defined surgical steps and each surgical step may include a plurality of pre-defined surgical tasks. For example, the surgical procedure plan template may be a template for a laparoscopic sigmoid colectomy procedure. The plurality of pre-defined surgical steps in the template may be the following surgical steps as described in the surgical procedure plan 33000: initiate, access, mobilize colon, resect sigmoid, perform anastomosis, and conclude.

The surgeon 33060 may select a surgical task within a surgical step for which to simulate surgical choices. For example, the surgeon 33060 may select surgical task "make incisions". In response to the selection, the surgical procedure planning user interface 33052 may send the surgical task selection 33062 of "make incisions" to a simulation engine 33056.

In response to the surgical task selection 33062 of "make incisions", the simulation engine 33056 may send the selection 33062 to a surgical choice generator module 33054 for generation of surgical choices to simulate. In response to the selection 33062, the surgical choice generator module 33054 may generate one or more surgical choices for making incisions for trocar placement (e.g., as further described in FIGS. 31A-B and FIGS. 32A-B) and corresponding surgical outcomes.

Figures 31A, 31B:
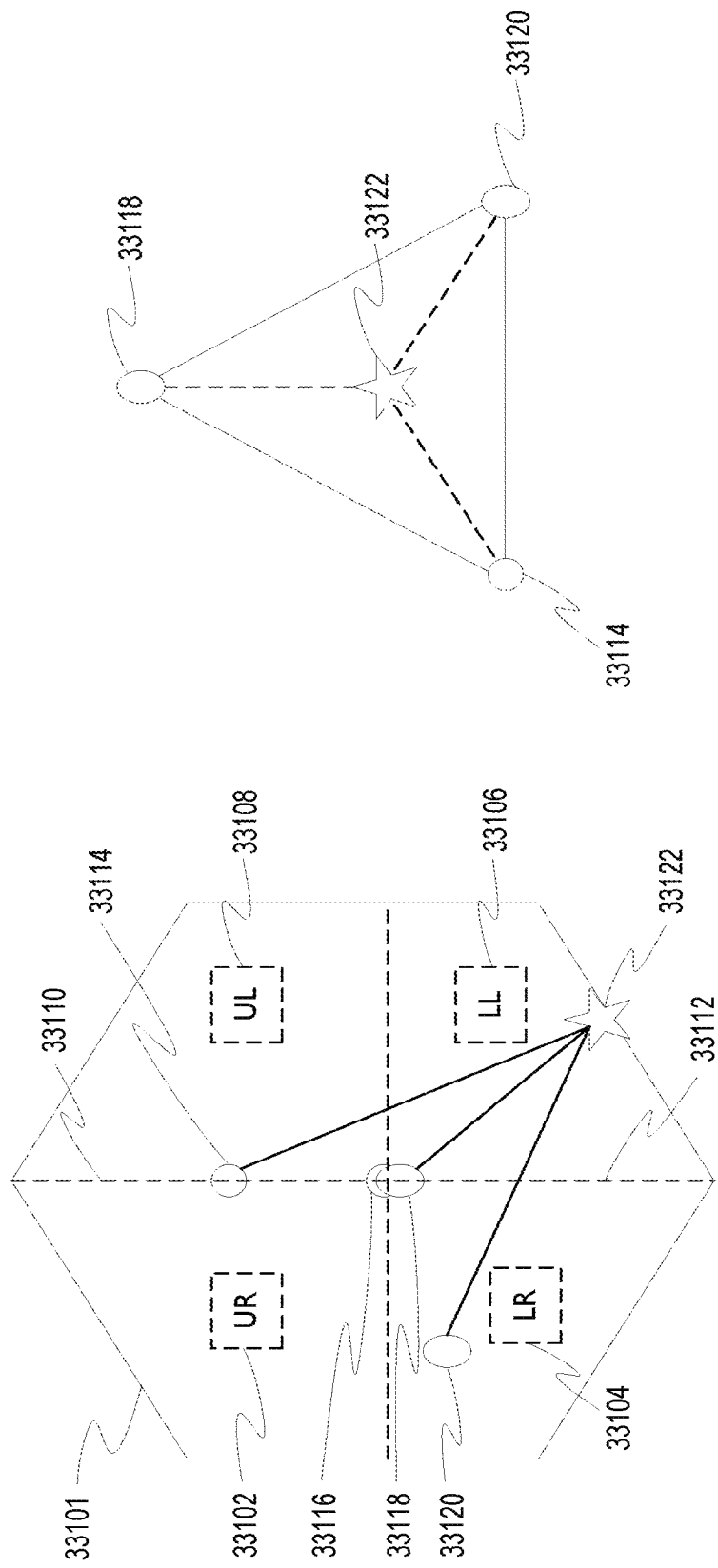
FIGS. 31A and 31B illustrate an example set of surgical choices for a surgical task for use with a computer-implemented interactive surgical system and/or a surgical simulator.

FIG. 31A and FIG. 31B illustrate an example set of surgical choices for a surgical task for use with a computer-implemented interactive surgical system and/or a surgical simulator. The computer-implemented interactive surgical system and/or a surgical simulator may be the simulation device 30000 (e.g., described in FIGS. 7 and 8). The example set of surgical choices may be implemented by the simulation device 30000. The example set of surgical choices may be implemented by the processor 30034 of the simulation device 30000.

As shown in FIG. 31A, a shape 33101 represents the abdomen of a patient's front. The shape 33101 is divided into upper right quadrant (UR) 33102, upper left quadrant (UL) 33108, lower right quadrant (LR) 33104, and lower left quadrant (LL) 33106, with umbilicus 33116 in the center. A midline consisting of an upper midline 33110 and a lower midline 33112 divides the shape 33101 into equal left and right halves. An oval shape 33118 overlapping with umbilicus 33116 represents a location of an 12 mm incision for a laparoscope's trocar port. An oval shape 33120 in the LR area represents a location of a 12 mm incision for a harmonic energy device's trocar port. A circle shape 33114 on the upper midline 33110 represents a location of a 5 mm incision for a grasper's trocar port. A star shape 33122 represents a location of a target anatomy (e.g., sigmoid colon in a laparoscopic sigmoid colectomy). 33118, 33120, 33112 represent surgical choices of incision location for an incision for a trocar port. Solid lines between 33120 and 33122, between 33118 and 33122, between 33114 and 33122 represent the spatially relationships among the laparoscope, the harmonic device, the grasper when the three of them are all pointed at the target anatomy 33122 during a surgical procedure. Such spatial relationships represent a spatial arrangement of laparoscope and two surgical instruments that provide sufficient visibility of the surgical instruments as the three of them are working on the target anatomy. Such arrangement may be referred to as "triangulation" by a person skilled in the art.

FIG. 31B shows a field-of-view perspective of the spatial relationships among the laparoscope, the harmonic device, and the grasper when the three of them are all pointed at the target anatomy 33122 during a surgical procedure. As such, the sight of the harmonic device and the sight of the grasper are maximized when the three of them are both pointed at and working on the target anatomy 33122 during a surgical procedure.

FIG. 32A and FIG. 32B illustrate an example set of surgical choices for a surgical task for use with a computer-implemented interactive surgical system and/or a surgical simulator. The computer-implemented interactive surgical system and/or a surgical simulator may be the simulation device 30000 (e.g., described in FIGS. 7 and 8). The example set of surgical choices may be implemented by the simulation device 30000. The example set of surgical choices may be implemented by the processor 30034 of the simulation device 30000.

FIG. 32A illustrates the same surgical choice of an incision location for a laparoscope's trocar port as illustrated in FIG. 31A, the same surgical choice of an incision location for a harmonic device's trocar port as illustrated in FIG. 31A, and a different surgical choice of an incision location for a grasper 33114' from that is illustrated in FIG. 31A. FIG. 32B shows a field-of-view perspective of the spatial relationships among the laparoscope, the harmonic device, and the grasper when the three of them are all pointed at the target anatomy 33122 during a surgical procedure. As such, the sight of the grasper is significantly limited due to the close proximity of 33114' to 33122 and 33118 spatially.

Referring to FIG. 30, the surgical choices 33064 of incision locations shown in FIGS. 31A-B may be generated by the surgical choice generator module 33054 and sent to the simulation engine 33056. A surgical outcome 33066 corresponding to the surgical choices 33064 may also be sent by the module 33054. In such case, the surgical outcome 33066 may be "no surgical complication". A "no complication" surgical outcome may indicate no surgical complication results from the surgical choices 33064.

The surgical choices 33064 of incision locations shown in FIGS. 32A-B may be generated by the surgical choice generator module 33054 and sent to the simulation engine 33056. A surgical outcome 33066 corresponding to the surgical choices 33064 may also be generated by the module 33054. Such surgical outcome 33066 may be a surgical complication that the incision location 33114' for the grasper port 33114' is aborted and the incision is closed (e.g., due to the limited sight of the grasper).

The simulation engine 33056 may send the surgical choices 33064 of incision locations shown in FIGS. 31A-B and FIGS. 32A-B and the corresponding surgical outcomes 33066 to a simulation visualization module 33058. The simulation visualization module 33058 may be integrated into the surgical procedure planning user interface 33052 or separate from the user interface 33052. In response, the surgical procedure planning user interface 33052 may visualize the simulation of the surgical choices 33064 of incision locations and the corresponding surgical outcomes 33066, e.g., in an automated process. The automated process may visualize the surgical choices 33064 of incision locations shown in FIGS. 31A-B and the corresponding surgical outcome 33066 of "no surgical complication" and continue to visualize the surgical choices 33064 of incision locations shown in FIGS. 32A-B and the corresponding surgical outcome 33066 of the surgical complication described herein.

In response to the visualization of the surgical choices 33064 of incision locations and the corresponding surgical outcomes 33066, the surgeon 33060 may select the surgical choices 33064 of incision locations shown in FIGS. 31A and 31B. In such case, the surgical procedure planning user interface 33052 may store such surgical choices of incision locations under the surgical task of "make incisions" that is a part of the surgical step "initiate" of a surgical procedure plan 33000 for a laparoscopic sigmoid colectomy. The surgeon 33060 may not select the surgical choices 33064 of incision locations shown in FIGS. 32A and 32B (e.g., due to the surgical complications described). In such case, the surgical procedure planning user interface 33052 may discard such surgical choices. In such matter, the remaining surgical steps, surgical tasks, and surgical choices may be generated for the surgical procedure plan 33000 for a laparoscopic sigmoid colectomy.

Referring now to the surgical choice generator module 33054, the module 33054 may generate surgical choices 33064 and corresponding surgical outcomes 33066 based on the given surgical task 33062 using machine learning models.

For example, a generative machine learning model may be trained using past pre-surgical data and/or past surgical procedure data in a remote system (e.g., the cloud 17 as described in FIG. 1 and the remote system 31008 as described in FIG. 15). The generative machine learning model may be any suitable generative model, such as generative adversarial networks (GANs) or a Markov chain-based model.

For example, a machine learning model based on GANs (GANs model) may be trained using past surgical procedure data from laparoscopic sigmoid colectomy procedures. The GANs model may model that data pattern that given a surgical step, a list surgical tasks may be performed. The GANs model may model the probability distribution of the surgical tasks present in the past surgical procedure data. That is, when the GANs model generates a surgical task from the list of possible surgical tasks, the surgical task is generated at a probability according to the probability distribution. In an example, the GANs model may generate a surgical task of making incisions for trocar placement for surgical step "initiate" at a probability of 100% because all laparoscopic sigmoid colectomy procedures start with such surgical task.

Similarly, the GANs model may model the data pattern that given a surgical task, a list of surgical choices may be made. The GANs model may model the probability distribution of the surgical choices present in the past surgical procedure data. That is, when the GANs model generates a surgical choice from the list of possible surgical choices given a surgical task, the surgical choice is generated at a probability according to the probability distribution. In an example, the GANs model may generate a surgical choice, e.g., a surgical choice of a laparoscope's trocar port's incision location at the umbilicus, at a probability of 95% because it may be a standard technique for a laparoscopic sigmoid colectomy procedure and reflected in the past surgical procedure data for laparoscopic sigmoid colectomy procedures.

Similarly, the GANs model may model the data pattern that given a surgical choice, one or more surgical outcomes may follow. The GANs model may model the probability distribution of the surgical outcomes present in the past surgical procedure data. That is, when the GANs model generates a surgical outcome from the list of possible surgical outcomes given a surgical outcome, the surgical outcome is generated at a probability according to the probability distribution. In an example, the GANs model may generate a surgical outcome of "surgical complication", e.g., for a surgical choice of a harmonic device trocar port's incision location being at the lower left quadrant of the abdomen, at a probability of 90%. Such probability of a surgical complication may be due to the significantly limited sight of the harmonic device in laparoscope's view regardless of the incision location for a grasper.

As such, the GANs model may generate a surgical choice or a surgical outcome with an associated probability. For example, when the surgical choice generator module 33054 generates a surgical choice using the GANs model, the module 33054 may generate a surgical choice 33064 and a corresponding surgical outcome 33066 with an associated probability. The simulation engine 33056 may send the surgical choice 33064 and the corresponding surgical outcome 33066 with the associated probability to the simulation visualization module 33058. In response, the surgeon 33060 may view the surgical choice 33064 and the corresponding surgical outcome 33066 in the context of its probability. In an example, a high probability of a negative surgical outcome may dissuade the surgeon 33060 from selecting the associated surgical choice. In an example, a low probability of a negative surgical outcome may not be singly determinative of whether the surgeon 33060 may select the associated surgical choice. For example, the surgeon 33060 may simulate other surgical choices to review if their corresponding surgical outcomes may be negative and if so whether their probabilities are higher or lower before selecting which surgical choice to add to the surgical procedure plan.

Figure 33:
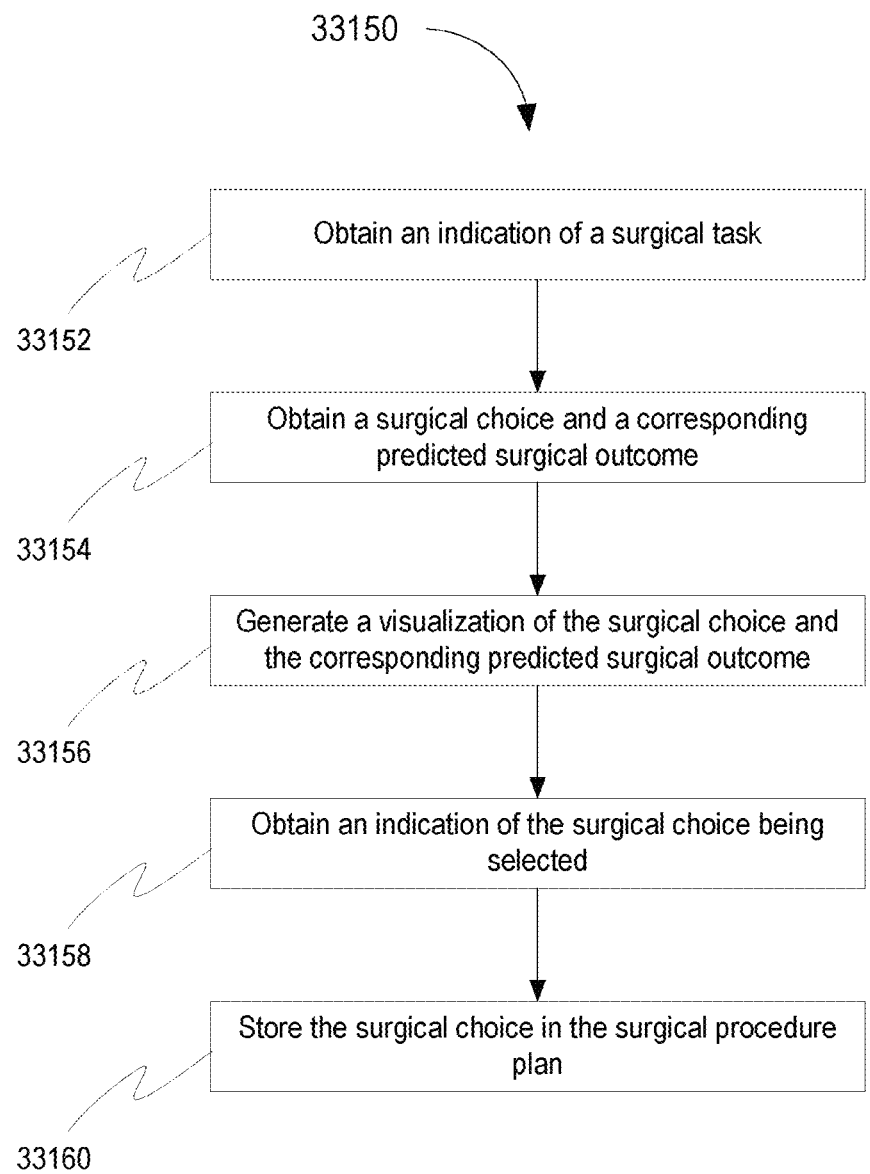
FIG. 33 is a flow chart of an example operation of simulation-assisted surgical procedure planning.

FIG. 33 is a flow chart 31150 of an example operation of simulation-assisted surgical procedure planning. For example, the example operation may include a process to determine a surgical choice and a corresponding surgical outcome to perform a simulated surgical task in a simulated environment. The process may store a selected surgical choice and a selected corresponding surgical outcome in a surgical procedure plan.

At 33152, an indication of a surgical task may be obtained. The surgical task may be associated a surgical step of a surgical procedure plan. For example, the indication of the surgical task may be obtained from a surgical procedure planning user interface. For example, the indication of the surgical task may include identifying information of the surgical procedure plan, identifying information of the surgical task, and/or identifying information of the surgical step.

At 33154, a surgical choice and a corresponding predicted surgical outcome may be obtained. The surgical choice and the corresponding predicted surgical outcome may be associated with the surgical task. For example, a machine learning (ML) model may be trained using data of a plurality of past surgical procedures. The ML model may generate the surgical choice and the corresponding predicated surgical outcome using the ML model. The surgical choice and the corresponding predicted surgical outcome may be obtained from the ML model.

At 31156, a visualization of the surgical choice and the corresponding predicted surgical outcome in a simulated environment may be generated.

At 33158, an indication of the surgical choice being selected may be obtained.

At 33160, the surgical choice in the surgical procedure plan may be stored. For example, the surgical choice may be a first surgical choice and the corresponding predicted surgical outcome may be a first corresponding predicted surgical outcome. A second surgical choice and a second corresponding predicated surgical outcome may be obtained. The second surgical choice and the second corresponding predicted surgical outcome may be associated with the surgical task. A visualization of the second surgical choice and the second corresponding predicted surgical outcome may be generated in the simulated environment. An indication of the second surgical choice being not selected may be obtained. The second surgical choice may be discarded.

Surgical procedure planning (e.g., including tool setup) may be based on simulation (e.g., automated simulation runs).

A surgical procedure planning system may be integrated with an artificial intelligence (AI) driven simulation system to visualize surgical steps and anticipated outcomes for a chosen surgical procedure plan and chosen surgical steps. The surgical procedure planning system may assist a user in assembling a surgical procedure plan and running multiple iterations of simulations to identify aspects of the plan that lead to variable outcomes or complications to show both options and the range of results of the assembled plan. The automated simulation may include probability range results from an aggregated set of procedures and outcomes.

The aggregated set of procedures and outcomes may be resulting from previous local surgeries of the user or the facility. The aggregated set of procedures and outcomes may be a larger set from a remote system or a cloud server which has aggregated regional or would-wide datasets. The surgical procedure planning system may include a digital interface. The digital interface may allow a surgeon to choose and plan surgical steps and step through the possible outcomes, including information of the likelihood of an outcome or result, and why. The results shown may include the steps, reasons, complications, etc. that are the highest probable source of the results. The results may be of the entire plan, a step of the plan or a predefined patient complication to the plan. The digital interface may display mitigation that may be used to minimize or maximize results with differing choices.

Operating room setup simulations may be performed with adaptable variables for instruments, equipment, approach and room aspects.

Equipment needs and instrument needs may be simulated based on a surgical procedure plan (e.g., for a patient) and compared with the surgical procedure plan. Examples of equipment may be C-arm or ultra-sound. The simulation of equipment needs and/or instrument needs and the procedure plan may be compared to determine if all the equipment and/or instruments needed for the procedure are included in the surgical procedure plan. An AI-based simulation may look through all the options of the surgical procedure steps and the associated instruments and tools to determine the equipment and/or instrument needs. The simulation may highlight any issues or other combinations of instruments that may be swapped for the instruments that have been included in the surgical procedure plan.

Robot configuration, setup and steps for hybrid and/or complete robot surgeries may be simulated based on a surgical procedure plan to determine different robot supplementations of a surgeon. Patient positioning on an operating table may be simulated. Operating table configuration may be simulated. Examples of operation table configuration may be tilt, leg board positions or removal, or bed slide to main column for C-arm or O-arm. Bar configuration may be simulated. Examples of bar configuration may be tilt, up or down, or slide. Arm configuration may be simulated. Examples of arm configuration may be stowed or deployed, or arm positions on bar. Arm to cannula configuration may be simulated. Arm to natural orifice configurations may be simulated. For example, no cannula, such as uManip, gastrointestinal (GI) scope, or cStapler, may be used in the simulation. Arm to perc access configurations may be simulated. For example, no cannula, such as liver retractor, may be used in the simulation. Actions of the surgeon may be automated in the simulation. For example, the simulation may simulate breaking out key steps with variations. Setups such as the following may be simulated: port placements, arm placements, bar or robot, or parking spots of other cart-based robots. Actions of other assistants in certain steps of a procedure may be automated in the simulation. The simulation may be based on statistical sampling of port placements, e.g., to assign optimized positioning for key surgical steps.

Figure 34:
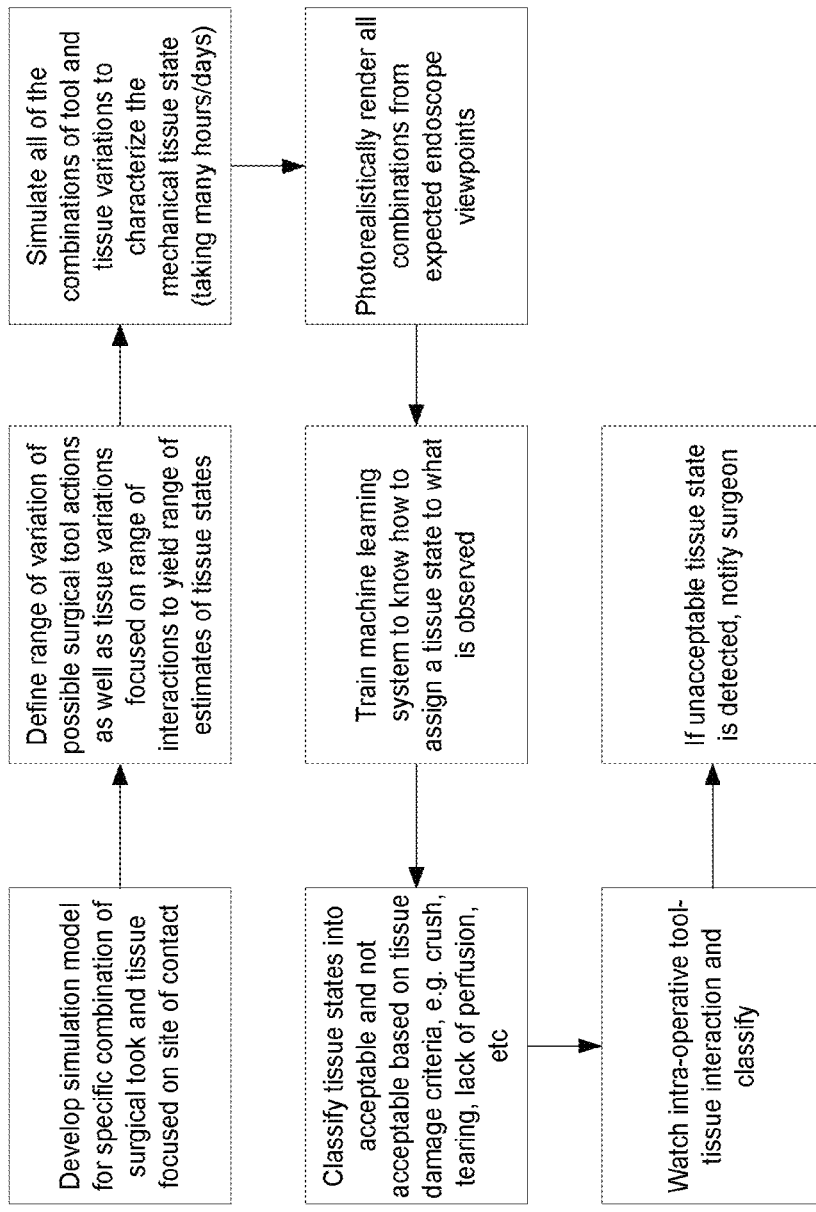
FIG. 34 illustrates a machine learning-assisted simulation process for avoiding tissue-manipulation errors.

The simulator may simulate tool-tissue interaction to avoid tissue-manipulation errors. FIG. 34 illustrates a machine learning-assisted simulation process 33170 for avoiding tissue-manipulation errors.

Figure 35:
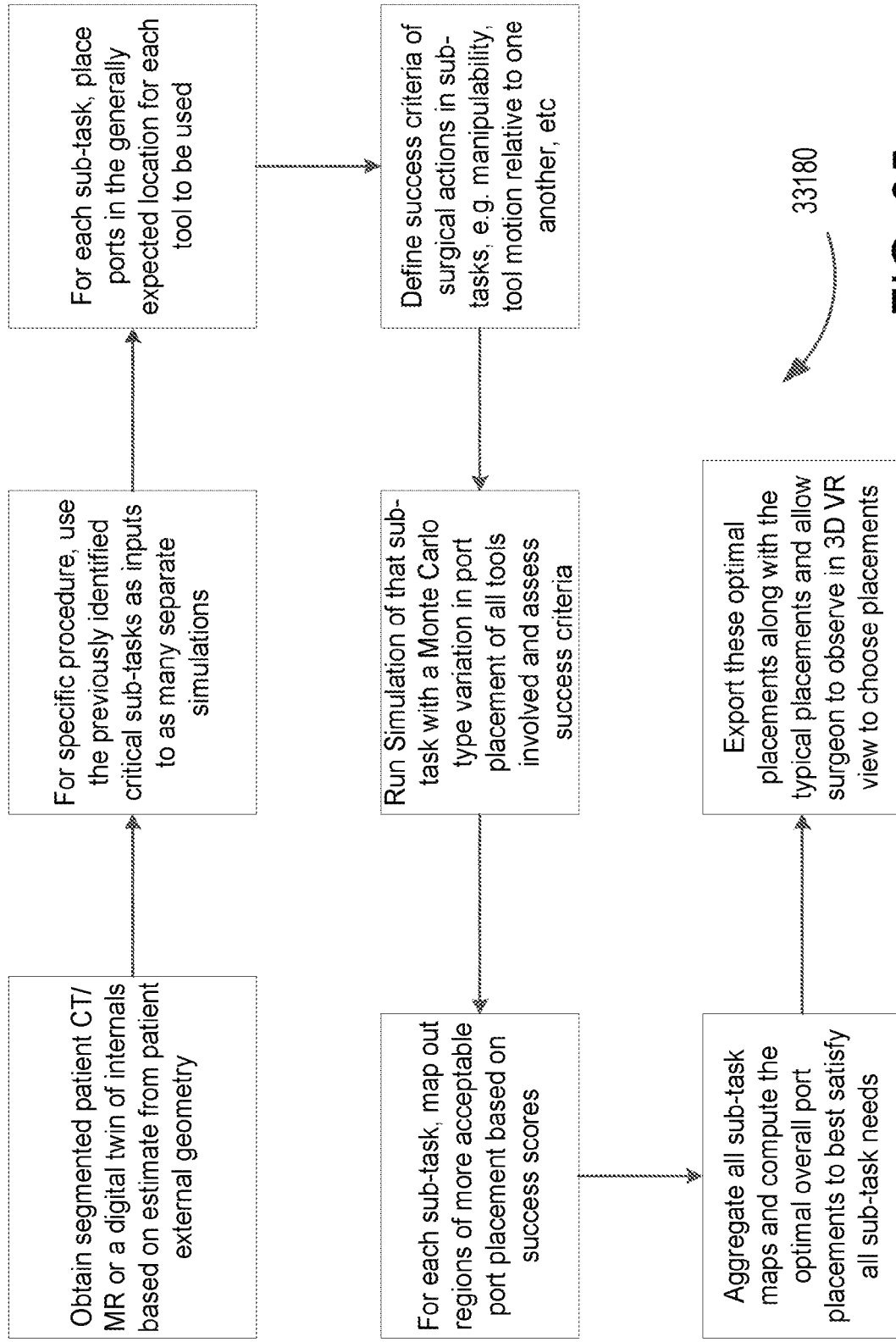
FIG. 35 illustrates an example process of determining optimality of patient specific port placement for an overall surgical procedure.

Surgeon location and relocations needed relative to a patient's orientation and/or positioning for completion of a surgical procedure may be simulated based on a surgical procedure plan. The simulation may identify drive-up robots to supplement single surgeon access. The simulation may simulate multiple options of repositioning of the access of the robot or the lap positing via virtual reality (VR) room visualization. The simulation may simulate organ access implicated by instruments of different lengths. The simulation may simulate and determine a needed patient setup, e.g., robot arm under leg for hysterectomy or endoscopic colon assisted lap. The simulation may simulate port placement and associated implications. FIG. 35 illustrates an example process 33180 of determining optimality of patient specific port placement for an overall surgical procedure.

The simulation may automate understanding of the implications of how the OR may be set up, e.g., how the OR setup may achieve reach, access, all steps of procedure. The simulator may communicate back to OR staff the probability of a setup being successful to outcomes. The simulation system may run through multiple differing runs to determine all of the possible combinations of the equipment, its location, and the efficiency of that placement. The variation may be displayed out to provide the choices the staff has for the options and the implications of each of the options.

The simulator may run simulations to determine patient body and/or limb positioning to minimize setup time or patient injury while providing the best access to a surgical site with the least amount of repositioning. Prior to a surgery a patient may be transferred to the operating table. The final position of the patient may be important, and may require planning and coordination by the OR team. Such planning and coordination may require time prior to the surgery and may cause delays during surgery to stop and reposition. For example, simulations may be used to train the staff based on patient characteristics and/or profile, procedure type, room layout, and/or equipment position. The simulator may provide information to the OR team of the optimal position of the patient on the bed to reduce the setup time by not requiring the OR team to plan and may coordinate and direct focus to other tasks. The simulator may provide details to the user on the proper placement and/or position to have least impact to the patient based on condition, and/or when proper placement was met. During surgery prevention of injury may require proper positioning of the patient throughout the surgery. A range of injuries may occur when a patient has been placed or moved improperly during surgery. There may be a set number of diagnoses that may come from such a situation. For example, simulations may be used to teach staff of cues or identifiers of when patient should be moved and how to move them to prevent injury. Examples of common injuries may be Ulnar nerve, Brachial plexus, and Spinal cord. Feedback of divergence from best or trained practice in positioning may be used to baseline the simulator.

The simulation may identify potential issues and options for resolution or changing outcomes. The simulator may identify deviations and/or recovery options from a surgical procedure plan and pre-operative simulations. The simulator may generate notification(s) of the identified deviations and/or recovery options. The simulation may employ virtual geofencing, e.g., for highlighting when surgical action is off preplanned simulation. The simulation may employ mechanical geofencing, e.g., for creating mechanical drive boundary when surgical action is off preplanned simulation. The simulation may provide feedback during approach. The feedback may be via geofencing of critical structures and/or adaptation during action.

The simulator may employ reactive simulation with integrated potential complications and issues for procedural and approach development. For example, new approaches may be developed by HCPs and hospitals, using existing instruments (e.g., IE, novel port positioning, hybrid use of assistant with/without devices), e.g., for procedural development. For example, procedural development may be unique to patient, e.g., how to take clinical inputs (e.g., tumor location, adhesions) into consideration.

Figure 36:
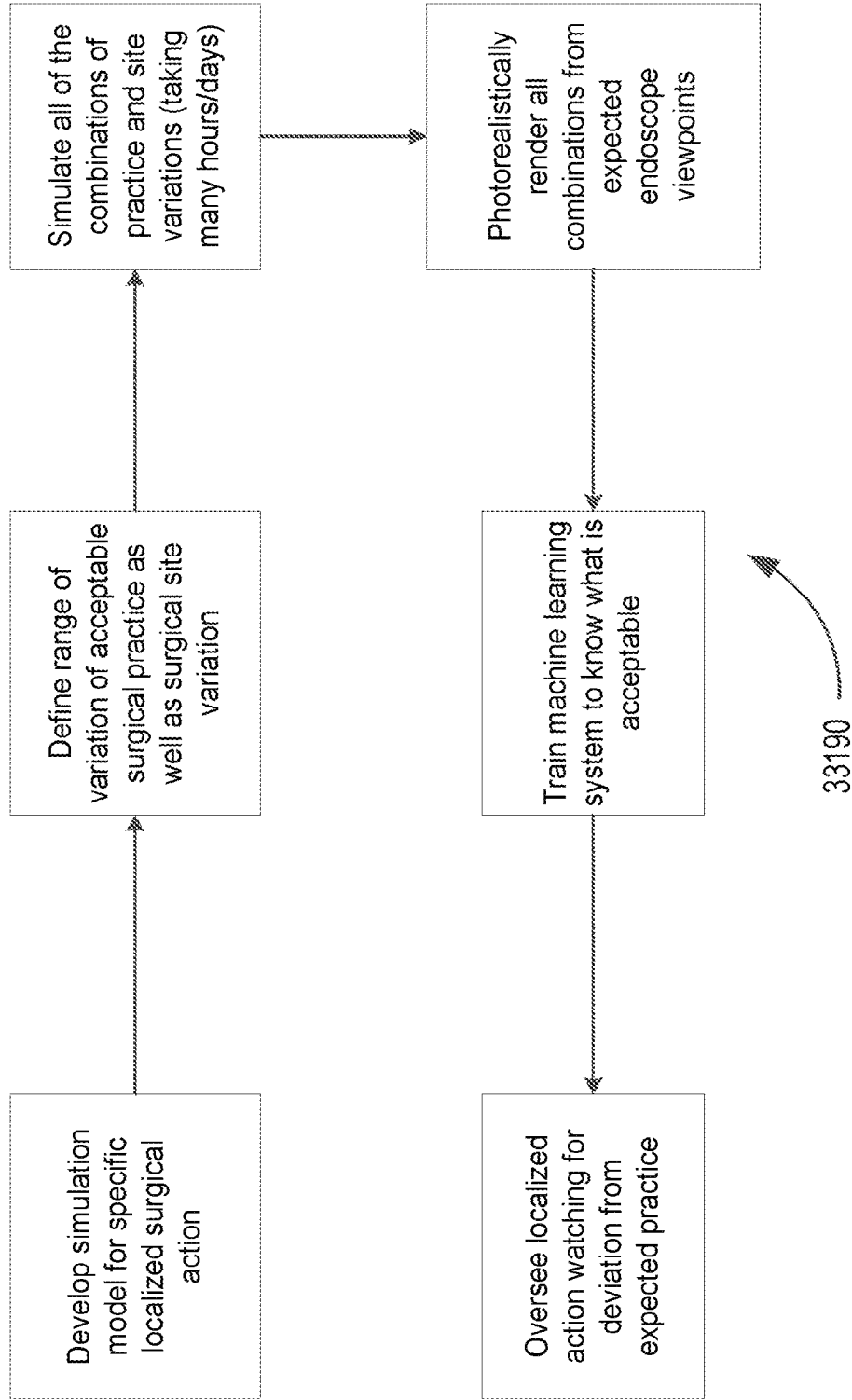
FIG. 36 illustrates an example process of detecting deviations from expected practice using ML-assisted simulation.

Predictive modeling may be employed in simulations. Critical surgical actions for a given procedure may be simulated to develop predictive models (e.g., machine learning models). Predictive models developed for the surgical actions may be employed in surgical procedures that include the surgical actions. A machine learning (ML) model may be employed to identify the stage of a surgical procedure so that the appropriate ML model for a surgical action may be invoked to perform predictions based on localized behaviors observed in simulations. FIG. 36 illustrates an example process 33190 of detecting deviations from expected practice using ML-assisted simulation.

Figure 37:
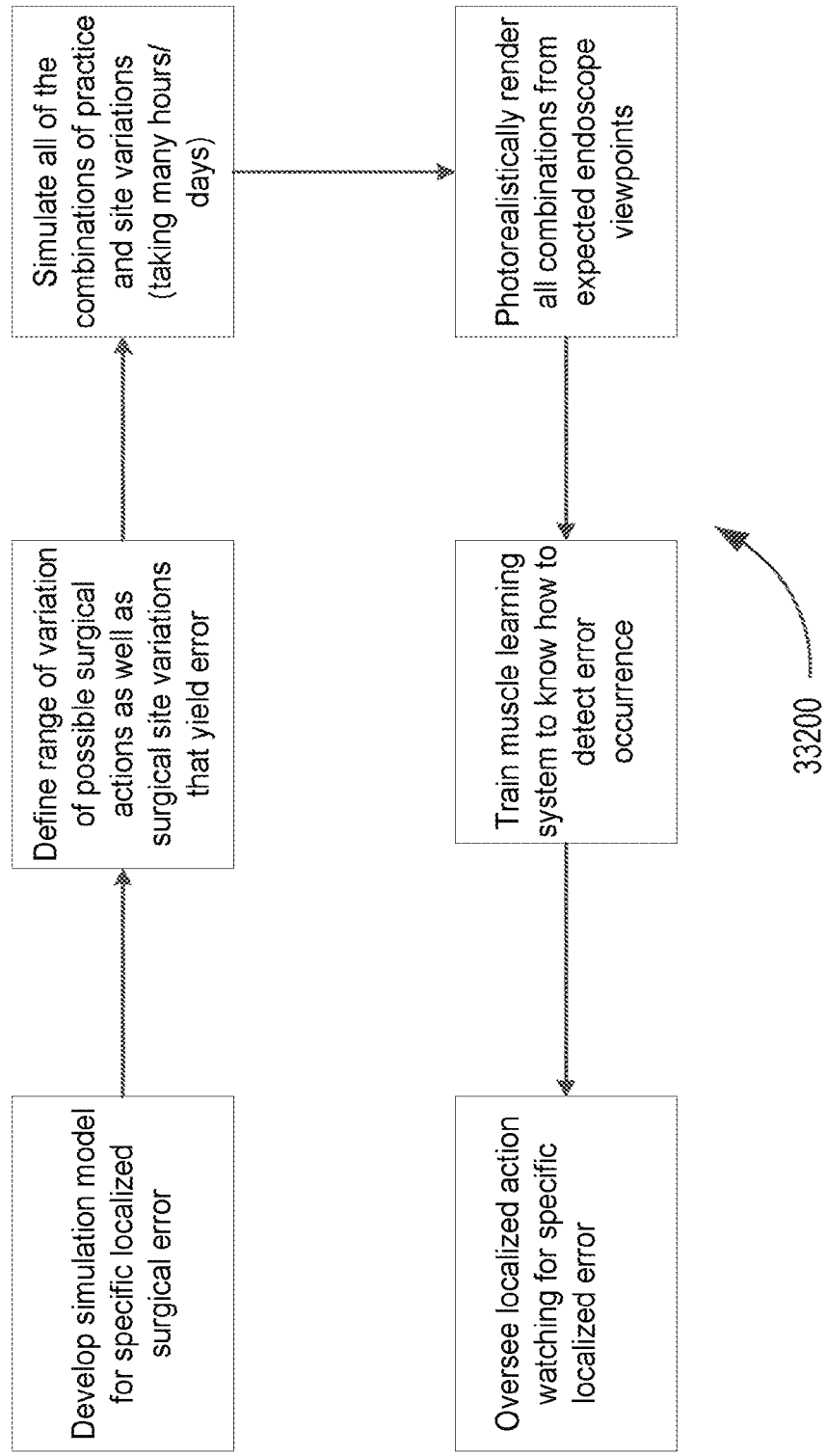
FIG. 37 illustrates an example process of detecting surgical errors using ML-assisted simulation.

Critical surgical errors for a given procedure may be simulated to develop predictive models (e.g., ML models). Predictive models developed for the surgical errors may be employed in surgical procedures that include the surgical errors. A ML model may be employed to identify the stage of a surgical procedure so that the appropriate ML model for a surgical error may be invoked to perform predictions based on localized errors at that stage. FIG. 37 illustrates an example process 33200 of detecting surgical errors using ML-assisted simulation.

Simulations may be performed pre-operatively to assess and/or optimize patient outcomes based on patient input. The simulations may provide indication and/or notification of most likely complications or adjustments within an impending surgical procedure to alert surgeon and/or staff and/or facility. For example, patient data, and/or patient vitals and/or patient physical characteristics may be used as inputs for simulations prior to a surgical procedure. The simulations may represent a realistic training and/or preparation prior to the surgical procedure. For example, patients' pre-operative data and/or patients' vitals and/or patients' physical characteristics may be inputted back into the simulator to identify any changes and/or modifications to be made and may provide notification(s) of the changes and/or modifications to an OR team, e.g., through an app and/or monitor and/or message. The changes and/or modifications may minimize complications and/or optimize efficiency within the OR. In an example, pre-surgery check may occur up to two weeks in advance, factors such as the following may change within that time period that may impact patient outcomes and/or approaches the surgeon takes: blood pressure, heart rate, or breathing changes. Real-time information of such factors may be added to the previous simulator runs to indicate recommendations to improve outcomes. For example, changes in pre-surgery checkup verses pre-op inputs baselined against gold standards or facility procedures to provide notifications, changes, and/or optimization to modify and/or adjust facility influencers for better outcomes and optimization on efficiencies. Identification of operating room may be diverted based on equipment or room layout, the staff location within the room, the staff skill set or experience required, based on the changes and/or impact of complication(s) to improve outcomes, and based on knowing when and/or how to react. Identifying when additional staff and/or resources are needed. In an example, additional scrub and/or circulating nurse, and/or additional specialty surgeon on standby may be needed. In an example, if surgery was for cholecystectomy and patient showed possible lung or heart issues then a Pulmonologist or Cardiologist may be on standby if complications were to arise.

The simulator may display and may provide review of automated simulation(s) with feedback, recommendations, and/or alternatives highlighted for a simulation user. For example, the simulator may display and may provide review of automated surgical step operation based on a setup and/or or configurations. The simulator may highlight when the automated surgical step operation does not work. The simulator may compare the automated result to real-world and/or human operated options. The simulator may show key differences from the comparison. The simulator may learn options for the surgical step from automation. The simulator may obtain feedback on the options for the surgical step from a simulator user (e.g., a surgeon). The simulator may indicate which earlier setup steps may result in later steps having robotic and/or patient collisions and/or access limitations.

The simulator may predicate and communicate the probability of a surgeon's skill being able to achieve success given simulation of setup and patient parameters. The surgeon's skill may be from earlier training run inputs and/or from CSATS scores. Statistics may be created based on a plurality of simulation runs from a plurality of surgeons. The statistics may be used to build a database. The simulation may predict outcomes based on the procedure, the difficulty of the procedure, its plan, the approaches and the surgeon skill. The simulation may predict setup shortfalls and/or where the setup shortfalls may be in the setup and/or what outcome the setup shortfalls affect. The simulation may highlight tasks that are more challenging for the surgeon based on previous simulation runs of recorded skill level and may make recommendations to lower the difficulty of the task or may suggest alternative approaches, access locations, and/or instrument mixes that would improve the outcomes, e.g., including hybrid or full robotics.

Simulation OR efficiency behaviors and/or boundaries may be performed to refine boundaries and/or notifications from a surgical data system (e.g., a surgical hub). Data captured from using the simulator may be used to model and/or identify the extent of contamination and/or size of the exposure zone of highly contagious infections. Such information may be communicated to the monitoring systems (e.g., to control/direct patients). For example, the Covid pandemic created new situations for hospital facilities in which the hospital facilities were not prepared. The simulator may be used to determine one or more methods for how a facility may handle the flow of incoming patients to minimize infection to the facility. For example, the Covid pandemic created new situations in which varying array of symptoms were displayed by individuals differently. The simulator may identify and/or capture symptoms and may provide the facility a checklist of signs to look for. The simulator may communicate to the facility monitoring system for incoming patients to direct them to a controlled environment to minimize the potential contamination and/or infection to the facility.

Figure 38:
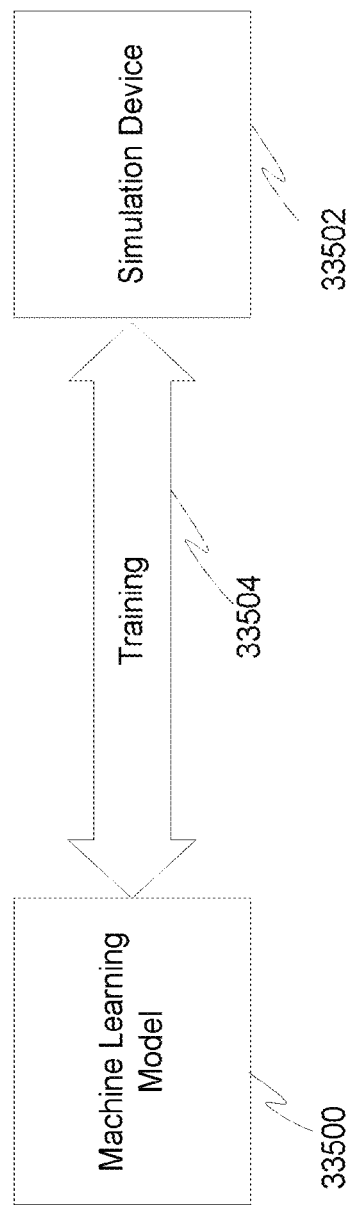
FIG. 38 is a block diagram of an example machine learning framework.

FIG. 38 is a block diagram of an example machine learning framework. Machine learning is a branch of artificial intelligence that seeks to build computer systems that may learn from data without human intervention. These techniques may rely on the creation of analytical models that may be trained to recognize patterns within a dataset, such as a data collection. These models may be deployed to apply these patterns to data, such as biomarkers, to improve performance without further guidance. For example, such a model may include the machine learning module 33500.

Machine learning may be supervised (e.g., supervised learning). A supervised learning algorithm may create a mathematical model from training a dataset (e.g., training data). The training data may consist of a set of training examples. A training example may include one or more inputs and one or more labeled outputs. The labeled output(s) may serve as supervisory feedback. In a mathematical model, a training example may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been a part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may contain inputs and may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each train example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

In an example framework, a simulation device 33502 may enable the training 33504 of the machine learning model 33500. The simulation device 33502 may represent a complex system that receives setup information, such as simulated procedure and/or surgical task, anatomy, physiology, equipment, instruments, and the like. The simulation device 33502 may represent a complex system that receives activity information, such as instrument manipulation, simulated tasks and/or simulated surgical activity primitives, and the like. The simulation device 33502 may represent a complex system that receives setup information and activity information, and in response, outputs one or more results, such as final procedure state, a performance score, an efficiency score, a simulated patient outcome, and the like. For example, the result may include a particular state, value, metric, or the like. For example, the result may include a function, such as a weighed function, of a particular state, value, metric, or the like. The datasets represented by the combinations of respective setup information, activity information, and results associated with the simulation device 33502 may be used to train 33504 the machine learning model 33500. As disclosed herein, the training 33504 may be supervised learning, unsupervised learning, reinforcement learning, cognitive computing, and the like.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronic medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g., logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

In the example framework, the machine learning model 33500 may be used to model solutions that drive toward a specific result. For example, the model 33500 may be structured and/or trained to receive as input an instance of setup information and to output corresponding activity information. For example, the model 33500 may be structured and/or trained to receive as input an instance of activity information and to output corresponding setup information. In an example, the machine learning model 33500 may be used to model solutions that drive toward a variable result. For example, the model 33500 may be structured and/or trained to receive as input an instance of setup information and a desired result and to output corresponding activity information. For example, the model 33500 may be structured and/or trained to receive as input an instance of activity information and a desired result and to output corresponding setup information.

An example training set may include the results of a simulation of all setups and/or activities that have a result within a predefined range of acceptance. To illustrate, the model may address suture placement. For example, the setup, activity, and results may include elements such as suture pattern, tension, wound healing, and the like. In an example, the simulation may determine tension on colon when reconnected in a low anterior resection (LAR) anastomosis and may include predicted resultant profusion in the results. In an example, the simulation may determine lung volume post expansion following a segmentectomy and/or lobectomy. An example training set may include the results of multiple run automated simulations of a particular surgical procedure with an activity set, and the model may enable to determine outcomes of a preestablished starting set.

In an example, the training data may be aggregated to provide a summary view of possible choices and/or variations, such as choices and/or variations within a predefined number of variable steps. The choices and/or variations may include those where the outcome is with a acceptable result-set. Such summary may include a proposed approach path for best outcomes. For example, such summary may propose an approach based on expert review, customer satisfaction surveys, outcomes feedback, and the like. For example, such summary may communicate an adverse event risk score. The adverse event risk score may update progressively up or down as choices evolve. The summary may include an interactive tool to comparing and/or contrasting different approaches. The interactive tool may enable comparing and/or contrasting multiple autorun simulations.

In an example, the simulation device 33502 may be used to create ground truth data sets for machine learning and/or artificial intelligence training. For example, the simulation device 33502 may produce situations to establish bounding parameters and/or edge cases for machine learning and/or artificial intelligence training. For example, the simulation device 33502 may provide output of robotic path guidance. Such guidance may be direct guidance, geofenced, or the like. For example, the simulation device 33502 may provide feedback data. For example, data may be used from a simulation that is driven from database. The data may include information regarding similar cases. The database may include machine learning and/or artificial intelligence model information trained with similar cases. For example, the simulation device 33502 may use a machine learning model to predict medical risks. The prediction may include information of what devices, equipment, and/or consumables may be appropriate in view of the predicted risk, for example.

In an example, a machine learning model 33500 may be trained to apply notations, comment, and/or annotations to surgical videos. For example, such notations, comment, and/or annotations may be incorporated into a training set, such that future videos and/or future simulations may be processed according to the model for review. The model may output notations, comment, and/or annotations at appropriate points within the processed video and/or simulation. For example, the machine learning model 33500 may be trained to present complex simulations in real time.

In an example, the simulation device 33502 may be used to create supplemental training sets (e.g., training sets to supplement real-world training sets). For example, the simulation device 33502 may be used to create supplemental training sets that include cases that are rare in the real-world, such as rare anatomic conditions, rare physiology, and/or rare adverse events. Such supplemental training sets may be used to for training 33504 a machine learning model 33500 for example. Similarly, the simulation device 33502 may be used to create patient specific hybrid data sets. For an example, the simulation device 33502 (e.g., via an application module) and/or a machine learning model 33500 may be used to check input parameters of patient specific topics. Such checking may result in changes to the simulated anatomy via modifications to and/or addition of certain objects and/or object properties. For example, the patient specific anatomy an include adding irregularities, such as multiple pulmonary artery branches and/or tumor ingrowths for example, to the simulation. For example, such patient specific modification may be input from remote healthcare inputs and/or pre-operative monitoring. Such patient specific data sets may be included for simulation to generate datasets for machine learning model training, for example. The simulation device 33502 may be used to create supplemental training sets that incorporate rare patient-specific irregularities.

In an example, the simulation device 33502 may be used to create training data sets related to procedure platform, such as robotic, laparoscopic, open, hybrid, and the like. Here, similar surgical goals may be simulated using various platforms and/or variation within a particular platform. Such setup data and activity data may be used with their corresponding simulated results to train a machine learning model 33500 to recommend approaches for future surgeries, for example.

Figure 39:
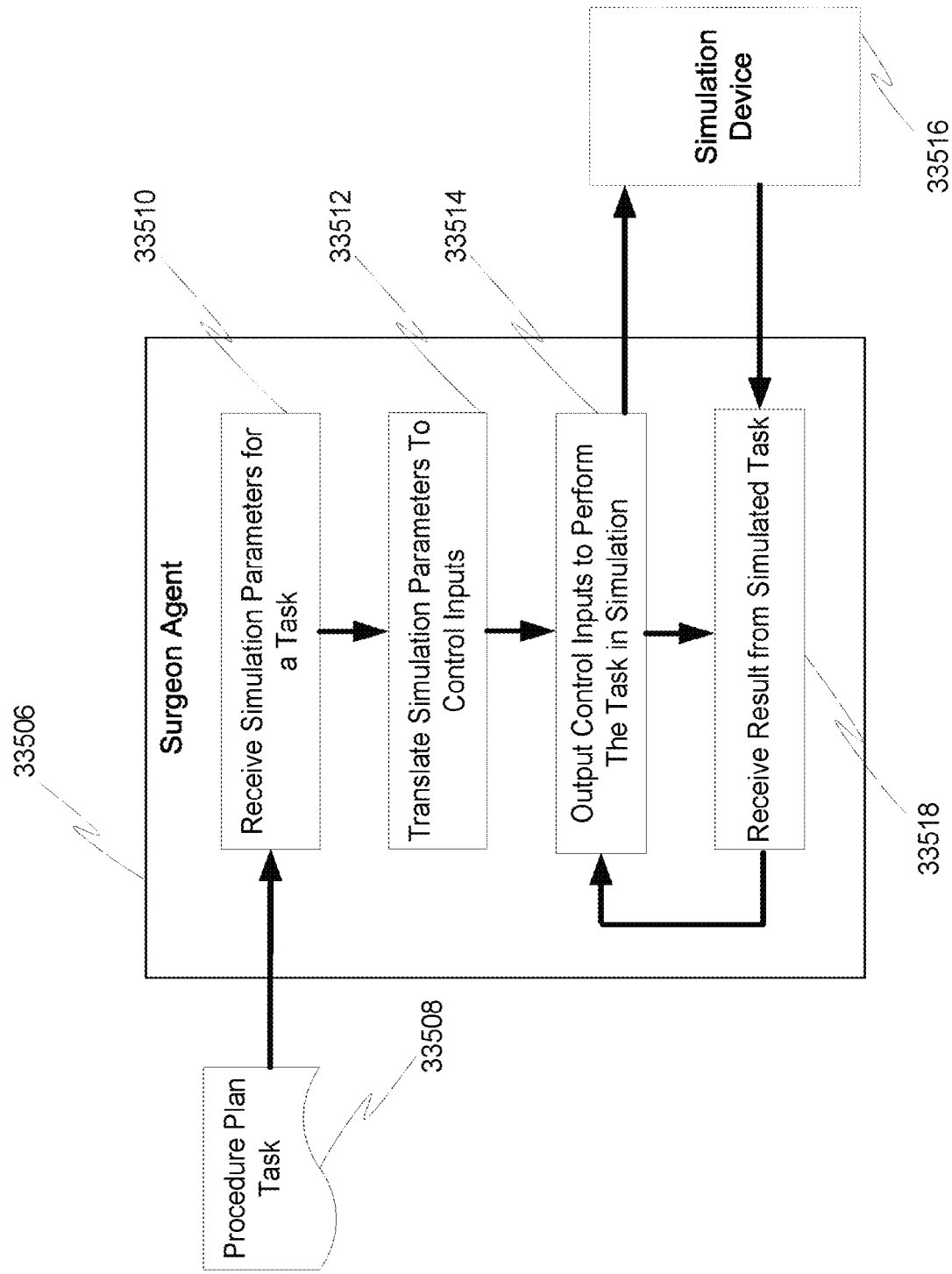
FIG. 39 is a block diagram of an example surgeon agent.

FIG. 39 is a block diagram of an example surgeon agent 33506. The surgeon agent 33506 may include the surgeon agent 30006 disclosed herein with reference to FIG. 7, for example. The surgeon agent 33506 may provide computer-based control of a simulated task. Such a surgeon agent 33506 may be used to simulate many variations of the surgical task. Such simulations may be used to generate large datasets for analysis and/or for training a machine learning model, such as machine learning model 33500, for example. Such datasets may be used to analyze and/or model aspects of the surgical task subject to variation.

In an example the surgeon agent 33506 may receive procedure plan task data 33508. The procedure plan task data 33508 may include information about a particular surgical task. For example, the procedure plan task data 33508 may include one or more simulation parameters related to the surgical task. Such simulation parameter may provide information on how a particular surgical task is to be handled in simulation. Simulation parameters for the surgical task may include a parameterized representation of the surgical task, each of which include, for example, one or more specific manipulations and one or more reference locations. For example, for a suturing task, an example parameterized representation may include a manipulation, such as an initial suture insertion, with angle, for example, and a reference location, such as a point defined relative to a simulated wound. The procedure plan task data 333508 may be structured as disclosed herein with regard to FIGS. 11A-B for example.

At 33510, the surgeon agent 33506 may receive one or more simulation parameters from the procedure plan task data 33508. The surgeon agent 33506 may include logic to translate simulation parameters into one or more control inputs to a simulation. For example, the surgeon agent 33506 may mimic control inputs based on a determination made from the simulation parameters. For example, the surgeon agent 33506 may engage an application programming interface (API) of the simulation to determine control inputs and/or as a method to control the simulation. At 33512, the surgeon agent may translate the one or more simulation parameters into one or more control inputs.

At 33514, the surgeon agent 33506 may output the control inputs to a simulation device 33516. The simulation device 33516 may perform a simulation cycle based on such control inputs and in turn send an output to the surgeon agent. The output may include a representation of the simulation state in view of the control inputs. The output may include one or results metrics for example.

At 33518, the surgeon agent may receive the simulation output. The surgeon agent may loop to subsequent control inputs, if present. Subsequent control inputs may be translated from additional simulation parameters. Such additional simulation parameters may have been received from the procedure plan task data 33508 and/or a subsequent reception of additional procedure plan task data 33508. Such a surgeon agent may enable computer-based control of a surgical simulation according to a set of parameterized input data. As a building block, one or more instances of surgeon agents may be used with one or more simulations to test many variations of a particular task through simulation. Such building blocks may be combined to test variations of surgical activities of any length, for example. For example, a one or more surgeon agents may be used with one or more elements of corresponding procedure plan task data to enable computer-based control of many variations of entire surgical procedures in simulation.

Figure 40:
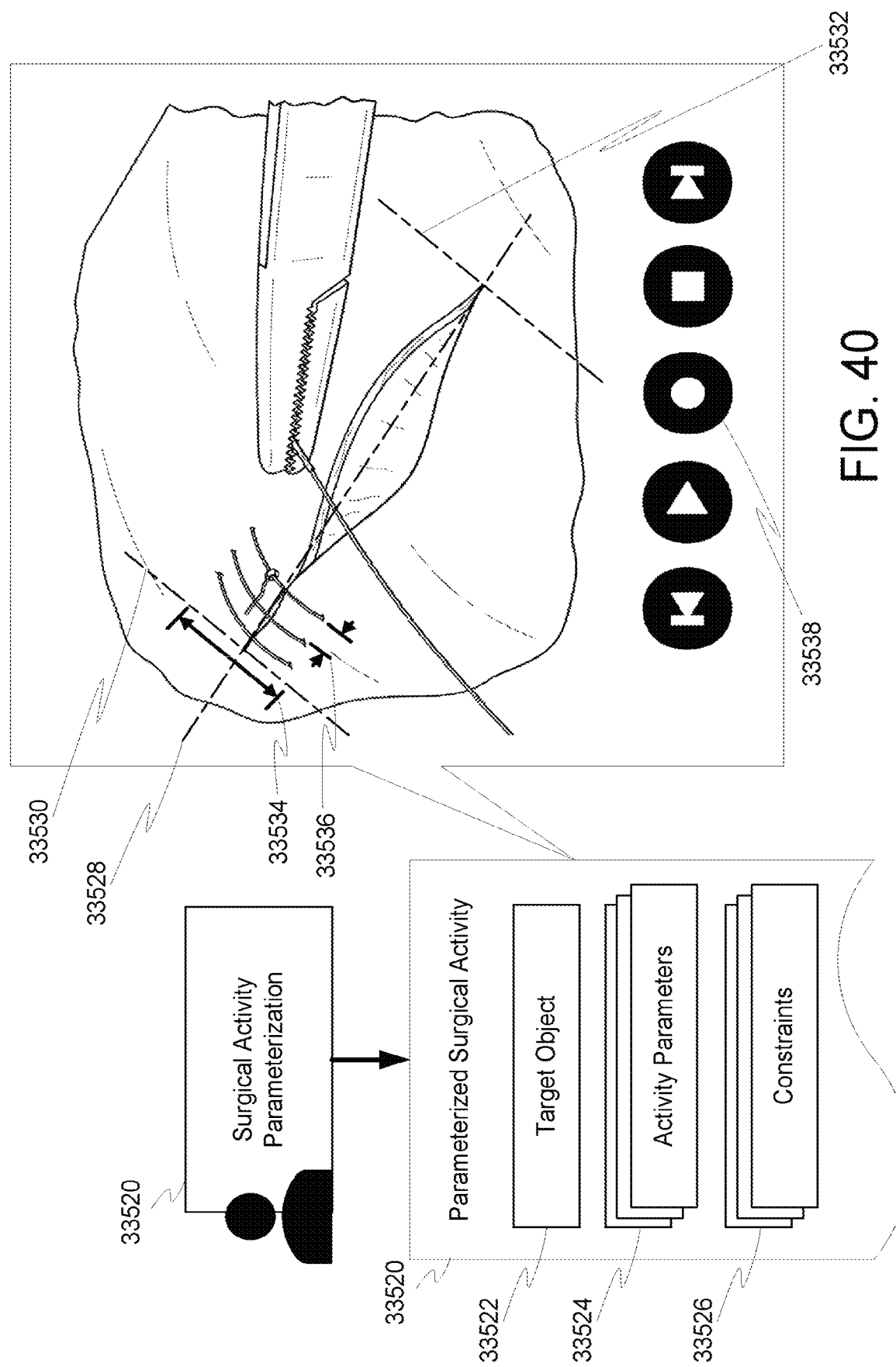
FIG. 40 illustrates an example simulation activity parameterization data set.

FIG. 40 illustrates an example simulation activity parameterization data set. The parameterization of a surgical activity for simulation via computer-based control may include the operation of a surgical activity parameterization tool 33520. The surgical activity parameterization tool 33520 may be used to generation parameterized surgical activity data 33522. The surgical activity parameterization tool 33520 may be based on a simulation platform. For example, the surgical activity parameterization tool 33520 may be implemented in an application module 30010 of the simulation device 30000 disclosed herein with regard to FIG. 7. The surgical activity parameterization tool 33520 may be a stand-alone tool.

The surgical activity parameterization tool 33520 may include a processor configured to perform the step, functions, and/or capabilities disclosed here. The surgical activity parameterization tool 33520 may enable a user to define one or more parameters to represent a surgical activity. For example, the surgical activity parameterization tool 33520 may enable a user to define one or more parameters to represent a surgical activity, such that a computer-based control agent, like the surgeon agent device 30006 as disclosed herein with regard to FIG. 7 for example, may perform the surgical activity. Such parameters may represent a parameterized surgical activity data 33520.

In an example, parameterized surgical activity data 33520 may include a target object 33522, one or more activity parameters 33524, and/or one or more constraints 33526. The target object 33522 may include information that indicates a particular object, collection of objects, and/or portion of an object within the simulation environment with which the surgical activity is to be done. The activity parameters 33524 may include information that indicates the particular data elements and/or values that define the variations available in performing the activity. The constraints 33526 may include information that indicates any limitations associated with activity, such limitations may be used by the simulation to prevent certain interpolating activity from being performed.

To illustrate, parameterized surgical activity data 33520 may be used to define a wound closure activity. In such an example, the target object 33522 may include information indicative of the simulated wound, including for example, the tissue object within which the wound is located, geometric information about the location, size, and shape of the wound, the wound depth, subsurface objects, and the like. For example, parameterized data such as coordinates of a center line 33528, an upper edge 33530, a lower edge, 33532, and the like, may be used to indicate location of the wound in simulation. The activity parameters 33524 may include information that indicates what manipulations are expected relative to the target object 33522. For example, parameterized data such a suture width 33534, suture spacing, suture pattern, suture tension, suture depth, suture type, and the like, may be used to indicate the nature and quality of the suturing activity. For example, other parameterized data such as suture technique, instrument, suture material, needle type, knot type, and the like may be used to define aspects of how the activity is to be performed. The constraints 33526 may include data that indicates any specific limitations to constrain the activity operation. For example, the constraints 33526 may include duration, dexterity, precision, accuracy, collision constraints, applied pressure, adjacent tissue contact, and the like.

The parameterize surgical activity 33520 may provide a structure to represent many different ways to perform a particular activity. For example, a number of different sutures that may be performed by applying various combinations and/or permutations of parameter values.

The surgical activity parameterization tool 33520 may include a user interface to enable the definition of the data elements and/or their values. In an embodiment, the surgical activity parameterization tool 33520 may provide a "macro" recording capability to record actual user input controls and to populate the parameterized surgical activity data 33520 with elements, values, and/or elements and values based on the recorded user input. The surgical activity parameterization tool 33520 may include a media player-like user interface 33538 to record, playback, edit, and the like, user input controls.

Figure 41:
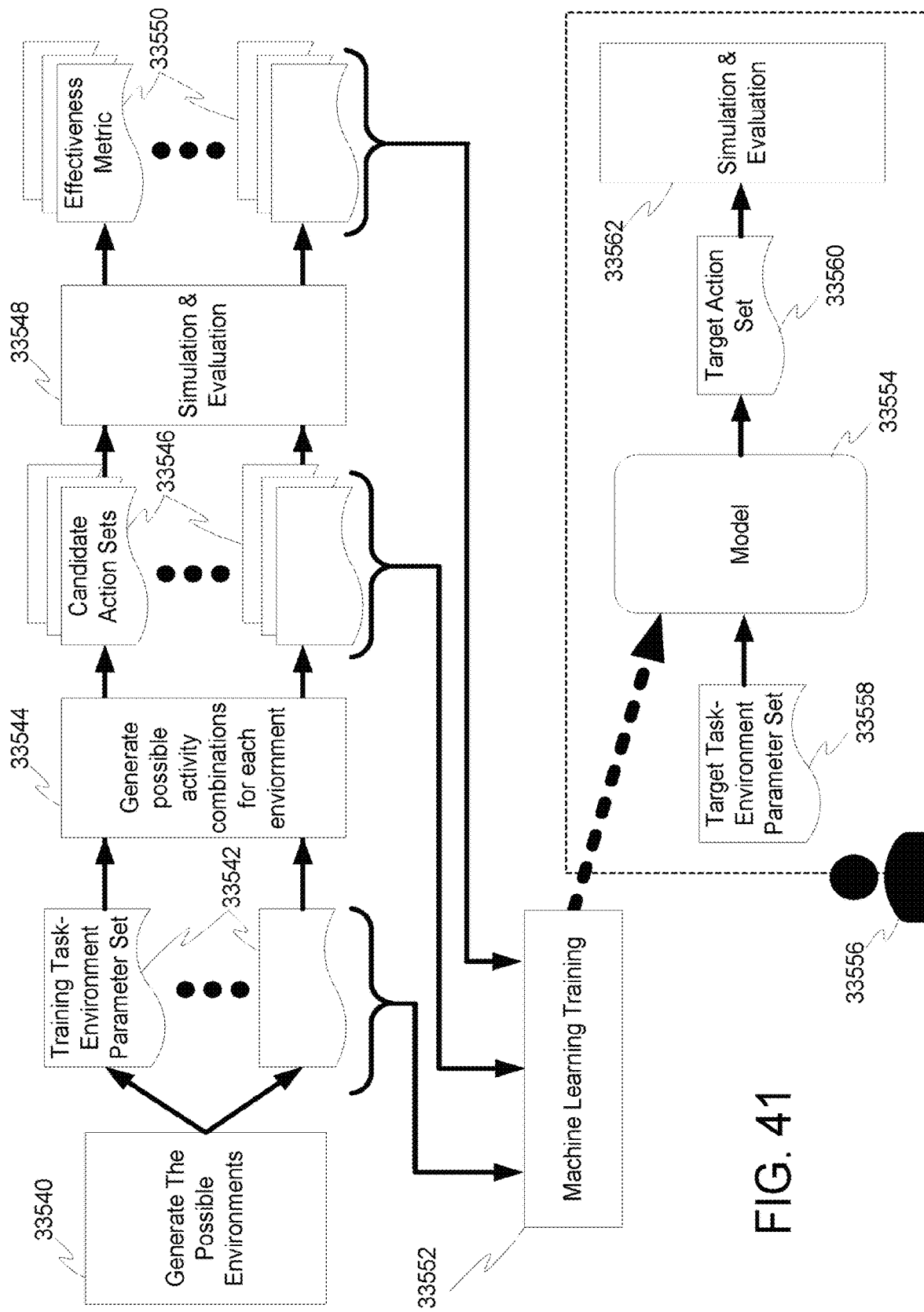
FIG. 41 illustrates an example surgical simulation flow for machine learning training.

FIG. 41 illustrates an example surgical simulation flow for machine learning training. The parameterize surgical activity data structure may enable a computationally effective approach to simulation-based training of a machine learning models. In an example, at 33540, one or more simulation environments may be generated. For example, the one or more simulation environments may be generated by a combination and/or permutation of setup data elements, such as the setup data 30088, 30090, 30092 as disclosed herein with regard to FIG. 11B for example. Such generation may result in one or more training task-environment parameter sets 33542.

At 33544, for each training task-environment parameter set 33542, possible activity combinations may be generated. For example, such generation may include various combinations and/or permutations of procedural task and/or activity data, such as task data 30094, 30096, 30098 disclosed herein with regard to FIG. 11B and/or parameterized surgical activity data 33520 disclosed herein with regard to FIG. 40 for example. Such generation may output one or more candidate action sets 33546. In an example, each training task-environment parameter sets 33542 may have one or more candidate action sets 33546 associated with it. In this way, various surgical setups and/or various surgical approaches may be generated for simulation under computer-based control input. The combination of training task-environment parameter sets 33542 and candidate action sets 33546 may represent the input space being simulated. The combination of training task-environment parameter sets 33542 and candidate action sets 33546 may represent a portion of the training data that may be used for a machine learning model.

In an example, the training task-environment parameter sets may be received from a surgical data system, such as the surgical data system 30008 disclosed herein with regard to FIG. 7 for example. The surgical data system may records real-world environment data from real-world performances of a surgical task. The surgical data system may use such real-world environment data to generates the plurality of training task-environment parameter sets. With this approach, the training task-environment parameter sets may better represent a typical anatomy, physiology, and the like. Similarly, this approach may be used so the training task-environment parameter sets may better represent anatomy, physiology, and the like for a particular patient population, for example.

At 33548, candidate action set 33546 with its corresponding training task-environment parameter set 33542 may be simulated and/or evaluated. For example, the candidate action set 33546 with its corresponding training task-environment parameter set 33542 may be provided as input to a simulation device, such as the simulation device 30000 disclosed herein with regard to FIG. 7, for example. For example, the training task-environment parameter set 33542 may be provided as setup information to the simulation. For example, the candidate action set 33546 may be driven by a surgeon agent, such as surgeon agent 30006 for example, to operate the simulation.

The evaluation of the performance of each respective candidate action set 33546 and training task-environment parameter set 33542 pair may result in one or more effectiveness metrics 33550. The evaluation may include any performance metric appropriate in view of the desired machine learning training. For example, the evaluation may include a comparison of the final simulation state to a preferred target simulation state. For example, the evaluation may include an assessment of certain performance characteristics, such as procedure duration, procedure movement, equipment changes, instrument usage, consumable usage, and the like. In an example, the effectiveness metric 33550 may include a function, such as a weighted function, of one or more performance results. In an example, the effectiveness metric 33550 may include a vector of one or more performance results.

At 33552, each candidate action set 33546 and training task-environment parameter set 33542 pair and its respective effectiveness metric 33550 may serve as training data for training a machine learning model. The training may include any training algorithm appropriate in view of the model objective and the nature of the training data. For example, the training may include supervised learning, unsupervised learning, reinforcement learning, cognitive computing, and the like.

The output of such training may include a model 33554. And at 33556, the model may be employed to determine new candidate action set 33546 and training task-environment parameter set 33542 pairs that are consistent with the training and the effectiveness metrics 33550. In an example, the model 33554 may receive a "new" task-environment parameter set (e.g., a target task-environment parameter set 33558). And the model may output a corresponding "new" action set (e.g., a target action set 33560). In an example, the model may be trained such that it may receive a "new" action set and output a corresponding "new" task-environment parameter set. In this sense, the simulation data may be used to model surgical environments, surgical activities, and their corresponding results to determine new environments (e.g., surgical setups) and/or new activities (e.g., procedures) that aim to achieve (e.g., maximize, minimize, or the like) a result (e.g., a particular performance objective).

The determined target action set 33560 and training task-environment parameter set 33558 pair may be simulated at 33562. The simulation may include an evaluation and a corresponding effectiveness metric. Such metric may be used to verify the model 33554, for example.

To illustrate the process, in an example, the procedure may include a suturing procedure. One or more environments may be defined. For example, a predefined surgical site may be warped to establish one or more training task-environment parameter sets. For example, a single predefined surgical site may be used to generate a single training task-environment parameter set for modeling.

One or more suturing approached may be defined. For example, a simulation of a needle passing through tissue on either side of a suture site may be developed (e.g., developed using a tool, such as the surgical activity parameterization tool 33520). For example, a computer vision-based approach may be applied to extract relevant geometric parameters from the suture site. For example, the suture site and/or the suturing activity may be parametrically defined.

The suture bites may be placed in simulation and evaluated according to effectiveness metric, such as wound interfacial pressure. For example, the effectiveness metric may be used to train a model to maximize the effectiveness metric across a number of variations, such as suture placement, depth, count, force, and the like. In an example, the model may continue learning/automation across the various options and in view of the global suture force to compute the best goal criteria over the entire suture site. The module may be used with a target environment to output a suture approach that maximizes the effectiveness metric for the suture site.

Figure 42:
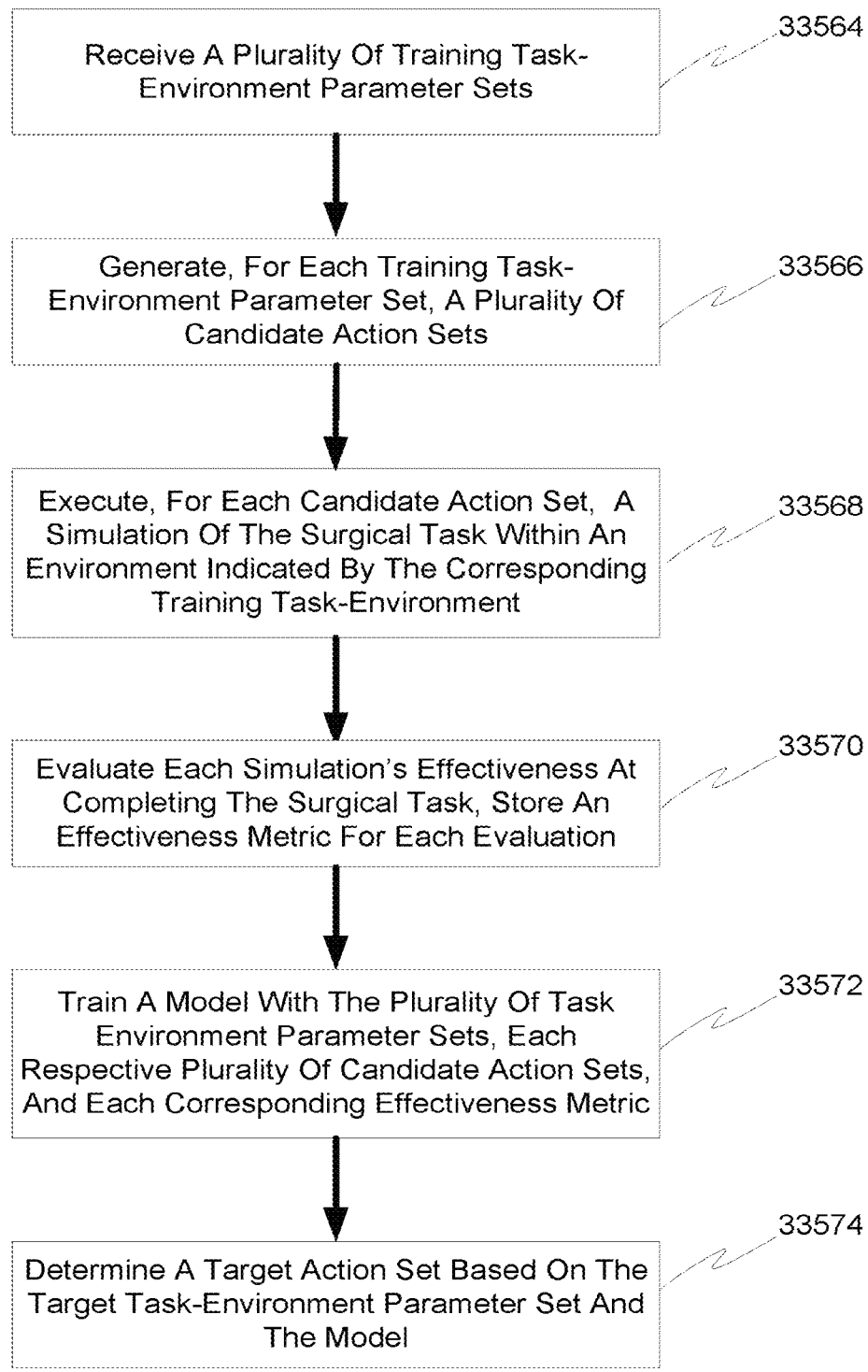
FIG. 42 is a flow chart of an example surgical simulation operation.

FIG. 42 is a flow chart of an example surgical simulation operation. For example, the example surgical simulation operation may include a process to determine a target action set to perform a simulated surgical task in a simulated environment. The simulated environment for the simulation surgical task may be indicated by a target task-environment parameter set.

At 33564, a plurality of training task-environment parameter sets may be received. Each training task-environment parameter set may indicate a respective simulated environment within which a simulated surgical task is to be completed. For example, the plurality of training task-environment parameter sets may be received from a surgical data system. The surgical data system may record real-world environment data from real-world performances of the surgical task. The surgical data system may generate the plurality of training task-environment parameter sets from the real-world environment data. For example, each training task-environment parameter set may include anatomical information, physiological information, and/or surgical setup information.

At 33566, for each training task-environment parameter set, a plurality of candidate action sets may be generated. Each candidate action set may include a parameterized surgical activity within the respective simulated environment. For example, the parameterized activity may include a simulated transection parameterized by any of relative anatomical location, instrument selection, and/or instrument application direction. For example, the parameterized activity may include suturing parameterized by any of suture location, suture pattern, suture number, suture material, and suture tension. For example, the parameterized activity may include a surgical robotic guidance path.

At 335658, Each candidate action set may be executed within a simulated environment indicated by the corresponding training task-environment set. And when the candidate action set is so executed, it may cause performance of the simulated surgical task. Such performance may have an effectiveness that is indicated by a corresponding effectiveness metric. For example, each performance may be evaluated, at 33570, to determine its effectiveness metric. The corresponding effectiveness metrics may be stored. In an example, an output may be generated. The output may be a human-readable aggregation of the plurality of task environment parameter sets, each respective plurality of candidate action sets, and each corresponding effectiveness metric.

At 33572, a model may be trained. For example, the plurality of task environment parameter sets, each respective plurality of candidate action sets, and each corresponding effectiveness metric may be used to train the model.

At 33574, a target action set may be determined based on the target task-environment parameter set and the model.

The training may be based on a machine learning algorithm, such as a supervised learning algorithm, an unsupervised learning algorithm, a reinforcement learning algorithm, and the like.

In an example, an action set (e.g. a candidate action set, a target action set, or an input action set) may refer to a set of parameters which define one or more actions taken during a surgery. For example, an action set may refer to a number of surgical choices taken by an operator. For example, an action set may include specific layout decisions (both of the surgical staff and of the surgical instrumentation). An action set may also refer to the specific equipment used during a surgery. In other words, it may refer to portions of a surgical procedure which have consequences on the surgery, both in duration, surgical outcomes, effectiveness of the procedure, etc. For example, the candidate, target, and input action sets may each employ a compatible and/or same format. A machine-learning model can be trained, for example, on the basis of a candidate action set to help define a relationship between any arbitrary "input" action set. This allows the machine-learning model to be used to find a target action set within a given simulation having a certain effectiveness.

Similarly, an environment parameter set (e.g. an environment parameter set, a target environment parameter set, or an input environment parameter set) may refer to a set of parameters which define the overall environment of a surgical simulation. It may refer to the parameters which initialize and define the constraints and physics of a surgical simulation. The target and environment parameter sets, for example, may employ a compatible and/or same format as that of the environment parameter set. A machine-learning model may be trained, for example, on the basis of an environment parameter set to help define a relationship between any arbitrary "input" environment parameter set. This allows the machine-learning model to be used to find a target action set within a given simulation having a certain effectiveness.

In an example, the machine-learning model may be trained using a set of labelled data to train the model in a supervised fashion. For example, the combination of the environment parameter set and the action set may be considered to be the input data (as this refers to a specific set of actions run within a specific simulation environment). This data for training purposes may be "labelled" with its associated effectiveness metric (i.e. the output of the simulation, which relates to how effective the specific action was within that simulation). By feeding this labelled data into the machine-learning model, the model can generate a relationship between different actions/environments and the associated effectiveness.

The simulated surgical task and the effectiveness metric may include any surgical activity subject to simulation with an objective goal subject to computer evaluation. For example, the simulated surgical task may include a lower anterior resection anastomosis. And the effectiveness metric may include perfusion resulting from the performance of the simulated surgical task. For example, the simulated surgical task may include any of segmentectomy and lobectomy. And the effectiveness metric may include an indication of output lung volume resulting from the performance of the simulated surgical task.

Figure 43:
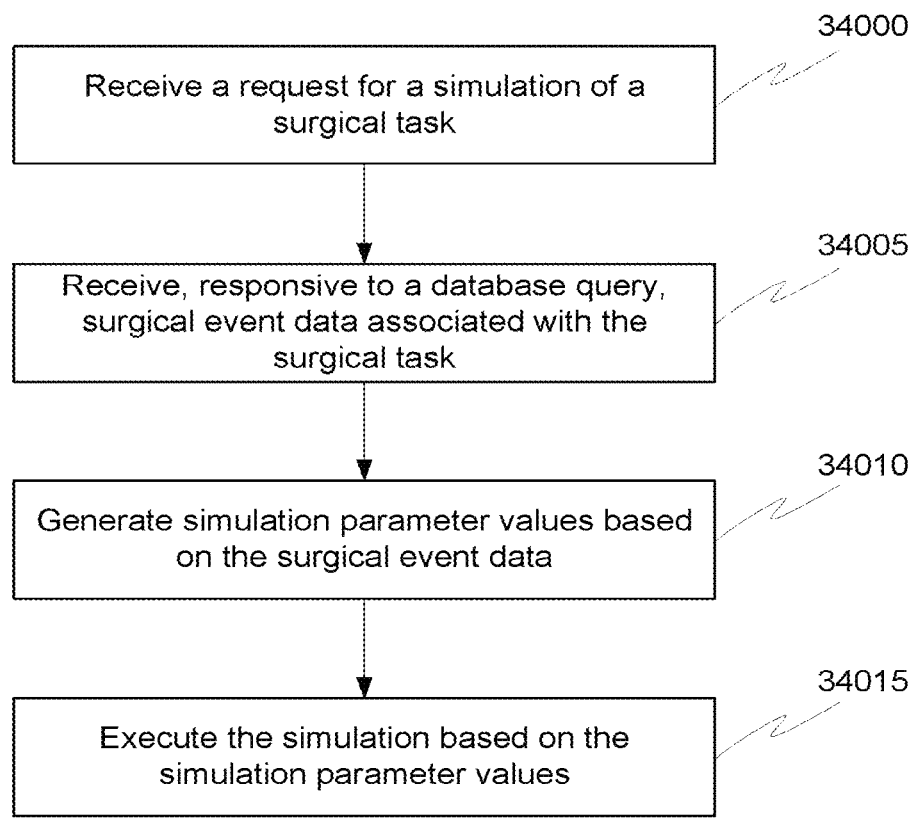
FIG. 43 shows example surgical task simulation with parameter values.

FIG. 43 shows example surgical task simulation with parameter values.

At 34000, a request for a simulation of a surgical task may be received. The request may be sent from a surgical data system as described with respect to FIG. 7 to a simulator, for example, that may execute the simulation. The simulator may include a core simulation module as described with respect to FIG. 7. The simulator may include one or more application modules as described with respect to FIG. 7.

The surgical task may comprise a medical procedure and a medical procedure context. In examples, the medical procedure may be a colorectal surgery. The medical procedure context may include information related to one or more qualities of the medical procedure. For example, the medical procedure context may include information related to one or more qualities of the colorectal surgery. For example, the medical context may include information that conveys the inferior mesenteric artery (IMA) is thin. In examples, the information may include the diameter of the IMA. The medical context may include information that conveys that the patient receiving the colorectal surgery is prone to an allergic response. The medical context may be determined by the object properties module as described with respect to FIG. 7. For example, the object properties module may be a module included in the simulator.

At 34005, surgical event data associated with the surgical task may be received. In examples, the surgical event data may be received responsive to a database query. For example, the simulator may query a database included in the surgical data system as described with respect to FIG. 7. In examples, the simulator may send a message including the medical procedure and/or the medical procedure context to a query module. In such a case, the query module may perform the query of the database.

The database may store information related to historical data associated with medical procedures and medical procedure contexts. For example, the historical data may be associated with colorectal surgery. The historical data may be associated with colorectal surgery, for example, when the IMA was thin. The historical data may be local data associated with medical facility. For example, the local data may be stored on a surgical hub of the medical facility. The local data may be based on medical procedures and medical procedure contexts that the medical staff of the medical facility experienced. For example, the medical staff may perform 50 colorectal surgeries in a year. Each colorectal surgery may comprise one or more respective qualities. Each colorectal surgery along with the respective qualities may be stored on the surgical hub associated with the medical facility.

The database may store information related to a consequence associated with the medical procedure and/or medical procedure context. For example, the medical procedure may be a colorectal surgery and the medical procedure context may be the pulmonary artery is thick. A consequence associated with the colorectal surgery when the pulmonary artery is thick may be a pulmonary artery tear. The pulmonary artery tear may be linked to the medical procedure and the medical procedure context. The consequence may be based on a historical data associated with medical procedures and/or medical procedure contexts. The consequence may be local data based on the medical procedures of a medical facility.

The database may return surgical event data based on the query. In examples, the surgical event data may be associated with the medical procedure and/or the medical procedure context. In examples, the surgical event data may be filtered based on the medical procedure and the medical procedure context. For example, the surgical event data may be associated with colorectal surgery when the pulmonary artery (PA) is thin. The surgical event data may include the consequence described herein. The surgical event data may be sent to a parameter value generator.

At 34010, one or more simulation parameter value may be generated. The simulation parameter value(s) may be generated based on the surgical event data. For example, the surgical event data may indicate that when the PA is thin during a colorectal surgery, the PA tends to tear when the surgeon applies a force to it. Simulation parameter values may be generated to represent the surgical event data.

At 34015, a simulation may be executed based on the simulation parameter values. In examples, the simulation parameter values may be sent to the simulator, for example, after the simulation parameter values are generated. A simulator may comprise a script with executable instructions. The simulator may execute the script, for example, when executing the simulation. The script may be configured with parameters and each parameter may comprise a parameter value. The simulator may set the parameters values with the generated simulation parameter values.

Update parameter values may be received. In examples, the update parameter values may be received by the simulator periodically. The update parameter values may be based on user interaction data. The update parameter values may be base on a physics modules as described with respect to FIG. 7.

Figure 44:
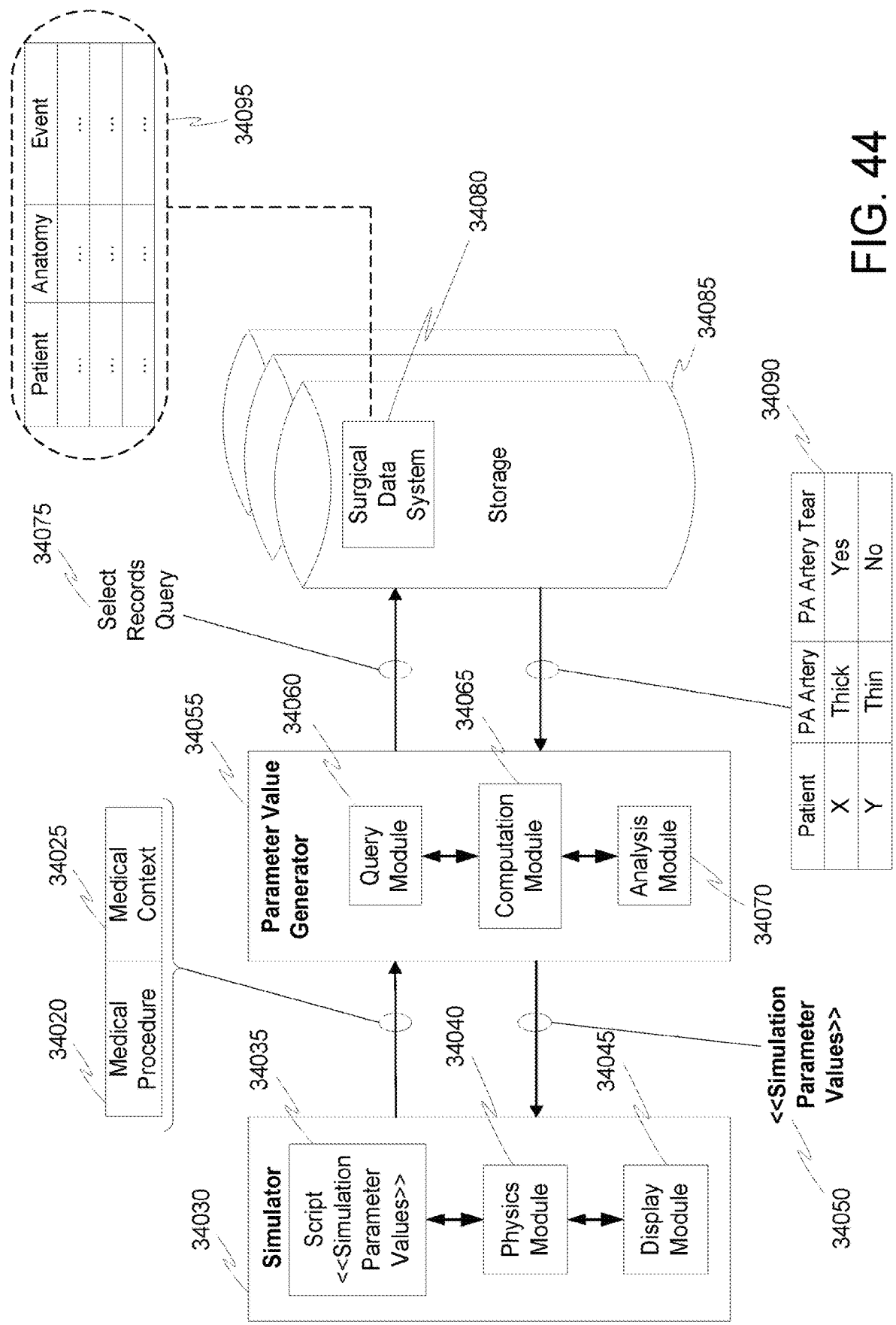
FIG. 44 shows an example layout of surgical task simulation with parameters values.

FIG. 44 shows an example layout of surgical task simulation with parameters values.

A simulator 34030 may include a script 34035 as described with respect to FIG. 43. The script 34035 may be configured with simulation parameters and each simulation parameter may comprise a simulation parameter value. The script 34035 may be in communication with a physics module 34040. The physics module 34040 may receive user interaction data from an input device. For example, the input device may be a robotic controller. A user may move the robotic controller and data related to the user's movement may be sent to the physics module 34040. The physics module 34040 may coordinate the user interaction data and send the user interaction data to the script 34035.

The physics module 34040 and the script 34035 may be in communication with a display module 34045. The display module 34045 may generate images to be used in a simulation environment. The images may represent the anatomy and/or physiology of the simulation environment. Update values may be sent from the physics module 34040 to the display module 34045 and the display module 34045 may generate images corresponding to the update values. The generated images may be used by the simulator 34030 to depict an updated simulated environment to the user. The display module 34045 may be in communication with the three-dimensional (3D) graphics pipeline as described with respect to FIG. 7. In examples, the display module 34045 may be an application module as described with respect to FIG. 7.

The simulator 34030 may send a message to a parameter value generator 34055. The message may comprise the medical procedure 34020 and the medical procedure context 34025 as described with respect to FIG. 43. The parameter value generator 34055 may comprise a query module 34060 as described with respect to FIG. 43. The query module 34060 may send a select records query 34075 to a storage 34085 that may include the surgical data system 34080 as described with respect to FIG. 7. The surgical data system 34080 may include a database that holds historical data associated with a medical procedure 34020 and a medical procedure context 34025. The surgical data system 34080 may analyze the select records query 34075 and may select one or more data entries from the database. The data entries may correspond to the medical procedure 34020 and the medical procedure context 34025. The storage 34085 may send a message that includes the data entries.

In examples, the message may be sent to a parameter value generator 34055. The parameter value generator 34055 may generate simulation parameter values 34050 as described with respect to FIG. 43. In examples, the parameter value generator 34055 may comprise a query module 34060, a computation module 34065, and an analysis module 34070. The modules may be in communication with each other. The parameter value generator 34055 may send the simulation parameter values 34050 to the simulator 34030. The simulator 34030 may set the script parameter values with the simulation parameter values 34050.

Procedure simulations with predefined obstacles, complication, approach issues, and/or critical event options for training in Laparoscopic, Open, and robotic surgeries (e.g., hybrid and full) may be provided.

Parameterized simulation for training having predefined complications and/or adverse events to enable recovery and procedure progress improvements may be provided. The simulation may comprise selectable predefined starting and/or anatomy aspects. The simulation may comprise adjustable complications for training people to encounter and overcome. The anatomy may be a summation of real-world surgical procedure datasets. The selectable and adjustable complications may be a summary or aggregation of aspects of other procedures. The aggregation of complications may result from compiled results and/or outcomes from a predefined dataset. —The predefined datasets may have been derived from an AI simulation, for example, to choose appropriate parameters. The adjustable parameters may allow the head of education to choose and/or adjust multiple key issues and complications.

Automated simulations to determine the best parameterized training simulator based on the experience level of the users may be provided. Simulator recordings and/or process scenarios completed may identify best practices, training needs and procedure development within the facility to improve outcomes, efficiency and/or how to respond to a new pandemic.

In examples, the recordings of the simulated scenarios may be used to identify best practices and/or gold standard approaches. Reviewing the multiple user inputs and patient differences, the inputs and outputs may be reviewed to identify how to get successful outcomes and/or facility efficiency to develop procedures and/or training needs. may be fed into a machine learning system that may identify the differences in the approaches and results. From the difference, the machine learning system may define the parameters that may be varied for training individuals of that level, for example. to improve results.

In examples. utilizing known inputs, multiple scenarios may be created simulating more variables and/or variation and optimal treatment to determine an effective treatment plan (e.g., patient placement such as face-up or face down while on a ventilator). The variations may be used to identify heavily impacting parameters that may become the training simulator's parameters to train new people in response to the variables.

Simulation of various robotic intervention approaches may include teleop, DaVinci, Verb, Hugo, CMR, OTTAVA, autonomous non-tissue affecting jobs (e.g., motion of circular stapler anvil to hed, for example, on circular IP MAP and/or cooperation of endoluminal scope to lap arm end-effector, for example, on endoluminal IP MAP), autonomous tissue affecting jobs (e.g., suturing and/or biopsy), or teleoperation readiness for autonomous subsequent steps. Teleoperation readiness for autonomous steps may include a simulation of procedural steps that precede autonomous jobs providing readiness for autonomous steps, for example, evaluation of teleoperative or manually controlled surgical jobs. An example may include mobilization of LAR descending colon and positioning of circular stapler anvil such that situation connection is ready and the simulation of the autonomous action (e.g., connecting the anvil to the circular stapler head) from the point of teleoperation. Teleoperation readiness for autonomous steps may include indication of obstacles in autonomous path. Teleoperation readiness for autonomous steps may include indication of state readiness for autonomous path.

A way to simulate unique clinical situations may be provided. For HCP institution, a way to manage tumor in growth to adjacent organs for oncology debulking maneuvers may be provided. The way to manage tumor in growth may be to provide information and a simulated pre-op review of what devices and imaging overlays are needed. The simulation may determine in what way to set up the procedure for the best approach.

The approach may be provided in a patient format for patient understanding and consultation and/or communication patient to care team. The approach may be linked to the DRG codes for institution reimbursement.

The simulation may comprise predefined adjustable parameters that may enable the person setting up the simulation to define the anatomy, disease type, irregularities, and/or micro-outcome responses, for example, as a means of configuring the simulation for the user to interact with.

Training may include general intra op robot control training, OR set up and workflow training, and/or emergency situation training (e.g., patient access with arms out of the way and/or robot enabled interventions such as arms in new positions, arms with docking of hemostat delivery device, hemostat clamp, or ligation device). The simulation may include procedure planning.

Simulation of where patient limbs are on table held supports in various anatomic positions, for example, where table supports can be robotic manipulated or in simulations may be provided. In examples, for arms, legs, and angles for ortho, the positions may be based on robotic arm holding that limb. Feedback of divergence from best or trained practice in limb positioning may be provided. Limb may be on non-robotic arm and tracked through IR and fiducials.

Adverse events simulation where the procedure may be setup to culminate in differing adverse events and may allow for the procedure suspended and the adverse events to be dealt with may be provided.

Emergency situation training may include patient access with arms out of the way. Emergency situation training may involve robot enabled interventions (e.g., arms in new positions, arms with docking of hemostat delivery device, hemostat clamp, or ligation device).

Adverse events simulation may include uncontrolled bleeding. Uncontrolled bleeding may result from a tear in the PA/PV transection jobs of a lobectomy. Steps needed to bring the patient to a stable state may be provided. Adverse events simulation may include malfunction of an instrument or jamming of the instrument on the patient.

Steps highlighting how to simulate recovery may be provided. The steps may include how to control hemorrhage, to reduce tension, anatomic presentation of where to have traction and counter traction to allow presentation of dissection planes, and/or position of other robotic or assist instruments to enable traction and counter traction. Steps highlighting what additional people are needed such as assistants may be provided. Steps highlighting what additional clinical checks to make (e.g., blood pressure, anesthesia checks, blood gas O2 saturation, etc.) may be provided.

The simulation may indicate an end of an event and follow-on checks to do. In examples, emergency situations and outside influencers may be indicated. An emergency situations may include an unplanned event that may disrupt the staff and/or environment if not adequately trained or prepared on how to properly react (e.g., power outage, fire, earthquake, hurricane/tornado, and or disgruntle employee or intruder abruption). The outside stressor may be used to train and/or prepare the staff for unforeseen environmental disruptions that may occur during a surgery and the reaction and/or response may limit available options. For example, during a surgery an adverse advent may occur (e.g., fire) and the staff may be trained to respond by immediately removing risk to any possible bleeding and may work to minimize contamination by addressing the sterile area and maintain patient safety.

Figure 45:
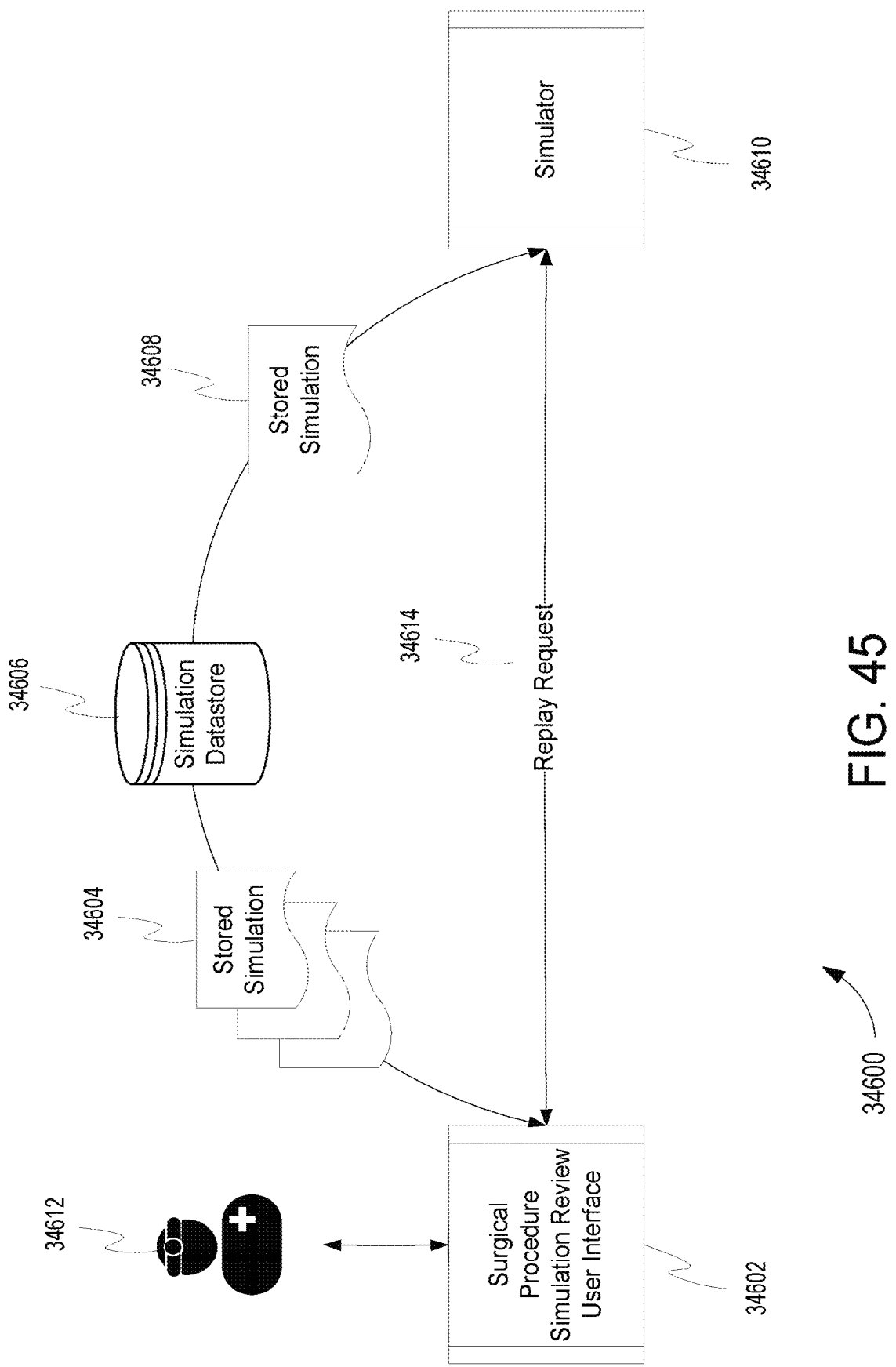
FIG. 45 is an example data flow of surgical procedure simulation review.

FIG. 45 is an example data flow 34600 of surgical procedure simulation review. The data flow 34600 may be performed by the simulation device 30000 (e.g., described in FIGS. 7 and 8). The data flow 34600 may be performed by the processor 30034 of the simulation device 30000.

A surgical procedure simulation review user interface 34602 may be used by a user 34612. The user 34612 may be a medical instructor or trainer, such as a surgeon. The user 34612 may be a medical trainee, such as a medical student or a resident.

The surgical procedure simulation review user interface 34602 may be used to review surgical procedure simulations that have been previously run. The user interface 34602 may retrieve summary information of one or more previous simulations for viewing (e.g., as further described in FIGS. 46 and 47A-B). The user interface 34602 may retrieve a previous simulation for replaying a part or all parts of the simulation. The summary information of a previous simulation may be configured to provide a choice to replay the simulation.

For example, the user interface 34602 may retrieve summary information of one or more stored simulations 34604 from a simulation datastore 34606 to display to the user 34612. The summary information of a stored simulation may include a summary of information regarding the simulation's surgical steps, surgical tasks within steps, surgical choices with surgical tasks. The summary information may include breakdown information and/or aggregated information. Further details are described in FIGS. 46 and 47A-B.

For example, a stored simulation displaying summary information may be configured to replay. In an example, when displaying summary information, a stored simulation 34068 in the one or more stored simulations 34604 may provide a choice (e.g., a link or a button) to replay the simulation. In response to the user's 34612 selection to replay the simulation, the surgical procedure simulation review user interface 34602 may send a replay request 34614 to a simulator 34610. In response, the simulator 34610 may retrieve a complete dataset of the stored simulation 34608 from the simulation datastore 34606 to replay (e.g., in a visualization module). For example, a stored simulation displaying summary information may be configured to replay a part of the simulation, such as one surgical step of a simulated surgical procedure. In such case, the simulator 34610 may retrieve one surgical step of the simulated surgical procedure to replay.

FIG. 46 is an example output 34650 of an example surgical procedure simulation review user interface. The example output 34650 may be generated by the simulation device 30000 (e.g., described in FIGS. 7 and 8). The example output 34650 may be generated by the processor 30034 of the simulation device 30000.

The example output 34650 may be an example output of a surgical procedure simulation review user interface 34602. The example output 34650 presents summary information of two simulated sigmoid colectomy procedures, simulated sigmoid colectomy 1 and simulated sigmoid colectomy 2. The two simulated sigmoid colectomy procedures may have been simulated with the same simulation configurations, including the simulation configurations for the simulated patient. Each of the two simulated sigmoid colectomy procedures presents summary information for surgical steps initiate 34652, access 34654, mobilize colon 34656, resect sigmoid 34658, perform anastomosis 34660, and conclude 34662. Each surgical step presents summary information of surgical tasks, including surgical choices, surgical outcomes and how surgical choices relate to surgical outcomes.

A surgical step "initiate" 34652 may include summary information for surgical tasks: make incisions and trocar placement. For simulated sigmoid colectomy 1, the "make incisions" surgical task for a laparoscope's trocar port presents an incision location of umbilicus, an incision length of 12 mm, an incision time duration of two minutes and one second, information that the incision time duration is 15 seconds above an aggregated data point generated by the user interface 34602, namely, the average incision time duration of the two simulated sigmoid colectomies. In comparison, for simulated sigmoid colectomy 2, "make incisions" surgical task for a laparoscope's trocar port presents an incision location of umbilicus, an incision length of 12 mm, an incision time duration of one minutes and 31 seconds, information that the incision time duration is 15 seconds below the average incision time duration of the two simulated sigmoid colectomies.

For simulated sigmoid colectomy 1, the "make incisions" surgical task for a grasper's trocar port presents an incision location of upper right quadrant of abdomen, an incision length of 5 mm, an incision time duration of one minute and one second, information that the incision time duration is eight seconds above the average incision time duration of the two simulated sigmoid colectomies. In comparison, for simulated sigmoid colectomy 2, "make incisions" surgical task for a laparoscope's trocar port presents an incision location of upper midline, an incision length of 5 mm, an incision time duration of 45 seconds, information that the incision time duration is 8 seconds below the average incision time duration of the two simulated sigmoid colectomies.

For simulated sigmoid colectomy 1, the "make incisions" surgical task for a harmonic device's trocar port presents an incision location of lower right quadrant of abdomen, an incision length of 12 mm, an incision time duration of one minute and 46 seconds, information that the incision time duration is eight seconds above the average incision time duration of the two simulated sigmoid colectomies. In comparison, for simulated sigmoid colectomy 2, "make incisions" surgical task for a harmonic device's trocar port presents an incision location of lower right quadrant of abdomen, an incision length of 12 mm, an incision time duration of one minute and 30 seconds, information that the incision time duration is 8 seconds below the average incision time duration of the two simulated sigmoid colectomies.

As shown, a replay option 34672 may be provided for the "make incisions" surgical tasks in the surgical step "initiate" 34652 of simulated sigmoid colectomy 1. When selected, the replay option 34672 may replay the simulation of the surgical step in a simulator (e.g., the simulator 34610 as described in FIG. 45). A replay option such as the replay option 34672 may be provided for any surgical step, any surgical task in a surgical step, and/or for an entire simulated surgical procedure.

A replay option 34674 for the "make incisions" surgical tasks in the surgical step "initiate" 34652 of simulated sigmoid colectomy 2 may be provided. The replay option 34674 may operate similarly to the replay option 34672 as described.

A surgical step "access" 34654 may include summary information for surgical tasks: dissect mesentery, identify inferior mesenteric artery (IMA) branches, and identify ureter. The surgical step access 34654 may be completed without performing surgical task "identify IMA branches" or surgical task "identify ureter". Not performing a surgical task as such may be interpreted as a surgical choice (e.g., an implicit surgical choice). In such case, surgical complications, such as bleeding or damaged ureter, may result.

As shown, for simulated sigmoid colectomy 1, the surgical task "dissect mesentery" presents a total dissection time duration of 38 minutes and 1 second and information that the dissection time duration is eight minutes and 49 seconds above the average dissection time duration of the two simulated sigmoid colectomies. In comparison, for simulated sigmoid colectomy 2, the surgical task "dissect mesentery" presents a total dissection time duration of 20 minutes and 23 seconds and information that the dissection time duration is eight minutes and 49 seconds below the average dissection time duration of the two simulated sigmoid colectomies.

As shown, "medial-to-lateral" is a surgical choice for the dissection direction of the surgical task "dissect mesentery" for simulated sigmoid colectomy 1 and simulated sigmoid colectomy 2.

As shown, surgical task "identify IMA branches" was performed for simulated sigmoid colectomy 1 and was not performed for simulated sigmoid colectomy 2. A causal relationship between surgical task "identify IMA branches" and corresponding surgical outcomes is illustrated. A causal relationship arrow originates from a surgical choice of IMA branches being identified and ends at a surgical outcome of no complications. In comparison, a causal relationship arrow originates from a surgical choice of IMA branches not being identified and ends at a surgical outcome of a surgical complication of moderate bleeding. Further details of how causal relationships such as these may be determined are illustrated in FIGS. 47A and 47B.

As shown, surgical task "identify ureter" was performed for simulated sigmoid colectomy 1 and simulated sigmoid colectomy 2. A causal relationship between surgical task "identify ureter" and corresponding surgical outcome for simulated sigmoid colectomy 1 is illustrated. A causal relationship arrow originates from a surgical choice of identifying ureter and ends at a surgical outcome of no complications. Further details of how causal relationships such as these may be determined are illustrated in FIGS. 47A and 47B.

A surgical step "mobilize colon" 34656 may include summary information for surgical tasks: ligate IMA, mobilize upper sigmoid, mobilize descending colon, and mobilize rectum and sigmoid.

As shown, for simulated sigmoid colectomy 1, the surgical task "ligate IMA" presents a total ligation time duration of 6 minutes and 31 second and information that the ligation time duration is 39 seconds above the average IMA ligation time duration of the two simulated sigmoid colectomies. In comparison, for simulated sigmoid colectomy 2, the surgical task "ligate IMA" presents a total ligation time duration of five minutes and twelve seconds and information that the dissection time duration is 39 seconds below the average IMA ligation time duration of the two simulated sigmoid colectomies.

As shown, surgical choices of order in which IMA was ligated are different between simulated sigmoid colectomy 1 and simulated sigmoid colectomy 2. For example, IMA branches were ligated before the IMA root in simulated sigmoid colectomy 1. In comparison, the IMA root was ligated before the IMA branches in simulated sigmoid colectomy 2. A causal relationship between IMA ligation surgical choice "branches before root" and a corresponding surgical outcome is illustrated. A causal relationship arrow originates from the "branches before root" surgical choice and ends at a surgical outcome of no surgical complications and minimum bleeding. Similarly, a causal relationship between IMA ligation surgical choice "root before branches" and a corresponding surgical outcome is illustrated. A causal relationship arrow originates from the "root before branches" surgical choice and ends at a surgical outcome of some complications and moderate bleeding. Further details of how causal relationships such as these may be determined are illustrated in FIGS. 47A and 47B.

A surgical step "resect sigmoid" 34658 may include similar summary information for surgical tasks: transect bowel, remove sigmoid, and set anvil for circular stapler. A surgical step "perform anastomosis" 34660 may include similar summary information for surgical tasks: prepare rectum, insert circular stapler, align anvil with rectum, attach anvil to circular stapler, and fire circular stapler. A surgical step "conclude" 34662 may include similar summary information for surgical tasks: inflate colon, check for leaks, remove trocars, and close incisions.

FIGS. 47A and 47B illustrate an example implementation of an aspect of a surgical procedure simulation review. The example implementation may be performed by the simulation device 30000 (e.g., described in FIGS. 7 and 8). The example implementation may be performed by the processor 30034 of the simulation device 30000.

As described in FIG. 46, a causal relationship between a surgical choice and a corresponding surgical outcome may be determined from a plurality of simulated surgical procedures. For example, as shown in FIG. 46, a causal relationship between IMA ligation surgical choice "branches before root" and corresponding absence of bleeding complication may be determined, e.g., from a plurality of simulated sigmoid colectomy procedures, such as those configured with the same simulation configurations. A causal relationship between IMA ligation surgical choice "root before branches" and a corresponding bleeding complication may be determined, e.g., from a plurality of simulated sigmoid colectomy procedures, such as those configured with the same simulation configurations.

FIGS. 47A and 47B demonstrate an example analysis method using multiple linear regression for determining such causal relationships. As shown in FIG. 47A, input data for the analysis are two independent variables 34702 "IMA ligation root v. branch order" and "IMA ligation branches order" and a target variable 34704 "bleeding amount". Independent variable "IMA ligation root v. branch order" represents a surgical choice selection point at which different surgical choices may be selected. Examples of surgical choices at the surgical choice selection point may include "root before branches" and "branches before root". Independent variable "IMA ligation branches order" represents a second surgical choice selection point. Examples of surgical choices at the surgical choice selection point may include "thinnest to thickest", "thickest to thinnest", and "other".

Target variable "bleeding amount" represents a surgical outcome corresponding to the "IMA ligation root v. branch order" surgical choice selection point and/or "IMA ligation branches order" surgical choice selection point. Examples of the surgical outcome may include "minimum", "moderate", and "severe". A surgical outcome of "moderate" or "severe" may be interpreted as a surgical complication.

Values in the independent variables columns 34702 and target variable column 34704 are in text format here for the ease of description. The values have their corresponding numeric values under the multiple linear regression analysis method. For example, "root before branches" may be a value of 1 and "branches before root" may be a value of 0. For example, "thinnest to thickest" may be a value of 1, "thickest to thinnest" may be a value of 0, and "other" may be a value of 2. For example, "minimum" may be a value of 0.1, moderate may be a value of 5, "severe" may be a value of 20.

As shown in FIG. 47B, example output data for the example analysis using the multiple linear regression analysis method are coefficients and p-value for the independent variables 34702 "IMA ligation root v. branch order" and "IMA ligation branches order". A value of 3.45 indicates that with one unit increase in "IMA ligation root v. branch order" there is 3.45 times increase in "bleeding amount". Consistent with the coefficient value 3.45, p-value for independent variable "IMA ligation root v. branch order" is 0.01, which is a value less than 0.05. The coefficient value and the p-value indicate independent variable "IMA ligation root v. branch order" is an important factor in predicting target variable "bleeding amount". Hence, a causal relationship is determined to be present between the two variables.

A coefficient value of 0.14 for "IMA ligation branches order" indicates that with one unit increase in "IMA ligation branches order" there is 0.14 times increase in "bleeding amount". Consistent with the coefficient value 0.14, p-value for independent variable "IMA ligation branches order" is 0.64, which is a value greater than 0.05. The coefficient value and the p-value indicate independent variable "IMA ligation branches order" is not an important factor in predicting target value "bleeding amount". Hence, a causal relationship is determined to be not present between the two variables.

Figure 48:
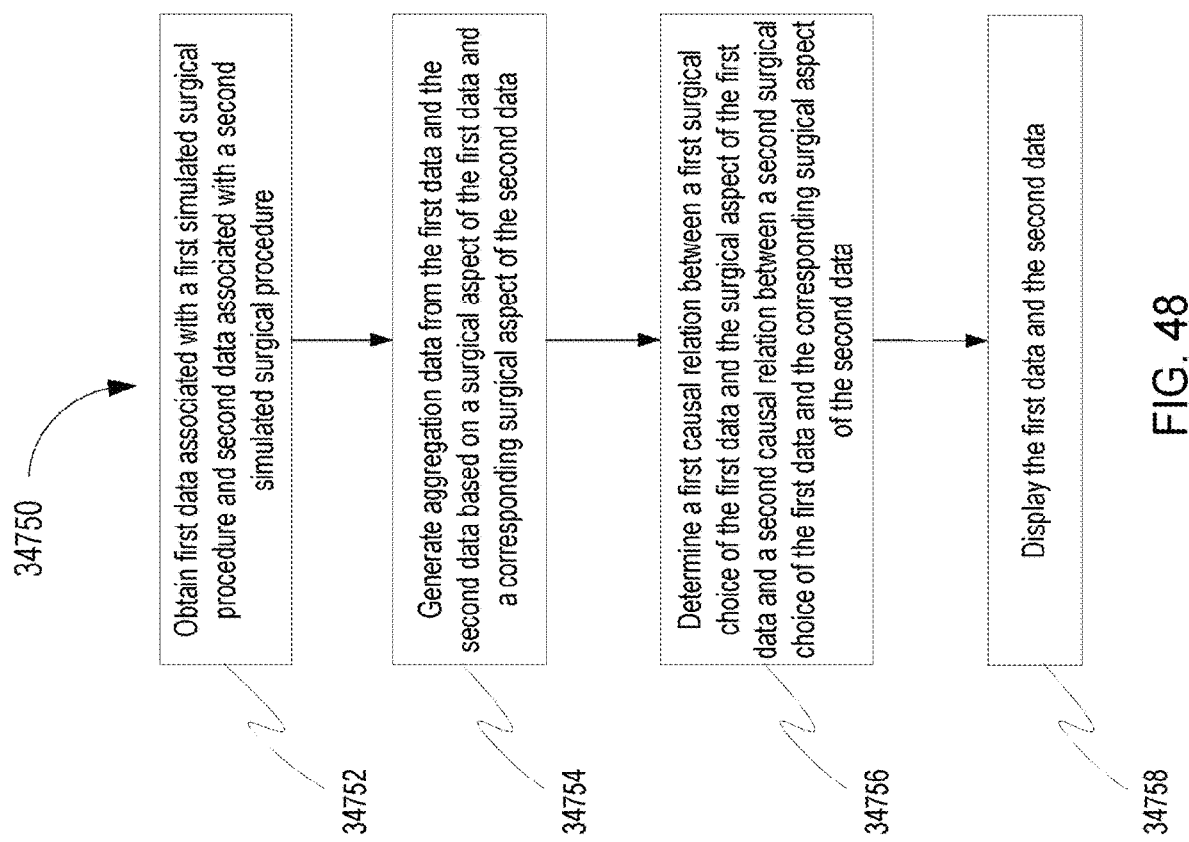
FIG. 48 is a flow chart of an example operation of surgical procedure simulation review.

FIG. 48 is a flow chart 34750 of an example operation of surgical procedure simulation review. For example, the example operation may include a process to obtain stored simulation data for data aggregation. The process may determine causal relationship(s) between surgical choices(s) and corresponding surgical aspect(s).

At 34752, first data associated with a first simulated surgical procedure and second data associated with a second simulated surgical procedure may be obtained. The first simulated surgical procedure and the second simulated surgical procedure may simulate a surgical procedure. The first data and second data may be associated with a surgical task of the surgical procedure. For example, the first simulated surgical procedure and the second simulated surgical procedure may be configured with a same simulation configuration or a same set of simulation configurations. For example, the first simulated surgical procedure may be a user-simulated procedure and the second simulated surgical procedure may be a computer-simulated procedure.

At 34752, aggregation data from the first data and the second data may be generated based on a surgical aspect of the first data and a corresponding surgical aspect of the second data. For example, the surgical aspect may be associated with one of the following: a time duration of a surgical task, a surgical instrument usage, a surgical outcome, or a surgical complication. For example, the surgical aspect of the first data may include a first numeric value and the corresponding surgical aspect of the second data may include a second numeric value. In such case, the process may display the aggregation data.

At 34756, a first causal relation between a first surgical choice of the first data and the surgical aspect of the first data and a second causal relation between a second surgical choice of the first data and the corresponding surgical aspect of the second data may be determined from the aggregation data. For example, the first surgical choice of the first data may be a first selection from a plurality of surgical choices of a surgical choice selection point. The second surgical choice of the second data may be a second selection from the plurality of surgical choices of the surgical choice selection point. The surgical choice selection point may be a part of the surgical task. The surgical aspect of the first data may include a surgical complication. The corresponding surgical aspect of the second data may not include the surgical complication.

At 34758, the first data and the second data may be displayed.

For example, a request to replay a simulation of the first surgical choice of the first data and the surgical aspect of the first data may be received. The surgical aspect of the first data may include a surgical outcome or a surgical complication. a visualization of the simulation of the first surgical choice of the first data and the surgical aspect of the first data may be generated.

For example, a request to simulate the plurality of surgical choices of the surgical choice selection point in the first surgical procedure may be received. A visualization of the plurality of surgical choices of the surgical choice selection point in the first surgical procedure may be generated.

A surgical analysis system may present a summary and/or an overview of multiple simulations to identify differences, impacts, and/or key impacts.

The surgical analysis system may provide an overview interface. The overview interface may aggregate multiple simulations, e.g., regarding reactions, usage and/or outcomes. The overview interface may contrast the multiple simulations, e.g., regarding reactions, usage and outcomes. The surgical analysis system may be capable of compiling the reactions, complications, and/or outcomes of a simulation dataset. The surgical analysis system may be capable of aggregating the reactions, complications, and/or outcomes of the simulation dataset. The multiple simulations may be simulations run by a same user, different users, and/or a computer. Key learned or instruction sets may be an aggregation of specific local reactions for specific events and/or key events. The key learned or instruction sets may be overlaid to show best practices or key generated views from a teacher or instructor.

Multiple simulation users (e.g., residents) may practice on a simulator set up the same way (e.g., for training purposes). The summary may be used as a means to debrief how each person did and/or the pluses and/or minuses of what each person did and/or the minor differences resulted from the pluses and minuses. A group or class of simulation users (e.g., students) may interact with the simulation set up in the same or similar way. Aggregation of each of their approaches, instrument usage, step-of-use, outcomes, and complications may be shown side by side for a debrief of what works and what challenges they faced. For example, in teaching hospitals, summary and overview may include input from teaching staff, e.g., chief residency training surgeon or clinical specialty chairs. The resulted differences may include approach, time per task, details of the instrument usage and techniques, outcomes, cost, staff efficiency, or robot or alternative equipment positioning and usage, etc.

Figure 49:
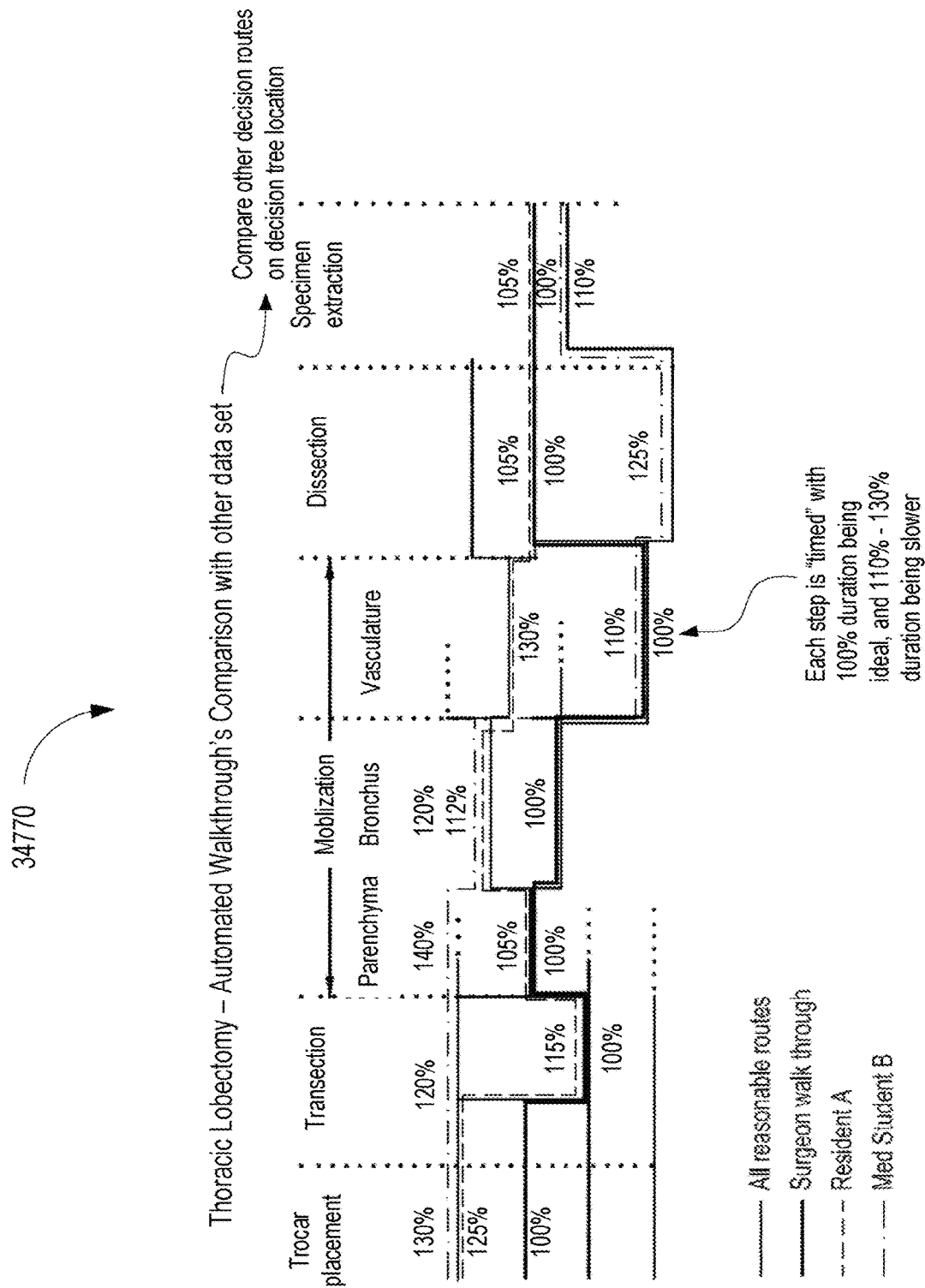
FIG. 49 illustrates comparisons of timings for a plurality of simulation walkthroughs for a thoracic lobotomy surgical procedure.

The surgical analysis system may perform automated walkthroughs of simulations. The automated simulation walkthroughs may be compared to a surgeon walkthrough or other single dataset to give a procedure planning surgeon options at different decision tree locations. The surgeon planned and simulated procedure may be displayed side-to-side, e.g., in an ethnographic layout format to allow the surgeon to compare his or her choices with other options from best practices, alternative approaches, and/or anticipated complications. This decision tree may allow the surgeon to choose between different options at different points in the procedure plan. The surgeon's choice may be fed back into the simulation for hands-on interaction to practice and/or visualize the adjustments and/or options for the plan. FIG. 49 is an illustration 34770 of comparisons of timings for a plurality of simulation walkthroughs for a thoracic lobotomy surgical procedure.

The surgical analysis system may allow a user to see options at each decision point and expand out options and outcomes from each choice (e.g., similar to a gaming scenario review). Each step may be zoomed in on and allow a user (e.g., a surgeon) see and visualize each of multiple possible steps resulting from the zoomed-in-on event. The user may cascade them out from that choice, and see multiple steps in the future and what results and complications each choice dictates. The surgical analysis system may provide summation and outcomes review. The surgical analysis system may provide feedback to AI algorithm(s).

The surgical analysis system may detect and highlight possible adverse events via simulations (e.g., for training a simulation user to learn to avoid such events in a real surgical procedure). Following each step, the surgical analysis system may provide simulation of what adverse event(s) may look like, such as pulmonary vein rupture due to dissection pressure; roux limb tension; colon anastomotic tension; or ureter damage during dissection. The simulation by the surgical analysis system may obtain CSATS actual video(s) to augment the simulation. The simulation by the surgical analysis system may obtain simulation data from stored simulations (e.g., pure simulation). Examples of adverse events may be bleeding or weeping, air leaks, tissue tension resulting in restricted blood flow, damage to a adjacent critical structure like a ureter or nerve, collateral thermal damage from energy devices, incomplete or excessive ablation, etc.

The simulation may be a multi-person simulation. Multi-person digital simulation may enable multiple healthcare professionals (HCP) to interact with a same simulated patient in a same surgical procedure simultaneously. The multi-person digital simulation may develop the needed interactive rapport to assist in highly complex procedures.

Digital simulation may be a tool that could be used to teach, train or practice surgery that may provide real-life visualization, responses and feedback without the risk to people. Having the entire OR staff in a multi-person virtual reality condition may add the interactions, errors and other unknowns that may occur during a real surgical procedure to provide more realistic environment.

For example, a scrub nurse may assist surgeons directly and may be actively involved in the operation. Multi-person VR may simulate instrument hand offs, scenarios of handing wrong instrument, or defective instruments to train for reactions of team and/or prepare the nurse for unplanned scenario. Such simulation may prepare the team of possible outcomes so everyone is trained and/or prepared to react as opposed to the surgeon having to direct and/or communicate to everyone, which may distract him from the patient. Such simulation may train the nurse to know when to pass equipment and/or when to monitor certain patient conditions, which may improve efficiency and minimize distractions from the patient.

For example, a circulating nurse may ensure that operating rooms are sterilized and that they remain sterile during procedures. Multi-person VR may simulate unsterile conditions, when to open sterile packaging, or when equipment may be needed in the sterile field. Such simulation may provide preparation and knowledge to timing of needs to minimize time within the OR. Such simulation may train the circulating nurse on when to open packaging and/or move equipment with the least disruption to cause contamination to the surgical site, e.g., not to open or move when the door is open or about to be open, and/or when people are actively moving in the OR.

For example, a surgeon and an anesthesiologist may be key players in the operating room (OR), aiming for a common goal, e.g., safety and good outcome for patient. Behind the mask, they may not read each other's minds. Training scenarios may keep each other informed of actions impacting their responses to the patient. The surgeon-anesthesiologist relationship may lead to interventions that may improve the relationship and may have the effect of increasing patient safety and the quality of perioperative care.

Multi-person digital simulation may be used to retrain a surgeon and/or staff to learn new and/or different methods. Most surgeons may continue to operate and use the tools based on their training or teacher, e.g., typically, they may continue this approach throughout their career because they may be able to focus on the operation without having to worry and/or think about the task at hand, e.g., the device in their hand, location or energy activation or firing. It may become instinctive to the surgeon so not to distract. As technology advances, gold standards may be set for a facility and/or procedure, or method within each facility may be different. Multi-person digital simulation may be a method for the surgeon/staff to be retrained in order to feel comfortable before going into a real-life scenarios. The simulation may baseline different techniques and/or practice until the efficiency requirements were met.

Figure 50:
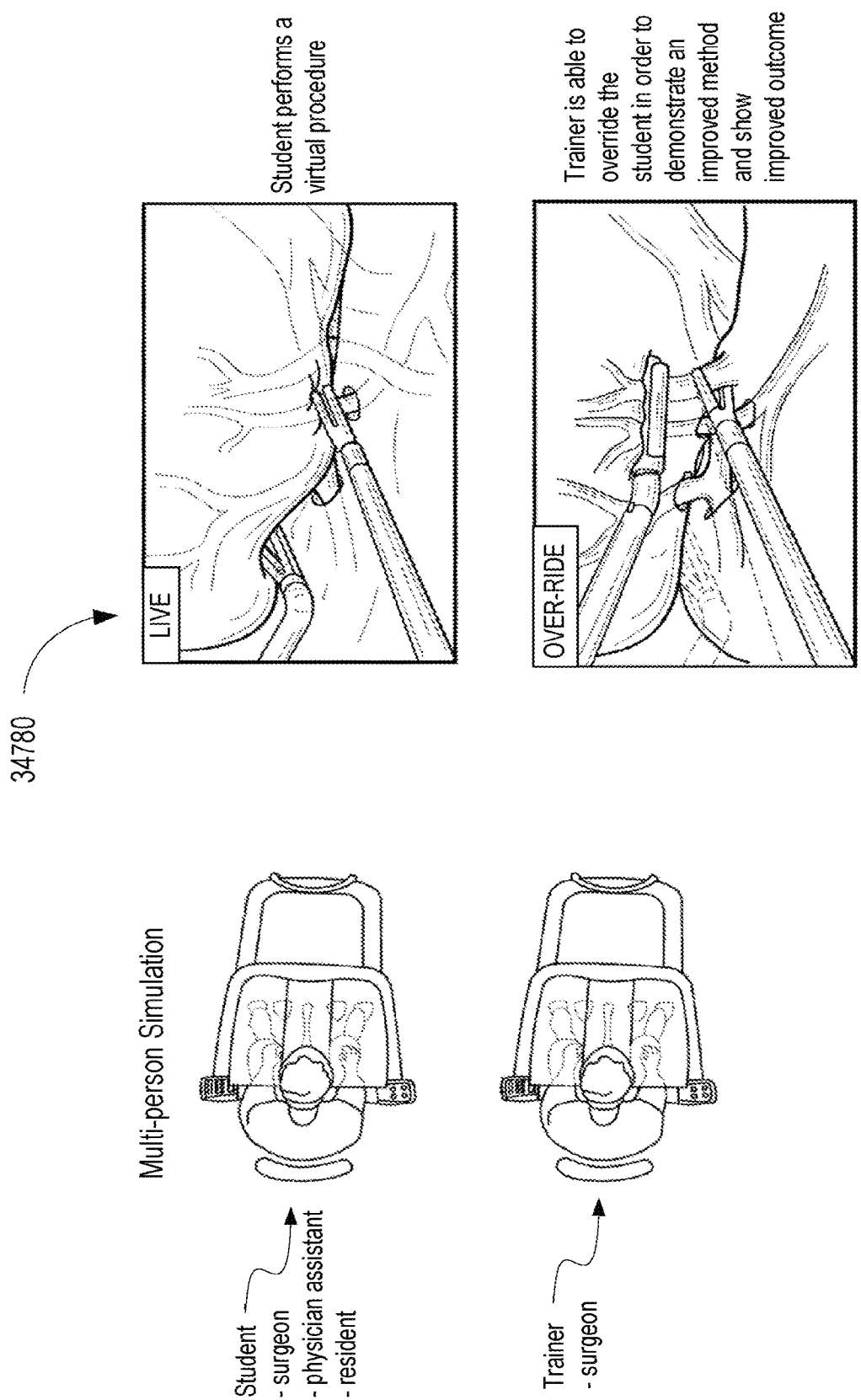
FIG. 50 is an illustration of a physician and the physician assistant working cooperatively within a simulation to achieve a result together.

FIG. 50 is an illustration 34780 of a physician and a physician assistant working cooperatively within a simulation to achieve a result together.

A simulator (e.g., a simulator for training) may indicate to a user with a score and/or a reward system to drive competition, drive individual development/improvement, and/or require a defined score in order to certify or allow an individual to perform actions within the facility. For example, the score may be used to provide the user an understanding of how well the user did in order to baseline against others or drive development to improve in defined areas. For example, the score may provide the facility the confidence and/or indication that the user was properly trained to perform the actions prior to a real event. For example, the facility may use the score as a reward system to train and/or develop its staff members, e.g., high score and/or certain levels. For example, the facility may use the score to provide justification and/or confirmation that the staff/individual was properly trained for legal issues or litigation. The score may be related to a key task that is being trained, efficiency, value, outcomes, etc., The score may be used to reinforce good behavior and/or reduce variation.

The following non-exhaustive list of embodiments also forms part of the present disclosure.

Embodiment 2.1. A computing device, the computing device comprising:
  a processor configured to:
   receive first two-dimensional (2D) image data of a first human organ, wherein the first 2D image data comprises first 2D visible image data captured inside a first patient and first three-dimension (3D) reconstruction reference data;
   receive second 2D image data of a second human organ, wherein the second 2D image data comprises second 2D visible image data captured inside a second patient and second 3D reconstruction reference data;
   generate 3D image data from an aggregation of the first 2D visible image data and the second 2D visible image data and based on the first 3D reconstruction reference data and the second 3D reconstruction reference data, wherein the 3D image data comprises spatial information and visual information;
   map a shape of a deformable 3D model of a human organ to correspond to the spatial information of the 3D image data;
   map a surface of the deformable 3D model of the human organ to correspond to the visual information of the 3D image data; and
   output the deformable 3D model.

It may be understood that a "deformable 3D model" can refer to any volumetric model which comprises a plurality of spatial data points (such as a model of a human organ which is rendered in 3D). This allows the model to be easily "deformed" (or interacted with, so as to change the shape/size of the model), through the modification of the spatial data points in the model.

It may also be understood that "mapping" a shape/surface of a first model refers to modifying the shape/surface of the first model based on a separate 3D model (i.e. 3D image data). It may include using a point-to-point mapping, whereby each point on the model can be adjusted to minimize a difference to the separate 3D model (in this case, the 3D image data which has been generated).

One technical effect of this embodiment is that the accuracy of both the shape and the surface detail on a 3D model can be improved, through the capture and processing of 2D images.

Embodiment 2.2. The computing device of embodiment 2.1, wherein the processor is configured to simulate a surgical procedure.

Embodiment 2.3. The computing device of any one embodiments 2.1 to 2.2, wherein the 3D model of a human organ is a 3D model of a simulated human organ.

Embodiment 2.4. The computing device of any one of embodiments 2.1 to 2.3, wherein the first human organ and the second human organ are a same type of human organ.

Embodiment 2.5. The computing device of any one of embodiments 2.1 to 2.4, where the first patient is the same as the second patient.

Embodiment 2.6. The computing device of any one of embodiments 2.1 to 2.5, wherein the 2D image data is captured using structured light imaging.

Embodiment 2.7. The computing device of any one of embodiments 2.1 to 2.6, wherein the processor is further configured to:
receive tissue property data of the one or more human organs, wherein the tissue property data is determined at least by tracking a displacement of a physical fiducial marker attached on the one or more human organs; and
when a simulated force is applied to the deformable 3D model, deform the deformable 3D model based on the physical property data.

Embodiment 2.8. The computing device of any one of embodiments 2.1 to 2.7, wherein the first 2D image data further comprises first invisible image data that is captured inside the first patient, wherein the second 2D image data further comprises second invisible image data that is captured inside the second patient, wherein the processor is further configured to generate the 3D image data from the aggregation of the first visible image data and the second visible image data, based on the first reference and the second reference, and based on the first invisible image data and the second invisible image data, wherein the 3D image data further comprises non-visual information, and wherein the processor is further configured to generate sub-surface data of the deformable 3D model of the human organ based on the non-visual information of the 3D image data.

Embodiment 2.9. The computing device of any one of embodiments 2.1 to 2.8, wherein the processor is further configured to:
receive patient specific data; and
map the surface of the deformable 3D model of the human organ to correspond to the visual information of the 3D image data and the patient specific data.

Embodiment 2.10. A computing device of any one of embodiments 2.2 to 2.9, when dependent on embodiment 2.2, wherein the processor is further configured to:
define an expected aspect of the simulated surgical procedure, wherein the expected aspect is one of a surgical step, a job that is a part of the surgical step, a location in a surgical scene, or a surgical instrument;
monitor an input data, from a user, to the simulated surgical procedure; and
when the input data is determined to correspond to the expected aspect, present a relevant instruction to the user.

Embodiment 2.11. The computing device of any one of embodiments 2.2 to 2.9, when dependent on embodiment 2.2, wherein the processor is further configured to:
define an expected aspect of the simulated surgical procedure, wherein the expected aspect is one of a surgical step, a job that is a part of the surgical step, a location in a surgical site, or a surgical instrument;
monitor an input data, from a user, to the simulated surgical procedure; and
when the input data is determined to correspond to the expected aspect, present to an instructor a choice of initiating an instructive interaction with the user.

Embodiment 2.12. A computing device of any one of embodiments 2.2 to 2.9, when dependent on embodiment 2.2, wherein the processor is further configured to:
define an expected surgical step of the simulated surgical procedure;
monitor an input data to the simulated surgical procedure from a user; and
when the input data is determined to correspond to the expected surgical step, presents to the user a choice of viewing a corresponding segment of one or more actual surgical procedure videos, wherein the one or more actual surgical procedure videos comprise segments that are indexed on surgical steps.

Embodiment 2.13. A computing device of embodiment 2.12, wherein the choice of viewing the corresponding segment of the one or more actual surgical procedure videos may be further customized by a surgical complication or a surgical outcome.

Embodiment 2.14. A computer-implemented method, the computing-implemented method comprising:
receiving first two-dimensional (2D) image data of a first human organ, wherein the first 2D image data comprises first 2D visible image data captured inside a first patient and first three-dimension (3D) reconstruction reference data;
receiving second 2D image data of a second human organ, wherein the second 2D image data comprises second 2D visible image data captured inside a second patient and second 3D reconstruction reference data;
generating 3D image data from an aggregation of the first 2D visible image data and the second 2D visible image data and based on the first 3D reconstruction reference data and the second 3D reconstruction reference data, wherein the 3D image data comprises spatial information and visual information;
mapping a shape of a deformable 3D model of a human organ to correspond to the spatial information of the 3D image data;
mapping a surface of the deformable 3D model of the human organ to correspond to the visual information of the 3D image data; and
outputting the deformable 3D model.

Embodiment 2.15. The computer-implemented method of embodiment 2.14, wherein the 3D model of a human organ is a 3D model of a simulated human organ.

Embodiment 2.16. The computer-implemented method of any one of embodiments 2.14 to 2.15, wherein the first human organ and the second human organ are a same type of human organ.

Embodiment 2.17. The computer-implemented method of any one of embodiments 2.14 to 2.16, where the first patient is the same as the second patient.

Embodiment 2.18. The computer-implemented method of any one of embodiments 2.14 to 2.17, wherein the 2D image data is captured using structured light imaging.

Embodiment 2.19. The computer-implemented method of any one of embodiments 2.14 to 2.18 further comprising:
receiving tissue property data of the one or more human organs, wherein the tissue property data is determined at least by tracking a displacement of a physical fiducial marker attached on the one or more human organs; and
when a simulated force is applied to the deformable 3D model, deforming the deformable 3D model based on the physical property data.

Embodiment 2.20. The computer-implemented method of any one of embodiments 2.14 to 2.19, wherein the first 2D image data further comprises first invisible image data that is captured inside the first patient, wherein the second 2D image data further comprises second invisible image data that is captured inside the second patient, wherein the processor is further configured to generate the 3D image data from the aggregation of the first visible image data and the second visible image data, based on the first reference and the second reference, and based on the first invisible image data and the second invisible image data, wherein the 3D image data further comprises non-visual information, and wherein the processor is further configured to generate sub-surface data of the deformable 3D model of the human organ based on the non-visual information of the 3D image data.

Embodiment 2.21. The computer-implemented method of any one of embodiments 2.14 to 2.20, wherein the processor is further configured to:
  receiving patient specific data; and
  mapping the surface of the deformable 3D model of the human organ to correspond to the visual information of the 3D image data and the patient specific data.

Embodiment 2.22. The computer-implemented method of any one of embodiments 2.14 to 2.21, further comprising:
  defining an expected aspect of the simulated surgical procedure, wherein the expected aspect is one of a surgical step, a job that is a part of the surgical step, a location in a surgical scene, or a surgical instrument;
  monitoring an input data, from a user, to the simulated surgical procedure; and
  when the input data is determined to correspond to the expected aspect, presenting a relevant instruction to the user.

Embodiment 2.23. The computer-implemented method of any one of embodiments 2.14 to 2.22, further comprising:
  defining an expected aspect of the simulated surgical procedure, wherein the expected aspect is one of a surgical step, a job that is a part of the surgical step, a location in a surgical site, or a surgical instrument;
  monitoring an input data, from a user, to the simulated surgical procedure; and
  when the input data is determined to correspond to the expected aspect, presenting to an instructor a choice of initiating an instructive interaction with the user.

Embodiment 2.24. The computer-implemented method of any one of embodiments 2.14 to 2.23, wherein the processor is further configured to:
  defining an expected surgical step of the simulated surgical procedure;
  monitoring an input data to the simulated surgical procedure from a user; and
  when the input data is determined to correspond to the expected surgical step, presenting to the user a choice of viewing a corresponding segment of one or more actual surgical procedure videos, wherein the one or more actual surgical procedure videos comprise segments that are indexed on surgical steps.

Embodiment 2.25. The computer-implemented method of embodiment 2.24, wherein the choice of viewing the corresponding segment of the one or more actual surgical procedure videos may be further customized by a surgical complication or a surgical outcome.

Embodiment 2.26. A computer-readable medium comprising instructions which, when executed by a computer, cause the computer to carry out the method of any one of embodiments 2.14 to 2.25.

Embodiment 3.1. A device for providing simulation support in a live surgical procedure, the device comprising:
  a processor configured to:
  identify a procedure plan for a live surgical procedure;
  identify a stored simulation of a surgical procedure that corresponds to the procedure plan;
  determine, from information received during the live surgical procedure, a present portion of the live surgical procedure;
  retrieve, from the stored simulation, a portion of the stored simulation that corresponds to the present portion of the live surgical procedure; and
  present, for user interaction, the portion of the simulation that corresponds to the present portion of the live surgical procedure.

In this embodiment, "simulation support" may refer to the use of a surgical simulation during a live surgical procedure so as to provide active guidance to the surgeon during a surgery. In some embodiments, "simulation support" may refer to having a simulation environment that runs simultaneously and continuously with the live surgical procedure. Alternatively, "simulation support" may refer to a simulation which is not actively being run simultaneously with the live surgical procedure, but one which can be queried so as to present a portion of a simulation which has been run at least once. Each of these embodiments can be considered to provide support, or guidance, to a surgeon during a live surgical procedure.

"User interaction" may also refer to "user guidance". In other words, the portion of the simulation may be presented or displayed to the surgeon for the purposes of guiding the surgery.

It may be understood that "live surgical procedure" refers to a surgical procedure that is happening in real-time. In other words, the live surgical procedure can be happening concurrently with the operation of the simulation.

The processor of this embodiment is configured to determine a portion of the live surgical procedure through information received (e.g. through image processing or through information received from a surgical hub, configured to determine surgical context). The benefit of this situational awareness is that the processor can retrieve information from a stored simulation to guide the surgeon in performing the most optimum surgery.

One technical effect of this embodiment is that the user is assisted in performing a surgery through a guided interaction. This guidance leads to improved patient outcomes, and shorter surgical times, both of which are advantageous to the patient.

Embodiment 3.2. The device of embodiment 3.1, wherein the procedure plan comprises a set of tasks, and wherein the stored simulation comprises information indicative of simulated activity indexed according to the set of tasks.

Embodiment 3.3. The device of embodiment 3.2, wherein the processor is further configured to determine the present portion of the live surgical procedure by determining a present task from the procedure plan.

Embodiment 3.4. The device of embodiment 3.3, wherein the processor is further configured to retrieve a portion of the simulation that corresponds to the present portion of the live surgical procedure by retrieving a selected portion of the information indicative of simulated activity that is indexed the present task.

Embodiment 3.5. The device of any one of embodiments 3.1 to 3.4, wherein the processor is further configured present a visualization of the present portion of the live surgical procedure concurrently with a presentation of the portion of the simulation that corresponds to the present portion of the live surgical procedure.

Embodiment 3.6. The device of any one of embodiments 3.1 to 3.5, wherein the user interaction comprises a timeline user control to view the stored simulation at a time other than that which corresponds to the present portion of the live surgical procedure.

The functionality of this embodiment allows a surgeon to view potential consequences of future actions, which can inform their decisions and thereby improve surgical outcomes. This improved guidance can be advantageous for surgeons, particularly in instances where foresight of future actions in uncertain circumstances can be beneficial for patient health.

Embodiment 3.7. The device of embodiment 3.6, wherein the processor is configured to retrieve a different portion of the stored simulation based on a user's selection of the timeline control.

Embodiment 3.8. The device of any one of embodiments 3.1 to 3.8, wherein the user interaction comprises a procedure plan user control to view a different portion of stored simulation that corresponds to that selected by the procedure plan user control.

Embodiment 3.9. The device of embodiment 3.8, wherein the processor is configured to retrieve a different portion of the stored simulation based on a user's selection of the procedure plan control.

Embodiment 3.10. The device of any one of embodiments 3.1 to 3.9, wherein the processor is further configured to receive control input during the live procedure, for the portion of the stored simulation that corresponds to the present portion of the live surgical procedure, and to execute, with the control input, a live simulation that corresponds to the portion of the stored simulation that corresponds to the present portion of the live surgical procedure.

Embodiment 3.11. The device of embodiment 3.10, wherein the control input is a modification of the user activity in the stored simulation.

Embodiment 3.12. The device of embodiment 3.11, wherein the user activity comprises any of instrument selection, instrument configuration, technique selection, or application location.

Embodiment 3.13. The device of any one of embodiments 3.10 to 3.12, wherein the control input is a modification of the simulation settings.

Embodiment 3.14. The device of any one of embodiments 3.10 to 3.13, wherein the control input is a modification of simulated anatomy.

Embodiment 3.15. A computer-implemented method for providing simulation support in a live surgical procedure, the method comprising:
  identifying a procedure plan for a live surgical procedure;
  identifying a stored simulation of a surgical procedure that corresponds to the procedure plan;
  determining, from information received during the live surgical procedure, a present portion of the live surgical procedure;
  retrieving, from the stored simulation, a portion of the stored simulation that corresponds to the present portion of the live surgical procedure; and
  presenting, for user interaction, the portion of the simulation that corresponds to the present portion of the live surgical procedure.

Embodiment 3.16. The computer-implemented method of embodiment 3.15, wherein the procedure plan comprises a set of tasks, and wherein the stored simulation comprises information indicative of simulated activity indexed according to the set of tasks.

Embodiment 3.17. The computer-implemented method of embodiment 3.16, further comprising determining the present portion of the live surgical procedure by determining a present task from the procedure plan.

Embodiment 3.18. The computer-implemented method of embodiment 3.17, further comprising retrieving a portion of the simulation that corresponds to the present portion of the live surgical procedure by retrieving a selected portion of the information indicative of simulated activity that is indexed the present task.

Embodiment 3.19. The computer-implemented method of any one of embodiments 3.15 to 3.18, further comprising presenting a visualization of the present portion of the live surgical procedure concurrently with a presentation of the portion of the simulation that corresponds to the present portion of the live surgical procedure.

Embodiment 3.20. The computer-implemented method of any one of embodiments 3.15 to 3.19, wherein the user interaction comprises a timeline user control to view the stored simulation at a time other than that which corresponds to the present portion of the live surgical procedure.

Embodiment 3.21. The computer-implemented method of embodiment 3.20, further comprising retrieving a different portion of the stored simulation based on a user's selection of the timeline control.

Embodiment 3.22. The computer-implemented method of any one of embodiments 3.15 to 3.21, wherein the user interaction comprises a procedure plan user control to view a different portion of stored simulation that corresponds to that selected by the procedure plan user control.

Embodiment 3.23. The computer-implemented method of embodiment 3.22, further comprising retrieving a different portion of the stored simulation based on a user's selection of the procedure plan control.

Embodiment 3.24. The computer-implemented method of any one of embodiments 3.15 to 3.23, further comprising receiving control input during the live procedure, for the portion of the simulation that corresponds to the present portion of the live surgical procedure, and to execute, with the control input, a live simulation that corresponds to the portion of the stored simulation that corresponds to the present portion of the live surgical procedure.

Embodiment 3.25. The computer-implemented method of embodiment 3.24, wherein the control input is a modification of the user activity in the stored simulation.

Embodiment 3.26. The computer-implemented method of embodiment 3.25, wherein the user activity comprises any of instrument selection, instrument configuration, technique selection, or application location.

Embodiment 3.27. The computer-implemented method of any one of embodiments 3.24 to 3.26, wherein the control input is a modification of the simulation settings.

Embodiment 3.28. The computer-implemented method of any one of embodiments 3.24 to 3.27, wherein the control input is a modification of simulated anatomy.

Embodiment 3.29. A device for providing simulation support in a live surgical procedure, the device comprising:
  a processor configured to:
  identify a procedure plan for a live surgical procedure;
  identify a stored simulation of a surgical procedure that corresponds to the procedure plan;
  retrieve, from the stored simulation, a portion of the stored simulation that corresponds to a portion of the live surgical procedure;
  present, for user interaction, the portion of the stored simulation that corresponds to the present portion of the live surgical procedure;
  receive control input during the live procedure; and
  execute, with the control input, a live simulation that corresponds to the portion of the stored simulation that corresponds to the portion of the live surgical procedure.

Embodiment 3.30. The device of embodiment 3.29, wherein the control input is any of a modification of user activity in the stored simulation, a modification of the simulation settings, or a modification of simulated anatomy.

Embodiment 3.31. A computer-readable medium comprising instructions which, when executed by a computer, cause the computer to carry out the method of any one of embodiments 3.15 to 3.28.

Embodiment 4.1. A device comprising:
a processor configured to:
execute a simulation of a surgical procedure; wherein the surgical procedure is simulated in a simulated surgical environment;
generate a first visual representation of a portion of the simulated surgical environment, wherein the first visual representation corresponds to a primary view within the simulated surgical environment;
generate a second visual representation of a portion of the simulated surgical environment, wherein the second visual representation corresponds to a simulation of supplemental view within the simulated surgical environment;
coordinate generation of the first visual representation and generation of the second visual generation such that the first visual representation and the second visual representation correspond to a common event in the surgical procedure; and
present the first visual representation and the second visual representation for user interaction within the simulated surgical environment.

The benefit of this embodiment is that a supplemental view within a simulated surgical environment (such as a view from a medical imaging device) can be simultaneously delivered along with a primary view, thus providing more information to a user within a virtual or simulated environment. The coordination of the two views may allow for real-time training using multiple sources of information (e.g. views from different instruments).

In some embodiments, a "portion of the simulated surgical environment" may refer to a portion of a 3D surgical environment rendered for a virtual reality environment. In this way, a visual representation of this portion refers to a view that would be seen when looking into the rendered simulation.

One technical effect can therefore be considered an improved realism of a simulation environment, which results in improved training outcomes for surgeons.

Embodiment 4.2. The device of embodiment 4.1, wherein the primary view comprises a point-of-view of a surgeon within the surgical environment.

Embodiment 4.3. The device of embodiment 4.1, wherein the primary view comprises an endoscopic view of the surgical procedure.

Embodiment 4.4. The devoice of any one of embodiments 4.1 to 4.3, wherein the secondary view comprises any of a computerized tomography view, a magnetic resonance imaging view, an x-ray view, or trans-orifice scopic view of the surgical procedure.

Traditional surgical simulations fail to disclose supplementary views from surgical instrumentation, such as CT scans, within a simulated surgical environment. The advantage of this is that a significantly more comprehensive surgical training environment can be created and the realism of the simulation can be further enhanced.

Embodiment 4.5. The device of embodiment 4.2, wherein the second visual representation is mapped, within the first visual representation, to register to a simulated medical equipment display.

Embodiment 4.6. The device of embodiment 4.5, wherein the processor is further configured to present the second visual representation for user interaction by simulating a traditional user interface for the simulated medical equipment display for the user.

The benefit of this embodiment is that the second visual representation can be shown on a display within the first visual representation, which corresponds to a point of view of the surgeon. In other words, this embodiment is advantageous because the supplemental view can be mapped onto a simulated physical display, which improves the realism of a virtual reality simulated environment. This will improve the effectiveness of a virtual reality training set-up.

Embodiment 4.7. The device of embodiment 4.6, wherein the processor is further configured to present the first visual representation and the second visual representation to any of a virtual reality or augmented reality interface for user interaction.

Embodiment 4.8. The device of embodiment 4.7, wherein the processor is further configured to receive live biomarker information associated with the user, wherein the processor is further configured to modify execution of the simulation of the surgical procedure based on the live biomarker information.

Embodiment 4.9. The device of any one of embodiments 4.1 to 4.6, wherein the processor is further configured to present the first visual representation and the second visual representation to a computer display.

In this embodiment, the first and second visual representations can be provided on a simulation that is running on a computer. This allows for similar advantages to be provided where a virtual reality headset is not being used (i.e. when a simulation training program is being run on a computer).

Embodiment 4.10. The device of any one of embodiments 4.1 to 4.9, wherein the first visual representation is generated from the simulation of the surgical procedure and the second visual representation is generated from the simulation of the surgical procedure.

Embodiment 4.11. The device of any one of embodiments 4.1 to 4.10, wherein the first visual representation and the second visual representation are synchronized.

Embodiment 4.12. The device of any one of embodiments 4.1 to 4.11, wherein the processor is further configured to present the first visual representation for user interaction by simulating interaction with instrumentation outside of the sterile field for the user.

Embodiment 4.13. The device of embodiment 4.2, wherein the second visual representation is mapped, within the first visual representation, to register to common anatomy within the simulated surgical environment.

Embodiment 4.14. The device of embodiment 4.1, wherein the first visual representation corresponds to a first point-of-view of first health care professional within the simulated surgical environment; and wherein the processor is further configured to generate a third visual representation of the simulated surgical environment; wherein the third visual representation corresponding a second point-of-view of a second health care professional within the simulated surgical environment.

Embodiment 4.15. The device of embodiment 4.14, wherein the processor is further configured to present the first visual representation and the second visual representation to any of a first virtual reality or first augmented reality interface for user interaction of the first health care professional, and wherein the processor is further configured to present the third visual representation to any of a second virtual reality or second augmented reality interface for user interaction of the second health care professional.

Embodiment 4.16. The device of embodiment 4.15, wherein the processor is further configured to receive first live biomarker information associated with the first health care professional and second live biomarker information associated with the second health care professional, wherein the processor is further configured to modify execution of the simulation of the surgical procedure based on the first live biomarker information and the second live biomarker information.

Embodiment 4.17. A computer-implemented method comprising:
  executing a simulation of a surgical procedure; wherein the surgical procedure is simulated in a simulated surgical environment;
  generating a first visual representation of a portion of the simulated surgical environment, wherein the first visual representation corresponds to a primary view within the simulated surgical environment;
  generating a second visual representation of a portion of the simulated surgical environment, wherein the second visual representation corresponds to a simulation of supplemental view within the simulated surgical environment;
  coordinating generation of the first visual representation and generation of the second visual generation such that the first visual representation and the second visual representation correspond to a common event in the surgical procedure; and
  presenting the first visual representation and the second visual representation for user interaction within the simulated surgical environment.

Embodiment 4.18. The computer-implemented method of embodiment 4.17, wherein the primary view comprises a point-of-view of a surgeon within the surgical environment.

Embodiment 4.19. The computer-implemented method of embodiment 4.17, wherein the primary view comprises an endoscopic view of the surgical procedure.

Embodiment 4.20. The computer-implemented method of any one of embodiments 4.17 to 4.19, wherein the secondary view comprises any of a computerized tomography view, a magnetic resonance imaging view, an x-ray view, or transorifice scopic view of the surgical procedure.

Embodiment 4.21. The computer-implemented method of embodiment 4.18, wherein the second visual representation is mapped, within the first visual representation, to register to a simulated medical equipment display.

Embodiment 4.22. The computer-implemented method of embodiment 4.20, further comprising presenting the second visual representation for user interaction by simulating a traditional user interface for the simulated medical equipment display for the user.

Embodiment 4.23. The computer-implemented method of embodiment 4.22, further comprising presenting the first visual representation and the second visual representation to any of a virtual reality or augmented reality interface for user interaction.

Embodiment 4.24. The computer-implemented method of embodiment 4.23, further comprising receiving live biomarker information associated with the user, and modifying execution of the simulation of the surgical procedure based on the live biomarker information.

Embodiment 4.25. The computer-implemented method of any one of embodiments 4.17 to 4.21, further comprising presenting the first visual representation and the second visual representation to a computer display.

Embodiment 4.26. The computer-implemented method of any one of embodiments 4.17 to 4.25, wherein the first visual representation is generated from the simulation of the surgical procedure and the second visual representation is generated from the simulation of the surgical procedure.

Embodiment 4.27. The computer-implemented method of any one of embodiments 4.17 to 4.26, wherein the first visual representation and the second visual representation are synchronized.

Embodiment 4.28. The computer-implemented method of any one of embodiments 4.17 to 4.27, further comprising presenting the first visual representation for user interaction by simulating interaction with instrumentation outside of the sterile field for the user.

Embodiment 4.29. The computer-implemented method of embodiment 4.18, wherein the second visual representation is mapped, within the first visual representation, to register to common anatomy within the simulated surgical environment.

Embodiment 4.30. The computer-implemented method of embodiment 4.17, wherein the first visual representation corresponds to a first point-of-view of first health care professional within the simulated surgical environment; and wherein the method further comprises generating a third visual representation of the simulated surgical environment; wherein the third visual representation corresponding a second point-of-view of a second health care professional within the simulated surgical environment.

Embodiment 4.31. The computer-implemented method of embodiment 4.30, further comprising presenting the first visual representation and the second visual representation to any of a first virtual reality or first augmented reality interface for user interaction of the first health care professional, and presenting the third visual representation to any of a second virtual reality or second augmented reality interface for user interaction of the second health care professional.

Embodiment 4.32. The computer-implemented method of embodiment 4.31, wherein the further comprising receiving first live biomarker information associated with the first health care professional and second live biomarker information associated with the second health care professional, and modifying execution of the simulation of the surgical procedure based on the first live biomarker information and the second live biomarker information.

Embodiment 4.33. A device comprising:
  a processor configured to:
  execute a simulation of a surgical procedure; wherein the surgical procedure is simulated in a simulated surgical environment;
  generate a first visual representation of a portion of the simulated surgical environment, wherein the first visual representation corresponds to a primary view within the surgical environment, wherein the first visual representation is generated from the simulation of the surgical;
  generate a second visual representation of a portion of the simulated surgical environment, wherein the second visual representation corresponds to a simulation of supplemental view within the surgical environment procedure, wherein the second visual representation is generated from the simulation of the surgical procedure;
  present the first visual representation and the second visual representation for user interaction.

Embodiment 4.34. The device of embodiment 4.33, wherein the processor is further configured to synchronize generation of the first visual representation and generation of the second visual generation such that the first visual representation and the second visual representation correspond to a common activity throughout the surgical procedure.

Embodiment 4.35. A computer-readable medium comprising instructions which, when executed by a computer, cause the computer to carry out the method of any one of embodiments 4.17 to 4.32.

Embodiment 5.1: A device for simulating a surgical setup, the device comprising:
 a processor configured to:
  execute a simulation of a surgical procedure, wherein the simulation simulates activity in a surgical operating room with a surgical setup, wherein each surgical setup comprises a respective surgical equipment setup and a respective surgical staff setup;
  generate a performance score, wherein the performance score corresponds to the surgical setup and is based on a performance of the surgical setup in simulation.

Embodiment 5.2. A device for simulating a surgical setup, the device comprising:
 a processor configured to:
  execute a plurality of simulations of a surgical procedure, wherein each simulation simulates activity in a surgical operating room with a respective one of a plurality of surgical setups, wherein each surgical setup comprises a respective surgical equipment setup and a respective surgical staff setup;
  generate a plurality of performance scores, wherein each of the plurality of performance scores corresponds to a respective surgical setup, wherein each of the plurality of performance scores is based on a performance of the respective surgical setup in simulation;
  determine a first surgical setup from the plurality of surgical setups based on the plurality of performance scores; and
  output the first surgical setup.

This embodiment provides a simulator which is configured to run a simulation and model the surgical staff setup and surgical equipment setup, to determine which of these setups is preferred. In one embodiment, the device can generate a performance score based on the different surgical setups, to determine which of these is most optimal. In some embodiments, the performance score corresponds to a duration of a surgery. In some embodiments, the performance score corresponds to an amount of movement required during surgery. In other embodiments, the performance score corresponds to a number of surgical complications. In other embodiments, the performance score corresponds to patient outcomes.

Through analyzing the effect of surgical setups on the above parameters (which may be broadly referred to as surgical costs and which may relate to non-financial, opportunity costs incurred during a surgery), the output of the simulation can be used to improve surgical outcomes. That is, the device of the present embodiment can be used to inform decisions which, e.g., reduce the time required during a surgery, or improve patient outcomes.

In other words, the use of this device, which analyzes the placement and movement of the surgical staff and surgical equipment can inform decisions which minimize surgical duration, improve patient outcomes, etc.

Where a plurality of simulations are executed by the processor of the device, the device can be further configured to compare the respective performance scores and to determine a specific surgical setup which provides the most optimum surgical setup that achieves the above effects.

Embodiment 5.3. The device of embodiment 5.1 or 5.2, wherein each surgical equipment setup comprises number of equipment, respective positions of equipment, and type of equipment, wherein each surgical staff setup comprises number of staff, respective positions of staff, and role of staff.

Embodiment 5.4. The device of any one of embodiments 5.1 to 5.3, wherein generating the performance scores is based on a surgical duration.

Embodiment 5.5. The device of any one of embodiments 5.1 to 5.4, wherein generating the performance scores is based on surgical movement.

Embodiment 5.6. The device of any one of embodiments 5.1 to 5.5, wherein generating the performance scores is based on surgical complications.

Embodiment 5.7. The device of any one of embodiments 5.1 to 5.6, wherein generating the performance scores is based on patient outcomes.

In some embodiments, the performance score may be a metric for assessing the effectiveness of a certain surgical setup, so as to improve patient outcomes, reduce surgical complications, reduce surgical durations, or limit surgical movement (which has a knock-on effect on surgical durations).

Embodiment 5.8. The device of any one of embodiments 5.2 to 5.7, wherein the processor is further configured to:
 receive a scoring function; and
 generate the plurality of performance scores using the scoring function.

Embodiment 5.9. The device of any one of embodiments 5.1 to 5.8, wherein the processor is further configured to:
 determine a procedure plan based on the output; and
 send the procedure plan to a surgical hub.

Embodiment 5.10. The device of any one of embodiments 5.2 to 5.9, wherein the processor is further configured to:
 generate the plurality of surgical setups, wherein generating the plurality of surgical setups comprises receiving a manifest of surgical equipment and a manifest of surgical staff and generating all combinations of surgical setups using the surgical equipment and surgical staff on the manifest.

Embodiment 5.11. The device of any one of embodiment 5.1 to 5.10, wherein the processor is further configured to:
 receive information indicative of the surgical procedure.

Embodiment 5.12. The device of embodiment 5.11, wherein the information indicative of the surgical procedure is received from a surgical hub.

Embodiment 5.13. The device of any one of embodiments 5.1 to 5.12, wherein the processor is further configured to:
 receive a task associated with the surgical procedure; and
 determine a task impact for the task based on each of the plurality of the surgical setups.

Embodiment 5.14. A method, comprising:
 executing a simulation of a surgical procedure, wherein the simulation simulates activity in a surgical operating room with a surgical setup, wherein the surgical setup comprises a respective surgical equipment setup and a respective surgical staff setup;
 generating a performance score, wherein the performance score corresponds to the surgical setup, and the performance score is based on a performance of the surgical setup in simulation.

Embodiment 5.15. A computer-implemented method, comprising:
 executing a plurality of simulations of a surgical procedure, wherein each simulation simulates activity in a surgical operating room with a respective one of a plurality of surgical setups, wherein each surgical setup comprises a respective surgical equipment setup and a respective surgical staff setup;

generating a plurality of performance scores, wherein each of the plurality of performance scores corresponds to a respective surgical setup, wherein each of the plurality of performance scores is based on a performance of the respective surgical setup in simulation;

determining a first surgical setup from the plurality of surgical setups based on the plurality of performance scores; and outputting the first surgical setup.

Embodiment 5.16. The computer-implemented method of embodiment 5.14 or 5.15, wherein each surgical equipment setup comprises number of equipment, respective positions of equipment, and type of equipment, wherein each surgical staff setup comprises number of staff, respective positions of staff, and role of staff.

Embodiment 5.17. The computer-implemented method of any one of embodiments 5.14 to 5.16, wherein generating the performance scores is based on a surgical duration.

Embodiment 5.18. The computer-implemented method of any one of embodiments 5.14 to 5.17 wherein generating the performance scores is based on surgical movement.

Embodiment 5.19. The computer-implemented method of any one of embodiments 5.14 to 5.18, wherein generating the performance scores is based on surgical complications.

Embodiment 5.20. The computer-implemented method of any one of embodiments 5.14 to 5.19, wherein generating the performance scores is based on patient outcomes.

Embodiment 5.21. The computer-implemented method of any one of embodiments 5.14 to 5.20, further comprising:
receiving a scoring function; and
generating the plurality of performance scores using the scoring function.

Embodiment 5.22. The computer-implemented method of any one of embodiments 5.14 to 5.21, further comprising:
determining a procedure plan based on the output; and
sending the procedure plan to a surgical hub.

Embodiment 5.23. The computer-implemented method of any one of embodiments 5.14 to 5.22, further comprising:
generating the plurality of surgical setups, wherein generating the plurality of surgical setups comprises receiving a manifest of surgical equipment and a manifest of surgical staff and generating all combinations of surgical setups using the surgical equipment and surgical staff on the manifest.

Embodiment 5.24. The computer-implemented method of any one of embodiments 5.14 to 5.23, further comprising:
receiving information indicative of the surgical procedure.

Embodiment 5.25. The computer-implemented method of embodiment 5.24, wherein the information indicative of the surgical procedure is received from a surgical hub.

Embodiment 5.26. The computer-implemented method of any one of embodiments 5.14 to 5.25, further comprising:
receiving a surgical task associated with the surgical procedure; and
determining a surgical task impact for the surgical task based on each of the plurality of the surgical setups.

Embodiment 5.27. A device for simulating a surgical setup, the device comprising:
a processor configured to:
receive a surgical task associated with a surgical procedure;
execute a plurality of simulations of a surgical procedure, wherein each simulation simulates activity related to performing the surgical task in a surgical operating room with a respective one of a plurality of surgical setups, wherein each surgical setup comprises a respective surgical equipment setup and a respective surgical staff setup;

generate a plurality of surgical task impacts, wherein each of the plurality of surgical task impacts corresponds to a respective surgical setup, wherein each of the plurality of surgical task impacts is based on a performance of the surgical task of the respective surgical setup in simulation;

determine a first surgical setup from the plurality of surgical setups based on the plurality of surgical task impacts; and output the first surgical setup.

Embodiment 5.28. A computer-readable medium comprising instructions which, when executed by a computer, cause the computer to carry out the method of any one of embodiments 5.13 to 5.26.

Embodiment 6.1. A computing device for generating a surgical procedure plan, the computing device comprising:
a processor configured to:
obtain, from a user, an indication of a surgical task;
obtain, from a surgical choice generator module, a surgical choice and a corresponding predicted surgical outcome, wherein the surgical choice and the corresponding predicted surgical outcome are associated with the surgical task;
generate, in a simulated environment, a visualization of the surgical choice and the corresponding predicted surgical outcome;
obtain an indication of the surgical choice being selected; and
store the surgical choice as a part of a surgical step in a surgical procedure plan.

It may be understood that a "surgical procedure plan" refers to a list of surgical tasks/choices that are performed in a surgery. In other words, this can be considered a preferred itinerary of actions, each of which has a certain surgical consequence.

The use a simulator to inform decisions regarding the selection of certain tasks within a surgery can provide improved surgical outcomes. That is, by obtaining surgical choices and corresponding predicted surgical outcomes from a surgical choice generator, a person generating a surgical procedure plan can make more informed decisions (e.g. to mitigate risk during surgery) and improve surgical outcomes.

By generating a visualization of a surgical choice and the respective outcome in a simulated environment, the user is guided with a distinct set of information that they would not have previously had access to, allowing them to select the most optimum surgical choices, which again have a beneficial effect to surgical outcomes during surgery.

Embodiment 6.2. The computing device of embodiment 6.1, wherein the indication of the surgical task is obtained from a surgical procedure planning user interface.

Embodiment 6.3. The computing device of any one of embodiments 6.1 to 6.2, wherein the indication of the surgical task comprises identifying information of the surgical procedure plan, identifying information of the surgical task, and identifying information of the surgical step.

Embodiment 6.4. The computing device of any one of embodiments 6.1 to 6.3, wherein the surgical task comprises a surgical task that contributes to completion of a surgical step of the surgical procedure plan.

Embodiment 6.5. The computing device of any one of embodiments 6.1 to 6.4, wherein the processor is further configured to train a machine learning (ML) model using data of a plurality of past surgical procedures, wherein the processor is further configured to generate the surgical choice and the corresponding predicted surgical outcome using the ML model, and wherein the processor is further configured to obtain the surgical choice and the corresponding predicted surgical outcome.

It is understood that a machine learning algorithm may be trained using a supervised training or unsupervised training method. When a supervised training method is used, the model may be trained on a set of labelled data. In some embodiments, the machine learning algorithm may be trained using a set of data comprising surgical choices, wherein each surgical choice is labelled with a certain predicted surgical outcome. As a result of training a machine learning model in this way, the processor, using the trained machine learning model, can be configured to generate predicted surgical outcomes from different surgical choices, or vice versa.

Embodiment 6.6. The computing device of any one of embodiments 6.1 to 6.5, wherein the surgical choice is a first surgical choice and the corresponding predicted surgical outcome is a first corresponding predicted surgical outcome, and wherein the processor is further configured to:
  obtain, from the surgical choice generator module, a second surgical choice and a second corresponding predicted surgical outcome, wherein the second surgical choice and the second corresponding predicted surgical outcome are associated with the surgical task;
  generate, in the simulated environment, a visualization of the second surgical choice and the second corresponding predicted surgical outcome;
  obtain an indication of the second surgical choice being not selected; and
  discard the second surgical choice.

By generating a visualization of a first and second surgical choice in a simulated environment, along with the respective surgical consequences, the user can see different options for surgery simultaneously, which can provide improved selections. By visualizing different alternatives for a surgical choice together, the user is guided more effectively to select a certain option for the surgical procedure plan.

Embodiment 6.7. A computer-implemented method for generating a surgical procedure plan via surgical simulation, the method comprising:
  obtaining, from a user, an indication of a surgical task;
  obtaining, from a surgical choice generator module, a surgical choice and a corresponding predicted surgical outcome, wherein the surgical choice and the corresponding predicted surgical outcome are associated with the surgical task;
  generating, in a simulated environment, a visualization of the surgical choice and the corresponding predicted surgical outcome;
  obtaining an indication of the surgical choice being selected; and
  storing the surgical choice as a part of a surgical step in a surgical procedure plan.

Embodiment 6.8. The computer-implemented method of embodiment 6.7, wherein the indication of the surgical task is obtained from a surgical procedure planning user interface.

Embodiment 6.9. The computer-implemented method of embodiment 6.7 or 6.8, wherein the indication of the surgical task comprises identifying information of the surgical procedure plan, identifying information of the surgical task, and identifying information of the surgical step.

Embodiment 6.10. The computer-implemented method of any one of embodiments 6.7 to 6.9, wherein the surgical task being associated with the surgical step of the surgical procedure plan comprises a surgical task that contributes to completion of the surgical step of the surgical procedure plan.

Embodiment 6.11. The computer-implemented method of any one of embodiments 6.7 to 6.10, further comprising:
  training a machine learning (ML) model using data of a plurality of past surgical procedures;
  generating the surgical choice and the corresponding predicted surgical outcome using the ML model; and
  obtaining the surgical choice and the corresponding predicted surgical outcome.

Embodiment 6.12. The computer-implemented method of any one of embodiments 6.7 to 6.11, wherein the surgical choice is a first surgical choice and the corresponding predicted surgical outcome is a first corresponding predicted surgical outcome, and wherein the method further comprises:
  obtaining, from a surgical choice generator module, a second surgical choice and a second corresponding predicted surgical outcome, wherein the second surgical choice and the second corresponding predicted surgical outcome are associated with the surgical task;
  generating, in the simulated environment, a visualization of the second surgical choice and the second corresponding predicted surgical outcome;
  obtaining an indication of the second surgical choice being not selected; and
  discarding the second surgical choice.

Embodiment 6.13. A computer-readable medium comprising instructions which, when executed by a computer, cause the computer to carry out the method of any one of embodiments 6.7 to 6.12.

Embodiment 7.1. A computer-implemented method for determining a target action set, the method comprising:
  receiving a plurality of environment parameter sets, wherein each environment parameter set corresponds to a respective simulated environment within which a simulated surgical task is to be completed;
  generating, for each environment parameter set, a plurality of candidate action sets, wherein each candidate action set, when executed within the respective simulated environment, causes performance of the respective simulated surgical task with an effectiveness that is indicated by a corresponding effectiveness metric;
  training a machine-learning model with the plurality of environment parameter sets, each respective plurality of candidate action sets, and each corresponding effectiveness metric, such that the trained machine-learning model may comprise a functional relationship between a model input and a model output, wherein the model input comprises an input environment parameter set and an input action set, and wherein the output comprises an output effectiveness metric; and
  determining a target action set based on a target environment parameter set and a corresponding effectiveness metric which is output by the trained machine-learning model.

It may be understood that an action set (e.g. a candidate action set, a target action set, or an input action set) can refer to a set of parameters which define one or more actions taken during a surgery. In some embodiments, an action set can refer to a number of surgical choices taken by an operator.

In some embodiments, an action set can include specific layout decisions (both of the surgical staff and of the surgical instrumentation). It can also refer to the specific equipment used during a surgery. In other words, it may refer to portions of a surgical procedure which have consequences on the surgery, both in duration, surgical outcomes, effectiveness of the procedure, etc. It is to be understood that the candidate, target, and input action sets are all data sets having the same format. That is, a machine-learning model can be trained on the basis of a candidate action set to help define a relationship between any arbitrary "input" action set. This allows the machine-learning model to be used to find a target action set within a given simulation having a certain effectiveness.

It may also be understood that an environment parameter set (e.g. an environment parameter set, a target environment parameter set, or an input environment parameter set) can refer to a set of parameters which define the overall environment of a surgical simulation. In other words, it refers to the parameters which initialize and define the constraints and physics of a surgical simulation. It is to be understood that the target and environment parameter sets are all data sets having the same format as that of the environment parameter set. That is, a machine-learning model can be trained on the basis of an environment parameter set to help define a relationship between any arbitrary "input" environment parameter set. This allows the machine-learning model to be used to find a target action set within a given simulation having a certain effectiveness.

In one embodiment "training a machine-learning model" may refer to using a set of labelled data to train the model in a supervised fashion. In this case, the combination of the environment parameter set and the action set can be considered to be the input data (as this refers to a specific set of actions run within a specific simulation environment). This data for training purposes can be "labelled" with its associated effectiveness metric (i.e. the output of the simulation, which relates to how effective the specific action was within that simulation). By feeding this labelled data into the machine-learning model, the model can generate a relationship between different actions/environments and the associated effectiveness.

For the avoidance of doubt, where the present embodiment refers to an "environment parameter set", this may be the same parameter set that the application refers to as a "training task-environment parameter set" (i.e. a parameter set that can be used to train the machine learning model).

Both the initialization of the surgical simulation (which is defined by the environment parameter set) and the specific choices/actions taken within the simulation (which is defined by the candidate action set) have implications on the overall effectiveness of the surgery (defined by the effectiveness metric).

In one embodiment, "determining a target action set" may refer to selecting an action set from a plurality of action sets within a predetermined simulation (as defined by an environment parameter set). The target action set may be selected based on which target action set (as an input to the machine learning model) produces the best output efficiency metric from the machine learning model.

In other words, the present invention uses the output data of a simulation to improve the training of a machine learning model, and then uses the improved trained artificial intelligence to make an improved conclusion regarding surgical actions/choices that can be performed within a certain surgical set-up.

One advantage of this is that a machine-learning model (such as a neural network) can be trained with additional data which may not arise commonly during a live surgical procedure. In other words, the simulation can provide data regarding "riskier" surgical choices and their consequences to a machine learning model. The informed intelligence coming from the machine learning model can inform future decisions on surgery, by highlighting which decisions actually have beneficial effects without needing to risk real patients to gather the appropriate data.

The consequence of improving the training of a machine learning model in the way of the present embodiment is that improved surgical outcomes can be achieved via the target action set determined.

Embodiment 7.2. The computer-implemented method of embodiment 7.1, wherein receiving the plurality of environment parameter sets comprises receiving the plurality of environment parameter sets from a surgical data system that records real-world environment data from real-world performances of the surgical task and that generates the plurality of environment parameter sets from the real-world environment data.

Embodiment 7.3. The computer-implemented method of any one of embodiments 7.1 to 7.2, wherein each environment parameter set comprises anatomical information, physiological information, and surgical setup information.

Embodiment 7.4. The computer-implemented method of any one of embodiments 7.1 to 7.3, wherein each candidate action set comprises a parameterized surgical activity within the respective simulated environment.

Embodiment 7.5. The computer-implemented method of embodiment 7.4, wherein the parameterized activity comprises a simulated transection parameterized by any of relative anatomical location, instrument selection, and instrument application direction.

Embodiment 7.6. The computer-implemented method of embodiment 7.4, wherein the parameterized activity comprises a simulated suturing parameterized by any of suture location, suture pattern, suture number, suture material, and suture tension.

Embodiment 7.7. The computer-implemented method of embodiment 7.4, wherein the parameterized activity comprises a surgical robotic guidance path.

Embodiment 7.8. The computer-implemented method of any one of embodiments 7.1 to 7.7, wherein the simulated surgical task comprises lower anterior resection anastomosis; wherein each candidate action set, when executed within the simulated environment indicated by the corresponding environment set causes performance of the simulated surgical task with effectiveness that is indicated by the corresponding effectiveness metric, wherein the corresponding effectiveness metric is an indication of perfusion resulting from the performance of the simulated surgical task.

Embodiment 7.9. The computer-implemented method of any one of embodiments 7.1 to 7.8, wherein the simulated surgical task comprises any of segmentectomy and lobectomy; wherein each candidate action set, when executed within the simulated environment indicated by the corresponding environment set causes performance of the simulated surgical task with effectiveness that is indicated by the corresponding effectiveness metric, wherein the corresponding effectiveness metric is an indication of output lung volume resulting from the performance of the simulated surgical task.

Embodiment 7.10. The computer-implemented method of any one of embodiments 7.1 to 7.9, further comprising generating an output that is a human-readable aggregation of the plurality of task environment parameter sets, each respective plurality of candidate action sets, and each corresponding effectiveness metric.

Embodiment 7.11. The computer-implemented method of any one of embodiments 7.1 to 7.10, wherein training the machine-learning model comprises training the machine-learning model with any of a supervised learning algorithm, an unsupervised learning algorithm, and a reinforcement learning algorithm.

Embodiment 7.12. A device for determining a target action set, the device comprising:
 a processor configured to:
  receive a plurality of environment parameter sets from a surgical data system, wherein each environment parameter set corresponds to a respective simulated environment within which a simulated surgical task is to be completed;
  generate, for each environment parameter set, a plurality of candidate action sets, wherein each candidate action set, when executed within the respective simulated environment corresponding to the corresponding environment set causes performance of the respective simulated surgical task with an effectiveness that is indicated by a corresponding effectiveness metric;
  train a machine-learning model with the plurality of environment parameter sets, each respective plurality of candidate action sets, and each corresponding effectiveness metric, such that the trained machine-learning model may comprise a functional relationship between a model input and a model output, wherein the model input comprises an input environment parameter set and an input action set, and wherein the output comprises an output effectiveness metric; and
  determine a target action set based on a target environment parameter set and a corresponding effectiveness metric which is output by the trained machine-learning model.

Embodiment 7.13. The device of embodiment 7.12, wherein the surgical data system is configured to record real-world environment data from real-world performances of the surgical task and is further configured to generate the plurality of environment parameter sets from the real-world environment data.

Embodiment 7.14. The device of any one of embodiments 7.12 to 7.13, wherein each environment parameter set comprises anatomical information, physiological information, and surgical setup information.

Embodiment 7.15. The device of any one of embodiments 7.12 to 7.14, wherein each candidate action set comprises a parameterized surgical activity within the respective simulated environment.

Embodiment 7.16. The device of embodiment 7.15, wherein the parameterized activity comprises a simulated transection parameterized by any of relative anatomical location, instrument selection, and instrument application direction.

Embodiment 7.17. The device of embodiment 7.15, wherein the parameterized activity comprises a simulated suturing parameterized by any of suture location, suture pattern, suture number, suture material, and suture tension.

Embodiment 7.18. The device of embodiment 7.15, wherein the parameterized activity comprises a surgical robotic guidance path.

Embodiment 7.19. The device of any one embodiments 7.12 to 7.18, wherein the simulated surgical task comprises lower anterior resection anastomosis; wherein each candidate action set, when executed within the simulated environment indicated by the corresponding environment set causes performance of the simulated surgical task with effectiveness that is indicated by the corresponding effectiveness metric, wherein the corresponding effectiveness metric is an indication of perfusion resulting from the performance of the simulated surgical task.

Embodiment 7.20. The device of any one embodiments 7.12 to 7.18, wherein the simulated surgical task comprises any of segmentectomy and lobectomy; wherein each candidate action set, when executed within the simulated environment indicated by the corresponding environment set causes performance of the simulated surgical task with effectiveness that is indicated by the corresponding effectiveness metric, wherein the corresponding effectiveness metric is an indication of output lung volume resulting from the performance of the simulated surgical task.

Embodiment 7.21. The device of any one of embodiments 7.12 to 7.20, wherein the processor is further configured to generate an output that is a human-readable aggregation of the plurality of task environment parameter sets, each respective plurality of candidate action sets, and each corresponding effectiveness metric.

Embodiment 7.22. The device of any one of embodiments 7.12 to 7.21, wherein the processor is configured to train the machine-learning model with any of a supervised learning algorithm, an unsupervised learning algorithm, and a reinforcement learning algorithm.

Embodiment 7.23. A device for determining a target action set, the device comprising:
 a processor configured to:
  receive a plurality of environment parameter sets from a surgical data system, wherein each environment parameter set corresponds to a respective simulated environment within which a simulated surgical task is to be completed;
  generate, for each environment parameter set, a plurality of candidate action sets, wherein each candidate action set, when executed within the respective simulated environment causes performance of the simulated surgical task with an effectiveness that is indicated by a corresponding effectiveness metric;
  train a machine-learning model with the plurality of environment parameter sets, each respective plurality of candidate action sets, and each corresponding effectiveness metric, such that the trained machine-learning model comprises a functional relationship between a model input and a model output, wherein the model input comprises an input environment parameter set and an input action set, and wherein the output comprises an output effectiveness metric; and
  determine a target action set based on a target environment parameter set and a corresponding effectiveness metric which is output by the trained machine-learning model.

Embodiment 7.24. The device of embodiment 7.23, wherein the surgical data system is configured to record real-world environment data from real-world performances of the surgical task and is further configured to generate the plurality of environment parameter sets from the real-world environment data.

Embodiment 7.25. The device of any one of embodiments 7.23 to 7.24, wherein each environment parameter set comprises anatomical information, physiological information, and surgical setup information.

Embodiment 7.26. The device of any one of embodiments 7.23 to 7.25, wherein each candidate action set comprises a parameterized surgical activity within the respective simulated environment.

Embodiment 7.27. A device for determining a target action set, the device comprising:
a processor configured to:
receive a machine-learning model trained with the plurality of environment parameter sets, respective plurality of candidate action sets, and corresponding effectiveness metrics, such that the trained machine-learning model comprises a functional relationship between a model input and a model output, wherein the model input comprises an input environment parameter set and an input action set, and wherein the output comprises an output effectiveness metric,
determine a target action set based on the environment parameter set and the machine-learning model;
wherein each environment parameter set corresponds to the respective simulated environment within which the simulated surgical task is to be completed;
wherein the plurality of environment parameter sets are from a surgical data system,
wherein for each environment parameter set, a plurality of candidate action sets when executed within the simulated environment corresponding to the corresponding environment set causes performance of the simulated surgical task with an effectiveness that is indicated by the corresponding effectiveness metric.

Embodiment 7.28. The device of embodiment 7.27, wherein each environment parameter set comprises anatomical information, physiological information, and surgical setup information, and wherein each candidate action set comprises a parameterized surgical activity within the respective simulated environment.

Embodiment 7.29. A computer-readable medium comprising instructions which, when executed by a computer, cause the computer to carry out the method of any one of embodiments 7.1 to 7.11.

Embodiment 8.1. A device for simulating a surgical task comprising:
a processor configured to:
receive a request for a simulation of the surgical task;
receive, responsive to a database query, surgical event data associated with the surgical task;
generate simulation parameter values based on the surgical event data; and
execute the simulation based on the simulation parameter values.

It may be understood that surgical event data which can be received from a database can be used in the generation of simulation parameter values. The benefit is that external data from a database can be used to modify the parameters (and thus, the operation of) a simulation running on the device.

In some embodiments, "surgical event data" may refer to any data which has been gathered in relation to previously performed surgeries. In one embodiment, it may refer to paired sets of data (including surgical actions performed and the surgical consequences). Alternatively, or additionally, it may also comprise data which includes physiological parameters of the patient, to further contextualize any surgical consequences which may have arisen due to the specific patient.

This embodiment provides a mechanism for a processor running a simulation to send a query for surgical event data, process this data into parameters which can be used in the simulation, and then run the simulation based on these processed values. It was not previously known for a surgical simulation set-up to be interconnected with surgical databases, such as the ones coupled with a surgical hub.

In other words, this allows the device of the embodiment 1 to inject complications into a pre-existing simulation. That is, a set of data including known inputs and outputs (e.g. from historical data of previous surgeries performed in a hospital) can be processed and used to improve a known simulation environment.

One technical advantage of this is that a surgical simulator can request access to information which can improve the realism of the simulation. This can improve the realism of the surgical simulation environment. It can further enable a single surgical simulation to be adaptable with new methods and techniques in surgery. The consequence of improved training is that surgical outcomes can be improved, as the surgeons will be better prepared for surgical complications.

Embodiment 8.2. The device of embodiment 8.1, wherein the surgical task comprises a medical procedure and medical procedure context.

It may be understood that a medical procedure context can refer to a type of procedure being performed. It may also refer to a condition of the simulated patient's anatomy and/or physiology.

Embodiment 8.3. The device of embodiment 8.2, wherein the surgical event data comprises historical data associated with the medical procedure and context data associated with the medical procedure context.

It may be understood that "historical data" can refer to data stored in memory which corresponds to one or more surgeries which have been previously performed. In these cases, a surgical hub can be configured to monitor a variety of parameters during the surgery, and store this data synchronously so that it can be later accessed to detect trends and certain consequences which result from different actions.

Embodiment 8.4. The device of embodiment 8.3, wherein the historical data and the context data are local data associated with a medical facility.

Embodiment 8.5. The device of embodiment 8.3 or embodiment 8.4, wherein the processor is further configured to:
filter the surgical event data to filtered surgical event data that matches the medical procedure and the medical procedure context; and
generate simulation parameter values based on the filtered surgical event data.

The benefit of this embodiment is that a reduced processing power is required to parse the surgical interaction data. A further benefit of this embodiment is that, by first filtering the surgical event data, the simulation can be more precisely initialized for an improved training outcome. For example, there may be a large array of available data related to the ligation of a blood vessel (each piece of data associated with a surgical outcome or consequence). However, there may be differing consequences due to a ligation based on the type of surgery being performed. Thus, by filtering the array of available data (i.e. the surgical event data) to limit to a certain medical procedure/context, and only using the corresponding pairs of triggering events/consequence environment parameters to generate the parameters for modifying the simulator, the resultant simulation can be generally improved.

Embodiment 8.6. The device of any one of embodiments 8.1 to 8.5, wherein generating simulation parameter values comprises calculating probabilities of surgical events.

The benefit to a probabilistic approach to generating simulation parameter values is to further improve the realism of a surgical training environment. In particular, if a specific consequence only occurs a proportion of the time, this detail can be imported into the simulation to further improve the realism of the training environment.

Embodiment 8.7. The device of any one of embodiments 8.1 to 8.6, wherein the processor is further configured to:
periodically receive update parameter values based on user interaction data; and
periodically update the simulation parameter values based on the update parameter values.

Embodiment 8.8. The device of any one of embodiments 8.1 to 8.7, wherein the processor is further configured to:
determine surgical event data criteria based on the surgical task;
send the surgical event data criteria to a surgical hub database; and
receive, responsive to a database query, surgical event data that satisfies the surgical event data criteria.

Embodiment 8.9. The device of any one of embodiments 8.1 to 8.8, wherein executing the simulation comprises executing a script, wherein the script is configured with the simulation parameter values.

Embodiment 8.10. A computer-implemented method for simulating a surgical task comprising:
receiving a request for a simulation of the surgical task;
receiving, responsive to a database query, surgical event data associated with the surgical task;
generating simulation parameter values based on the surgical event data; and
executing the simulation based on the simulation parameter values.

Embodiment 8.11. The computer-implemented method of embodiment 8.10, wherein the surgical task comprises a medical procedure and medical procedure context.

Embodiment 8.12. The computer-implemented method of embodiment 8.11, wherein the surgical event data comprises historical data associated with the medical procedure and context data associated with the medical procedure context.

Embodiment 8.13. The computer-implemented method of embodiment 8.12, wherein the historical data and the context data are local data associated with a medical facility.

Embodiment 8.14. The computer-implemented method of embodiment 8.12 or 8.13, wherein the processor is further configured to:
filter the surgical event data to filtered surgical event data that matches the medical procedure and the medical procedure context; and
generate simulation parameter values based on the filtered surgical event data.

Embodiment 8.15. The computer-implemented method of any one of embodiments 8.10 to 8.14, wherein generating simulation parameter values comprises calculating probabilities of surgical events.

Embodiment 8.16. The computer-implemented method of any one of embodiments 8.10 to 8.15, further comprising:
periodically receiving update parameter values based on user interaction data; and
periodically updating the simulation parameter values based on the update parameter values.

Embodiment 8.17. The computer-implemented method of any one of embodiments 8.10 to 8.16, further comprising:
determining surgical event data criteria based on the surgical task;
sending the surgical event data criteria to a surgical hub database; and
receive, responsive to a database query, surgical event data that satisfies the surgical event data criteria.

Embodiment 8.18. The computer-implemented method of any one of embodiments 8.10 to 8.17, wherein executing the simulation comprises executing a script, wherein the script is configured with the simulation parameter values.

Embodiment 8.19. A device for simulating a surgical task comprising:
a processor configured to:
receive a request for a simulation of the surgical task, wherein the surgical task comprises a medical procedure and medical procedure context;
receive, responsive to a database query, surgical event data associated with the surgical task;
generate simulation parameter values based on the surgical event data; and
execute the simulation based on the simulation parameter values.

Embodiment 8.20. A computer-readable medium comprising instructions which, when executed by a computer, cause the computer to execute the method of any one of embodiments 8.10 to 8.18.

Embodiment 9.1. A computing device for simulating a surgical procedure, the computing device comprising:
a processor configured to:
obtain first data associated with a first simulated surgical procedure and second data associated with a second simulated surgical procedure, wherein the first simulated surgical procedure and the second simulated surgical procedure each simulate a surgical procedure, and the first data and second data are each associated with a surgical task of the surgical procedure;
determine a first causal relation between a first surgical choice of the first data and a surgical aspect of the first data and a second causal relation between a second surgical choice of the first data and a corresponding surgical aspect of the second data;
display the first data and the second data, wherein the first causal relation is displayed with the first data and the second causal relation is displayed with the second data.

In some embodiments, there may be a plurality of surgical choices associated with a single surgical task, and this set of surgical choices can be stored in a respective data set (i.e. the first data/second data). Each of the surgical choices may be associated with a numeric value (e.g. one surgical choice may be assigned a value of 0, whilst another surgical choice may be assigned a value of 1). In some embodiments, the numerical value assigned to each surgical choice in a respective data set may refer to a row number, or other pointer to a data location within the data set.

In some embodiments, the "causal relationship" may include a linear or non-linear relationship between the numerical value assigned to each of the surgical choices and a surgical outcome. Therefore, the causal relationship may comprise a coefficient defining how an independent variable affects a dependent variable. The "causal relationship" may further include a value of statistical significance (e.g. a P-number), which indicates the statistical strength of the determined relationship. In some embodiments, both the coefficient and the value of statistical significance can be displayed to a user.

It may be understood that where the embodiment recites "the first simulated surgical procedure and the second simulated surgical procedure each simulate a surgical procedure", it can refer to a case where each of these procedures simulate the same type of surgical procedure. That is, the surgical procure simulated in the first simulated surgical procedure is the same surgical procedure simulated in the second simulated surgical procedure.

Similarly, where the embodiment recites that "the first data and second data are each associated with a surgical task of the surgical procedure", this can refer to each set of data being associated with the same surgical task of the procedure. That is, the surgical task associated with the first data can be the same as the surgical task associated with the second data.

In some cases, each of the respective simulated surgical procedures may, however, comprise different surgical choices (i.e. different actions being taken with respect to a specific surgical task in the procedure).

In some embodiments, the "surgical aspect" can refer to a specific surgical outcome or a surgical complication. For example, the first and second data sets can be aggregated and analyzed for causal relationships on the basis of a surgical outcome or a surgical complication.

The benefit of performing a statistic analysis (i.e. determining a causal relationship) between different surgical choices taken in different simulations (simulating the same task in a surgical procedure) and their corresponding surgical aspects (e.g. a surgical outcome) is that the processor can be configured to determine the effect certain choices have on different aspects of surgery. This information can be presented to a user in a way which allows them to make informed decisions about which surgical choice to elect in a future surgery. This will have a positive effect on the overall wellbeing of a patient, as the appropriate selection of surgical choices based on a simulation can lower operation times, improve patient outcomes, reduce surgical complications, etc.

Embodiment 9.2. The computing device of embodiment 9.1, wherein the first simulated surgical procedure and the second simulated surgical procedure are configured with a same simulation configuration or a same set of simulation configurations.

Embodiment 9.3. The computing device of any one of embodiments 9.1 to 9.2, wherein the surgical aspect is associated with one of the following: a time duration of a surgical task, a surgical instrument usage, a surgical outcome, or a surgical complication.

Embodiment 9.4. The computing device of any one of embodiments 9.1 to 9.3, wherein the first surgical choice of the first data is a selection from a plurality of surgical choices at a surgical choice selection point, wherein the second surgical choice of the second data is a selection from the plurality of surgical choices of the surgical choice selection point, wherein the surgical choice selection point is a part of the surgical task, wherein the surgical aspect of the first data comprises a surgical complication, and wherein the corresponding surgical aspect of the second data does not comprise the surgical complication.

Embodiment 9.5. The computing device of any one of embodiments 9.1 to 9.4, wherein the surgical aspect of the first data comprises a first numeric value, wherein the corresponding surgical aspect of the second data comprises a second numeric value, and wherein the processor is further configured to display the aggregation data.

Embodiment 9.6. The computing device of any one of embodiments 9.1 to 9.5, wherein the first simulated surgical procedure is a user-simulated procedure and the second simulated surgical procedure is a computer-simulated procedure.

Embodiment 9.7. The computing device of any one of embodiments 9.1 to 9.6, wherein the processor is further configured to:
receive a request to replay a simulation of the first surgical choice of the first data and the surgical aspect of the first data, wherein the surgical aspect of the first data comprises a surgical outcome or a surgical complication; and
generate a visualization of the simulation of the first surgical choice of the first data and the surgical aspect of the first data.

Embodiment 9.8. The computing device of any one of embodiments 9.4 to 9.7, wherein the first simulated surgical procedure is a computer-simulated procedure, and wherein the processor is further configured to:
receive a request to simulate the plurality of surgical choices of the surgical choice selection point; and
generate a visualization of the plurality of surgical choices of the surgical choice selection point.

Embodiment 9.9. A computer-implemented method for performing surgical analysis via surgical simulation, the method comprising:
obtaining first data associated with a first simulated surgical procedure and second data associated with a second simulated surgical procedure, wherein the first simulated surgical procedure and the second simulated surgical procedure each simulate a surgical procedure, and the first data and second data are each associated with a surgical task of the surgical procedure;
determining a first causal relation between a first surgical choice of the first data and a surgical aspect of the first data and a second causal relation between a second surgical choice of the first data and a corresponding surgical aspect of the second data;
displaying the first data and the second data, wherein the first causal relation is displayed with the first data and the second causal relation is displayed with the second data.

Embodiment 9.10. The computer-implemented method of embodiment 9.9, wherein the first simulated surgical procedure and the second simulated surgical procedure are configured with a same simulation configuration or a same set of simulation configurations.

Embodiment 9.11. The computer-implemented method of embodiment 9.9 or 9.10, wherein the surgical aspect is associated with one of the following: a time duration of a surgical task, a surgical instrument usage, a surgical outcome, or a surgical complication.

Embodiment 9.12. The computer-implemented method of any one of embodiments 9.9 to 9.11, wherein the first surgical choice of the first data is a selection from a plurality of surgical choices at a surgical choice selection point, wherein the second surgical choice of the second data is a selection from the plurality of surgical choices of the surgical choice selection point, wherein the surgical choice selection point is a part of the surgical task, wherein the surgical aspect of the first data comprises a surgical complication, and wherein the corresponding surgical aspect of the second data does not comprise the surgical complication.

Embodiment 9.13. The computer-implemented method of any one of embodiments 9.9 to 9.12, wherein the surgical aspect of the first data comprises a first numeric value, wherein the corresponding surgical aspect of the second data comprises a second numeric value, and wherein the processor is further configured to display the aggregation data.

Embodiment 9.14. The computer-implemented method of any one of embodiments 9.9 to 9.13, wherein the first simulated surgical procedure is a user-simulated procedure and the second simulated surgical procedure is a computer-simulated procedure.

Embodiment 9.15. The computer-implemented method of any one of embodiments 9.9 to 9.14, further comprising:
receiving a request to replay a simulation of the first surgical choice of the first data and the surgical aspect of the first data, wherein the surgical aspect of the first data comprises a surgical outcome or a surgical complication; and
generating a visualization of the simulation of the first surgical choice of the first data and the surgical aspect of the first data.

Embodiment 9.16. The computer-implemented method of any one of embodiments 9.9 to 9.15, further comprising:
receiving a request to simulate the plurality of surgical choices of the surgical choice selection point in the first surgical procedure; and
generating a visualization of the plurality of surgical choices of the surgical choice selection point in the first surgical procedure.

Embodiment 9.17. The computing device of any one of embodiments 9.1 to 9.8, wherein the processor is further configured to generate aggregation data from the first data and the second data based on the surgical aspect of the first data and the corresponding surgical aspect of the second data, and wherein the processor is configured to determine the first causal relationship and the second causal relationship from the aggregation data.

Embodiment 9.18. The computing device of any one of embodiments 9.1 to 9.8, wherein the causal relationship between the first surgical choice of the first data and the surgical aspect of the first data and the causal relationship between the second surgical choice of the second data and the surgical aspect of the second data each comprise one or more coefficient value and, optionally, a value of statistical significance.

Embodiment 9.19. The computer-implemented method of any one of embodiments 9.9 to 9.16, further comprising generating aggregation data from the first data and the second data based on the surgical aspect of the first data and the corresponding surgical aspect of the second data, and wherein the determining the first causal relationship and the second causal relationship comprises determining the first causal relationship and the second causal relationship from the aggregation data.

Embodiment 9.20. The computer-implemented method of any one of embodiments 9.9 to 9.16, wherein the causal relationship between the first surgical choice of the first data and the surgical aspect of the first data and the causal relationship between the second surgical choice of the second data and the surgical aspect of the second data each comprise one or more coefficient value and, optionally, a value of statistical significance.

Embodiment 9.21. A computer-readable medium comprising instructions which, when executed by a computer, cause the computer to perform the method of any one of embodiments 9.9 to 9.16, 9.19, and 9.20.

Embodiment 1.1. A device for managing surgical consequences in a simulated surgical task, the device comprising:
a processor configured to:
receive a simulation environment to simulate a surgical task defined by a set of environmental parameters;
receive surgical interaction data, wherein the surgical interaction data comprises an indication of a triggering event and an indication of consequence environmental parameters associated with the triggering event;
receive user interaction data based on a user action within the simulation environment and associated with the surgical task; and
on a condition that the received user interaction data matches the triggering event, modify the simulation environment based on the consequence environmental parameters.

By receiving surgical interaction data, the device of the embodiment 1.1 is configured to modify a pre-existing simulation environment based on this data. This allows the device of the embodiment 1.1 to inject complications into the simulation. In other words, a set of data including known inputs and outputs (e.g. from historical data of previous surgeries performed in a hospital) can be used to improve a known simulation environment.

One technical advantage of this is to improve the realism of a simulation environment, which can improve the efficacy of training exercises. The consequence of improved training is that surgical outcomes can be improved, as the surgeons will be better prepared for surgical complications.

Embodiment 1.2. The device of embodiment 1.1, wherein the surgical interaction data is associated with the surgical task and the surgical task comprises a medical procedure and a medical procedure context.

It may be understood that a medical procedure context can refer to a type of procedure being performed. It may also refer to a condition of the simulated patient's anatomy and/or physiology.

Embodiment 1.3. The device of embodiment 1.2, wherein the triggering event and the consequence environmental parameters are based on historical data associated with the medical procedure and the medical procedure context, wherein the historical data is based on previously performed live procedures recorded by a surgical hub.

The benefit of receiving surgical interaction data which is based on historical data is that a known simulation model can be iteratively improved and made more accurate based on real-world complications. In other words, the simulation environment can be iteratively improved based on known surgical choices and their respective surgical outcomes.

It may be understood that "historical data" can refer to data stored in memory which corresponds to one or more surgeries which have been previously performed. In these cases, a surgical hub can be configured to monitor a variety of parameters during the surgery, and store this data synchronously so that it can be later accessed to detect trends and certain consequences which arrive from different actions.

Embodiment 1.4. The device of embodiment 1.3, wherein the historical data is local data associated with a medical facility, wherein the previously performed live procedures are performed by medical staff associated with the medical facility, wherein the surgical hub is controlled by the medical facility.

Embodiment 1.5. The device of any one of embodiments 1.1 to 1.4, wherein the processor is further configured to:
determine a probability that the triggering event occurs;
determine an update simulation event based on the probability; and
on a condition that the update simulation event occurs, modify the simulation environment based on the consequence environmental parameters.

The benefit to a probabilistic approach to triggering events is to further improve the realism of a surgical training environment. In particular, if a specific consequence only occurs a proportion of the time, this detail can be imported into the simulation to further improve the realism of the training environment.

Embodiment 1.6. The device of any one of embodiments 1.2 to 1.5, wherein the processor is further configured to:
filter the surgical interaction data to filtered surgical interaction data, wherein the filtered surgical interaction data comprises an indication of a filtered triggering event and an indication of filtered consequence environment parameters, wherein the filtered triggering event is based on the medical procedure and the medical procedure context.

The benefit of this embodiment is that a reduced processing power is required to parse the surgical interaction data. A further benefit of this embodiment is that, by receiving a triggering event and corresponding consequence environment parameters related to a specific surgical task, the simulation can be more precisely initialized for an improved training outcome. For example, there may be a large array of available data related to the ligation of a blood vessel (each piece of data associated with a surgical outcome or consequence). However, there may be differing consequences due to a ligation based on the type of surgery being performed. Thus, by filtering the array of available data to limit to a certain medical procedure/context, and only using the corresponding pairs of triggering events/consequence environment parameters as parameters for modifying the simulator, the resultant simulation may be generally improved.

Embodiment 1.7. The device of any one of embodiments 1.1 to 1.6, wherein the processor is further configured to:
determine a triggering threshold associated with the surgical interaction data; and
on a condition that the user interaction data crosses the triggering threshold, modify the simulation environment based on the consequence environmental parameters.

The benefit of this embodiment is that the device can be configured to generate trigger conditions from a set of raw data. This can be achieved through, for example, machine-learning mechanisms, which can be used to identify patterns and thresholds at which triggers can cause different consequences in the surgical environments. By determining these thresholds, the surgical simulation can be made more realistic beyond what was previously possible.

Embodiment 1.8. The device of any one of embodiments 1.2 to 1.7, wherein the processor is further configured to:
determine surgical event interaction criteria based on the surgical task; and
on a condition that the received user interaction data satisfies the surgical event interaction criteria, modify the simulation environment based on the consequence environmental parameters.

Embodiment 1.9. The device of embodiment 1.8, wherein the surgical interaction criteria is associated with the medical procedure and the medical procedure context.

Embodiment 1.10. The device of any one of embodiments 1.1 to 1.9, wherein the set of environmental parameters indicates a baseline anatomy, wherein the consequence environmental parameters indicate a modified anatomy that is a result of a surgical interaction represented by the surgical interaction data.

Embodiment 1.11. The device of any one of embodiments 1.2 to 1.10, wherein the medical procedure context comprises at least one of: tissue friability, tissue fragility, blood flow, tissue perfusion, allergic reactions, blood pressure, or heart rate.

Embodiment 1.12. A computer-implemented method, comprising:
receiving a simulation environment to simulate a surgical task defined by a set of environmental parameters;
receiving surgical interaction data, wherein the surgical interaction data comprises an indication of a triggering event and an indication of consequence environmental parameters associated with the triggering event;
receiving user interaction data based on a user action within the simulation environment and associated with the surgical task; and
on a condition that the received user interaction data matches the triggering event, modifying the simulation environment based on the consequence environmental parameters.

Embodiment 1.13. The computer-implemented method of embodiment 1.12, wherein the surgical interaction data is associated with the surgical task and the surgical task comprises a medical procedure and a medical procedure context.

Embodiment 1.14. The computer-implemented method of embodiment 1.13, wherein the triggering event and the consequence environmental parameters are based on historical data associated with the medical procedure and the medical procedure context, wherein the historical data is based on previously performed live procedures recorded by a surgical hub.

Embodiment 1.15. The computer-implemented method of embodiment 1.14, wherein the historical data is local data associated with a medical facility, wherein the previously performed live procedures are performed by medical staff associated with the medical facility, wherein the surgical hub is controlled by the medical facility.

Embodiment 1.16. The computer-implemented method of any one of embodiments 1.12 to 1.15, further comprising determining a probability that the triggering event occurs; determining an update simulation event based on the probability; and on a condition that the update simulation event occurs, modify the simulation environment based on the consequence environmental parameters.

Embodiment 1.17. The computer-implemented method of any one of embodiments 1.13 to 1.16, further comprising:
filtering the surgical interaction data to filtered surgical interaction data, wherein the filtered surgical interaction data comprises an indication of a filtered triggering event and an indication of filtered consequence environment parameters, wherein the filtered triggering event is based on the medical procedure and the medical procedure context.

Embodiment 1.18. The computer-implemented method of any of embodiments 1.12 to 1.17, further comprising determining a triggering threshold associated with the surgical interaction data; and on a condition that the user interaction data crosses the triggering threshold, modifying the simulation environment based on the consequence environmental parameters.

Embodiment 1.19. The computer-implemented method of any one of embodiments 1.13 to 1.18, further comprising:
determining surgical event interaction criteria based on the surgical task; and
on a condition that the received user interaction data satisfies the surgical event interaction criteria, modifying the simulation environment based on the consequence environmental parameters.

Embodiment 1.20. The computer-implemented method of embodiment 1.19, wherein the surgical interaction criteria is associated with the medical procedure and the medical procedure context.

Embodiment 1.21. The computer-implemented method of any one of embodiments 1.12 to 1.20, wherein the set of environmental parameters indicates a baseline anatomy, wherein the consequence environmental parameters indicate a modified anatomy that is a result of a surgical interaction represented by the surgical interaction data.

Embodiment 1.22. The computer-implemented method of any one of embodiments 1.13 to 1.21, wherein the medical procedure context comprises at least one of: tissue friability, tissue fragility, blood flow, tissue perfusion, allergic reactions, blood pressure, or heart rate.

Embodiment 1.23. A device for managing surgical consequences in a simulated surgical task, the device comprising:
a processor configured to:
receive a simulation environment to simulate a surgical task defined by a set of environmental parameters;
receive surgical interaction data, wherein the surgical interaction data comprises an indication of a triggering event and an indication of consequence environmental parameters associated with the triggering event;
receive user interaction data based on a user action within the simulation environment and associated with the surgical task;
determine whether the received user interaction data matches the triggering event; and
modify, based on the determination whether the received user data matches the triggering event, the simulation environment based on the consequence environmental parameters.

Embodiment 1.24. The device of any one of embodiments 1.1 to 1.11 or embodiment 1.20, wherein the processor is configured to receive the surgical interaction data from a surgical data system.

Embodiment 1.25. A surgical system for adaptably simulating a surgical task, the system comprising the device of any one of embodiments 1.1 to 1.11, and a surgical data system, wherein the processor is configured to receive the surgical interaction data from the surgical data system.

Embodiment 1.26. The surgical system of embodiment 1.25, wherein the surgical data system is configured to analyze historical data and identify correlations between a surgeon's actions and environmental events, and to send the analyzed data to the processor as the surgical interaction data.

A surgical system according to the above embodiments can provide the capability for intensive data processing to occur on a surgical data system, such as the processing performed to parse out historical data and identify trends and triggering events. In some embodiments, once the surgical data system has performed the analysis, this data can be passed to the processor, such that certain parameters of a simulation running on the processor can be updated.

The surgical data system being configured to identify correlations allows the system to generate trigger conditions without user input, enabling a more automated process of updating simulations to improve the realism of the environment.

This allows a pre-existing simulation module to be adapted to compensate for certain triggers, which may not have been known at the time the simulation module was designed. This can improve the longevity and adaptability of pre-existing simulation modules.

Embodiment 1.27. The computer-implemented method of any one of embodiment 1.12 to 1.22, wherein the step of receiving surgical interaction data comprises receiving surgical interaction data from a surgical data system.

Embodiment 1.28. A computer-readable medium comprising instructions which, when executed by a computer, cause the computer to carry out the method of any one of embodiments 1.12 to 1.22 and 1.27.

The invention claimed is:

1. A method for improving surgical outcomes using a surgical simulator, the method comprising:
aggregating, by an operating-room-based surgical data system, surgical activity data indicative of a performance of a live surgical procedure;
communicating the surgical activity data from the operating-room-based surgical data system to a surgical simulation device, in communication with the operating-room-based surgical data system;
simulating a surgical task within a simulation environment based on the surgical activity data;
the operating-room-based surgical data system setting consequence environmental parameters and a triggering event based on the consequence environmental parameters;
the operating-room-based surgical data system sending surgical interaction data comprising a triggering threshold to the surgical simulation device;
the surgical simulation device identifying deviations from a surgical procedure plan from a pre-operative simulation and identifying recovery options;
the surgical simulation device identifying modifications to be made from the surgical procedure;
receiving, from a user of the surgical simulation device, user interaction data based on a user action within the simulation environment, the user interaction data related to a surgeon performing the surgical task and the identified modifications to be made from the surgical procedure;
determining that the user interaction data has crossed the triggering threshold received from the operating-room-based surgical data system;
based on the user interaction data crossing the triggering threshold, modifying the simulation environment by updating one or more values of environmental parameters with one or more values of consequence environmental parameters associated with the triggering event;
notifying the surgeon of the modified simulation environment indicative of the performance of a modified surgical procedure, wherein the notification indicates that the modified simulation environment implements improved surgical techniques; and
displaying the modified simulation environment via a surgical display module in the operating room;
wherein modified simulation environment allows the surgeon to view potential consequences of future actions and make informed decisions and improve surgical outcomes.

2. The method of claim 1, wherein the operating-room-based surgical data system aggregates the surgical activity data from a plurality of smart surgical instruments.

3. The method of claim 2, wherein the plurality of smart surgical instruments comprises at least one of a monopolar instrument, a bipolar instrument, an ultrasonic instrument, a smoke evacuation instrument, a suction instrument, an irrigation instrument, an imaging instrument, or a surgical robotic instrument.

4. The method of claim 1, further comprising a direct communications connection between the surgical simulation device and the operating-room-based surgical data system.

5. The method of claim 1, further comprising a data network providing connectivity between the operating-room-based surgical data system and a network adapter of the surgical simulation device.

6. The method of claim 1, wherein the user interaction data is received via a user interface device.

7. The method of claim 6, wherein the user interface device comprises any of a virtual reality headset or a robotic surgery surgeon's console.

8. The method of claim 1, wherein the surgical activity data is structured by a procedure plan data structure that is common to the operating-room-based surgical data system and the surgical simulation device, wherein the operating-room-based surgical data system is configured to employ the procedure plan data structure to record discrete elements of the live surgical procedure for structured analysis, and wherein the surgical simulation device is configured to employ the procedure plan data structure to establish a setting and an objective for a simulation session.

9. The method of claim 8, wherein the procedure plan data structure is configured to covey information indicative of equipment, technique, and surgical steps in a structured format such that the equipment, technique, and surgical steps of the live surgical procedure are reflected in the simulation environment.

10. A system for improving surgical outcomes using a surgical simulator, the system comprising:
   an operating-room-based surgical data system, wherein the operating-room based surgical data system aggregates surgical activity data indicative of a performance of a live surgical procedure; and
   a surgical simulation device, in communication with the operating-room-based surgical data system, wherein the surgical simulation device is configured to:
   receive the surgical activity data from the operating-room-based surgical data system,
   simulate a surgical task within a simulation environment based on the surgical activity data,
   receive, from the operating-room-based surgical data system, surgical interaction data comprising a trigger threshold, wherein the operating-room-based surgical data system sets consequence environmental parameters and a trigger event based on the consequence environmental parameters,
   identify deviations from a surgical procedure plan from a pre-operative simulation and identify recovery options,
   identify modifications to be made from the surgical procedure,
   receive, from a user of the surgical simulation device, user interaction data based on a user action within the simulation environment, the user interaction data related to a surgeon performing the surgical task and the identified modifications to be made from the surgical procedure,
   determine that the user interaction data has crossed the trigger threshold received from the operating-room-based surgical data system,
   based on the user interaction data crossing the trigger threshold, modify the simulation environment by updating one or more values of environmental parameters with one or more values of the consequence environmental parameters associated with the trigger event,
   notify the surgeon of the modified simulation environment indicative of the performance of a modified surgical procedure, wherein the notification indicates that the modified simulation environment implements improved surgical techniques, and
   display the modified simulation environment via a surgical display module in the operating room,
   wherein the modified simulation environment allows the surgeon to view potential consequences of future actions and make informed decisions and improve surgical outcomes.

11. The system of claim 10, further comprising:
   aggregating, by the operating-room-based surgical data system, the surgical activity data from a plurality of smart surgical instruments.

12. The system of claim 11, wherein the plurality of smart surgical instruments comprises at least one of a monopolar instrument, a bipolar instrument, an ultrasonic instrument, a smoke evacuation instrument, a suction instrument, an irrigation instrument, an imaging instrument, or a surgical robotic instrument.

13. The system of claim 10, wherein said communicating comprises communicating via a direct communications connection between the surgical simulation device and the operating-room-based surgical data system.

14. The system of claim 10, wherein said communicating comprises communicating via a data network providing connectivity between the operating-room-based surgical data system and a network adapter of the surgical simulation device.

15. The system of claim 10, wherein the user interaction is received via a user interface device.

16. The system of claim 15, wherein the user interface device comprises any of a virtual reality headset or a robotic surgery surgeon's console.

17. The system of claim 10, wherein the surgical activity data is structured by a procedure plan data structure that is common to the operating-room-based surgical data system and the surgical simulation device, further comprising:
   employing, by the operating-room-based surgical data system, the procedure plan data structure to record discrete elements of the live surgical procedure for structured analysis; and
   employing, by the surgical simulation device, the procedure plan data structure to establish a setting and an objective for a simulation session;
   wherein the procedure plan data structure is configured to covey information indicative of equipment, technique, and surgical steps in a structured format such that the equipment, technique, and surgical steps of the live surgical procedure are reflected in the simulation environment.

18. A system for improving surgical outcomes using a surgical simulator, the system comprising:
   an operating-room-based surgical data system, wherein the operating-room based surgical data system aggregates surgical activity data indicative of a performance of a live surgical procedure; and
   a surgical simulation device, in communication with the operating-room-based surgical data system, wherein the surgical simulation device is configured to:
   receive the surgical activity data from the operating-room-based surgical data system,
   simulate a surgical task within a simulation environment based on the surgical activity data such that the surgical simulation device enables at least one of dynamic adaptation, rectification of surgical simulation objects enhanced navigation, coordinated surgical imagining, simulated surgical equipment coordination, simulation-based surgical procedure planning, simulation-based directed surgical development, simulation of surgical adverse events, or simulation-based surgical analysis, receive, from the operating-room-based surgical data system, surgical interaction data comprising a trigger threshold, wherein the operating-room-based surgical data system sets consequence environmental parameters and a trigger event based on the consequence environmental parameters, identify deviations from a surgical procedure plan from a pre-operative simulation and identify recovery options, identify modifications to be made from the surgical procedure, receive, from a user of the surgical simulation device, user interaction data based on a user action within the simulation environment, the user interaction data related to a surgeon performing the surgical task and the identified modifications to be made from the surgical procedure, determine that the user interaction data has crossed the trigger threshold received from the operating-room-based surgical data system, based on the user interaction data crossing the trigger threshold, modify the simulation environment by updating one or more values of environmental parameters with one or more values of the consequence environmental parameters associated with the trigger event;

notify the surgeon of the modified simulation environment indicative of the performance of a modified surgical procedure, wherein the notification indicates that the modified simulation environment implements improved surgical techniques, and display the modified simulation environment via a surgical display module in the operating room;

wherein the modified simulation environment allows the surgeon to view potential consequences of future actions and make informed decisions and improve surgical outcomes.

* * * * *